US008227610B2

(12) United States Patent
Janjic et al.

(10) Patent No.: US 8,227,610 B2
(45) Date of Patent: Jul. 24, 2012

(54) COMPOSITIONS AND METHODS FOR PRODUCING CELLULAR LABELS FOR NUCLEAR MAGNETIC RESONANCE TECHNIQUES

(75) Inventors: Jelena Janjic, Pittsburgh, PA (US); Eric T. Ahrens, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 865 days.

(21) Appl. No.: 12/218,265

(22) Filed: Jul. 10, 2008

(65) Prior Publication Data
US 2009/0074673 A1    Mar. 19, 2009

Related U.S. Application Data

(60) Provisional application No. 61/062,710, filed on Jan. 28, 2008, provisional application No. 60/959,135, filed on Jul. 10, 2007.

(51) Int. Cl.
*C07D 221/06* (2006.01)
*C07D 233/00* (2006.01)

(52) U.S. Cl. ............... 546/79; 564/152; 564/159

(58) Field of Classification Search .................. None
See application file for complete search history.

(56) References Cited

U.S. PATENT DOCUMENTS

| | | |
|---|---|---|
| 4,094,911 A | 6/1978 | Zollinger |
| 4,558,279 A | 12/1985 | Ackerman et al. |
| 4,570,004 A | 2/1986 | Lagow et al. |
| 4,714,680 A | 12/1987 | Civin |
| 4,783,401 A | 11/1988 | Horan et al. |
| 4,838,274 A | 6/1989 | Schweighardt et al. |
| 4,935,223 A | 6/1990 | Phillips |
| 4,990,283 A | 2/1991 | Visca et al. |
| 4,996,041 A | 2/1991 | Arai et al. |
| 5,061,620 A | 10/1991 | Tsukamoto et al. |
| 5,114,703 A | 5/1992 | Wolf et al. |
| 5,196,348 A | 3/1993 | Schweighardt et al. |
| 5,330,681 A | 7/1994 | Brunetta et al. |
| 5,397,562 A | 3/1995 | Mason et al. |
| 5,437,994 A | 8/1995 | Emerson et al. |
| 5,460,800 A | 10/1995 | Walters |
| 5,486,359 A | 1/1996 | Caplan et al. |
| 5,539,059 A | 7/1996 | Bierschenk et al. |
| 5,589,376 A | 12/1996 | Anderson et al. |
| 5,643,741 A | 7/1997 | Tsukamoto et al. |
| 5,690,907 A | 11/1997 | Lanze et al. |
| 5,716,827 A | 2/1998 | Tsukamoto et al. |
| 5,750,397 A | 5/1998 | Tsukamoto et al. |
| 5,753,506 A | 5/1998 | Johe |
| 5,763,197 A | 6/1998 | Tsukamoto et al. |
| 5,766,948 A | 6/1998 | Gage et al. |
| 5,785,950 A | 7/1998 | Kaufman et al. |
| 5,824,489 A | 10/1998 | Anderson et al. |
| 5,827,735 A | 10/1998 | Young et al. |
| 5,843,780 A | 12/1998 | Thomson |
| 5,851,832 A | 12/1998 | Weiss et al. |
| 5,914,108 A | 6/1999 | Tsukamoto et al. |
| 5,925,567 A | 7/1999 | Kraus et al. |
| 5,942,225 A | 8/1999 | Bruder et al. |
| 5,958,371 A | 9/1999 | Lanza et al. |
| 5,972,703 A | 10/1999 | Long et al. |
| 6,040,180 A | 3/2000 | Johe |
| 6,090,622 A | 7/2000 | Gearhart et al. |
| 6,171,610 B1 | 1/2001 | Vacanti et al. |
| 6,190,910 B1 | 2/2001 | Kusakabe et al. |
| 6,200,806 B1 | 3/2001 | Thomson |
| 6,245,566 B1 | 6/2001 | Gearhart et al. |
| 6,331,406 B1 | 12/2001 | Gearhart et al. |
| 6,361,996 B1 | 3/2002 | Rao et al. |
| 6,468,794 B1 | 10/2002 | Uchida et al. |
| 6,511,967 B1 | 1/2003 | Weissleder et al. |
| 7,357,937 B2 | 4/2008 | Hsu et al. |
| 7,514,074 B2 | 4/2009 | Pittenger et al. |
| 2002/0016002 A1 | 2/2002 | Toma et al. |
| 2002/0045259 A1 | 4/2002 | Lim et al. |
| 2002/0068045 A1 | 6/2002 | Reubinoff et al. |
| 2002/0123143 A1 | 9/2002 | Toma et al. |
| 2002/0192688 A1 | 12/2002 | Yang et al. |
| 2003/0003574 A1 | 1/2003 | Toma et al. |
| 2004/0109824 A1 | 6/2004 | Hinds et al. |
| 2005/0008572 A1 | 1/2005 | Prokop et al. |
| 2005/0079131 A1 | 4/2005 | Lanza et al. |
| 2005/0244384 A1 | 11/2005 | Law |
| 2006/0040389 A1 | 2/2006 | Murry et al. |
| 2006/0239919 A1 | 10/2006 | Wickline et al. |
| 2007/0253910 A1 | 11/2007 | Ahrens et al. |
| 2007/0258886 A1 | 11/2007 | Ahrens et al. |
| 2009/0263329 A1 | 10/2009 | Wickline et al. |

FOREIGN PATENT DOCUMENTS

| | | |
|---|---|---|
| DE | 2 242 191 | 4/1972 |
| DE | 42 03 254 | 5/1996 |
| EP | 0 307 863 | 7/1991 |
| EP | 0 307 087 | 6/1994 |
| EP | 1 728 788 | 12/2006 |
| WO | WO91/14664 | 10/1991 |
| WO | WO-94/18954 | 9/1994 |
| WO | WO-94/21303 | 9/1994 |

(Continued)

OTHER PUBLICATIONS

Szabo, J. Fluorine Chem. 2005 vol. 126, pp. 641-652.*
Ablamunits et al., Acceleration of autoimmune diabetes by cyclophosphamide is associated with an enhanced IFN-gamma secretion pathway, J. Autoimmun. 13(4):383-392 (1999).
Ahrens et al., A model for MRI contrast enhancement using $T_1$ agents, Proc. Natl. Acad. Sci. USA 95:8443-8448 (1998).
Ahrens et al., In vivo imaging platform for tracking immunotherapeutic cells, Nat. Biotechnol. 23(8):983-987 (2005).
Ahrens et al., Peripheral somatosensory fMRI in mouse at 11.7T, NMR Biomed., 14:318-324 (2001).
Ahrens et al., Receptor-mediated endocytosis of iron-oxide particles provides efficient labeling of dendritic cells for in vivo MR imaging, Mag. Reson. Med. 49:1006-1013 (2003).
Allen et al., Cellular delivery of MRI contrast agents, Chem. Bio. 11(3):301-307 (2004).

(Continued)

*Primary Examiner* — Janet Andres
*Assistant Examiner* — Heidi Reese
(74) *Attorney, Agent, or Firm* — Ropes & Gray LLP

(57) ABSTRACT

The disclosure provides, in part, compositions of perfluoro polyether compounds and associated methods for producing cellular labels for tracking cells by MRI and methods for labeling, detecting and quantifying cell numbers in vivo.

30 Claims, 66 Drawing Sheets

FOREIGN PATENT DOCUMENTS

| | | |
|---|---|---|
| WO | WO-96/41647 | 12/1996 |
| WO | WO97/40679 | 11/1997 |
| WO | WO-98/20907 | 5/1998 |
| WO | WO-00/02654 | 1/2000 |
| WO | WO-00/53795 | 9/2000 |
| WO | WO-2005/072780 | 8/2005 |
| WO | WO-2006/096499 | 9/2006 |
| WO | WO-2007/100715 | 9/2007 |
| WO | WO 2008/119790 | 10/2008 |
| WO | WO-2008/144028 | 11/2008 |
| WO | WO2009/009105 | 1/2009 |

OTHER PUBLICATIONS

Anderson et al., Magnetic resonance imaging of labeled T-cells in a mouse model of multiple sclerosis, Ann. Neurol. 55(5):654-659 (2004).

Arbab et al., Efficient magnetic cell labeling with protamine sulfate complexed to ferumoxides for cellular MRI, Blood 15:104(4):1217-23 (2004).

Barnett et al., Radiopaque Alginate Microcapsules for X-ray Visualization and Immunoprotection of Cellular Therapeutics, Mol. Pharm. 3(5):531-538 (2006).

Billotey et al., T-cell homing to the pancreas in autoimmune mouse models of diabetes: in vivo MR imaging, Radiology 236(2):579-587 (2005).

Bulte et al., Preparation of magnetically labeled cells for cell tracking by magnetic resonance imaging. Method Enzymol. 386:275-299 (2004).

Cantor et al., Effector function of diabetogenic CD4 Th1 T cell clones: a central role for TNF-alpha, J. Immunol. 175(11):7738-7745 (2005).

Caruthers et al., In vitro demonstration using 19F magnetic resonance to augment molecular imaging with paramagnetic perfluorocarbon nanoparticles at 1.5 Tesla, Invest. Radiology 41(3):305-312, Mar. 2006.

Cheng et al., Characterization of aqueous dispersions of Fe(3)O(4) nanoparticles and their biomedical applications, Biomaterials 26(7):729-738 (2005).

Crowder, et al. "Unique perflourocarbon nanobeacons improve stem/progenitor cell tracking with MRI" FASEB Journal, vol. 20, No. 4, part 1. Mar. 2006, pp. A633, Abstract.

Dardzinski et al., Rapid tissue oxygen tension mapping using 19F inversion-recovery echo-planar imaging of perfluoro-15-crown-5-ether, Magn. Reson. Med. 32(1):88-97 (1994).

Derossi et al, The Third Helix of the Antennapedia Homeodomain Translocates through Biological Membranes, J. Biol. Chem. 269(14)10444-10450 (1994).

Derossi et al., Cell Internationalization of the Third Helix of the Antennapedia Homeodomain Is Receptor-Independent, J. Biol. Chem. 271(30):18188-18193 (1996).

Dodd et al., Normal T-cell response and in vivo magnetic resonance imaging of T cells loaded with HIV transactivator-peptide-derived superparamagnetic nanoparticles, J. Immun. Meth. 256(1-2):89-105 (2001).

Dousset et al., In vivo macrophage activity imaging in the central nervous system detected by magnetic resonance, Mag. Res. Med. 41(2): 329-333 (1999).

Duong et al., In vivo MR measurements of regional arterial and venous blood volume fractions in intact rat brain, Mag. Res. Med. 43(3):393-402 (2000).

Eidelberg et al., 19F NMR imaging of blood oxygenation in the brain, Mag. Res. Med. 6(3):344-52 (1988).

Elster et al., Dyke Award. Europium-DTPA: a gadolinium analogue traceable by fluorescence microscopy, Am. J. Neuroradiol. 10(6):1137-1144 (1989).

Evgenov et al., In vivo imaging of immune rejection in transplanted pancreatic islets, Diabetes 55(9):2419-2428 (2006).

Evgenov et al., In vivo imaging of islet transplantation, Nat. Med. 12(1):144-148 (2006).

Fabien et al., Pancreatic lymph nodes are early targets of T cells during adoptive transfer of diabetes in NOD mice, J. Autoimmun. 8(3):323-334 (1995).

Fan et al., MRI of perfluorocarbon emulsion kinetics in rodent mammary tumours, Phys. Med. & Biol. 51:211-220 (2006).

Feili-Hariri, et al., Immunotherapy of NOD mice with bone marrow-derived dendritic cells, Diabetes, 48:2300-2308 (1999).

Fishman et al., Oxygen-sensitive 19F NMR imaging of the vascular system in vivo, Magn. Reson. Imaging 5(4):279-285 (1987).

Floris et al., Blood-brain barrier permeability and monocyte infiltration in experimental allergic encephalomyelitis: a quantitative MRI study, Brain. 127(Pt 3):616-27 (2004).

Forstrom et al., 18F-FDG Labelling of Human Leukocytes, Nucl. Med. Comm. 21(7):691-694 (2000).

Frankel et al.,Cellular uptake of the tat protein from human immunodeficiency virus, Cell, 55:1189-1193 (1989).

Friedrich et al., Promoter traps in embryonic stem cells: a genetic screen to identify and mutate developmental genes in mice, Genes & Dev. 5:1513-1523 (1991).

Girolomoni et al., Establishment of a Cell-Line with Features of Early Dendritic Cell Precursors from Fetal Mouse Skin, Eur. J. Imm. 25(8):2163-2169 (1995).

Granot et al., Labeling fibroblasts with biotin-BSA-GdDTPA-FAM for tracking of tumor-associated stroma by fluorescence and MR imaging, Magn, Reson. Med. 54(4):789-797 (2005).

Green et al., Autonomous functional domains of chemically synthesized human immunodeficiency virus tat trans-activator protein, Cell, 55:1179-1188 (1988).

Gritti et al., Multipotent neural stem cells reside into the rostral extension and olfactory bulb of adult rodents, The Journal of Neuroscience, 22(2):437-445 (2002).

Gudbjartsson et al., The Rician distribution of noisy MRI data, Magn. Reson. Med. 34(6):910-914 (1995).

Helmer et al. On the correlation between the water diffusion coefficient and oxygen tension in RIF-1 tumors, NMR in Biomedicine, 11(3):120-130 (1998).

Hoehn et al., Monitoring of implanted stem cell migration in vivo: A highly resolved in vivo magnetic resonance imaging investigation of experimental stroke in rat, Proc. Natl. Acad. Sci. USA 99(25):16267-16272 (2002).

Janjic et al., Self-delivering nanoemulsions for dual fluorine-19 MRI and fluorescence detection, J. Amer. Chem. Soc. 130:2832-2841 (2008).

Jiang et al., The Design and Synthesis of Highly Branched and Spherically Symmetric Fluorinated Oils and Amphiles, Tetrahedron 63(19):3982-3988 (2007).

Josephson et al., High-efficiency intracellular magnetic labeling with novel superparamagnetic-tat peptide conjugates, Bioconjugate Chem. 10(2):186-191 (1999).

Kanno et al., Macrophage accumulation associated with rat cardiac allograft rejection detected by magnetic resonance imaging with ultrasmall superparamagnetic iron oxide particles, Circulation 104(8):934-938 (2001).

Kimura et al., Neurite outgrowth of PC12 cells is suppressed by wortmannin, a specific inhibitor of phosphatidylinositol 3-kinase, J. Biol. Chem. 269:18961-18967 (1994).

Kircher et al., In vivo high resolution three-dimensional imaging of antigen-specific cytotoxic T-lymphocyte trafficking to tumors, Cancer Res. 63(20):6838-6846 (2003).

Kraitchman et al., In vivo magnetic resonance imaging of mesenchymal stem cells in myocardial infarction, Circulation 107(18):2290-2293 (2003).

Krause et al., Multi-organ, multi-lineage engraftment by a single bone marrow-derived stem cell, Cell 105:369-377 (2001).

Kravtzoff et al., GD-DOTA Loaded into red blood cells. A new magnetic resonance imaging contrast agents for vascular system, Adv. in Exp. Med. and Biol. 326:347-326 (1992).

Kuppuswamy et al., Multiple functional domains of Tat, the trans-activator of HIV-1, defined by mutational analysis, Nucl. Acids Res. 17:3551-3561 (1989).

Lagasse et al., Purified hematopoietic stem cells can differentiate into hepatocytes in vivo, Nat. Med. 6(11):1229-1234 (2000).

Lanza et al., 1H/19F magnetic resonance molecular imaging with perfluorocarbon nanoparticles. In: Ahrens ET, editor. In vivo cellular and molecular imaging, Curr. Top. Dev. Biol. 70:58-78 (2005).

Lanza et al., A novel site-targeted ultrasonic contrast agent with broad biomedical application, Circulation 94(12):3334-3340 (1996).
Leiter et al., The nonobese diabetic (NOD) mouse, Am. J. Pathol. 128(2):380-383 (1987).
Lewin et al., Tat peptide-derivatized magnetic nanoparticles allow in vivo tracking and recovery of progenitor cells, Nat. Biotechnol. 18(4):410-414 (2000).
Lutz et al., Measurement of oxygen tensions in the abdominal cavity and in the skeletal muscle using 19F-MRI of neat PFC droplets, Adv. Exp. Med. Biol. 428:569-572 (1997).
Mason, Non-invasive physiology: $^{19}$F NMR of perfluorocarbons, Art. Cells, Blood Subs., and Immob. Biotech. 22(4):1141-1153 (1994).
McGoron et al., Perfluorocarbon distribution to liver, lung and spleen of emulsions of perfluorotributylamine (FTBA) in pigs and rats and perfluorooctyl bromide (PFOB) in rats and dogs by F-19 NMR-spectroscopy, Artificial Cells Blood Substitutes and Immobilization, Biotechnology 22(4):1243-1250 (1994).
McNab et al., Tissue oxygen tension measurements in the Shionogi model of prostate cancer using $^{19}$F MRS and MRI, MAGMA 17:288-295 (2004).
Means et al., Chemical modifications of proteins: history and applications, Bioconj. Chem. 1:2-12 (1990).
Meyer et al., Measurement of vascular volume in experimental rat tumors by 19F magnetic resonance imaging, Invest. Radiol. 28(8):710-719 (1993).
Miller et al., Imaging the single cell dynamics of CD4+ T cell activation by dendritic cells in lymph nodes, J. Exp. Med. 200(7):847-856 (2004).
Miyazaki et al., Predominance of lymphocytes-T in pancreatic-islets and spleen of pre-diabetic non-obese diabetic (NOD) mice—A longitudinal-study, Clin. Exp. Immunol. 60(3):622-630 (1985).
Modo et al., Mapping transplanted stem cell migration after a stroke: a serial, in vivo magnetic resonance imaging study, Neuroimage 21(1):311-317 (2004).
Moore et al., Tracking the recruitment of diabetogenic CD8+ T-cells to the pancreas in real time, Diabetes 53(6):1459-1466 (2004).
Moore et al., Uptake of dextran-coated monocrystalline iron oxides in tumor cells and macrophages, J. Mag. Reson. Imaging 7(6): 1140-1145 (1997).
Morawski et al., Quantitative magnetic resonance immunohistochemistry with ligand-targeted F-19 nanoparticles, Magn. Reson. Med. 52(6):1255-1262 (2004).
Morawski et al., Targeted Nanoparticles for Quantitative Imaging of Sparse Molecular Epitopes with MRK, Mag. Res. in Med. 51(3):480-486 (2004).
Neubauer et al., Endothelial stem cell detection in vivo with unique perflourocarbon nanoparticle labels using fluorine (F-19) MNRI at 1.5 T, Circulation 114(18)(Suppl. S): 251 (Abstract) (2006).
Noth et al., In vivo measurement of partial oxygen pressure in large vessels and in the reticuloendothelial system using fast 19F-MRI, Magn. Reson. Med. 34(5):738-745 (1995).
Noth et al., Perfluoro-15-crown-5-ether labelled macrophages in adoptive transfer experimental allergic encephalomyelitis, Artificial Cells Blood Substitutes and Immobilization Biotechnology 25(3): 243-254 (1997).
Pakala et al., T helper 2 (Th2) T cells induce acute pancreatitis and diabetes in immune-compromised nonobese diabetic (NOD) mice, J. Exp. Med. 186(2):299-306 (1997).
Partlow et al., 19F magnetic resonance imaging for stem/progenitor cell tracking with multiple unique perfluorocarbon nanobeacons, FASEB J. 21:1647-1654 (2007).
Pelchen-Matthews et al., Phorbol ester-induced downregulation of CD4 is a multistep process involving dissociation from p56lck, increased association with clathrin-coated pits, and altered endosomal sorting, J. Exp. Med. 178(4):1209-1222 (1993).
Perez et al., Antennapedia homeobox as a signal for the cellular internalization and nuclear addressing of a small exogenous peptide, J. Cell Sci. 102:717-722 (1992).
Phillips et al., MAdCAM-1 is needed for diabetes development mediated by the T cell clone, BDC-2.5, Immunology 116(4):525-531 (2005).
Phillips et al., Nondepleting anti-CD4 has an immediate action on diabetogenic effector cells, hafting their destruction of pancreatic beta cells, J. Immunol. 165(4):1949-1955 (2000).
Piacenti et al., Synthesis and characterization of fluorinated polyetheric amides, J. Fluor. Chem. 68:227-235 (1994).
Pintaske et al., A preparation technique for quantitative investigation of SPIO-containing solutions and SPIO-labelled cells by MRI. Biomed. Tech. 50(6):174-180 (2005) (English Abstract).
Pittenger et al., Multilineage potential of adult human mesenchymal stem cells, Science, 284:143-147 (1999).
Pluchino et al., Injection of adult neurospheres induces recovery in a chronic model of multiple sclerosis, Nature 422(6933): 688-694 (2003).
Qiu et al., Null mutation of Dlx-2 results in abnormal morphogenesis of proximal first and second branchial arch derivatives and abnormal differentiation in the forebrain, Genes & Dev. 9:2523-2538 (1995).
Ribeiro et al., In vivo dynamics of T cell activation, proliferation, and death in HIV-1 infection: why are CD4+ but not CD8+ T cells depleted? Proc. Natl. Acad. Sci. USA 99(24):15572-15577 (2002).
Rodriguez at al., In vitro characterization of an Fe(8) cluster as potential MRI contrast agent, NMR Biomed. 18(5):300-307 (2005).
Ruben et al., Structural and functional characterization of human immunodeficiency virus tat protein, J. Vir. 63:1-8 (1989).
Sanchez et al., Highly Concentrated 1,2-bis (perfluoroalkyl) iodoethene emulsions for use as contrast agents for diagnosis, J. Fluor. Chem. 73(2):259-264 (1995).
Schneider et al., In vivo microscopic evaluation of the microvascular behavior of FITC-labeled macromolecular MR contrast agents in the hamster skinfold chamber, Invest. Radiol. 35(9):564-570 (2000).
Schoepf et al., Intracellular magnetic labeling of lymphocytes for in vivo trafficking studies, Biotechniques 24(4): 642-651 (1998).
Schulze et al., Cellular uptake and trafficking of a prototypical magnetic iron oxide label in vitro, Invest. Radiol. 30(10):604-10 (1995).
Shapiro at al., In vivo detection of single cells by MRI, Magn. Reson. Med. 55(2):242-249 (2006).
Soloski, Synthesis of perfluoro (polyether) difunctional compounds, J. Fluor. Chem. 11:601-612 (1978).
Srinivas et al., Fluorine-19 MRI for visualization and quantification of cell migration in a diabetes model, Mag. Res. In Med. 58(4):725-734 (2007).
Tonelli et al., Linear perfluoropolyether difunctional oligomers: chemistry, properties and applications, J. Fluorine Chem. 95:51-70 (1999).
Tonelli at al., Perfluoropolyether alkyl diesters: Structure effects of the alkyl group on the kinetics of the hydrolysis reactions, J. Polym. Sci. Part A: Polym Chem. 40:4266-4280 (2002).
Tonelli et al., Perfluoropolyether functional oligomers: unusual reactivity in organic chemistry, J. Fluor. Chem. 118(1-2):107-121 (2002).
Turvey at al., Noninvasive imaging of pancreatic inflammation and its reversal in type 1 diabetes, J. Clin. Invest. 115(9):2454-2461 (2005).
Venanzi at al., Structural properties and photophysical behavior of conformationally constrained hexapeptides functionalized with a new fluorescent analog of tryptophan and a nitroxide radical quencher, Biopolymers 75(2):128-139 (2004).
Weissleder et al., Magnetically labeled cells can be detected by MR imaging. J. Mag. Res. Imag. 7(1): 258-263 (1997).
Wilson at al., Measurement of preretinal oxygen-tension in the vitrectomized human eye using F-19 magnetic resonance spectroscopy, Arch. Ophthalmol-Chic. 110(8)1098-1100 (1992).
Wisner at al., A modular lymphographic magnetic resonance imaging contrast agent: contrast enhancement with DNA transfection potential, J. Med. Chem. 40(25):3992-3996 (1997).
Wu et al., In situ labeling of immune cells with iron oxide particles: An approach to detect organ rejection by cellular MRI, Proc. Natl. Acad. Sci. USA 103(6):1852-1857 (2006).
Xia et al., Tumour oxygen dynamics measured simultaneously by near-infrared spectroscopy and F-19 magnetic resonance imaging in rats, Phys. Med. Biol. 51(1):45-60 (2006).
Ye et al., In vivo detection of acute rat renal allograft rejection by MRI with USPIO particles. Kid. Intl. 61(3):1124-1135 (2002).
Yeh et al., Intracellular labeling of T-cells with superparamagnetic contrast agents, Magn. Reson. Med. 30(5):617-625 (1993).

Yeh et al., In-vivo dynamic MRI tracking of rat T-cells labeled with superparamagnetic iron-oxide particles, Magn. Reson. Med. 33:200-208 (1995).

You et al., Detection and characterization of T cells specific for BDC2.5 T cell-stimulating peptides, J. Immunol. 170(8):4011-4020 (2003).

Yu et al., High-resolution MRI characterization of human thrombus using a novel fibrin-targeted paramagnetic nanoparticle contrast agent, Mag. Res. In Med. 44:867-872 (2000).

Zhang et al., Synthetic applications of fluorous solid-phase extraction (F-SPE), Tetrahedron 62:11837-11865 (2006).

Zhao et al., Human bone marrow stem cells exhibit neural phenotypes and ameliorate neurological deficits after grafting into the ischemic brain of rats, Exp. Neur. 174:11-20 (2002).

Basse-Lusebrink et al., Multi-color $^{19}$F CSI: Simultaneous detection of differently labeled cells in vivo, Abstract #806, Proc. Int. Soc. Mag. Reson. 17 (2009).

Hitchens et al., Comparison of iron-oxide- and perfluorocarbon-based cellular contrast agents for detecting immune Cell infiltration in models of organ transplant rejection, Abstract #931, Proc. Int. Soc. Mag. Reson. 17 (2009).

Kim et al., Interplay of tumor vascular oxygenation and tumor pO2 observed using near-infrared spectroscopy, an oxygen needle electrode, and 19F MR pO2 mapping, J. Biomed Opt 8:53-62; 2003.

Klug et al., 1H/19F molecular MR-imaging in mouse models of acute and chronic inflammation, Abstract #3172, Proc. Int, Soc. Mag. Reson. 17 (2009).

Laukemper-Ostendorf et al., 19F-MRI of perflubron for measurement of oxygen partial pressure in porcine lungs during partial liquid ventilation, Magn. Reson. Med. 47:82-89; 2002.

Mason et al., Hexafluorobenzene: a sensitive 19F NMR indicator of tumor oxygenation, NMR Biomed 9:125-134; 1996.

Sotak et al., A new perfluorocarbon for use on fluorine-19 magnetic resonance imaging and spectroscopy, Magn. Reson. Med. 29:188 (1993).

Taylor and Deutsch, 19F-nuclear magnetic resonance: measurements of [O2] and pH in biological systems, Biophys J. 53: 227-233 (1988).

Wilhelm et al., Magnetophoresis and ferromagnetic resonance of magnetically labeled cells, Eur. Biophys. J. 31:118-125 (2002).

Flögel et al., In vivo monitoring of inflammation after cardiac and cerebral ischemia by fluorine magnetic resonance imaging, Circulation 118:140-148 (2008).

Cunningham et al., Positive contrast magnetic resonance imaging of cells labeled with magnetic nanoparticles, Mag. Res. In Med. 53:999-1005 (2005).

* cited by examiner

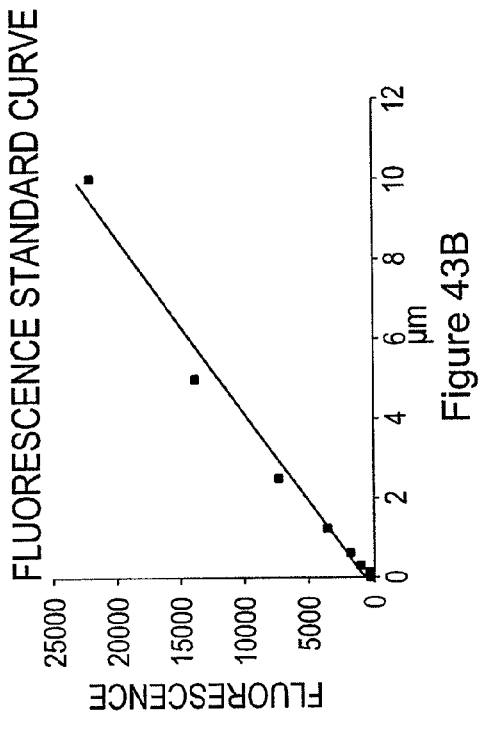
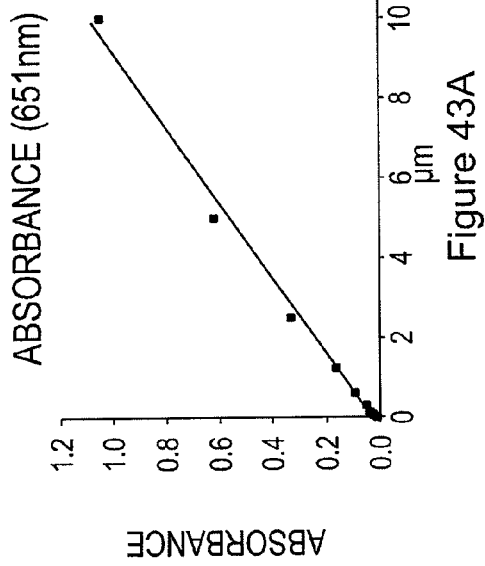
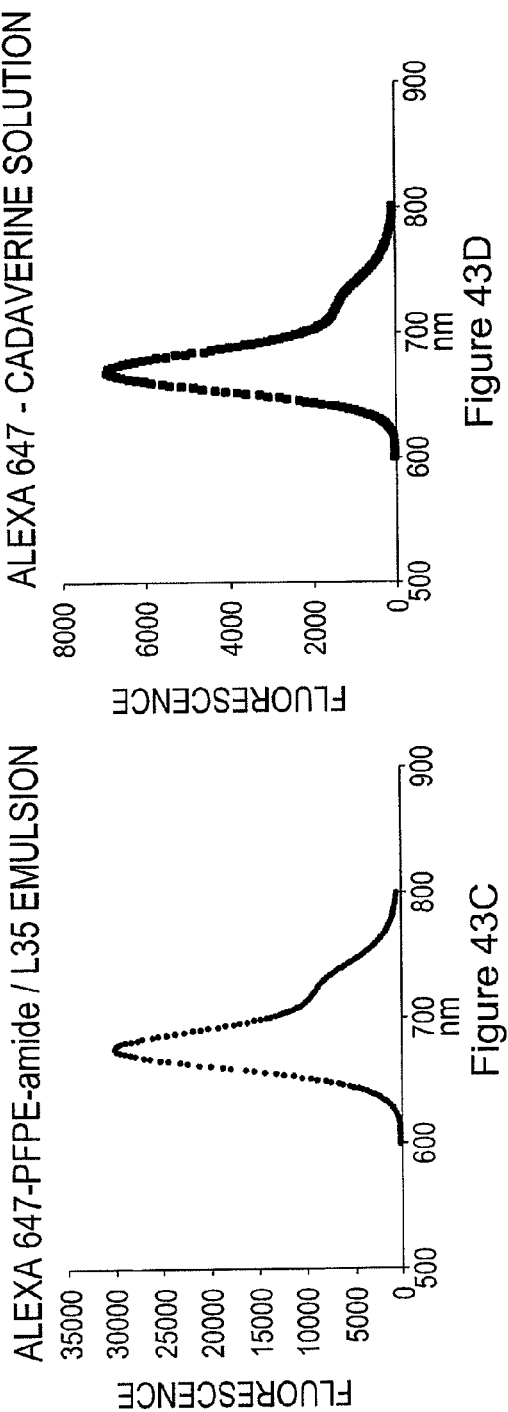

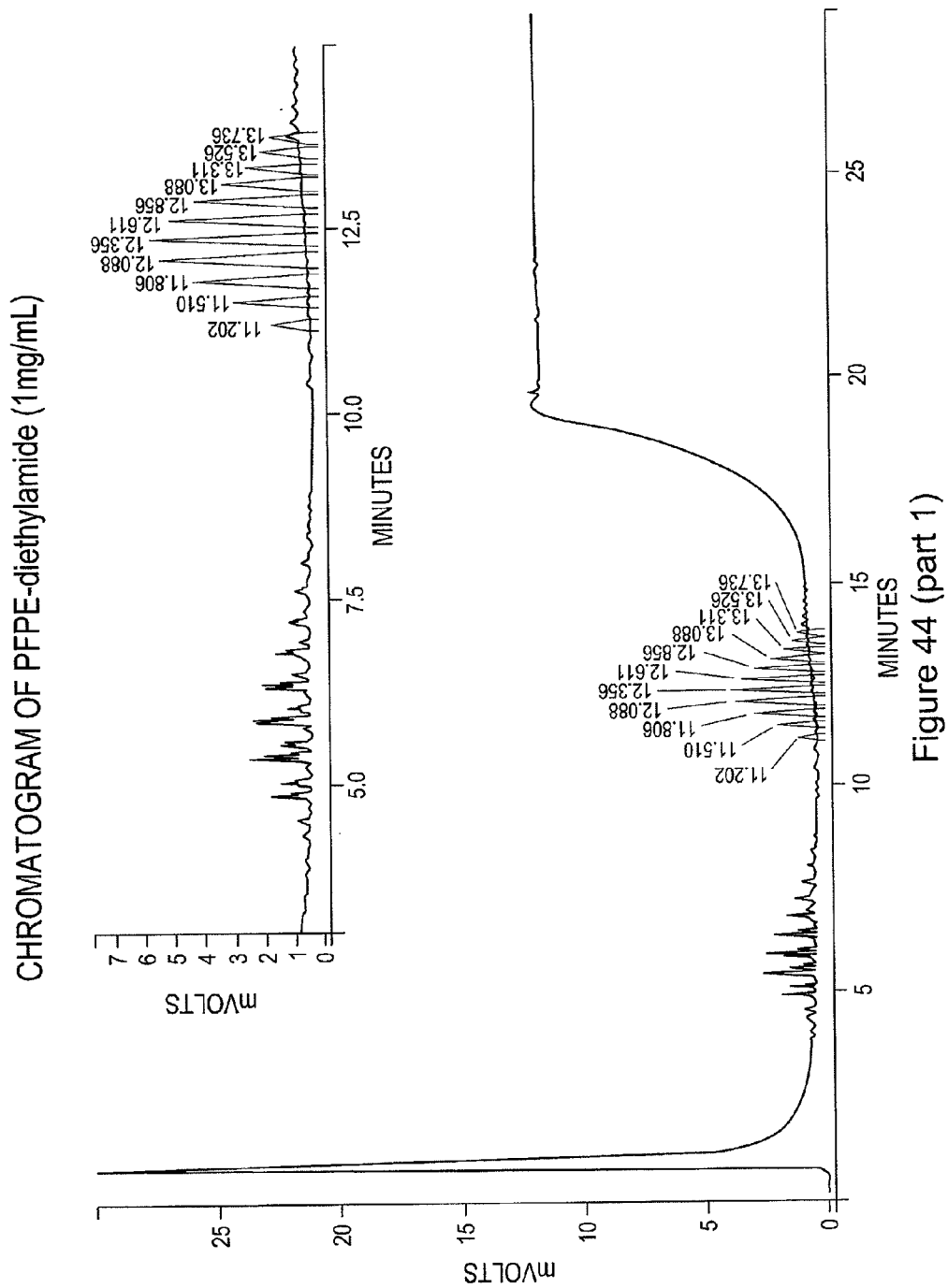
Figure 44 (part 1)

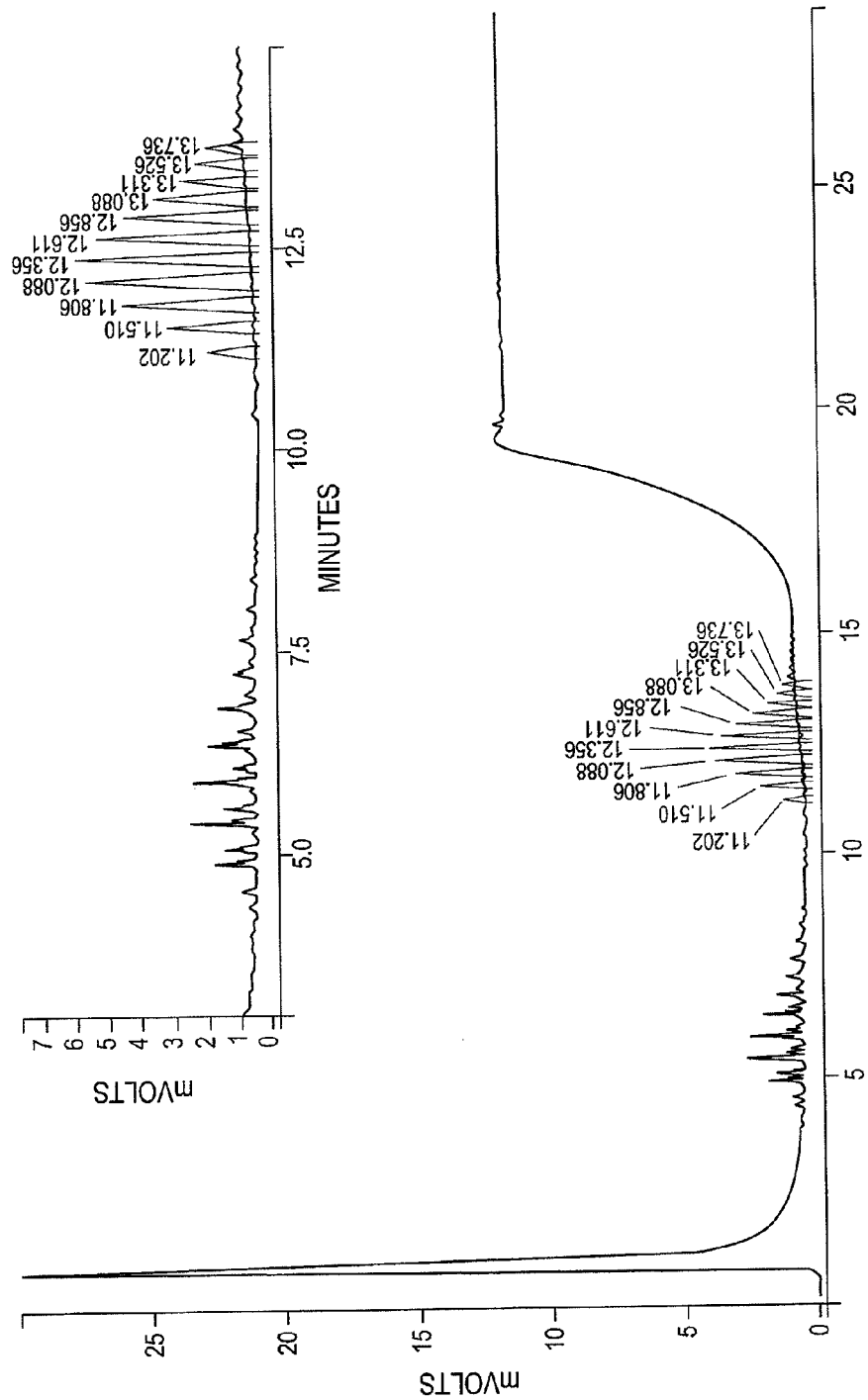
Figure 44 (part 2)

COMPOSITIONS AND METHODS FOR PRODUCING CELLULAR LABELS FOR NUCLEAR MAGNETIC RESONANCE TECHNIQUES

RELATED APPLICATIONS

This application claims the benefit of priority to U.S. provisional application Ser. Nos. 60/959,135, filed Jul. 10, 2007, and 61/062,710, filed Jan. 28, 2008. The disclosures of each of the foregoing applications are hereby incorporated by reference in their entirety.

BACKGROUND

Many biological processes are carried out by populations of cells. For example, cells of the immune system are recruited from the bloodstream to areas of inflammation or infection, resulting in an accumulation of immune cells at the affected site. A marked infiltration of immune cells often occurs in tissues affected by autoimmune diseases, cancers and infections. Likewise, transplant rejection is mediated by host immune cells that enter and destroy the transplanted tissue. There is also growing evidence that stem cells originating in the bone marrow migrate through the bloodstream and assist in the regeneration of damaged tissues.

Furthermore, the most immediately promising area of biologic therapy involves the emerging field of cellular therapy. Cellular therapy is broadly defined as the treatment of human disease by the administration of therapeutic cells that have been selected, multiplied, and pharmacologically treated outside the body, or ex vivo. These cells may be derived from the patient (autologous cells), from another human (allogenic cells), from other organisms (xenogenic cells), or from immortalized cell lines.

Cells represent the ultimate therapeutic system because of their ability to carry out complex functions and their responsiveness to changes in the surrounding tissue or host organism. In the simplest mode of cellular therapy, cells can be isolated, grown in quantity ex vivo, and implanted in patients to produce and secrete soluble factors that directly address the mechanism of disease. Cells can also accomplish tasks as complex as reconstitution of tissues, organs, or immune responses based on their ability to home to specific sites within the body, to exit from circulation, and to integrate into specific tissue or differentiate into new tissue. Other cellular therapeutics can be programmed for tumor killing or treating metastases (e.g., immunotherapeutics).

Although dynamic cell populations play a key role in significant diseases, present technologies for monitoring the location and movement of cells in vivo are quite limited. Typically, cell movements are monitored only in "snap shots" obtained by histological analysis of tissue biopsies. However, the process of sampling a tissue often alters the behavior of cells, and only a limited number of biopsies can be obtained from a particular tissue or organ. Some progress has been made studying cell movements via in vitro assays and isolated tissues ex-vivo. Existing instruments for non-invasive analysis of living organisms are, at present, ill-suited for tracking living cells. Light-based imaging technologies, such as bioluminescence (e.g. luciferases) technologies, are often ineffective at visualizing deep structures because most mammalian tissues are optically opaque. Positron emission tomography (PET) techniques using radioactively-labeled probes are highly sensitive. However, PET instrumentation is often limited to a resolution of several millimeters and is unable to resolve fine details of tissues and organs. Furthermore, labeled cells cannot be detected for time periods that extend beyond a typical PET radioisotope half-life, and generally PET is not useful for longitudinal studies. In order to gain a fundamental understanding of cellular processes, new ways to visualize and quantify the population dynamics of specific cell types in vivo must be developed.

Magnetic resonance imaging (MRI) is a widely used clinical diagnostic tool because it is non-invasive, allows views into optically opaque subjects, and provides contrast among soft tissues at reasonably high spatial resolution. Conventional MRI focuses almost exclusively on visualizing anatomy and has no specificity for any particular cell type. The 'probe' used by conventional MRI is the ubiquitous proton ($^1H$) in mobile water molecules. New classes of exogenous MRI probes or reagents are needed to facilitate cell-specific imaging in living subjects.

SUMMARY

In certain aspects, the disclosure provides novel methods and reagents for labeling cells ex vivo with an imaging reagent, such as fluorocarbon imaging reagent that can be detected by a nuclear magnetic resonance technique. In certain aspects, the disclosure provides methods and software for quantifying the numbers of labeled cells at particular locations in vivo. Cells may be labeled with a label including a fluorocarbon, for example a perfluoropolyether (PFPE), and since biological tissues have negligible endogenous fluorine content, in vivo $^{19}F$ MRI can provide an effective means of detecting labeled cells. In some embodiments these images are then superimposed on a conventional $^1H$ MRI to determine anatomical localization.

Labeled cells may be administered to a subject and subsequently detected by nuclear magnetic resonance techniques. Examples of nuclear magnetic resonance (NMR) techniques include MRI and localized magnetic resonance spectroscopy (MRS). Because nuclear magnetic resonance techniques are generally performed as non-invasive procedures, the labeled cells may be detected at one or more time points in a living subject. Labeled cells may also be detected in a cell culture or in essentially any other milieu on which a nuclear magnetic resonance technique can be performed, such as tissue explants, organs and tissues removed from a subject (possibly prior to transplant into a transplant recipient), artificially generated tissues and various matrices and structures seeded with cells.

In certain aspects, the disclosure provides methods for labeling a cell. Such methods may include contacting the cultured cells ex vivo with a fluorocarbon imaging reagent under conditions such that the fluorocarbon imaging reagent becomes associated with the cell. Perfluoropolyethers (PFPEs) are examples of suitable fluorocarbon imaging reagents. An imaging reagent may be formulated as an emulsion, often including a surfactant. Optionally, the cell may be contacted with the fluorocarbon imaging reagent in the presence of a reagent that enhances uptake of the fluorocarbon imaging reagent. Various cationic molecules, such as cationic lipids, protamine sulfate and polyethylenimine (PEI), are examples of a suitable uptake enhancing reagent; other such reagents are described herein and are, in view of this specification, known in the art. In certain embodiments, the composition of the surfactant may be designed to impart a cationic surface to the emulsion particle that enhances cellular uptake of the emulsion without the need of an enhancing reagent. In certain embodiments, the uptake enhancing compound is conjugated to the fluorocarbon. In certain embodiments, the cells are labeled with perfluorocarbon emulsion particles by electroporation.

While a fluorocarbon imaging reagent may be internalized by a cell, it may also associate with the extracellular surface of a cell. Association with an extracellular surface may be increased by conjugating the imaging reagent to a cellular targeting moiety. A cellular targeting moiety may be essentially any molecular entity that binds to the desired cells, such as an antibody that binds to an epitope that is exposed to the extracellular milieu. Uptake of an imaging reagent into a cell may be increased by conjugating the imaging reagent to an internalization moiety. An internalization moiety is any molecular entity that stimulates or promotes entry of the imaging reagent into the cell. Examples include internalizing peptides and moieties that bind to receptors or other cell surface proteins that are internalized by, for example, receptor mediated endocytosis. The cell may be essentially any cell, including prokaryotic and eukaryotic cells. In preferred embodiments, the cell is a mammalian cell. In certain embodiments the cell is a cell of the immune system, such as a dendritic cell or T cell. A cell may also be a stem cell or a cell that has been prepared for administration to a subject as part of a cellular therapy or a transplant, such as a peripheral blood stem cell transplant or bone marrow transplant. Other cell types can be labeled and imaged, for example an embryonic stem cell, a pancreatic islet, a hepatocyte, etc., perhaps in conjunction with a therapy.

In certain aspects, the disclosure provides methods of labeling cells with novel fluorocarbon imaging reagents. Preferred fluorocarbon imaging reagents have one or more of the following properties: reduced cytotoxicity; a $^{19}$F NMR spectrum that is simple, ideally having mostly a single, narrow resonance to minimize chemical shift artifacts; a large number of NMR-equivalent fluorine atoms per molecule; and suitability for formulation to permit efficient labeling of many cell types.

The present invention provides novel perfluoropolyether compounds (e.g., compounds of formulae 1-41), including purified preparations of those compounds, that may be used as imaging reagents in methods of the invention. The present invention also provides novel compositions comprising defined mixtures of the novel perfluoropolyether diamide compounds of the invention.

For example, in certain aspects, the disclosure provides a compound of any one of formulae 1-9:

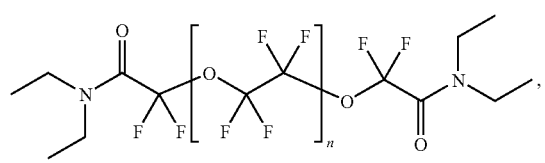

(1)

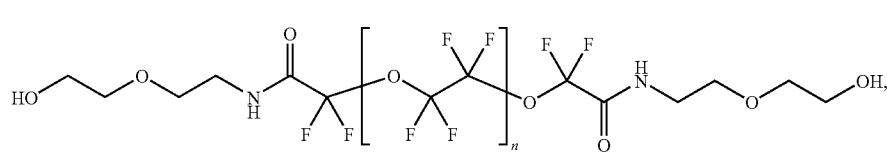

(2)

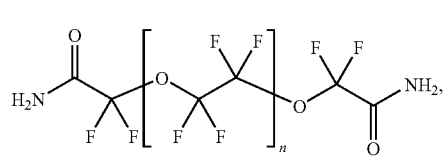

(3)

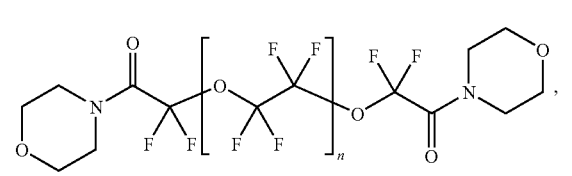

(4)

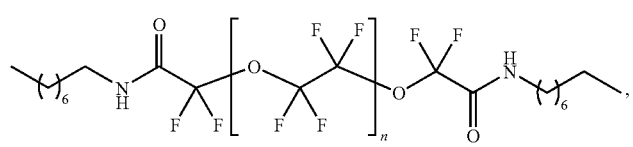

(5)

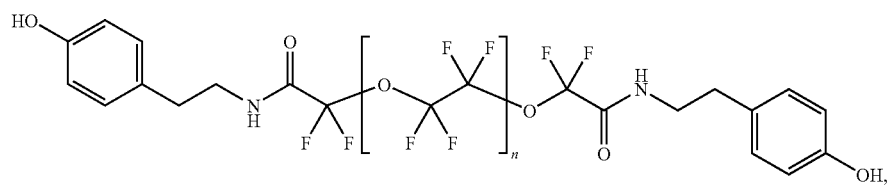

(6)

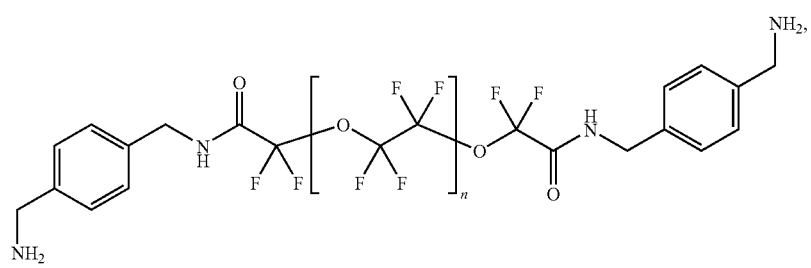

(7)

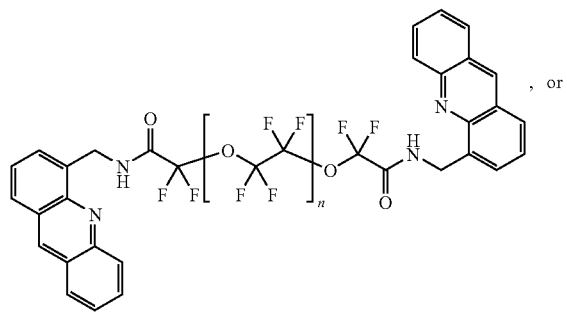 , or 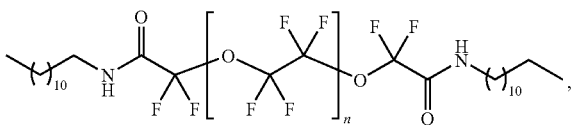
wherein
n, independently for each occurrence, represents an integer from 4 to 16.
In certain aspects, the disclosure provides a compound of any one of formulae 10-15:
wherein
n, independently for each occurrence, represents an integer from 4 to 16; and
m, independently for each occurrence, represents an integer from 4 to 16.
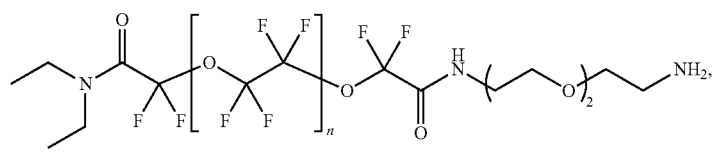
(10)
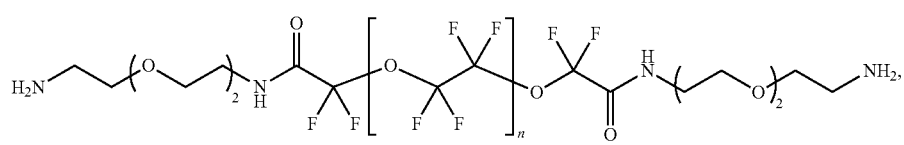
(11)
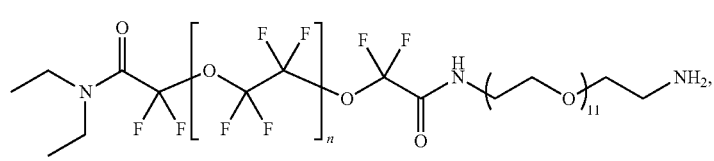
(12)
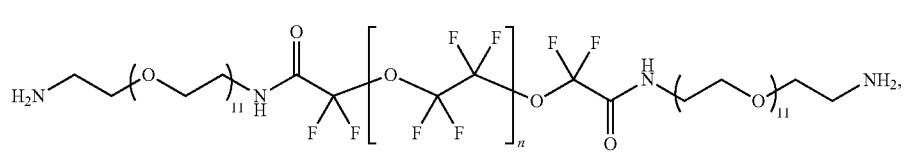
(13)
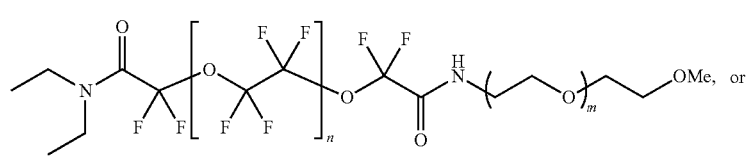
(14)
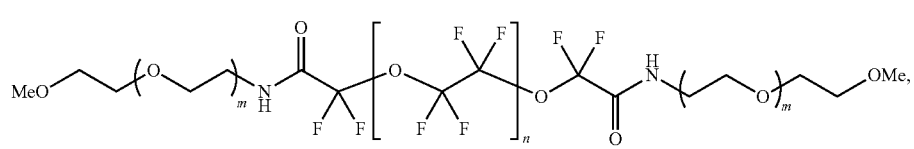
(15)

In certain aspects, the disclosure provides a compound of any one of formulae 16-17, or 40-41:
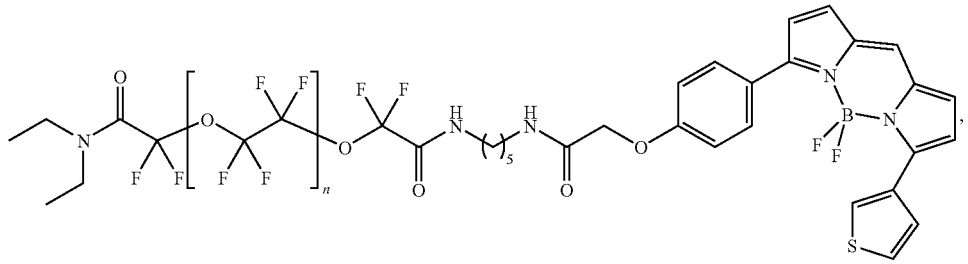
(16)
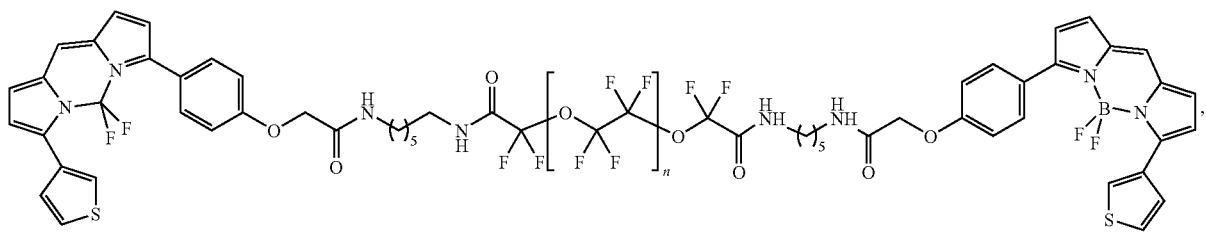
(17)
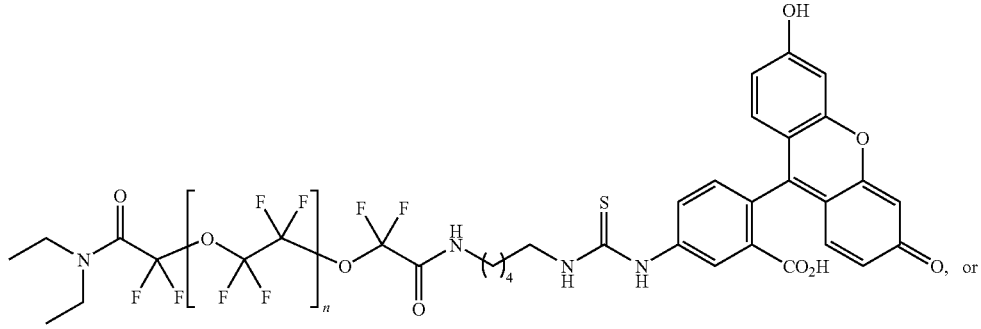
(40)
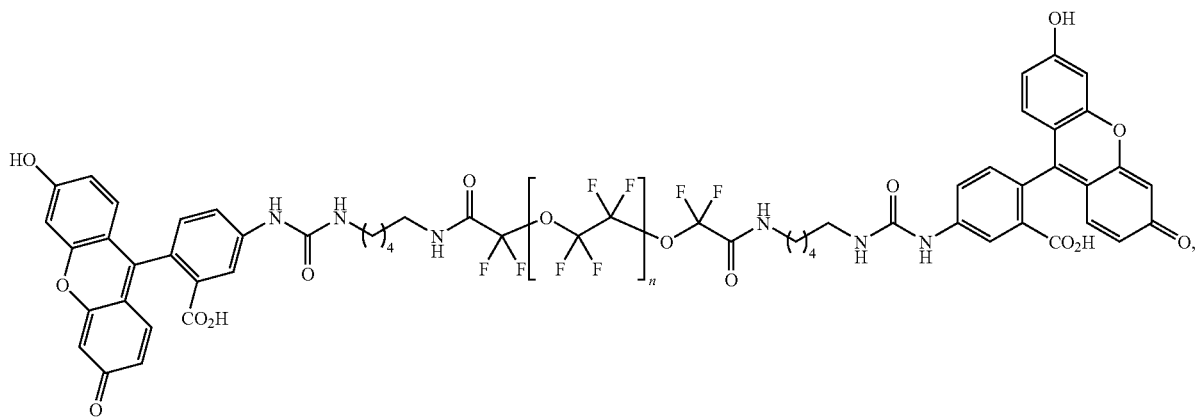
(41)
wherein
n, independently for each occurrence, represents an integer from 4 to 16.
In certain aspects, the disclosure provides a compound of any one of formulae 18 or 19:
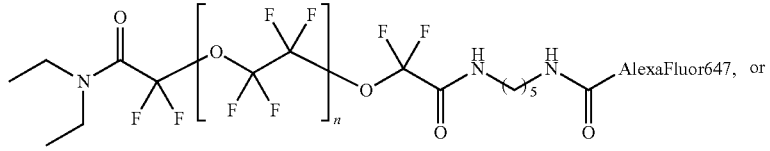
(18)

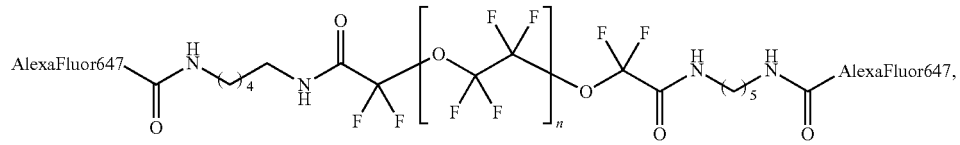
(19)

wherein
  n, independently for each occurrence, represents an integer from 4 to 16.

In certain aspects, the disclosure provides a compound of formula 26:

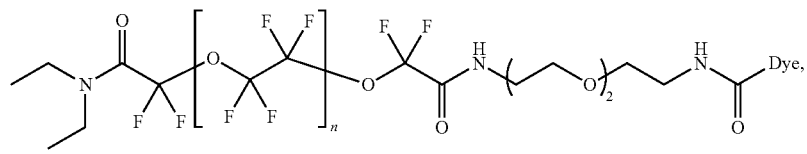
(26)

wherein
  n, independently for each occurrence, represents an integer from 4 to 16; and
  Dye represents a fluorescent detection moiety.

In certain such embodiments, the compound of formula 26 is a compound of formula 20:

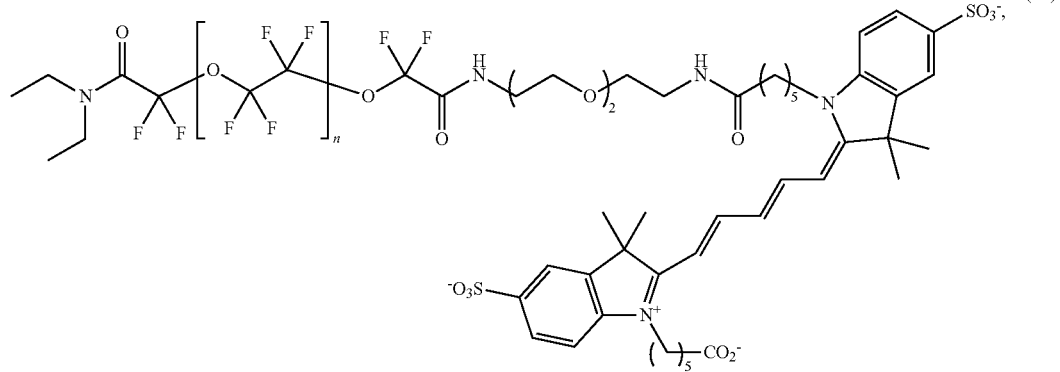
(20)

wherein
  n, independently for each occurrence, represents an integer from 4 to 16.

In certain aspects, the disclosure provides a compound of formula 27:

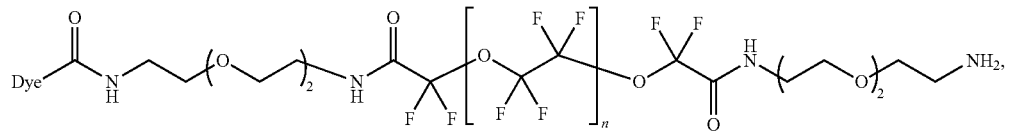
(27)

wherein
  n, independently for each occurrence, represents an integer from 4 to 16; and
  Dye represents a fluorescent detection moiety.

In certain such aspects, the compound of formula 27 is a compound of formula 21:

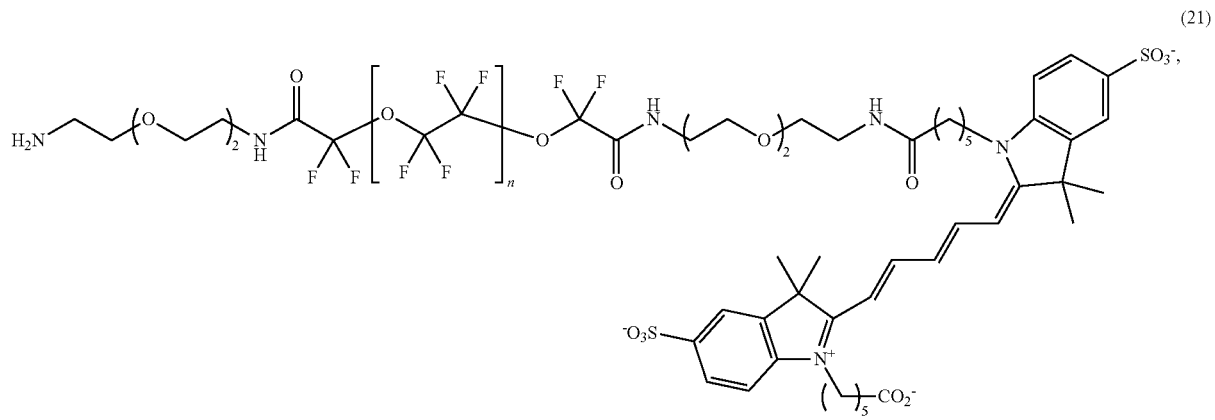

wherein
n, independently for each occurrence, represents an integer from 4 to 16.

In certain aspects, the disclosure provides a compound of formula 28:

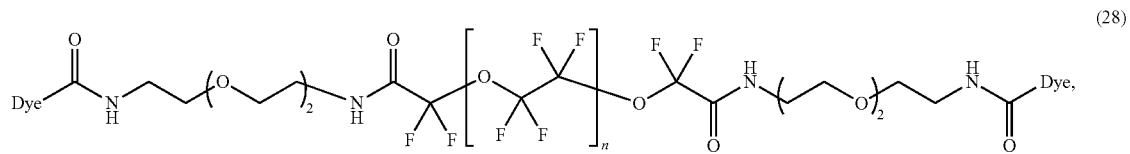

wherein
n, independently for each occurrence, represents an integer from 4 to 16; and
Dye represents a fluorescent detection moiety.

In certain such aspects, the compound of formula 28 is a compound of formula 22:

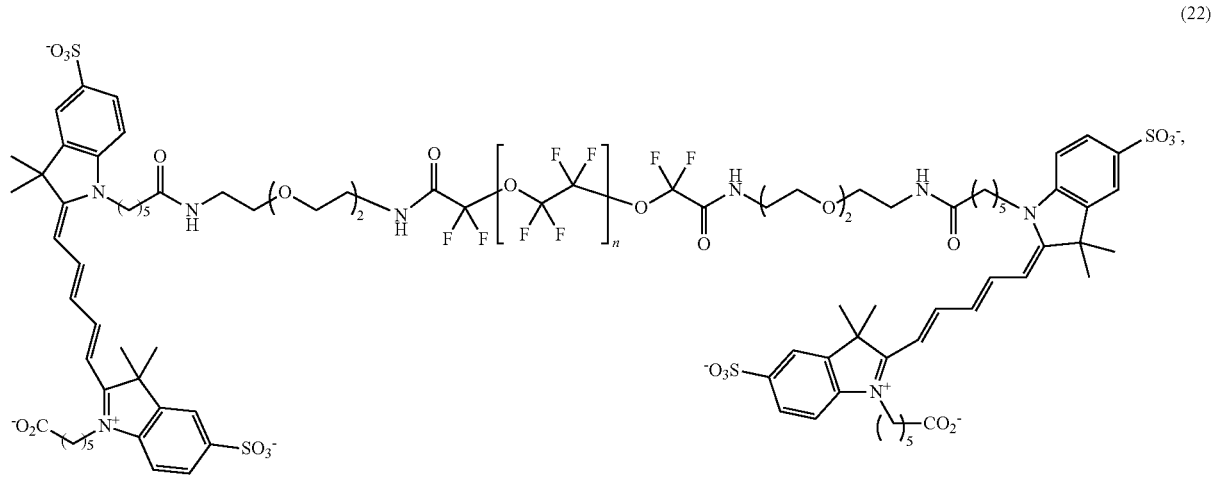

wherein
n, independently for each occurrence, represents an integer from 4 to 16.

In certain aspects, the disclosure provides a compound of formula 29:

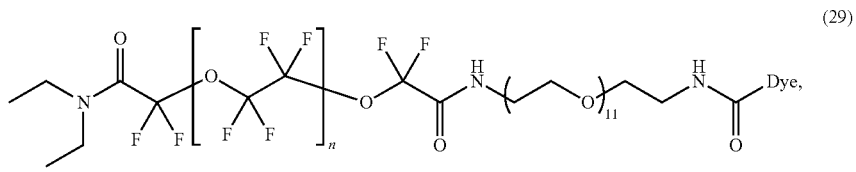
(29)

wherein
n, independently for each occurrence, represents an integer from 4 to 16; and
Dye represents a fluorescent detection moiety.
In certain such aspects, the compound of formula 29 is a compound of formula 23:

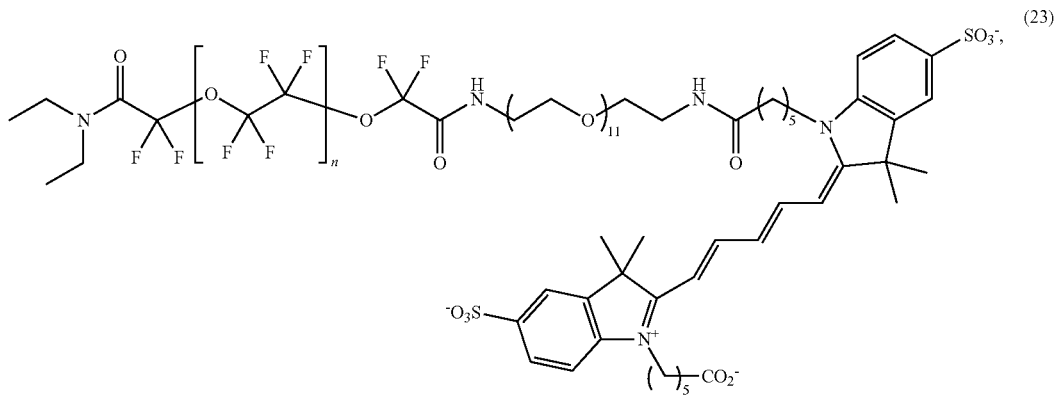
(23)

wherein
n, independently for each occurrence, represents an integer from 4 to 16.

In certain aspects, the disclosure provides a compound of formula 30:

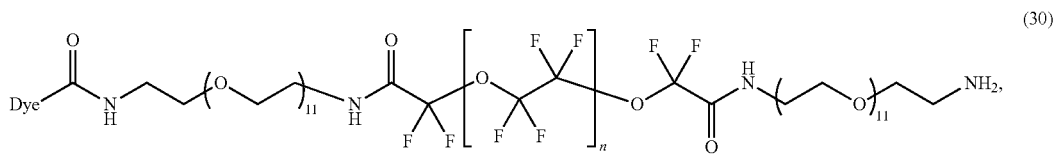
(30)

wherein
n, independently for each occurrence, represents an integer from 4 to 16; and
Dye represents a fluorescent detection moiety.
In certain such aspects, the compound of formula 30 is a compound of formula 24:

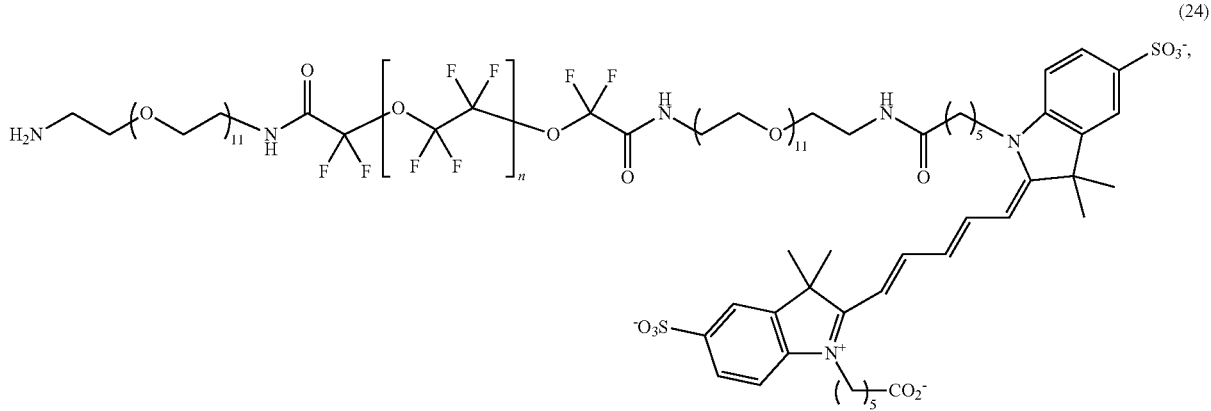
(24)

wherein
n, independently for each occurrence, represents an integer from 4 to 16.

In certain aspects, the disclosure provides a compound of formula 31:

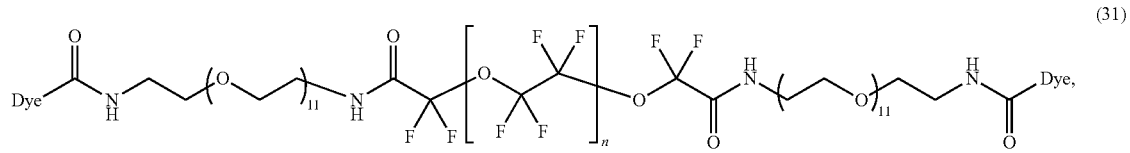
(31)

wherein
n, independently for each occurrence, represents an integer from 4 to 16; and
Dye represents a fluorescent detection moiety.

In certain such aspects, the compound of formula 31 is a compound of formula 25:

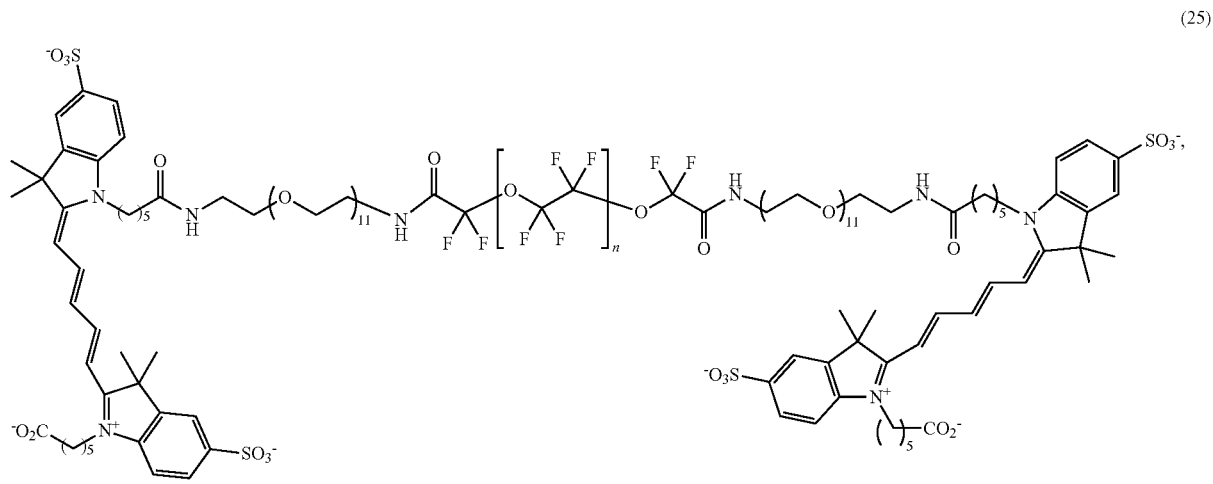
(25)

wherein
n, independently for each occurrence, represents an integer from 4 to 16.

In certain aspects, the disclosure provides a compound of any one of formulae 32-37:

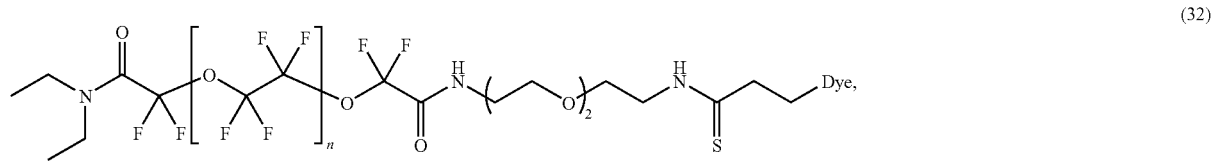
(32)

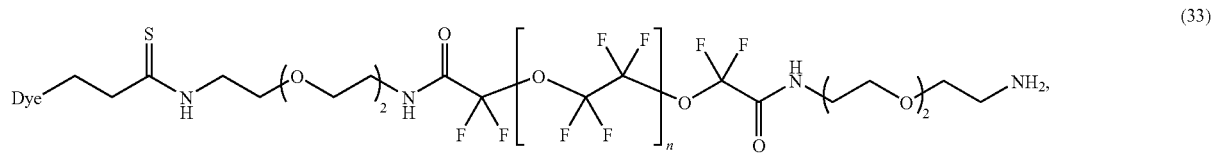
(33)

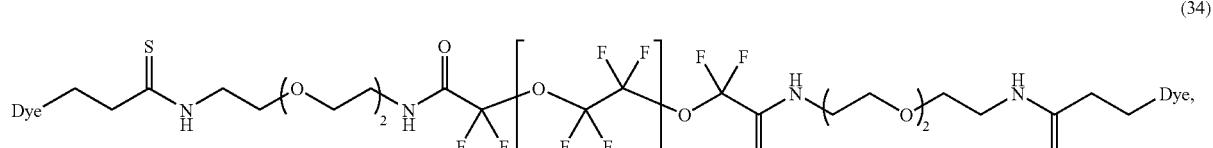
(34)

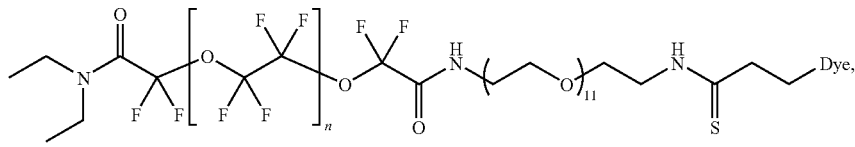

(35)

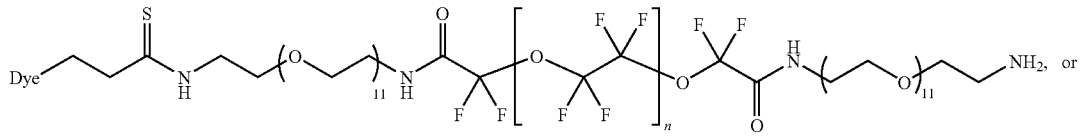

(36)

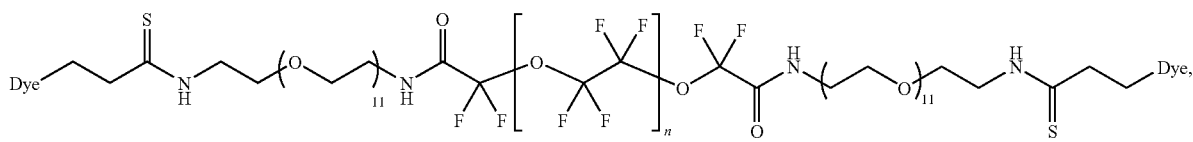

(37)

wherein n, independently for each occurrence, represents an integer from 4 to 16; and Dye, independently for each occurrence, represents a fluorescent detection moiety.

In certain aspects, the disclosure provides a composition comprising a compound of formula 10 and a compound of formula 1.

In certain aspects, the disclosure provides a composition comprising a compound of formula 12 and a compound of formula 1.

In certain aspects, the disclosure provides a composition comprising a compound of formula 14 and a compound of formula 1.

In certain aspects, the disclosure provides a composition comprising a compound of formula 16 and a compound of formula 1.

In certain aspects, the disclosure provides a composition comprising a compound of formula 40 and a compound of formula 1.

In certain aspects, the disclosure provides a composition comprising a compound of formula 16 and a compound of formula 17. In certain such embodiments, the composition further comprises a compound of formula 1.

In certain aspects, the disclosure provides a composition comprising a compound of formula 19 and a compound of formula 19. In certain such embodiments, the composition further comprises a compound of formula 1.

In certain aspects, the disclosure provides a composition comprising a compound of formula 40 and a compound of formula 41. In certain such embodiments, the composition further comprises a compound of formula 1.

In certain aspects, the disclosure provides a composition comprising a compound of formula 10 and a compound of formula 20.

In certain aspects, the disclosure provides a composition comprising a compound of formula 10, a compound of formula 20, and a compound of formula 1.

In certain aspects, the disclosure provides a composition comprising a compound of formula 11 and a compound of formula 21.

In certain aspects, the disclosure provides a composition comprising a compound of formula 11 and a compound of formula 22.

In certain aspects, the disclosure provides a composition comprising a compound of formula 12 and a compound of formula 23.

In certain aspects, the disclosure provides a composition comprising a compound of formula 12, a compound of formula 23, and a compound of formula 1.

In certain aspects, the disclosure provides a composition comprising a compound of formula 13 and a compound of formula 24.

In certain aspects, the disclosure provides a composition comprising a compound of formula 13 and a compound of formula 25.

In certain aspects, the disclosure provides a composition comprising a compound of formula 10 and a compound of formula 26.

In certain aspects, the disclosure provides a composition comprising a compound of formula 10, a compound of formula 26, and a compound of formula 1.

In certain aspects, the disclosure provides a composition comprising a compound of formula 11 and a compound of formula 27.

In certain aspects, the disclosure provides a composition comprising a compound of formula 11 and a compound of formula 28.

In certain aspects, the disclosure provides a composition comprising a compound of formula 12 and a compound of formula 29.

In certain aspects, the disclosure provides a composition comprising a compound of formula 12, a compound of formula 29, and a compound of formula 1.

In certain aspects, the disclosure provides a composition comprising a compound of formula 13 and a compound of formula 30.

In certain aspects, the disclosure provides a composition comprising a compound of formula 13 and a compound of formula 31.

In certain aspects, the disclosure provides a composition comprising a compound of formula 10 and a compound of formula 32.

In certain aspects, the disclosure provides a composition comprising a compound of formula 10, a compound of formula 32, and a compound of formula 1.

In certain aspects, the disclosure provides a composition comprising a compound of formula 11 and a compound of formula 33.

In certain aspects, the disclosure provides a composition comprising a compound of formula 11 and a compound of formula 34.

In certain aspects, the disclosure provides a composition comprising a compound of formula 12 and a compound of formula 35.

In certain aspects, the disclosure provides a composition comprising a compound of formula 12, a compound of formula 35, and a compound of formula 1.

In certain aspects, the disclosure provides a composition comprising a compound of formula 13 and a compound of formula 36.

In certain aspects, the disclosure provides a composition comprising a compound of formula 13 and a compound of formula 37.

In certain aspects, the disclosure provides a composition comprising one or more compounds of any one of formulae 1-17 or 20-37 or 40-41 and a compound of formula 1a. In certain embodiments, the composition may comprising one or more compounds of any one of formulae 1-37 or 40-41. In certain embodiments, the composition comprises 80-95% v/v of the compound of formula 1a.

In certain aspects, the disclosure provides a composition comprising one or more compound of any one of formulae 1-17 or 20-37 or 40-41 and perfluoro-15-crown-5 ether. In certain embodiments, the composition may comprising one or more compounds of any one of formulae 1-37 or 40-41. In certain embodiments, the composition comprises 80-95% v/v of perfluoro-15-crown-5 ether.

In certain aspects, the disclosure provides a composition comprising compound of formula:

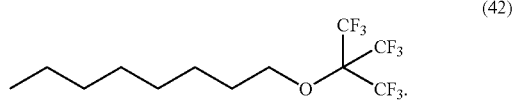

(42)

In certain aspects, the disclosure provides an emulsion comprising a compound of any one of formulae 1-17 or 20-37, 40-41, 1a, or perfluoro-15-crown-5 ether. In certain aspects, the disclosure provides an emulsion comprising a compound of any one of formulae 1-20-37, 40-41, 1a, or perfluoro-15-crown-5 ether. In certain aspects, the disclosure provides an emulsion comprising a composition comprising a compound of formula 10 and a compound of formula 1; a compound of formula 12 and a compound of formula 1; a compound of formula 14 and a compound of formula 1; a compound of formula 16 and a compound of formula 1; a compound of formula 10 and a compound of formula 20; a compound of formula 10, a compound of formula 20, and a compound of formula 1; a compound of formula 11 and a compound of formula 21; a compound of formula 11 and a compound of formula 22; a compound of formula 12 and a compound of formula 23; a compound of formula 12, a compound of formula 23, and a compound of formula 1; a compound of formula 13 and a compound of formula 24; a compound of formula 13 and a compound of formula 25; a compound of formula 10 and a compound of formula 26; a compound of formula 10, a compound of formula 26, and a compound of formula 1; a compound of formula 11 and a compound of formula 27; a compound of formula 11 and a compound of formula 28; a compound of formula 12 and a compound of formula 29; a compound of formula 12, a compound of formula 29, and a compound of formula 1; a compound of formula 13 and a compound of formula 30; a compound of formula 13 and a compound of formula 31; a compound of formula 10 and a compound of formula 32; a compound of formula 10, a compound of formula 32, and a compound of formula 1; a compound of formula 11 and a compound of formula 33; a compound of formula 11 and a compound of formula 34; a compound of formula 12 and a compound of formula 35; a compound of formula 12, a compound of formula 35, and a compound of formula 1; a compound of formula 13 and a compound of formula 36; or a compound of formula 13 and a compound of formula 37. In certain aspects, the emulsion further comprises a block copolymer. In certain embodiments, the block copolymer is a tri-block copolymer which comprises poly(ethylene oxide) and poly(propylene oxide). In certain such embodiments the block copolymer is poly(ethylene oxide)-poly(propylene oxide)-poly(ethylene oxide) (PEO-PPO-PEO) tri-block copolymer with an average molecular weight of 1900, an average number of PEO units of about 22, such as 21.59, and an average number of PPO units of about 16, such as 16.38. In certain such embodiments the block copolymer is poly(ethylene oxide)-poly(propylene oxide)-poly(ethylene oxide) (PEO-PPO-PEO) tri-block copolymer with an average molecular weight of 2900, an average number of PEO units of about 26, such as 26.36, and an average number of PPO units of about 30, such as 30.00. In certain such embodiments the block copolymer is poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97. In certain aspects, the emulsion further comprises a lipid. In certain such aspects, the lipid is DMPC. In certain aspects, the emulsion further comprising a lipid further comprises a block copolymer. In certain embodiments, the block copolymer is a tri-block copolymer which comprises poly(ethylene oxide) and poly(propylene oxide). In certain such embodiments the block copolymer is poly(ethylene oxide)-poly(propylene oxide)-poly(ethylene oxide) (PEO-PPO-PEO) tri-block copolymer with an average molecular weight of 1900, an average number of PEO units of about 22, such as 21.59, and an average number of PPO units of about 16, such as 16.38. In certain aspects, the emulsion further comprises polyethylenimine. In certain aspects, the emulsion further comprises protamine sulfate. In certain aspects, the emulsion further comprising protamine sulfate further comprises a block copolymer. In certain embodiments, the block copolymer is a tri-block copolymer which comprises poly(ethylene oxide) and poly(propylene oxide). In certain such embodiments the block copolymer is poly(ethylene oxide)-poly(propylene oxide)-poly(ethylene oxide) (PEO-PPO-PEO) tri-block copolymer with an average molecular weight of 1900, an average number of PEO units of about 22, such as 21.59, and an average number of PPO units of about 16, such as 16.38. In certain such embodiments the block copolymer is poly(ethylene oxide)-poly(propylene oxide)-poly(ethylene oxide) (PEO-PPO-PEO) tri-block copolymer with an average molecular weight of 2900, an average number of PEO units of about 26, such as 26.36, and an average number of PPO units of about 30, such as 30.00. In certain such embodiments the block copolymer is poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97. In certain aspects, the emulsion has a mean particle size of less than 200 nm in diameter. In certain aspects, the emulsion is stable at temperatures ranging from 4° C. to 37° C. In certain aspects, the emulsion has a polydispersity index ranging from 0.1 to 0.2.

In certain aspects, the disclosure provides an emulsion comprising a compound of formula 1, a compound of formula 16, a compound of formula 17, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1, a compound of formula 16, a compound of formula 17, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1, a compound of formula 16, a compound of formula 17, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1, a compound of formula 16, a compound of formula 17, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1, a compound of formula 16, a compound of formula 17, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1, a compound of formula 16, a compound of formula 17, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1, a compound of formula 18, a compound of formula 19, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1, a compound of formula 18, a compound of formula 19, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1, a compound of formula 18, a compound of formula 19, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1, a compound of formula 18, a compound of formula 19, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1, a compound of formula 18, a compound of formula 19, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1, a compound of formula 18, a compound of formula 19, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1, a compound of formula 40, a compound of formula 41, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1, a compound of formula 40, a compound of formula 41, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1, a compound of formula 40, a compound of formula 41, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1, a compound of formula 40, a compound of formula 41, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1, a compound of formula 40, a compound of formula 41, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1, a compound of formula 40, a compound of formula 41, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1a and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1, a compound of formula 16, a compound of formula 17, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1, a compound of formula 16, a compound of formula 17, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1, a compound of formula 16, a compound of formula 17, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;

a compound of formula 1, a compound of formula 18, a compound of formula 19, perfluoro-15-crown-ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1, a compound of formula 18, a compound of formula 19, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1, a compound of formula 18, a compound of formula 19, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1, a compound of formula 40, a compound of formula 41, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1, a compound of formula 40, a compound of formula 41, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1, a compound of formula 40, a compound of formula 41, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1a, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; a compound of formula 1a, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; a compound of formula 1a, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate; perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine; perfluoro-15-crown-5 ether and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29; a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate; a compound of formula 1a, a compound of formula 1, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate; a compound of formula 1a, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate; a compound of formula 1a, a compound of formula 1, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate; perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate; a compound of formula 1, a compound of formula 16, a compound of formula 17, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate; a compound of formula 1, a compound of formula 18, a compound of formula 19, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate; a compound of formula 1, a compound of formula 40, a compound of formula 41, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate; a compound of formula 1, a compound of formula 16, a compound of formula 17, a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate; a compound of formula 1, a compound of formula 18, a compound of formula 19, a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate; a compound of formula 1, a compound of formula 40, a compound of formula 41, a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate; or a compound of formula 42, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate.

In certain aspects, the disclosure provides a method for preparing a composition comprising a compound of formula 1 and a compound of formula 38:

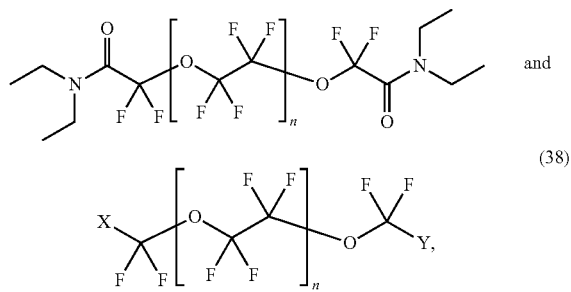

wherein n, independently for each occurrence, represents an integer from 4 to 16; and one or both of X and Y is an amide other than diethyl amide; comprising:

1) reacting perfluoropolyether methyl ester (39),

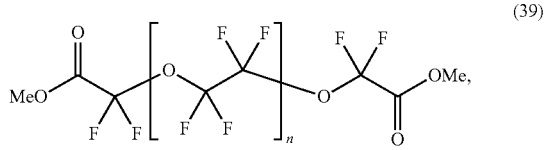

having two methyl ester end groups with a primary or secondary aliphatic amine other than diethyl amine;

2) reacting unmodified methyl ester end groups with excess diethyl amine; and 3) removing unreacted diethyl amine; and 4) optionally removing non volatile unreacted amine by selective extraction in fluorinated solvents or fluorous phase solid extraction and filtration Optionally, an imaging reagent may be formulated as an emulsion. Preferred emulsions will be stable at body temperature (37° C. for humans) and at a storage temperature, such as 4° C. or room temperature (20-25° C.). Preferably an emulsion is designed to facilitate uptake of the imaging agent by the subject cells. An emulsion may have an average particle (or droplet) size of less than 500 nm in diameter (meaning that the emulsion may contain particles larger than 500 nm in diameter, but having an arithmetical mean particle diameter falling less than 500 nm, as calculated by methods known in the art). In certain embodiments, the average particle diameter of the emulsion will be less than 400 nm, or less than 300 nm, or less than 200 nm, or less than 100 nm.

In certain aspects, the disclosure provides a method for preparing an emulsion of a PFPE derivative with a block copolymer using low energy methods. In certain embodiments, the block copolymer is a tri-block copolymer which comprises poly(ethylene oxide) and poly(propylene oxide). In certain embodiments, the method for preparing an emulsion comprising low energy methods may be used to prepare any of the emulsions of the application. In certain embodiments, the low energy method comprises a thin film method.

In certain aspects, the disclosure provides a method for preparing an emulsion of a PFPE derivative with a block copolymer using high energy methods. In certain embodiments, the block copolymer is a tri-block copolymer which comprises poly(ethylene oxide) and poly(propylene oxide). In certain embodiments, the method for preparing an emulsion comprising high energy methods may be used to prepare any of the emulsions of the application. In certain embodiments, the high energy method comprises microfluidization. In certain embodiments, the high energy method comprises homogenization. In certain embodiments, the high energy method comprises sonication.

In certain aspects, the disclosure provides dual fluorescence-$^{19}F$ MRI/MRS reagents formulated as an emulsion. A method may comprise fluorescent detection of labeled cells in vitro and in vivo.

In certain aspects, the disclosure provides methods for detecting a cell in a subject. A method may comprise: administering to the subject a cell that is labeled with a fluorocarbon imaging reagent and examining at least a portion of the subject by a nuclear magnetic resonance technique. Such analysis may include MRI or MRS, which may include collecting data for and generating an image of $^{19}F$ distribution. Imaging may also include collecting data for and generating a conventional anatomical $^{1}H$ image. In a preferred embodiment, $^{19}F$ and $^{1}H$ images are generated and compared, optionally by superposition or overlay. Optionally, labeled cells may be detected using $^{19}F$ MRS. In a preferred embodiment a conventional anatomical $^{1}H$ image is used as a template to guide the positions of one or more localized voxels for $^{19}F$ MRS. NMR data is understood to include both raw and processed data.

In certain aspects, the disclosure provides a method for quantifying cell number in vivo. A method may comprise administering to a subject, cells that are labeled with a fluorocarbon imaging reagent; and examining at least a portion of the subject by a nuclear magnetic resonance technique, thereby detecting labeled cells in the subject; and quantifying the number of labeled cells in a region of interest (ROI). In certain embodiments the disclosure provides a method for quantifying labeled cells in a recipient of a transplant that includes labeled cells.

Calibrating the mean "cellular dose" of labeling agent of a particular cell population may be a pre-requisite for in vivo quantitative determinations. The in vivo equivalent of the cellular dose will be referred to as the number of $^{19}F$ molecules per cell or cell quantity, but is understood to be any measure of the amount of label per cell in vivo. In certain embodiments the mean number of $^{19}$F molecules per cell or cell quantity of a labeled cell population is first measured (i.e., calibrated) in vitro prior to administration of cells to the subject or transplantation. In certain embodiments the mean number of $^{19}$F molecules per cell or cell quantity of a labeled cell population is measured (i.e., calibrated) contemporaneously with examination of labeled cells. In certain embodiments the mean number of $^{19}$F molecules per cell or cell quantity of a labeled cell population is calibrated after the labeled cells have been examined. In certain embodiments the mean number of $^{19}$F molecules per cell or cellular dose of a labeled cell population is calibrated in a test population of cells of a particular type, not necessarily destined for a patient, but used to calibrate cellular dose of labeling agent as a consequence of a particular labeling protocol or set of conditions; the value of cellular dose is then used to for future labeling and in vivo imaging experiments in the same population type of cells with the same labeling protocol. In certain embodiments the cellular dose or cell quantity of labeling agent is assayed using a variety of quantitative techniques, for example using the integrated area of a $^{19}$F NMR spectrum of a cell pellet of a known number of labeled cells. Besides $^{19}$F NMR, many other quantitative methods can be used to assay the cell quantity or cellular dose of the labeling reagent, as described herein. In certain embodiments, the cell quantity or cellular dose can be represented or deduced from prior data. In certain embodiments, the cellular dose or cell quantity may not be directly counted in $F^{19}$ molecules, but the units of the cellular dose of labeling reagent will be representative of this and will be understood to be equivalent.

In certain embodiments, quantifying includes using a calibrated $^{19}$F signal in the same field of view as the ROI. A calibrated $^{19}$F signal is a signal that, by virtue of any of the various calibration techniques described herein, or other techniques that will be apparent from this description, is such that one can deduce a relationship between the signal and the representative number of $^{19}$F molecules or cell quantity in the ROI within the subject. As an example, calibration may be achieved by placing a vial of known quantity of $^{19}$F molecules in the MRI detection field during imaging of the ROI. This permits one to calculate the relationship between the signal strength within the ROI and the number of $^{19}$F molecules. Alternatively, other nuclei can be used in the calibration standard, such as $^1$H.

In certain embodiments, the disclosure provides a method of quantifying the numbers of labeled cells in vivo within an ROI. For example, following cell administration, and in vivo $^{19}$F MRI/MRS, one can compare the total (e.g. integrated) $^{19}$F signal intensity in an ROI to a calibrated $^{19}$F reference. The $^{19}$F reference may be, for example, a vessel containing a solution with a known concentration of $^{19}$F nuclei. The vessel would be placed preferably externally or alongside, or optionally inside, the imaged subject or patient prior to data acquisition. In preferred embodiments, the reference is imaged along with the subject in the same image field of view. Optionally, the reference can be imaged in a separate scan, or no external reference can be used.

By computationally manipulating or combining a key set of parameters from the $^{19}$F MRI/MRS data set, one can calculate the number of labeled cells present in an ROI as described herein. For example, a key set of parameters may include: (i) the cellular dose of labeling agent (i.e., $F_c$) measured in vitro; (ii) in vivo $^{19}$F MRI/MRS data set taken in the subject at one or more time points following labeled cell administration; (iii) the voxel volume; (iv) the in-plane voxel area (i.e., area of the image pixel); (v) optionally, the MRI/MRS data set from the $^{19}$F reference standard; (vi) optionally, the measured Johnson noise of the $^{19}$F MRI/MRS data in the subject material; (vii) optionally, the measured signal-to-noise ratio (SNR) of one or more voxels of the $^{19}$F MRI/MRS data set in the subject material; (viii) optionally, the measured SNR of one or more voxels of the $^{19}$F MRI/MRS data set from the reference standard; (ix) optionally, the $^{19}$F NMR relaxation times (T1, T2, and T2*) of the subject material; (x) optionally, the $^{19}$F NMR relaxation times (T1, T2, and T2*) of the reference standard (for example, see *Magnetic Resonance Imaging, Third Edition*, chapter 4, editors D. D. Stark and W. G. Bradley, Mosby, Inc., St. Louis Mo. 1999). Those skilled in the art can derive other parameters, combinations of the above set, or derivations thereof, particularly from the $^{19}$F MRI/MRS dataset, that can be used to quantify the number of labeled cells in situ. In certain embodiments the above set of key parameters can be used to derive quantitative or statistical measures of the accuracy or confidence of the measured number of labeled cells.

There are many ways to combine the key parameters (i-x, above), any subsets of these, or any of their combinations or approximations, to estimate the effective number of labeled cells seen by $^{19}$F MRI in the subject material, denoted by $N_c$. For example, one can use an equation of the form $$N_c = \frac{[F_R]v}{I_R} \frac{1}{F_c} \sum_{i=1}^{N_{ROI}} I_c^{(i)}$$

where: $N_c$=total number of labeled cells in the ROI; $[F_R]$=concentration of $^{19}$F in the calibrated $^{19}$F reference solution (or gel); v=voxel volume; $I_R$=mean intensity of the calibrated $^{19}$F reference taken with the MRI/MRS scan, averaged over one or more voxels; $F_c$=average $^{19}$F cellular dose of the labeling agent measured in vitro; $N_{ROI}$=number of voxels in the ROI containing labeled cells; $I_c^{(i)}$=image intensity of the $i^{th}$ voxel in the ROI containing labeled cells; i=unitless index for voxels in the ROI containing labeled cells.

In certain aspects, the disclosure provides a calculating system for the quantification of $^{19}$F labeled cells and optionally, a statistical measure of the uncertainty in the measured cell number. In certain embodiments the disclosure provides a computer; a computer readable medium, operatively coupled to the computer, and computer readable medium program codes that can quantify the number of $^{19}$F labeled cells in a ROI in vivo. In certain embodiments the system calculates the number of labeled cells by ratios of the intensity of $^{19}$F signal and the volume of labeled cells in a ROI compared to a reference. In certain embodiments the system calculates the number of labeled cells according to a formula, an example of which is stated above. In certain embodiments the quantification comprises relating a calibrated NMR signal to a cellular dose.

In certain aspects, the disclosure provides a computer readable medium having computer readable program codes embodied therein for performing in vivo quantification of $^{19}$F labeled cells and optionally, a statistical measure of the uncertainty in the measured cell number. In certain aspects the computer readable medium program codes calculate the number of $^{19}$F labeled cells in a ROI detected by a magnetic resonance technique. In certain embodiments the system calculates the number of labeled cells by ratios of the intensity of $^{19}$F signal and the volume of labeled cells in a ROI compared to a reference. In certain embodiments the system calculates the number of labeled cells according to a formula. In certain embodiments the same computer can be used to calculate a statistical confidence coefficient accompanying the cell number calculation. In certain embodiments the quantification comprises relating a calibrated NMR signal to a cellular dose.

In certain aspects, the disclosure provides a method for labeling a cell, the method comprising contacting the cell ex vivo with a fluorocarbon imaging reagent comprising a compound of any one of formulae 1-17, 20-37, 40-42, 1a, or perfluoro-15-crown-5 ether under conditions such that the fluorocarbon imaging reagent becomes associated with the cell. In certain aspects, the disclosure provides an emulsion comprising a compound of any one of formulae 1-17 or 20-37, 40-42, 1a, or perfluoro-15-crown-5 ether. In certain aspects, the disclosure provides an fluorocarbon imaging reagent comprising a compound of any one of formulae 18 or 19.

In certain aspects, the disclosure provides a method for detecting a cell in a subject, the method comprising:
a) administering to the subject a cell that is labeled with a fluorocarbon imaging reagent comprising a compound of any one of formulae 1-17, 20-37, 40-42, 1a, or perfluoro-15-crown-5 ether; and
b) examining at least a portion of the subject by a nuclear magnetic resonance technique, thereby detecting a labeled cell in the subject.

In certain aspects, the disclosure provides a method for detecting transplanted cells in a transplant recipient, the method comprising:
a) administering cells for transplant to a transplant recipient, at least a portion of which cells for transplant are labeled with a fluorocarbon imaging reagent comprising a compound of any one of formulae 1-17, 20-37, 40-42, 1a, or perfluoro-15-crown-5 ether;
b) examining at least a portion of the subject by a nuclear magnetic resonance technique, thereby detecting the labeled cells.

In certain aspects, the disclosure provides a method for quantifying cell number in vivo, the method comprising:
a) administering to the subject cells that are labeled with a fluorocarbon imaging reagent comprising a compound of any one of formulae 1-17, 20-37, 40-42, 1a, or perfluoro-15-crown-5 ether;
b) examining at least a portion of the subject by a nuclear magnetic resonance technique, thereby detecting labeled cells in the subject; and
c) quantifying the number of labeled cells in a region of interest (ROI).

In certain aspects, the disclosure provides a method for labeling a cell, the method comprising contacting the cell in vivo with a fluorocarbon imaging reagent comprising a compound of any one of formulae 1-17, 20-37, 40-42, 1a, or perfluoro-15-crown-5 ether under conditions such that the fluorocarbon imaging reagent becomes associated with the cell.

In certain aspects, the disclosure provides a method for detecting a cell in a subject, the method comprising:
a) administering to the subject a fluorocarbon imaging reagent comprising a compound of any one of formulae 1-17, 20-37, 40-42, 1a, or perfluoro-15-crown-5 ether; and
b) examining at least a portion of the subject by a nuclear magnetic resonance technique, thereby detecting a labeled cell in the subject.

In certain aspects, the disclosure provides a labeled cellular formulation for administration to a subject, the formulation comprising:
a) a cell; and
b) a fluorocarbon imaging reagent comprising a compound of any one of formulae 1-17, 20-37, 40-42, 1a, or perfluoro-15-crown-5 ether that is associated with the cell.

In certain embodiments of the above methods, the disclosure provides an emulsion comprising a compound of any one of formulae 1-17 or 20-37, 40-42, 1a, or perfluoro-15-crown-5 ether. In certain embodiments of the above methods, the disclosure provides an fluorocarbon imaging reagent comprising a compound of any one of formulae 18 or 19.

As will be apparent from this disclosure, compositions and methods described herein will be useful in a variety of clinical procedures. For example, the disclosure provides methods for detecting donor cells in a recipient, such as a transplant recipient or a recipient of other types of cell-based therapy. Such a method may comprise administering cells for transplant to a transplant recipient, at least a portion of which cells for transplant are labeled with a fluorocarbon imaging reagent; and examining at least a portion of the subject by a nuclear magnetic resonance technique, thereby detecting the labeled cells. Detection of the labeled cells may be done once or repeatedly and may be performed so as to provide information about the location and trafficking of labeled cells in the transplant recipient. Examples of cell recipients include recipients of bone marrow transplants (or cellular fractions containing hematopoietic stem cells, commonly but not exclusively derived from bone marrow, peripheral blood or cord blood) and other cell or organ transplant recipients. Organ transplant recipients include recipients of donor organs such as liver, heart, lung, kidney, pancreatic tissue, neural tissue or other transplants. Recipients also include recipients of donor cells, which may be derived directly from a donor (in the case of autologous cells, the "donor" is the same individual as the recipient) or subjected to limited or extensive culturing prior to use. Donor cells may be derived from essentially any tissue that serves as a source of useful cells, and may include stem cells (including precursor cells), such as hematopoietic stem cells, hemangioblasts, hepatic stem cells, neural stem cells, muscle stem cells (e.g. satellite cells), cardiomyocyte precursor cells, pancreatic stem cells, vascular endothelial precursor cells, mesenchymal stem cells, bone or cartilage precursor cells, or may include mature cells, such as dendritic cells, immune cells (e.g., T cells, B cells), chondrocytes, osteoblasts, and the like. Cells for administration may be autologous, heterologous or even derived from another organism, such as a pig. Other aspects of the present invention will be apparent from the disclosure below.

BRIEF DESCRIPTION OF THE DRAWINGS

FIG. 43. Alexa647-PFPE amide/L35 emulsion measurements, where A) is the absorbance standard curve, B) is the fluorescence standard curve, and C) and D) show that the emulsion fluorescent emission spectrum is the same as that of the free dye.

FIG. 44. GC/FID traces of PFPE amide and the PFPE emulsion product. Both samples show the same polymer distribution and retention times under the conditions employed.

DETAILED DESCRIPTION

1. Overview

Figure 1:
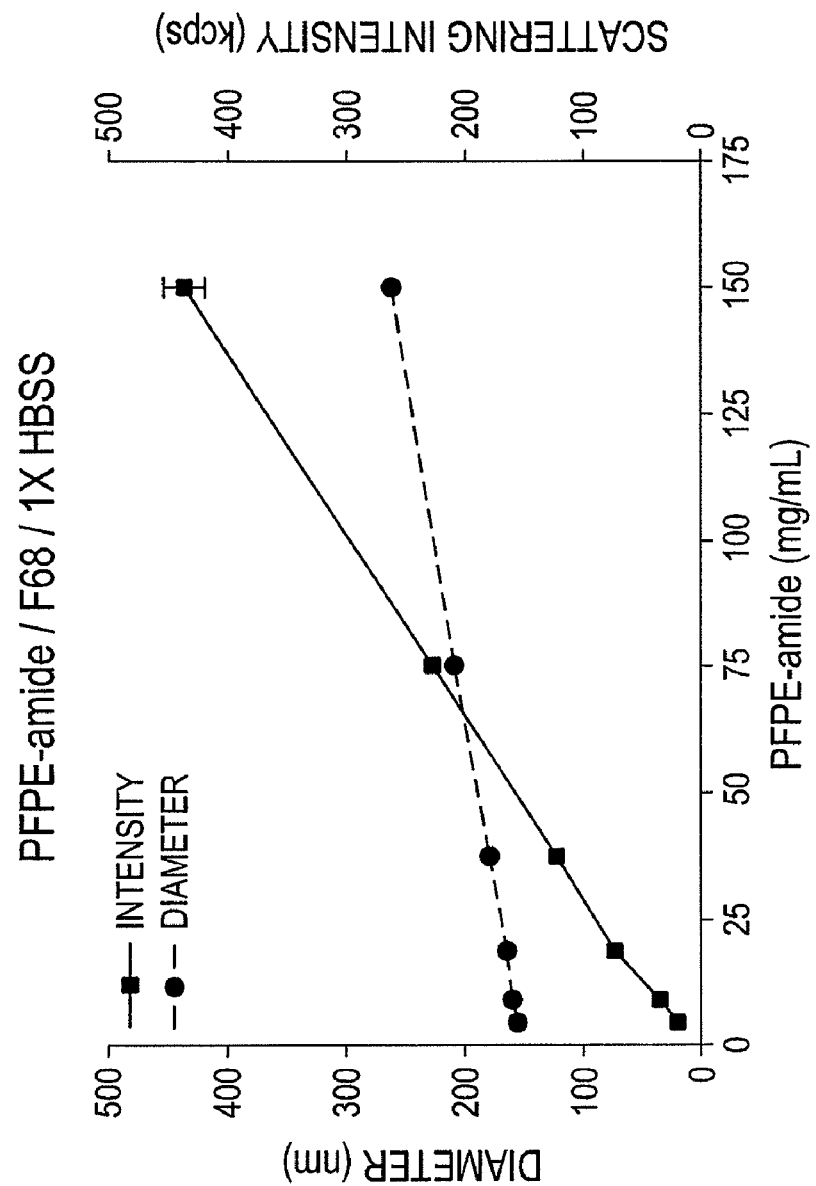
FIG. 1. PFPE amide 1 emulsified with Pluronic™ F68 by sonication in 1×HBSS buffer. Emulsion was diluted in 1×HBSS and particle size measured by Dynamic Light Scattering (DLS). Data represents average of two independent measurements, (mean±SD). Critical micelle concentration (CMC) of PFPE amide 1 is 22.2 mg/mL, in presence of 21.6 mol % F68 and 1×HBSS buffer, was estimated from the intersection of the graph of two curves. Measurements performed on Zetasizer Nano (Malvern, UK).

In certain aspects, the disclosure provides novel methods and reagents for labeling cells ex vivo with a nuclear magnetic resonance imaging reagent, such as a fluorocarbon imaging reagent and quantifying the labeled cells in vivo or ex vivo. In certain aspects, the disclosure provides novel methods and reagents for labeling cells in vivo with a nuclear magnetic resonance imaging reagent. Labeled cells may be detected by a $^{19}$F nuclear magnetic resonance technique (e.g., MRI/MRS) and quantified according to methods described herein. $^{19}$F nuclear magnetic resonance techniques are excellent imaging tools for biological systems because of the absence of endogenous background signals. Fluorine is present, if at all, at exceedingly low levels in living organisms, and generally not in a chemical form that is detectable by liquid-state nuclear magnetic resonance techniques. This is quite distinct from conventional $^1$H MRI which, while providing visualization of fine anatomical detail, does not permit selective detection of particular cell populations. Certain methods disclosed herein permit whole or partial body screening to visualize the distribution of labeled cells in a living subject. The precise anatomical location of labeled cells detected by $^{19}$F nuclear magnetic resonance may be determined by, for example, superimposition of a $^1$H MRI image that provides anatomical detail. In preferred embodiments, the $^1$H image is acquired during the same imaging session as the $^{19}$F image (without moving the subject) to ensure registration. Additionally, the nuclear magnetic resonance techniques disclosed herein may be applied effectively in ex vivo contexts, as in the case of tissue samples, excised organs and cell cultures. The imaging technology disclosed herein may be applied to a large number of biological and medical problems.

In certain aspects, a method of the invention may comprise labeling cells ex vivo with a $^{19}$F imaging reagent, administering the labeled cells to a subject, and detecting labeled cells in the subject. The cells to be labeled may be a crude cellular fraction or tissue sample, or the cells may be cultured and/or subjected to enrichment prior to labeling. For example, particular cell types may be selected by fluorescence activated cell sorting (FACS) prior to labeling. Other sorting or selective enrichment methods are known in the art for the various different cell types that may be of interest. The types of cells that are labeled may also be controlled by the nature of the imaging reagent. For example, simple colloidal suspensions of imaging reagent will tend to be taken up more quickly by cells with phagocytic activity. As another example, an imaging reagent may be formulated with or covalently bound to a targeting moiety that facilitates selective targeting of the imaging reagent to a particular population of cells. Imaging reagents are described further below. After labeling, cells may be immediately administered or the cells may be stored, further cultured, purified, enriched, segregated or processed in any way that is not incompatible with the intended use of such cells.

In certain aspects, labeled cells will be administered for a therapeutic purpose. Technology described herein may be used for monitoring the trafficking of cellular therapeutics in vivo or in any other desired milieu, such as a tissue explant. Bone marrow cell transplants have been widely used for many years in recipients of ablative therapies for cancers. Various purified cell populations have also been used in place of bone marrow, such as cell populations enriched for hematopoietic stem cells; for example cells may be harvested from umbilical cord blood or peripheral blood. After entering the bloodstream, the stem cells generally travel to the bone marrow, where they begin to produce new white blood cells, red blood cells, and platelets. This engraftment usually occurs within about 2 to 4 weeks after transplantation. Traditionally, engraftment is monitored by testing blood counts on a frequent basis, and complete recovery of immune function generally requires several months (for autologous transplant recipients) to years (for patients receiving allogeneic or syngeneic transplants). Cell sampling by bone marrow aspiration can provide further information on the function of the transplanted cells. These monitoring techniques may be enhanced by ex vivo labeling of the cells to be transplanted (or some small fraction of such cells), thus permitting non-invasive monitoring of the location and movement of transplanted cells by nuclear magnetic resonance techniques. Non-myeloablative allogeneic transplantation (i.e. reduced-intensity transplant) is a similar cell therapy that can be effective for treating several types of cancer. Generally, this technique relies on a lower dose of radiation and/or chemotherapeutic and a limited graft-versus-host disease (the action of immune cells from the transplant against any residual host cancer cells) to provide sufficient anti-cancer activity, as well as the hematopoietic potential of the graft cells to restore the patient's hematopoietic system. As with a traditional ablative graft, the techniques of the present invention may be used to monitor the locations and movements of graft cells in a non-myeloablative allogeneic transplantation.

Cellular therapeutics are also in development for use in the delivery of therapeutic proteins. In one embodiment, cells can be isolated, grown in quantity ex vivo and then implanted to produce and secrete soluble factors, which may be active either locally (e.g. enzymes, cytokines, and neurotransmitters) or at a distance (e.g. hormones and growth regulators). Cells may also be administered to a patient in order to accomplish complex therapeutic purposes, such as reconstitution of tissues, organs, or immune responses based on their ability to home to specific sites within the body, exit from the circulation, and integrate into surrounding tissue or differentiate to replace damaged tissue. Stem cell therapies have also been proposed for myriad diseases including neurological disorders, particularly those characterized by cell death (e.g., Parkinson's disease, stroke and brain injury caused by trauma), cardiovascular disorders (e.g., myocardial infarction), muscle regeneration (e.g., in patients suffering from cachexia or other wasting disorders), pancreatic regeneration in diabetes, liver regeneration, etc. In each instance, cells, or a subpopulation thereof, may be labeled with an imaging reagent ex vivo prior to administration, thus allowing the monitoring of these cells in vivo. In vivo monitoring by a nuclear magnetic resonance technique may be useful, for example, to evaluate the viability of the administered cells. A doctor may tailor a dosing schedule depending on the degree to which labeled cells are detected in a patient after administration. In vivo monitoring may also be useful in determining whether therapeutic cells have localized to a desired location. In general, it will be possible to investigate correlations between the migration behavior of therapeutic cells in vivo, as well as the number and/or survivorship of therapeutic cells in vivo, and therapeutic outcomes. When such correlations have been established, the in vivo imaging of therapeutic cells may be used as a prognostic indicator that may be helpful in selecting the appropriate dosage, administration modes and additional therapeutic interventions that will benefit the patient. Certain imaging advances of the invention will benefit a broad range of cellular therapeutic strategies because these imaging methodologies will be able to detect when, where and if the therapeutic cells have been delivered to the desired targets in vivo. Additionally, the detection of labeled cells may be enhanced by quantification of labeled cells in a ROI, such as a particular organ or tissue.

One example of an application of technology disclosed herein is in tracking dendritic cells (DCs). DCs are known to be the most efficient antigen presenting cells and have the capacity to stimulate naive T cells to initiate an immune response. Because DCs are the most potent stimulators of immune response in the body, DCs represent a possible therapeutic approach to increasing the "visibility" of tumors to a patient's immune system. DCs are the focus of tumor vaccines in development. Varying methods are used to expose the dendritic cells to tumor antigens ex vivo, after which educated dendritic cells are reinfused to stimulate development of T-cell mediated tumor killing. Data applying an embodiment of the present disclosure to the labeling and tracking of DCs and other cell types, presented in WO2005072780, is incorporated by reference herein.

In addition to DCs, other cell types have demonstrated promise for immunotherapy in cancer and other diseases such as diabetes, although their progress has been hampered by many factors, including the inability to observe their movement following transplantation into animals and humans. Natural killer (NK) cells, when harvested, treated ex vivo, and transplanted, have demonstrated the ability to kill metastatic tumor cells. Additional cell types treated ex vivo and transplanted to promote cancer immunity include lymphokine-activated killer (LAK) cells, tumor-infiltrating lymphocytes, and activated killer monocytes. Transplantation of T cells, which are white blood cells that attack pathogenic cells, has demonstrated promise against a variety of cancers, including pancreatic cancer, in which clinical trials are beginning, and against multiple sclerosis and HIV infection.

In certain aspects, labeled cells are administered to a subject for non-therapeutic purposes. For example, cells may be labeled ex vivo, administered to a subject and then detected, with the expectation that the labeled cells will behave similarly to like, unlabeled cells in vivo and may therefore be used to monitor the behavior of endogenous cell populations. Monitoring may be used for the purpose of tracking movements of cells, particularly in the case of cells that are known to be highly mobile, such as cells of the immune system, many types of stem cells and blood born cells. Monitoring may also be used for the purpose of tracking viability or adherence of non-mobile cells at the site of implant. Cells of many tissues, such as muscle, liver, pancreas, kidney, brain or skin will tend to be relatively stationary, but disappearance of label may indicate a high death rate, low adherence, or other information. Modern cell culture and sorting techniques allow the selective pooling and labeling of virtually any desired cell population, including various stem cell types, immune cell types, and other blood cell types. For example, cell surface markers can be used to sort mixed populations of cells to purify a population of interest. As described in WO2005072780 and U.S. provisional application No. 60/792,003 (both of which are herein incorporated by reference in their entirety), both T cells and dendritic cells may be labeled ex vivo and detected in vivo.

As an example, labeled immune cells may be used as detectable proxies for the movements of immune cells in a patient. Immune cells participate in and are markers for a host of inflammatory and autoimmune disorders, as well as cancer and atherosclerotic plaque formation. As a general methodology, any process involving the recruitment of immune cells may be detected in a patient by administering to the patient labeled immune cells. The accumulation of label in a particular area provides an indication of the degree of immune response occurring in that portion of the body. Traditionally, these types of studies involve histological techniques that are incompatible with living subjects. Certain methods of the disclosure may facilitate the development of therapeutic strategies for the treatment of human diseases. The ability to track selected populations of immune cells non-invasively, and without the use of radioisotopes, can impact many areas of basic and clinical immunology, such as multiple sclerosis, diabetes, monitoring organ transplant rejection, and cancer. For instance, tumors are often highly infiltrated by immune cells. Labeled cells may be imaged in a subject to reveal the location of a tumor, and in some instances may be useful as a non-invasive detection screen. Early detection of cancers has been a critical problem, as most early stage cancers are readily treated by surgery without resort to debilitating chemotherapeutic agents. Likewise, the progress of other inflammatory diseases may be monitored by tracking the dynamics of immune cells in the patient. The effectiveness of immunosuppressant therapy may be assessed as well. In the instance of an organ transplant recipient, the recipient could receive a dose of labeled immune cells prior to receiving the transplantation. In vivo monitoring of the accumulation of immune cells in the transplant could then be used as an early warning sign of rejection. In the case of transplants, the methods disclosed herein are particularly desirable because the alternative, biopsies, are well-known to increase the risk of organ rejection.

As an additional example, cells for use in a bone marrow cell transplant, or a peripheral blood stem cell transplant, may be labeled ex vivo as described herein, administered, and monitored in vivo by a nuclear magnetic resonance technique. Such monitoring may be used to evaluate the engraftment of donor cells in the recipient bone cavities, as well as survivorship and movement of labeled cells in the recipient. A physician can use information relating to the trafficking of donor cells in a recipient as an early indication of the likely success or failure of the procedure. This type of early detection will allow physicians to tailor the post-transplant therapeutic regimen accordingly. Another cellular cancer therapeutic where the detection technology can be applied is the allogeneic non-myeloablative, or reduced intensity transplant. This procedure may be used with a donor lymphocyte infusion to boost graft-versus-tumor effect which destroys cancer cells. Here the entire population, or a fraction, of transplanted cells could be labeled before infusion. A nuclear magnetic resonance technique could then be used determine where the cells traffic to in the body, which can be indicative of the efficacy of the procedure. As it is often desirable to limit the dose of allogeneic cells to minimize rejection, the cell's trafficking pattern may be used to calibrate dose. In the above cancer cell therapies it may be desirable to selectively label one or more sub-population of the transplanted cells (e.g., CD34+ stem cells or T cells) that are believed to have therapeutic efficacy.

As a further example, cells involved in formation of new tissue, such as in angiogenesis, can be labeled, administered to a subject, and detected to identify hotspots of tissue formation. For example, smooth muscle cells and/or endothelial precursor cells may be labeled and introduced into the bloodstream. Such cells are expected to accumulate at sites of angiogenic activity. Angiogenic activity may be associated with physiological and pathological events such as menstrual cycling, early pregnancy, collateral vessel formation in response to arterial blockages, tumor development and wound healing. Similarly, cells involved in wound healing, such as fibroblasts, may be labeled and administered systemically or to a site of suspected injury in order to monitor cellular behavior.

For example, a medicament or delivery device containing labeled cardiomyocyte lineage cell aggregates or cells derived therefrom may be provided for treatment of a human or animal body, including formulations for cardiac therapy. Cardiomyocyte lineage cells may be administered to a patient in a method for reconstituting or supplementing contractile and/or pacemaking activity in cardiac tissue (see US Patent Application No. 20060040389, 20050112104, 20050244384, which are incorporated in their entirety herein).

In accordance with the present invention labeled cardiomyocyte lineage cells are used to regenerate or repair striated cardiac muscle that has been damaged through disease or degeneration. The labeled cardiomyocyte lineage cells integrate with the healthy tissue of the recipient to replace the function of the dead or damaged cells, thereby regenerating the cardiac muscle as a whole. Cardiac muscle does not normally have reparative potential. The labeled cardiomyocyte lineage cells are used, for example, in cardiac muscle regeneration for a number of principal indications: (i) ischemic heart implantations, (ii) therapy for congestive heart failure patients, (iii) prevention of further disease for patients undergoing coronary artery bypass graft, (iv) conductive tissue regeneration, (v) vessel smooth muscle regeneration and (vi) valve regeneration.

The administration of the cells can be directed to the heart, by a variety of procedures. Localized administration is preferred. The mesenchymal stem cells can be from a spectrum of sources including, in order of preference: autologous, allogeneic, or xenogeneic. There are several embodiments to this aspect, including the following. The present invention allows monitoring of the progress of these cell in vivo.

The cardiomyocyte lineage cells may be cardiomyocyte precursor cells, or differentiated cardiomyocytes. Differentiated cardiomyocytes include one or more of primary cardiomyocytes, nodal (pacemaker) cardiomyocytes; conduction cardiomyocytes; and working (contractile) cardiomyocytes, which may be of atrial or ventricular type. In certain embodiments, cells come from a muscle sample (or other sample) that contains muscle progenitor cells such as satellite cells (see US Patent Application No. 20050244384). In certain embodiments, cells are mesenchymal stem cells (MSCs) (see US Patent Application No. 20050112104).

A "cardiomyocyte precursor" is defined as a cell that is capable (without dedifferentiation or reprogramming) of giving rise to progeny that include cardiomyocytes. Such precursors may express markers typical of the lineage, including, without limitation, cardiac troponin I (cTnI), cardiac troponin T (cTnT), sarcomeric myosin heavy chain (MHC), GATA4, NRx2.5, N-cadherin, .beta.1-adrenoceptor (.beta.1-AR), ANF, the MEF-2 family of transcription factors, creatine kinase MB (CK-MB), myoglobin, or atrial natriuretic factor (ANF).

In certain instances, cells may prove to be so thoroughly associated with a biological site or structure of interest that the labeled cells may be administered for the sole purpose of aiding in the visualization of such a structure. As mentioned above, immune cells characteristically infiltrate tumors. Accordingly, labeled immune cells may be administered for the purpose of visualizing tumors.

Technology disclosed herein may be applied to studies of animal models of human diseases. Various animal models of diseases may evince altered dynamics or survival of one or more cell populations. Such cell populations may be labeled, administered to the animal and monitored. For example, the infiltration of immune cells into the pancreas of the NOD mouse model for diabetes may be monitored. Other examples of animal models include: experimental allergic encephalomyelitis (multiple sclerosis model), gliosarcoma tumor models, and organ-transplant rejection. By tracking phenotypically-defined populations of immune cells in these models, one can elucidate aspects of the disease etiology and monitor how cell trafficking is affected by therapeutics. This method may be used, for example, to screen for drugs that have a desired effect in an animal model. A drug screening assay may comprise administering labeled cells to an animal and detecting the cells in vivo in the presence of a test agent. Changes in cell behavior that are correlated with the presence of the test agent may be indicative of a therapeutic effect. Such changes may be detected by comparison to a suitable reference, including, for example, the same animal before and after treatment with the test agent or a separate, untreated animal. In addition to a test agent, the methods may be used to evaluate the effects of test conditions, such as an exercise regimen, injury, genetic alteration, etc. As an example, it is expected that a drug for treatment of an autoimmune disease would decrease the tendency of immune cells to accumulate in an affected tissue. In addition to steady state evaluations, methods disclosed herein may be used to evaluate kinetic properties of cells, such as the rate at which cells arrive at a particular site and the time of signal persistence at a site. Drug screening assays may be particularly powerful when combined with in vivo monitoring of tightly defined cell populations, such as certain groups of immune cells that are implicated in various disorders. For example, monitoring of labeled cytotoxic T cells may be particularly useful in identifying drugs that may be useful in preventing transplant rejection. The ability to monitor cells in vivo provides a powerful assay that may be applied to the analysis of essentially any experimental animal, including, for example, any of the various transgenic or otherwise mutant mice that have been generated.

Several groups have studied labeling and visualizing immune cells using MRI contrast agents. Other researchers have used MRI contrast agents to label cell types such as stem cells and neuronal precursors. The majority of these studies render the cells magnetically-distinct via the incorporation of superparamagnetic iron-oxide (SPIO) agents. Cells labeled with contrast agents incorporating other types of metal ions, particularly gadolinium and manganese have also been used. In studies utilizing these metal-ion based agents, the compounds are not directly imaged; instead, one observes their indirect effect on surrounding waters. The presence of the agent tends to shorten the relaxation times ($T_1$, $T_2$, or $T_2^*$) of water in proximity to the compound; these effects can be detected in relaxation time-weighted images. SPIO agents, for example, impart contrast to conventional $^1H$ images by locally perturbing the magnetic field experienced by the nearby mobile water molecules, which in turn modulates $T_1$, $T_2$, or $T_2^*$. Methods described herein are distinctly different from all methods using metal ion based contrast agents because signals from $^{19}F$ nuclei in the imaging reagents may be directly detected and, optionally, imaged.

An inherent drawback to detecting labeled cells using metal-ion based contrast agents is that one is often in a situation where it is necessary to interpret subtle changes in grayscale contrast in regions that are believed to contain labeled cells. The large $^1H$ background signal from the high concentration of mobile water present in tissues can make it difficult to unambiguously identify regions containing labeled cells; this is especially problematic if the labeled cell biodistribution is not known a priori. The results of a 'snapshot' image are often ambiguous as to whether labeled cells are present in a specific tissue. This is a particularly vexing problem when trying to detect SPIO labeled cells in iron-laden organs that intrinsically appear dark in anatomical ($T_2$- or $T_2^*$-weighted) images, such as in the liver or the spleen. Often one must resort to detecting the time-lapse image intensity changes in a particular organ over a period of several hours to verify that labeled cells have accumulated. Furthermore, quantification of labeled cells in vivo in regions of interest using metal-ion based contrast agents is problematic, and there is generally no simple and reliable way to do this using relaxation-time weighted MRI or by using quantitative relaxation-time MRI maps.

In certain aspects, the disclosure provides multispectral 19F MRI reagents. In certain embodiments, a wide spectral separation between MRI reagents is useful for two channel MRI imaging, because it allows imaging of one cell type (e.g. DCs labeled at one frequency) simultaneously with another cell type (e.g. T cells, labeled with PFPE). In certain embodiments, this allows for studies of cell-cell interaction in vivo by 19F MRI. In certain embodiments, two-channel MRI is to be able to simultaneously track more then one cell type by noninvasive methods and study in vivo in real time cell-cell interactions. Such applications are highly relevant, for example, in the fields of cancer and inflammation.

Thus the methods and compositions disclosed herein provide much needed tools in the fields of medicine and biology.

2. Imaging Reagents and Formulations

The imaging reagent used in the subject methods is a fluorocarbon, i.e., a molecule including at least one carbon-fluorine bond. By virtue of the $^{19}F$ atoms, the imaging reagents disclosed herein may be detected by $^{19}F$ MRI and other nuclear magnetic resonance techniques, such as MRS techniques. In certain preferred embodiments, a fluorocarbon imaging reagent will have one or more of the following properties: 1) reduced cytotoxicity; 2) a $^{19}F$ NMR spectrum that is simple, ideally having a single, narrow resonance to minimize chemical shift artifacts; 3) high sensitivity with a large number of NMR-equivalent fluorine atoms in each molecule; 4) formulated to permit efficient labeling of many cell types and not restricted to phagocytic cells. Preferably, the imaging reagent comprises a plurality of fluorines bound to carbon, e.g., greater than 5, greater than 10, greater than 15 or greater than 20 fluorines bound to carbon. Preferably, at least 4, at least 8, at least 12 or at least 16 of the fluorines have a roughly equivalent NMR chemical shift.

For labeling cells in culture, the imaging reagents can be employed in one or more of at least three modalities: 1) imaging reagents that are internalized or otherwise absorbed by target cells without the formation of any covalent or other binding association; 2) imaging reagents that covalently attach to target cells; and 3) imaging reagents coupled to molecules, such as antibodies or ligands, that bind to molecules present on the target cells.

Imaging reagents of the first type include the perfluoro crown ethers and other perfluoropolyethers (PFPEs) that are taken up by cells and, preferably, are retained in the cell without degradation for a substantial period of time, e.g., having a half-life in the cell of at least 1 hour, at least 4 hours, at least about a day, at least about three days, or even at least about a week. For obvious reasons, it is preferred that the imaging reagent not interfere with ordinary cellular functions or exhibit cytotoxicity at the concentrations employed for labeling. As demonstrated herein, perfluoropolyethers show reduced toxic effect on the labeled cells.

Imaging reagents of the second type include electrophilic compounds that react with nucleophilic sites on the cell surface, such as exposed thiol, amino, and/or hydroxyl groups. Accordingly, imaging reagents such as maleimides, alkyl iodides, N-hydroxysuccinimide or N-hydroxysulfosuccinimide esters (NHS or sulfo-NHS esters), acyl succinimides, and the like can form covalent bonds with cell surfaces. Other techniques used in protein coupling can be adapted for coupling imaging reagents to cell surface proteins. See Means et al. (1990) *Bioconjugate Chemistry* 1:2-12, for additional approaches to such coupling.

Imaging reagents of the third type can be prepared by reacting imaging reagents of the second type not with the cells themselves, but with a functional moiety that is a cell-targeting ligand or antibody. Suitable ligands and antibodies can be selected for the application of interest. For example, a ligand that selectively targets hematopoietic cells could be labeled with an imaging reagent as described herein and administered to a patient, such as by injection.

Alternatively, an imaging reagent can be coupled to an indiscriminate internalizing peptide, such as antepennepedia protein, HIV transactivating (TAT) protein, mastoparan, melittin, bombolittin, delta hemolysin, pardaxin, Pseudomonas exotoxin A, clathrin, Diphtheria toxin, C9 complement protein, or a fragment of any of these. Cells treated with this indiscriminate molecule ex vivo will absorb the imaging reagent. When such labeled cells are implanted into an animal, such as a mammal, the imaging reagent can be used to visualize and/or track the implanted cells by nuclear magnetic resonance techniques.

In one embodiment, the internalizing peptide is derived from the drosophila antepennepedia protein, or homologs thereof. The 60-amino acid-long homeodomain of the homeo-protein antepennepedia has been demonstrated to translocate through biological membranes and can facilitate the translocation of heterologous polypeptides to which it is coupled. See for example Derossi et al. (1994) *J Biol Chem* 269:10444-10450; and Perez et al. (1992) *J Cell Sci* 102:717-722. It has been demonstrated that fragments as small as 16 amino acids long of this protein are sufficient to drive internalization. See Derossi et al. (1996) *J Biol Chem* 271:18188-18193.

Another example of an internalizing peptide is the HIV transactivator (TAT) protein. This protein appears to be divided into four domains (Kuppuswamy et al. (1989) *Nucl. Acids Res.* 17:3551-3561). Purified TAT protein is taken up by cells in tissue culture (Frankel and Pabo, (1989) *Cell* 55:1189-1193), and peptides, such as the fragment corresponding to residues 37-62 of TAT, are rapidly taken up by cell in vitro (Green and Loewenstein, (1989) *Cell* 55:1179-1188). The highly basic region mediates internalization and targeting of the internalizing moiety to the nucleus (Ruben et al., (1989) *J. Virol.* 63:1-8). Peptides or analogs that include a sequence present in the highly basic region can be conjugated to fluorinated imaging reagents to aid in internalization and targeting those reagents to the intracellular milieu.

Another PFPE composition of interest is linear PFPEs derivatized with a variety of end groups. The linear compounds have the advantage that one can conjugate a variety of functional entities to the end groups, such as functional moieties of various types. The $^{19}F$ NMR spectra of these linear compounds generally is more complex than the macrocyclic compounds, but a PFPE with two well-separated NMR signals can also be used. In this case it may be desirable to use an MRI pulse sequence that incorporates one or more off-resonance saturation pulses applied to the smaller resonance to eliminate any chemical shift artifacts.

The present invention provides certain novel perfluoropolyether diamide compounds, including purified preparations of those compounds that may be used as imaging reagents in methods of the invention. For instance, the invention provides compounds of any one of Formulae 1-9:

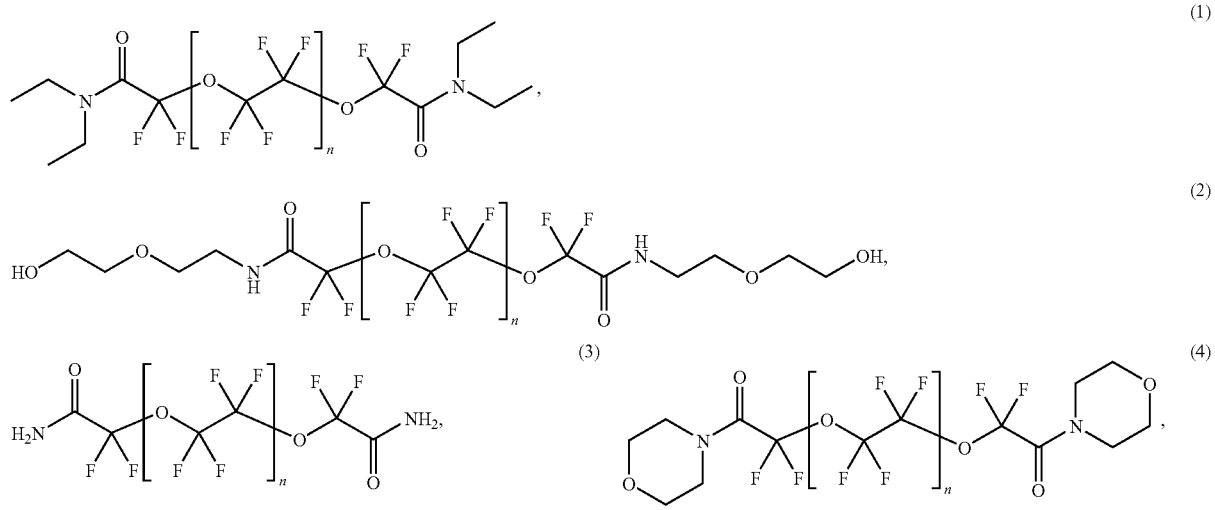

-continued

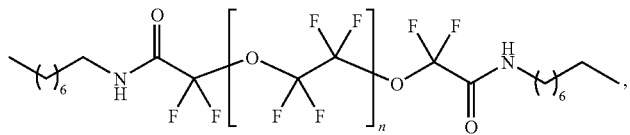
(5)

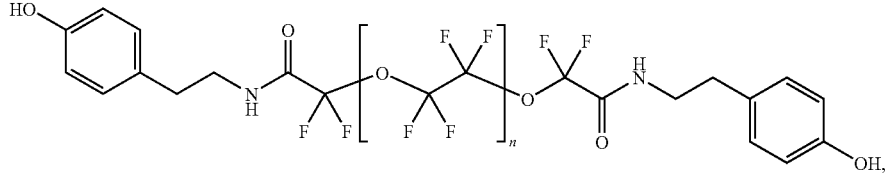
(6)

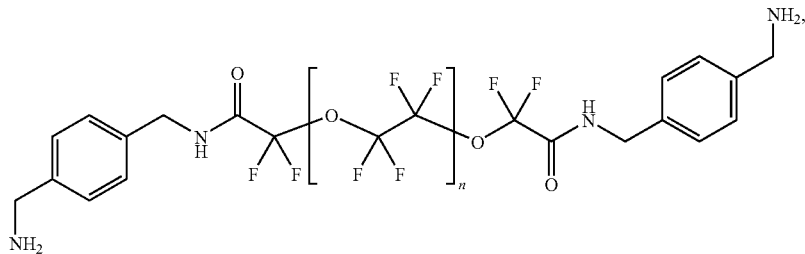
(7)

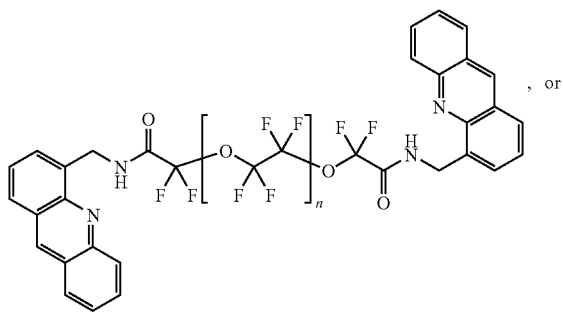
, or
(8)

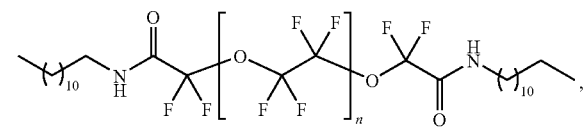
(9)

wherein n, independently for each occurrence, represents an integer from 4 to 16.

In certain embodiments, a linear perfluoropolyether may be derivatized with a relatively hydrophilic moiety at one or both ends. For example, the hydrophilic moiety may be a polyethylene glycol, thus forming a block copolymer with water-soluble regions on one or both end(s) and a hydrophobic region in the center. When mixed in an aqueous environment, imaging reagents of this type will tend to form micelles, with the PFPE core surrounded by a water-soluble coat. Amino-PEG blocks are commercially available with a range of molecular weights. In certain embodiments, the invention provides novel perfluoropolyether diamide compounds that contain one or more polyethylene glycol (PEG) groups. These derivatized perfluoropolyether diamide compounds may be used as imaging reagents in methods of the invention. For example, the invention provides compounds of any one of formulae 10-15:

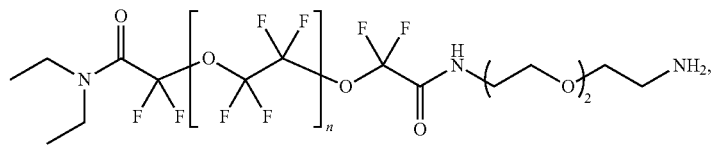
(10)

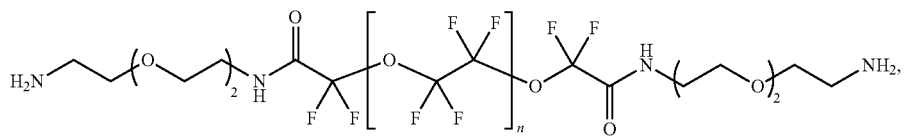
(11)

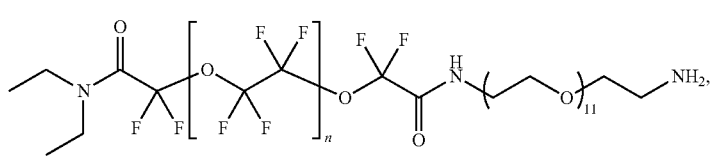

(12)

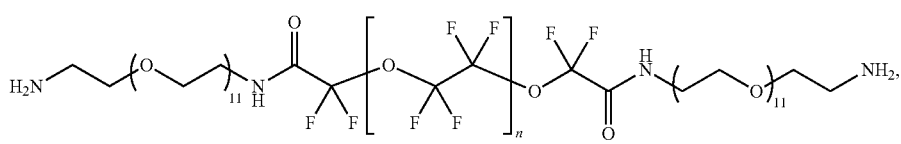

(13)

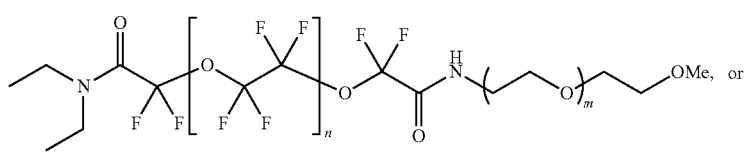

(14)

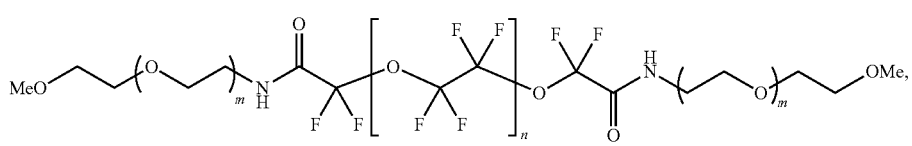

(15)

wherein n, independently for each occurrence, represents an integer from 4 to 16; and m, independently for each occurrence, represents an integer from 4 to 16.

A particularly useful application of linear PFPEs is the synthesis of a "dual mode" agent that can be detected by $^{19}$F nuclear magnetic resonance techniques and includes a detection moiety that facilitates detection by a second detection method. As an example, a fluorescent moiety attached to the end groups may be used to generate imaging reagents that can be visualized with $^{19}$F MRI and fluorescence microscopy. A wide range of fluorescent moieties may be used in a dual-mode agent. Many suitable fluorophores are known, including fluorescein and its derivatives (e.g., Oregon Green 488 and 514, Dichlorofluorescein, Carboxyfluorescein, etc., where all are available from Molecular Probes), lissamine, phycoerythrin, rhodamine (Perkin Elmer Cetus), Cy2, Cy3, Cy3.5, Cy5, Cy5.5, Cy7, Alexa dyes (Molecular Probes), BODIPy dyes (Molecular Probes) and Fluor X (Amersham). Fluorescent moieties include derivatives of fluorescein, benzoxadioazole, coumarin, eosin, Lucifer Yellow, pyridyloxazole and rhodamine. These and many other exemplary fluorescent moieties may be found in the Handbook of Fluorescent Probes and Research Chemicals (2000, Molecular Probes, Inc.). Additional fluorescent moieties include fluorescent nanocrystals, such as the "quantum dot" products available from Quantum Dot Corporation (Hayward, Calif.). Such nanocrystals may be constructed with a semiconductor core having an appropriate emission spectrum (e.g., CdS, CdSe, CdTe), a shell composed of a non-emissive transparent and relatively non-reactive material that can be efficiently wed to the underlying core material (e.g., ZnS), and a coating that provides desirable solubility (e.g., for solubility in aqueous, physiological solutions) and possible reactive groups for attachment to a fluorocarbon described herein.

Dual mode imaging reagents that permit fluorescent detection are particularly useful in a variety of applications. For example, fluorescent labeling permits the use of fluorescence-based cell sorting mechanisms, such as Fluorescence Activated Cell Sorting (FACS). Cell sorting may be desirable, for example, to enrich for a population of cells that have been successfully labeled. This may be particularly useful where labeling has been directed to rarer cell populations. Dual mode agents are also useful for finding and characterizing labeled cells after they have been implanted into a living subject. In this application, cells may be biopsied, or by some other means harvested, from the subject after they have resided there for some duration. Biological analysis of the harvested cells can then be performed. For example, FACS analysis can be performed on the harvested cells, where after positively selecting cells for the fluorescent PFPE label, the cells can be assayed for the expression of specific cell surface markers (using a different color fluorescent probe) to investigate any change in cell phenotype that occurred following implantation. Fluorescent labels may also be used for fluorescence microscopy of cells, particularly using three-dimensional confocal fluorescence microscopy. Fluorescence microscopy will not generally be useful for in vivo visualization of deep tissues containing labeled cells, but surface tissues may be visualized as well as tissue samples. Dual labeling will be particularly valuable in calibrating and validating any new fluorocarbon-based nuclear magnetic resonance labeling method. Results obtained by, for example, MRI/MRS may be compared to those obtained by fluorescence detection, both in cultured labeled cells (biopsied or otherwise) and in vivo, to the extent possible. A known fluorescence signal strength per unit molecule or nanoparticle may be used to calibrate the cellular dose in vitro (i.e., Fc).

In certain embodiments, the invention provides novel perfluoropolyether diamide compounds that contain one or more fluorescent detection groups. These derivatized perfluoropolyether diamide compounds may be used as imaging reagents in methods of the invention. For example, the invention provides compounds of any one of formulae 16-19 or 40-41:

(16)
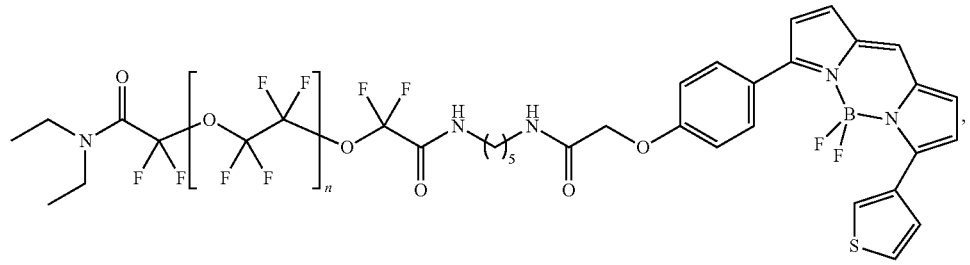
(17)
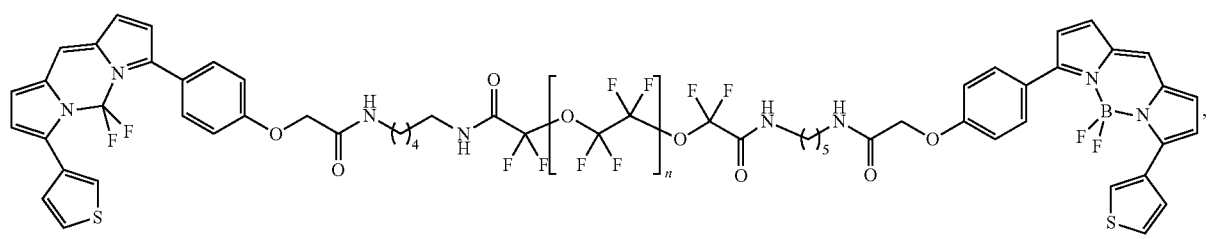
(18)
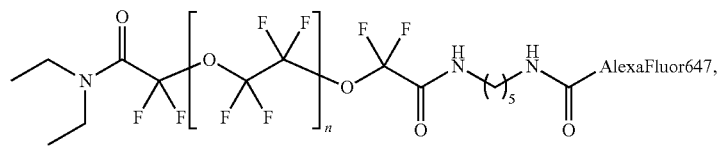
(19)
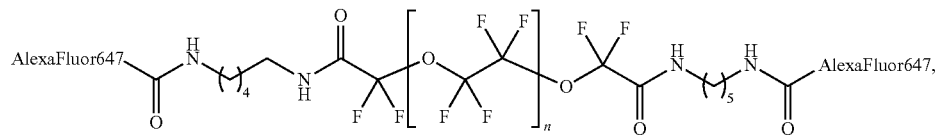
(40)
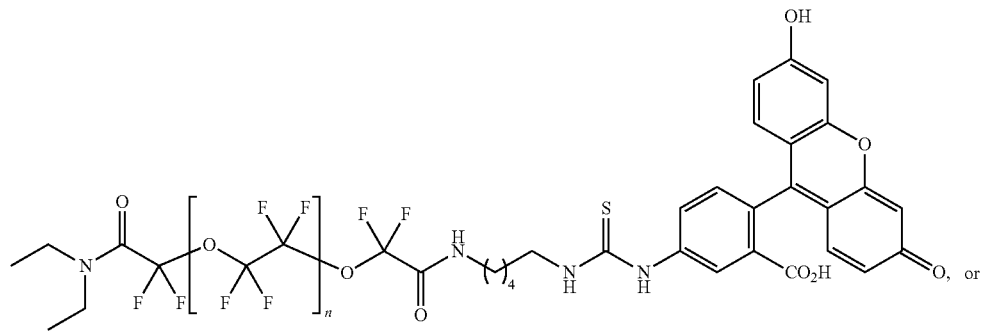
or
(41)
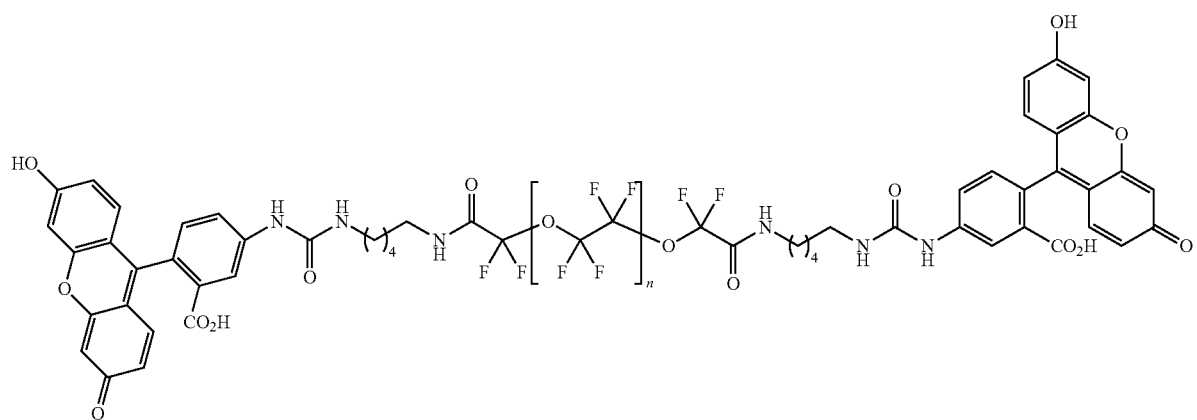

wherein n, independently for each occurrence, represents an integer from 4 to 16; and AlexaFluor647 is a residue of AlexaFluor647 fluorescent dye available from Molecular Probes™.

In certain embodiments, the invention provides novel perfluoropolyether diamide compounds that contain one or more fluorescent detection groups and one or more PEG groups. These derivatized perfluoropolyether diamide compounds may be used as imaging reagents in methods of the invention. For example, the invention provides compounds of any one of formulae 26-37:

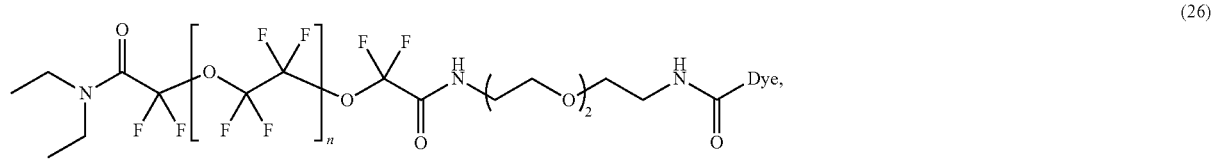
(26)

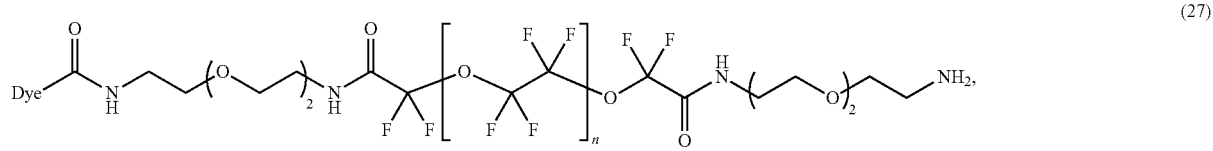
(27)

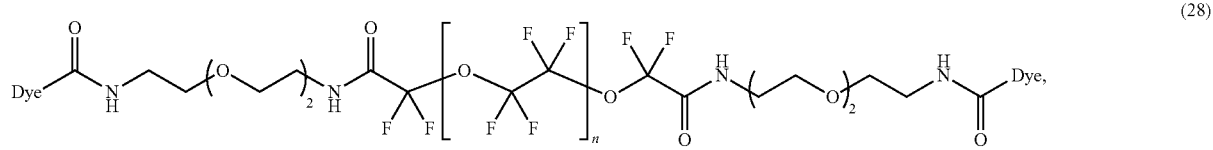
(28)

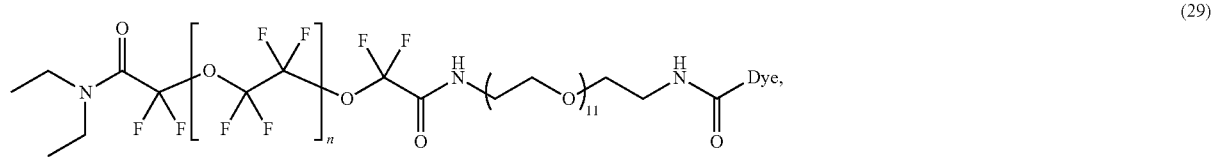
(29)

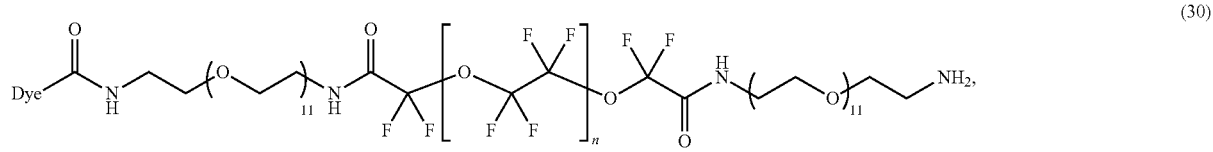
(30)

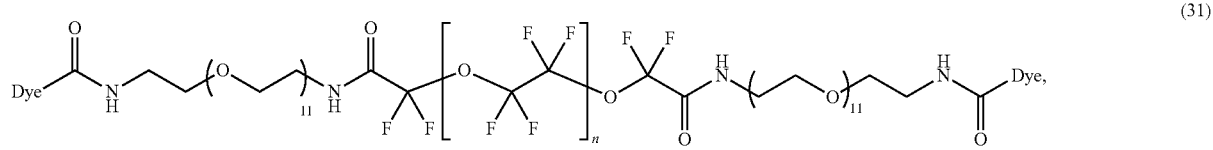
(31)

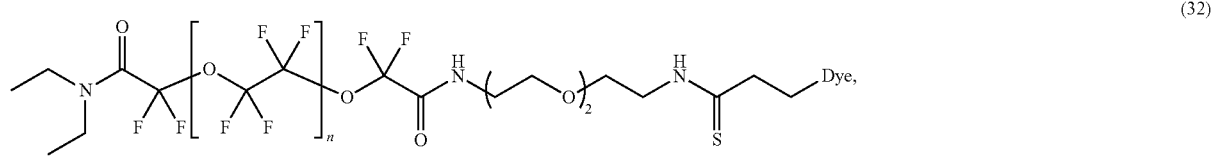
(32)

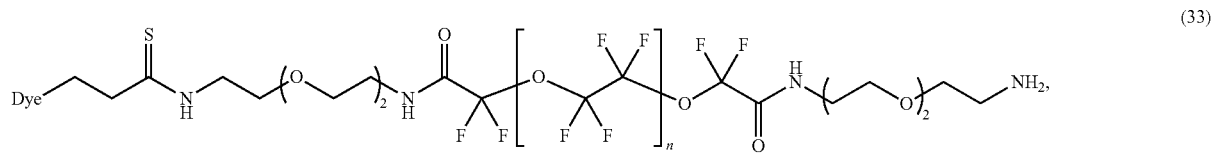
(33)

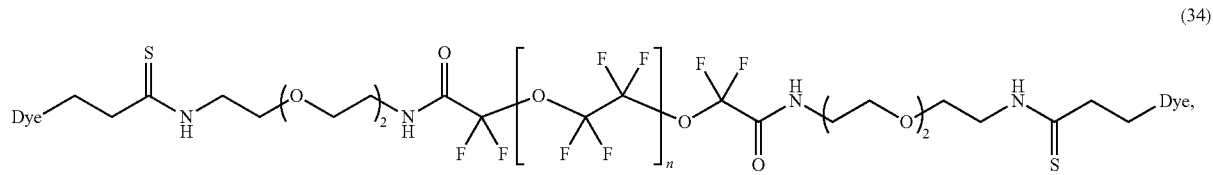
(34)

-continued

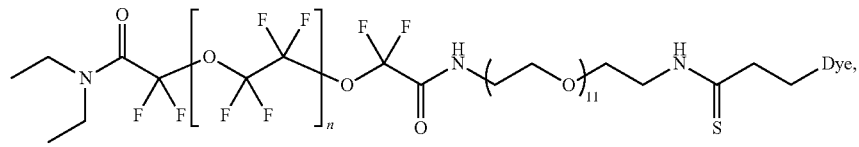
(35)

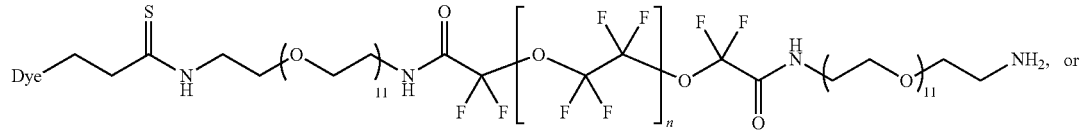
(36)

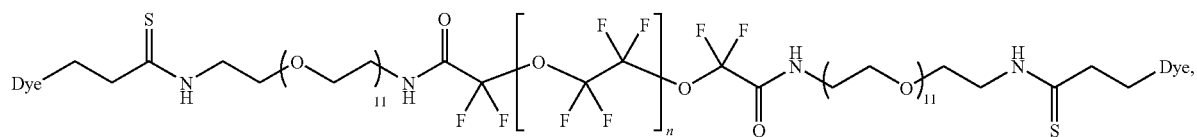
(37)

wherein
n, independently for each occurrence, represents an integer from 4 to 16; and
Dye represents a fluorescent detection moiety.

In certain embodiments, the compound of formula 26 is represented by a compound of formula 20:

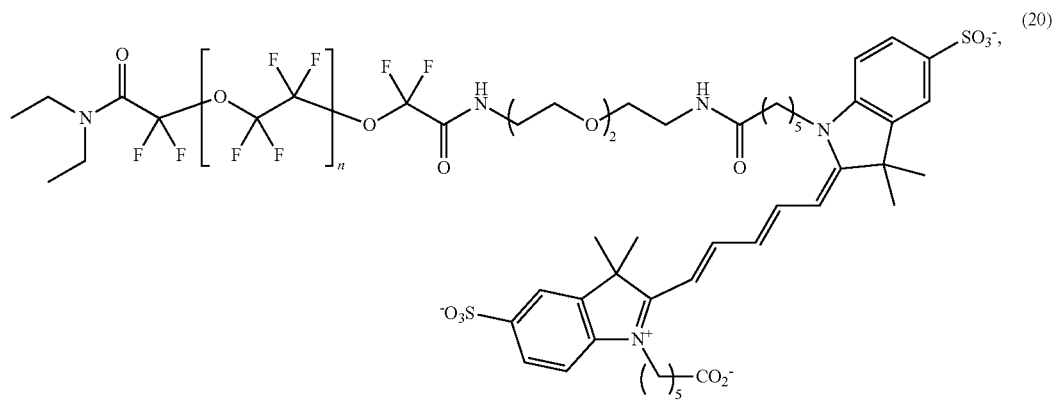
(20)

wherein
n, independently for each occurrence, represents an integer from 4 to 16.

In certain embodiments, the compound of formula 27 is represented by a compound of formula 21:

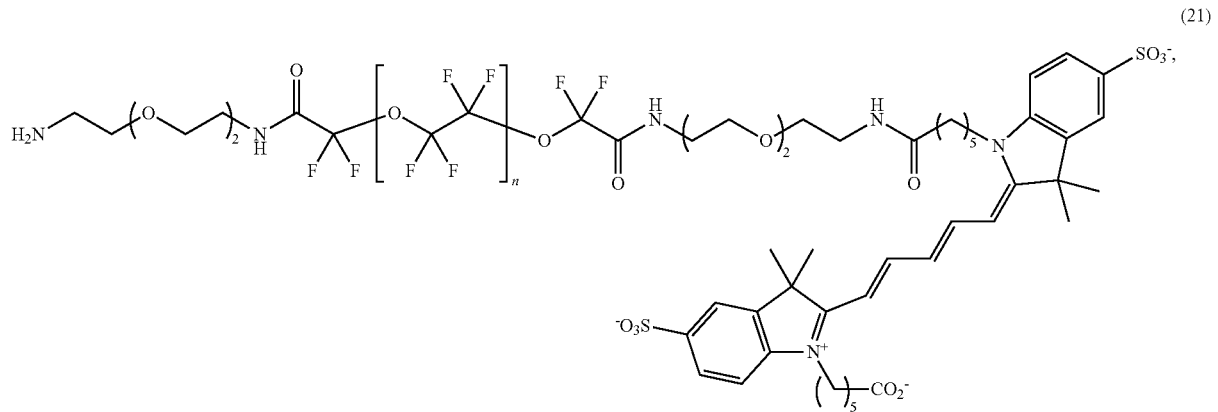
(21)

wherein
n, independently for each occurrence, represents an integer from 4 to 16.

In certain embodiments, the compound of formula 28 is represented by a compound of formula 22:

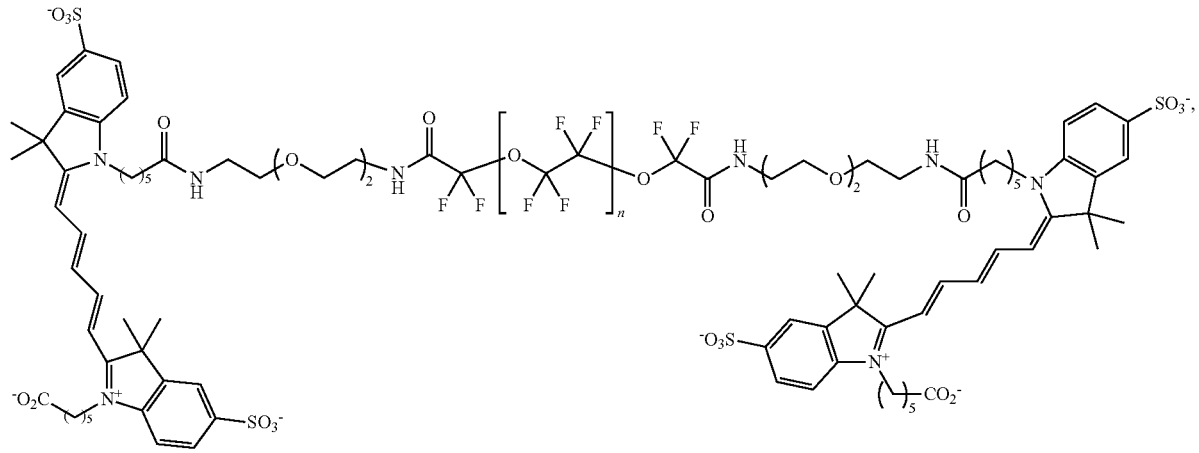

(22)

wherein
n, independently for each occurrence, represents an integer from 4 to 16.

In certain embodiments, the compound of formula 29 is represented by a compound of formula 23:

(23)

wherein
n, independently for each occurrence, represents an integer from 4 to 16.

In certain embodiments, the compound of formula 30 is represented by a compound of formula 24:

(24)

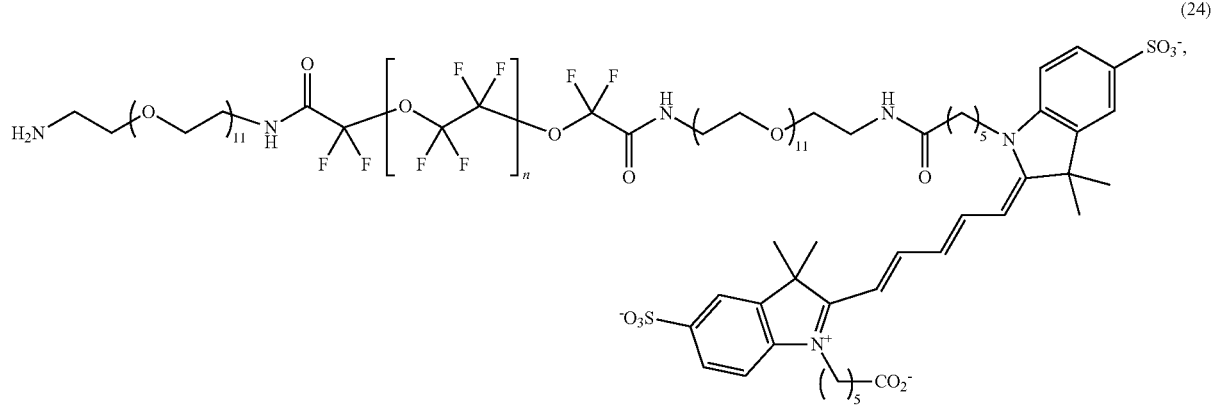

wherein n, independently for each occurrence, represents an integer from 4 to 16.

In certain embodiments, the compound of formula 31 is represented by a compound of formula 25:

mula 1. In certain embodiments, the composition comprising a compound of formula 14 and a compound of formula 1 contains the compound of formula 14 and the compound of formula 1 in a molar ratio from 1:1 to 1:100. In certain embodiments, the composition comprising a compound of (25)

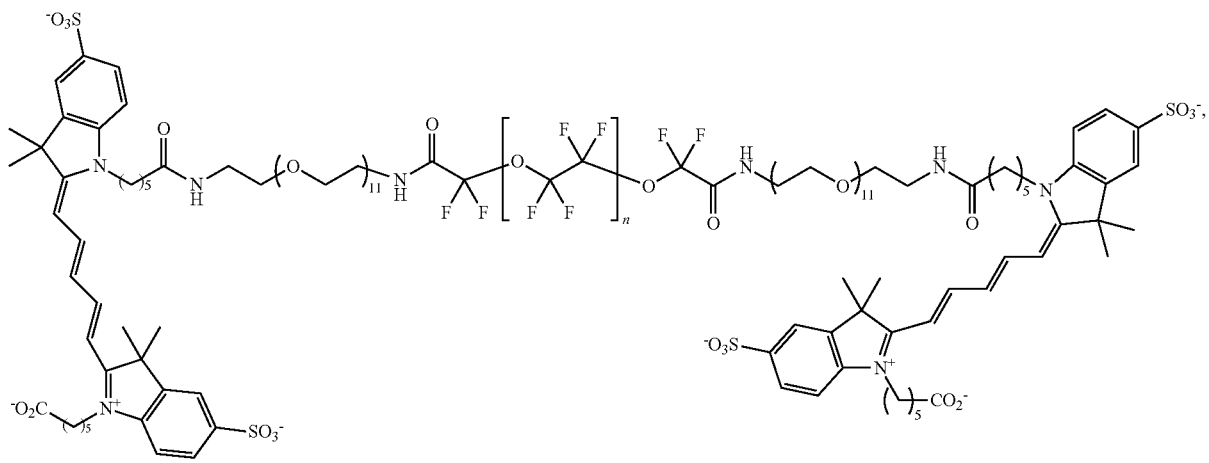

wherein n, independently for each occurrence, represents an integer from 4 to 16.

In certain embodiments, the invention provides a composition comprising two or more compounds of any one of formulae 1-37 or 40-41, e.g., with differing values of n.

The present invention provides certain compounds with a substantially different chemical shift from PFPE, including purified preparations of those compounds that may be used as imaging reagents in methods of the invention. For instance, the invention provides a compound of formula 42:

(42)

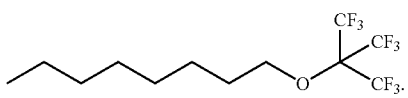

The present invention also provides novel compositions comprising combinations of the compounds recited above. For example, the present invention provides a composition comprising a compound of formula 10 and a compound of formula 1. In certain embodiments, the composition comprising a compound of formula 10 and a compound of formula 1 contains the compound of formula 10 and the compound of formula 1 in a molar ratio from 1:1 to 1:100. In certain embodiments, the composition comprising a compound of formula 10 and a compound of formula 1 contain the compound of formula 10 and the compound of formula 1 in a molar ratio of 1:2.

The present invention provides a further composition comprising a compound of formula 12 and a compound of formula 1. In certain embodiments, the composition comprising a compound of formula 12 and a compound of formula 1 contains the compound of formula 12 and the compound of formula 1 in a molar ratio from 1:1 to 1:100. In certain embodiments, the composition comprising a compound of formula 12 and a compound of formula 1 contain the compound of formula 12 and the compound of formula 1 in a molar ratio of 1:4.

The present invention provides a further composition comprising a compound of formula 14 and a compound of formula 1 contain the compound of formula 14 and the compound of formula 1 in a molar ratio of 1:10.

The present invention provides a further composition comprising a compound of formula 16 and a compound of formula 1. In certain embodiments, the composition comprising a compound of formula 16 and a compound of formula 1 contains the compound of formula 16 and the compound of formula 1 in a molar ratio from 1:1 to 1:100. In certain embodiments, the composition comprising a compound of formula 16 and a compound of formula 1 contain the compound of formula 16 and the compound of formula 1 in a molar ratio of 1:100.

The present invention provides a further composition comprising a compound of formula 18 and a compound of formula 1. In certain embodiments, the composition comprising a compound of formula 18 and a compound of formula 1 contains the compound of formula 18 and the compound of formula 1 in a molar ratio from 1:1 to 1:200. In certain embodiments, the composition comprising a compound of formula 18 and a compound of formula 1 contain the compound of formula 18 and the compound of formula 1 in a molar ratio of 1:50.

The present invention provides a further composition comprising a compound of formula 40 and a compound of formula 1. In certain embodiments, the composition comprising a compound of formula 40 and a compound of formula 1 contains the compound of formula 40 and the compound of formula 1 in a molar ratio from 1:1 to 1:200. In certain embodiments, the composition comprising a compound of formula 40 and a compound of formula 1 contain the compound of formula 40 and the compound of formula 1 in a molar ratio of 1:40.

The present invention provides a further composition comprising a compound of formula 16 and a compound of formula 17. In certain such embodiments, the composition further comprises a compound of formula 1.

The present invention provides a further composition comprising a compound of formula 19 and a compound of formula 19. In certain such embodiments, the composition further comprises a compound of formula 1.

The present invention provides a further composition comprising a compound of formula 40 and a compound of formula 41. In certain such embodiments, the composition further comprises a compound of formula 1.

The present invention provides a further composition comprising a compound of formula 10 and a compound of formula 20.

The present invention provides a further composition comprising a compound of formula 10, a compound of formula 20, and a compound of formula 1.

The present invention provides a further composition comprising a compound of formula 11 and a compound of formula 21.

The present invention provides a further composition comprising a compound of formula 11 and a compound of formula 22.

The present invention provides a further composition comprising a compound of formula 12 and a compound of formula 23.

The present invention provides a further composition comprising a compound of formula 12, a compound of formula 23, and a compound of formula 1.

The present invention provides a further composition comprising a compound of formula 13 and a compound of formula 24.

The present invention provides a further composition comprising a compound of formula 13 and a compound of formula 25.

The present invention provides a further composition comprising a compound of formula 10 and a compound of formula 26.

The present invention provides a further composition comprising a compound of formula 10, a compound of formula 26, and a compound of formula 1.

The present invention provides a further composition comprising a compound of formula 11 and a compound of formula 27.

The present invention provides a further composition comprising a compound of formula 11 and a compound of formula 28.

The present invention provides a further composition comprising a compound of formula 12 and a compound of formula 29.

The present invention provides a further composition comprising a compound of formula 12, a compound of formula 29, and a compound of formula 1.

The present invention provides a further composition comprising a compound of formula 13 and a compound of formula 30.

The present invention provides a further composition comprising a compound of formula 13 and a compound of formula 31.

The present invention provides a further composition comprising a compound of formula 10 and a compound of formula 32.

The present invention provides a further composition comprising a compound of formula 10, a compound of formula 32, and a compound of formula 1.

The present invention provides a further composition comprising a compound of formula 11 and a compound of formula 33.

The present invention provides a further composition comprising a compound of formula 11 and a compound of formula 34.

The present invention provides a further composition comprising a compound of formula 12 and a compound of formula 35.

The present invention provides a further composition comprising a compound of formula 12, a compound of formula 35, and a compound of formula 1.

The present invention provides a further composition comprising a compound of formula 13 and a compound of formula 36.

The present invention provides a further composition comprising a compound of formula 13 and a compound of formula 37.

The present invention also provides compositions comprising combinations of the compounds recited above and PFPE oxide, formula 1 a (Perfluoropoly(ethylene glycol) Dialkyl Ether, Exfluor Inc., TX),

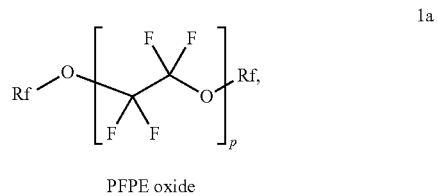

PFPE oxide wherein p represents an integer from 8 to 13; and

Rf is $CF_3$ and $CF_2CF_3$ in a ratio of 2:1, based on 19F NMR analysis.

For example, the present invention provides a composition comprising a compound of any one of formulae 1-9 and a compound of formula 1a. In certain embodiments, the present invention provides a composition comprising a compound of formula 1 and a compound of formula 1a. As a further example, the present invention provides a composition comprising a compound of formula 10 and a compound of formula 1a. The present invention provides a further composition comprising a compound of formula 10, a compound of formula 1, and a compound of formula 1a. The present invention provides a further composition comprising a compound of formula 12 and a compound of formula 1a. The present invention provides a further composition comprising a compound of formula 12, a compound of formula 1, and a compound of formula 1a. The present invention provides a further composition comprising a compound of formula 14 and a compound of formula 1a. The present invention provides a further composition comprising a compound of formula 14, a compound of formula 1, and a compound of formula 1a. The present invention provides a further composition comprising a compound of formula 16 and a compound of formula 1a. The present invention provides a further composition comprising a compound of formula 16, a compound of formula 1, and a compound of formula 1a. The present invention provides a further composition comprising a compound of formula 18 and a compound of formula 1a. The present invention provides a further composition comprising a compound of formula 18, a compound of formula 1, and a compound of formula 1a. The present invention provides a further composition comprising a compound of formula 40 and a compound of formula 1a. The present invention provides a further composition comprising a compound of formula 40, a compound of formula 1, and a compound of formula 1a. The present invention provides a further composition comprising a compound of formula 1, a compound of formula 16, a compound of formula 17, and a compound of formula 1a. The present invention provides a further composition comprising a compound of formula 1, a compound of formula 18, a compound of formula 19, and a compound of formula 1a. The present invention provides a further composition comprising a compound of formula 1, a compound of formula 40, a compound of formula 41, and a compound of formula 1a. The present invention provides a further composition comprising a compound of formula 10, a compound of formula 20, and a compound of formula 1a. The present invention provides a further composition comprising a compound of formula 10, a compound of formula 20, a compound of formula 1, and a compound of formula 1a. The present invention provides a further composition comprising a compound of formula 1, a compound of formula 21, and a compound of formula 1a. The present invention provides a further composition comprising a compound of formula 1, a compound of formula 22, and a compound of formula 1a. The present invention provides a further composition comprising a compound of formula 12, a compound of formula 23, and a compound of formula 1a. The present invention provides a further composition comprising a compound of formula 12, a compound of formula 23, a compound of formula 1, and a compound of formula 1a. The present invention provides a further composition comprising a compound of formula 13, a compound of formula 24, and a compound of formula 1a. The present invention provides a further composition comprising a compound of formula 13, a compound of formula 25, and a compound of formula 1a. The present invention provides a further composition comprising a compound of formula 10, a compound of formula 26, and a compound of formula 1a. The present invention provides a further composition comprising a compound of formula 10, a compound of formula 26, a compound of formula 1, and a compound of formula 1a. The present invention provides a further composition comprising a compound of formula 1, a compound of formula 27, and a compound of formula 1a. The present invention provides a further composition comprising a compound of formula 1, a compound of formula 28, and a compound of formula 1a. The present invention provides a further composition comprising a compound of formula 12, a compound of formula 29, and a compound of formula 1a. The present invention provides a further composition comprising a compound of formula 12, a compound of formula 29, a compound of formula 1, and a compound of formula 1a. The present invention provides a further composition comprising a compound of formula 13, a compound of formula 30, and a compound of formula 1a. The present invention provides a further composition comprising a compound of formula 13, a compound of formula 31, and a compound of formula 1a. The present invention provides a further composition comprising a compound of formula 10, a compound of formula 32, and a compound of formula 1a. The present invention provides a further composition comprising a compound of formula 10, a compound of formula 32, a compound of formula 1, and a compound of formula 1a. The present invention provides a further composition comprising a compound of formula 1, a compound of formula 33, and a compound of formula 1a. The present invention provides a further composition comprising a compound of formula 1, a compound of formula 34, and a compound of formula 1a. The present invention provides a further composition comprising a compound of formula 12, a compound of formula 35, and a compound of formula 1a. The present invention provides a further composition comprising a compound of formula 12, a compound of formula 35, a compound of formula 1, and a compound of formula 1a. The present invention provides a further composition comprising a compound of formula 13, a compound of formula 36, and a compound of formula 1a. The present invention provides a further composition comprising a compound of formula 13, a compound of formula 37, and a compound of formula 1a. In certain embodiments of any of the foregoing, the composition comprises 80-95% v/v of a compound of formula 1a, such as 80%, 81%, 82%, 83%, 84%, 85%, 86%, 87%, 88%, 89%, 90%, 91%, 92%, 93%, 94%, or 95% v/v of a compound of formula 1a.

The present invention also provides compositions comprising combinations of the compounds recited above and perfluoro-15-crown-5 ether. For example, the present invention provides a composition comprising a compound of any one of formulae 1-9 and perfluoro-15-crown-5 ether. In certain embodiments, the present invention provides a composition comprising a compound of formula 1 and perfluoro-15-crown-5 ether. The present invention further provides a composition comprising a compound of formula 1a and perfluoro-15-crown-5 ether. As a further example, the present invention provides a composition comprising a compound of formula 10 and perfluoro-15-crown-5 ether. As a further example, the present invention provides a composition comprising a compound of formula 10, a compound of formula 1, and perfluoro-15-crown-5 ether. The present invention provides a further composition comprising a compound of formula 12 and perfluoro-15-crown-5 ether. As a further example, the present invention provides a composition comprising a compound of formula 12, a compound of formula 1, and perfluoro-15-crown-5 ether. The present invention provides a further composition comprising a compound of formula 14 and perfluoro-15-crown-5 ether. As a further example, the present invention provides a composition comprising a compound of formula 14, a compound of formula 1, and perfluoro-15-crown-5 ether. The present invention provides a further composition comprising a compound of formula 16 and perfluoro-15-crown-5 ether. As a further example, the present invention provides a composition comprising a compound of formula 16, a compound of formula 1, and perfluoro-15-crown-5 ether. The present invention provides a further composition comprising a compound of formula 18 and perfluoro-15-crown-5 ether. As a further example, the present invention provides a composition comprising a compound of formula 18, a compound of formula 1, and perfluoro-15-crown-5 ether. The present invention provides a further composition comprising a compound of formula 40 and perfluoro-15-crown-5 ether. As a further example, the present invention provides a composition comprising a compound of formula 40, a compound of formula 1, and perfluoro-15-crown-5 ether. The present invention further provides a composition comprising a compound of formula 16, a compound of formula 17, a compound of formula 1, and perfluoro-15-crown-5 ether. The present invention further provides a composition comprising a compound of formula 18, a compound of formula 19, a compound of formula 1, and perfluoro-15-crown-5 ether. The present invention further provides a composition comprising a compound of formula 40, a compound of formula 41, a compound of formula 1, and perfluoro-15-crown-5 ether. The present invention provides a further composition comprising a compound of formula 10, a compound of formula 20, and perfluoro-15-crown-5 ether. The present invention provides a further composition comprising a compound of formula 10, a compound of formula 20, a compound of formula 1, and perfluoro-15-crown-5 ether. The present invention provides a further composition comprising a compound of formula 1, a compound of formula 21, and perfluoro-15-crown-5 ether. The present invention provides a further composition comprising a compound of formula 1, a compound of formula 22, and perfluoro-15-crown-5 ether. The present invention provides a further composition comprising a compound of formula 12, a compound of formula 23, and perfluoro-15-crown-5 ether. The present invention provides a further composition comprising a compound of formula 12, a compound of formula 23, a compound of formula 1, and perfluoro-15-crown-5 ether. The present invention provides a further composition comprising a compound of formula 13, a compound of formula 24, and perfluoro-15-crown-5 ether. The present invention provides a further composition comprising a compound of formula 13, a compound of formula 25, and perfluoro-15-crown-5 ether. The present invention provides a further composition comprising a compound of formula 10, a compound of formula 26, and perfluoro-15-crown-5 ether. The present invention provides a further composition comprising a compound of formula 10, a compound of formula 26, a compound of formula 1, and perfluoro-15-crown-5 ether. The present invention provides a further composition comprising a compound of formula 11, a compound of formula 27, and perfluoro-15-crown-5 ether. The present invention provides a further composition comprising a compound of formula 11, a compound of formula 28, and perfluoro-15-crown-5 ether. The present invention provides a further composition comprising a compound of formula 12, a compound of formula 29, and perfluoro-15-crown-5 ether. The present invention provides a further composition comprising a compound of formula 12, a compound of formula 29, and perfluoro-15-crown-5 ether. The present invention provides a further composition comprising a compound of formula 13, a compound of formula 30, and perfluoro-15-crown-5 ether. The present invention provides a further composition comprising a compound of formula 13, a compound of formula 31, and perfluoro-15-crown-5 ether. The present invention provides a further composition comprising a compound of formula 10, a compound of formula 32, and perfluoro-5-crown-5 ether. The present invention provides a further composition comprising a compound of formula 10, a compound of formula 32, a compound of formula 1, and perfluoro-15-crown-5 ether. The present invention provides a further composition comprising a compound of formula 11, a compound of formula 33, and perfluoro-15-crown-5 ether. The present invention provides a further composition comprising a compound of formula 11, a compound of formula 34, and perfluoro-15-crown-5 ether. The present invention provides a further composition comprising a compound of formula 12, a compound of formula 35, and perfluoro-5-crown-5 ether. The present invention provides a further composition comprising a compound of formula 12, a compound of formula 35, a compound of formula 1, and perfluoro-15-crown-5 ether. The present invention provides a further composition comprising a compound of formula 13, a compound of formula 36, and perfluoro-15-crown-5 ether. The present invention provides a further composition comprising a compound of formula 13, a compound of formula 37, and perfluoro-15-crown-5 ether. In certain embodiments of any of the foregoing, the composition comprises 80-95% v/v of perfluoro-15-crown-5 ether, such as 80%, 81%, 82%, 83%, 84%, 85%, 86%, 87%, 88%, 89%, 90%, 91%, 92%, 93%, 94%, or 95% v/v of perfluoro-15-crown-5 ether.

The present invention also provides formulations of the compounds or compositions of the present invention as described above that are suitable for uptake by cells. For example, the compounds or compositions of the present invention may be formulated as an emulsion. For example, the present invention provides an emulsion comprising a compound of any one of formulae 1-37 or 40-41. The present invention further provides an emulsion comprising a composition comprising a compound of formula 10 and a compound of formula 1; a composition comprising a compound of formula 12 and a compound of formula 1; a composition comprising a compound of formula 14 and a compound of formula 1; a composition comprising a compound of formula 16 and a compound of formula 1; a composition comprising a compound of formula 18 and a compound of formula 1; a composition comprising a compound of formula 40 and a compound of formula 1; a composition comprising a compound of formula 16 and a compound of formula 17; a composition comprising a compound of formula 16, a compound of formula 17, and a compound of formula 1; a composition comprising a compound of formula 18 and a compound of formula 19; a composition comprising a compound of formula 18, a compound of formula 19, and a compound of formula 1; a composition comprising a compound of formula 40 and a compound of formula 41; a composition comprising a compound of formula 40, a compound of formula 41, and a compound of formula 1; a composition comprising a compound of formula 10 and a compound of formula 20; a composition comprising a compound of formula 10, a compound of formula 20, and a compound of formula 1; a composition comprising a compound of formula 11 and a compound of formula 21; a composition comprising a compound of formula 11 and a compound of formula 22; a composition comprising a compound of formula 12 and a compound of formula 23; a composition comprising a compound of formula 12, a compound of formula 23, and a compound of formula 1; a composition comprising a compound of formula 13 and a compound of formula 24; a composition comprising a compound of formula 13 and a compound of formula 25; a composition comprising a compound of formula 10 and a compound of formula 26; a composition comprising a compound of formula 10, a compound of formula 26, and a compound of formula 1; a composition comprising a compound of formula 11 and a compound of formula 27; a composition comprising a compound of formula 11 and a compound of formula 28; a composition comprising a compound of formula 12 and a compound of formula 29; a composition comprising a compound of formula 12, a compound of formula 29, and a compound of formula 1; a composition comprising a compound of formula 13 and a compound of formula 30; a composition comprising a compound of formula 13 and a compound of formula 31; a composition comprising a compound of formula 10 and a compound of formula 32; a composition comprising a compound of formula 10, a compound of formula 32, and a compound of formula 1; a composition comprising a compound of formula 11 and a compound of formula 33; a composition comprising a compound of formula 11 and a compound of formula 34; a composition comprising a compound of formula 12 and a compound of formula 35; a composition comprising a compound of formula 12, a compound of formula 35, and a compound of formula 1; a composition comprising a compound of formula 13 and a compound of formula 36; or a composition comprising a compound of formula 13 and a compound of formula 37.

The present invention further provides an emulsion comprising a composition comprising a compound of any one of formulae 1-9 and a compound of formula 1a, such as a compound of formula 1 and a compound of formula 1a; a composition comprising a compound of formula 10 and a compound of formula 1a; a composition comprising a compound of formula 10, a compound of formula 1, and a compound of formula 1a; a composition comprising a compound of formula 12 and a compound of formula 1a; a composition comprising a compound of formula 12, a compound of formula 1, and a compound of formula 1a; a composition comprising a compound of formula 14 and a compound of formula 1a; a composition comprising a compound of formula 14, a compound of formula 1, and a compound of formula 1a; a composition comprising a compound of formula 16 and a compound of formula 1a; a composition comprising a compound of formula 16, a compound of formula 1, and a compound of formula 1a; a composition comprising a compound of formula 18 and a compound of formula 1a; a composition comprising a compound of formula 18, a compound of formula 1, and a compound of formula 1a; a composition comprising a compound of formula 40 and a compound of formula 1a; a composition comprising a compound of formula 40, a compound of formula 1, and a compound of formula 1a; a composition comprising a compound of formula 16, a compound of formula 17, a compound of formula 1, and a compound of formula 1a; a composition comprising a compound of formula 18, a compound of formula 19, a compound of formula 1, and a compound of formula 1a; a composition comprising a compound of formula 40, a compound of formula 41, a compound of formula 1, and a compound of formula 1a; a composition comprising a compound of formula 10, a compound of formula 20, and a compound of formula 1a; a composition comprising a compound of formula 10, a compound of formula 20, a compound of formula 1, and a compound of formula 1a; a composition comprising a compound of formula 11, a compound of formula 21, and a compound of formula 1a; a composition comprising a compound of formula 11, a compound of formula 22, and a compound of formula 1a; a composition comprising a compound of formula 12, a compound of formula 23, and a compound of formula 1a; a composition comprising a compound of formula 12, a compound of formula 23, a compound of formula 1, and a compound of formula 1a; a composition comprising a compound of formula 13, a compound of formula 24, and a compound of formula 1a; a composition comprising a compound of formula 13, a compound of formula 25, and a compound of formula 1a; a composition comprising a compound of formula 10, a compound of formula 26, and a compound of formula 1a; a composition comprising a compound of formula 10, a compound of formula 26, a compound of formula 1, and a compound of formula 1a; a composition comprising a compound of formula 11, a compound of formula 27, and a compound of formula 1a; a composition comprising a compound of formula 11, a compound of formula 28, and a compound of formula 1a; a composition comprising a compound of formula 12, a compound of formula 29, and a compound of formula 1a; a composition comprising a compound of formula 12, a compound of formula 29, a compound of formula 1, and a compound of formula 1a; a composition comprising a compound of formula 13, a compound of formula 30, and a compound of formula 1a; a composition comprising a compound of formula 13, a compound of formula 31, and a compound of formula 1a; a composition comprising a compound of formula 10, a compound of formula 32, and a compound of formula 1a; a composition comprising a compound of formula 10, a compound of formula 32, a compound of formula 1, and a compound of formula 1a; a composition comprising a compound of formula 11, a compound of formula 33, and a compound of formula 1a; a composition comprising a compound of formula 11, a compound of formula 34, and a compound of formula 1a; a composition comprising a compound of formula 12, a compound of formula 35, and a compound of formula 1a; a composition comprising a compound of formula 12, a compound of formula 35, a compound of formula 1, and a compound of formula 1a; a composition comprising a compound of formula 13, a compound of formula 36, and a compound of formula 1a; or a composition comprising a compound of formula 13, a compound of formula 37, and a compound of formula 1a. In certain embodiments of any of the foregoing, the composition comprises 80-95% v/v of a compound of formula 1a, such as 80%, 81%, 82%, 83%, 84%, 85%, 86%, 87%, 88%, 89%, 90%, 91%, 92%, 93%, 94%, or 95% v/v of a compound of formula 1a.

The present invention further provides an emulsion comprising a composition comprising a compound of any one of formulae 1-9 and perfluoro-15-crown-5 ether, such as a compound of formula 1 and perfluoro-15-crown-5 ether; a composition comprising a compound of formula 1a and perfluoro-15-crown-5 ether; a composition comprising a compound of formula 10 and perfluoro-15-crown-5 ether; a composition comprising a compound of formula 10, a compound of formula 1, and perfluoro-15-crown-5 ether; a composition comprising a compound of formula 12 and perfluoro-15-crown-5 ether; a composition comprising a compound of formula 12, a compound of formula 1, and perfluoro-15-crown-5 ether; a composition comprising a compound of formula 14 and perfluoro-15-crown-5 ether; a composition comprising a compound of formula 14, a compound of formula 1, and perfluoro-15-crown-5 ether; a composition comprising a compound of formula 16 and perfluoro-15-crown-5 ether; a composition comprising a compound of formula 16, a compound of formula 1, and perfluoro-15-crown-5 ether; a composition comprising a compound of formula 18 and perfluoro-15-crown-5 ether; a composition comprising a compound of formula 18, a compound of formula 1, and perfluoro-15-crown-5 ether; a composition comprising a compound of formula 40 and perfluoro-15-crown-5 ether; a composition comprising a compound of formula 40, a compound of formula 1, and perfluoro-15-crown-5 ether; a composition comprising a compound of formula 16, a compound of formula 17, a compound of formula 1, and perfluoro-15-crown-5 ether; a composition comprising a compound of formula 18, a compound of formula 19, a compound of formula 1, and perfluoro-15-crown-5 ether; a composition comprising a compound of formula 40, a compound of formula 41, a compound of formula 1, and perfluoro-15-crown-5 ether; a composition comprising a compound of formula 10, a compound of formula 20, and perfluoro-15-crown-5 ether; a composition comprising a compound of formula 10, a compound of formula 20, a compound of formula 1, and perfluoro-15-crown-5 ether; a composition comprising a compound of formula 1, a compound of formula 21, and perfluoro-15-crown-5 ether; a composition comprising a compound of formula 1, a compound of formula 22, and perfluoro-15-crown-5 ether; a composition comprising a compound of formula 12, a compound of formula 23, and perfluoro-15-crown-5 ether; a composition comprising a compound of formula 12, a compound of formula 23, a compound of formula 1, and perfluoro-15-crown-5 ether; a composition comprising a compound of formula 13, a compound of formula 24, and perfluoro-15-crown-5 ether; a composition comprising a compound of formula 13, a compound of formula 25, and perfluoro-15-crown-5 ether; a composition comprising a compound of formula 10, a compound of formula 26, and perfluoro-15-crown-5 ether; a composition comprising a compound of formula 10, a compound of formula 26, a compound of formula 1, and perfluoro-15-crown-5 ether; a composition comprising a compound of formula 11, a compound of formula 27, and perfluoro-15-crown-5 ether; a composition comprising a compound of formula 11, a compound of formula 28, and perfluoro-15-crown-5 ether; a composition comprising a compound of formula 12, a compound of formula 29, and perfluoro-15-crown-5 ether; a composition comprising a compound of formula 12, a compound of formula 29, a compound of formula 1, and perfluoro-15-crown-5 ether; a composition comprising a compound of formula 13, a compound of formula 30, and perfluoro-15-crown-5 ether; a composition comprising a compound of formula 13, a compound of formula 31, and perfluoro-15-crown-5 ether; a composition comprising a compound of formula 10, a compound of formula 32, and perfluoro-15-crown-5 ether; a composition comprising a compound of formula 10, a compound of formula 32, a compound of formula 1, and perfluoro-15-crown-5 ether; a composition comprising a compound of formula 11, a compound of formula 33, and perfluoro-15-crown-5 ether; a composition comprising a compound of formula 11, a compound of formula 34, and perfluoro-15-crown-5 ether; a composition comprising a compound of formula 12, a compound of formula 35, and perfluoro-15-crown-5 ether; a composition comprising a compound of formula 12, a compound of formula 35, a compound of formula 1, and perfluoro-15-crown-5 ether; a composition comprising a compound of formula 13, a compound of formula 36, and perfluoro-15-crown-5 ether; or a composition comprising a compound of formula 13, a compound of formula 37, and perfluoro-15-crown-5 ether. In certain embodiments of any of the foregoing, the composition comprises 80-95% v/v of perfluoro-15-crown-5 ether, such as 80%, 81%, 82%, 83%, 84%, 85%, 86%, 87%, 88%, 89%, 90%, 91%, 92%, 93%, 94%, or 95% v/v of perfluoro-15-crown-5 ether.

In certain embodiments, the emulsion may further comprise a block copolymer of polyethylene and polypropylene glycol. In certain embodiments, the emulsion may further comprise a Pluronic™. Nonionic Pluronic™ surfactants, polyethyleneoxide (PEO)/polypopyleneoxide (PPO)/polyethyleneoxide (PEO) block (ABA type), (PEO/PPO/PEO) block copolymers, exhibit a wide range of hydrophilicity/hydrophobicity as a function of the PEO/PPO ratio, so that one can expect to obtain different phase separated morphologies with polymers such as PLA as well as different degrees of hydration of the matrix. In particular, hydration plays an important role in determining polymer degradation via hydrolysis of the ester backbone. These polymeric surfactants exhibited minimal toxicities in vivo and some of them are in clinical use, as described by BASF Corporation in their 1989 Technical Bulletin; Attwood, et al., Int. J. Pharm. 26, 25

(1985); and U.S. Pat. No. 4,188,373 to Krezanoski. These materials can be obtained from BASF Corporation. In certain embodiments, emulsions of the present invention further comprise tri-block copolymer which comprises polyethyleneoxide and polypopyleneoxide.

In certain embodiments, emulsions of the present invention comprise a tri-block copolymer of poly(ethylene oxide)-poly(propylene oxide)-poly(ethylene oxide) (PEO-PPO-PEO) with an average molecular weight of 1900. In certain such embodiments, the tri-block copolymer comprises 50% PEO content with an average number of PEO units of about 22, such as 21.59, and an average number of PPO units of about 16, such as 16.38. In certain such embodiments, the hydrophilic-lipophilic balance (HLB) value of the tri-block copolymer is 19, wherein the HLB value can be calculated from the following equation:

$$HLB = -36\frac{m}{2n+m} + 33$$

where n represents the number of repeat units in the PEO segment of the polymer and m represents the number of repeat units in the PPO segment of the polymer. Exemplary tri-block copolymers can be obtained from BASF Corporation and are sold under the trade name of Pluronic™ L35.

In certain embodiments, emulsions of the present invention comprise a tri-block copolymer of poly(ethylene oxide)-poly(propylene oxide)-poly(ethylene oxide) (PEO-PPO-PEO) with an average molecular weight of 2900. In certain such embodiments, the tri-block copolymer comprises 40% PEO content with an average number of PEO units of about 26, such as 26.36, and an average number of PPO units of about 30, such as 30.00. In certain such embodiments, the hydrophilic-lipophilic balance (HLB) value of the tri-block copolymer is 15. Exemplary tri-block copolymers can be obtained from BASF Corporation and are sold under the trade name of Pluronic™ L64.

In certain embodiments, emulsions of the present invention comprise a tri-block copolymer of poly(ethylene oxide)-poly(propylene oxide)-poly(ethylene oxide) (PEO-PPO-PEO) with an average molecular weight of 8400. In certain such embodiments, the tri-block copolymer comprises 80% PEO content with an average number of PEO units of about 153, such as 152.73, and an average number of PPO units of about 29, such as 28.97. In certain such embodiments, the hydrophilic-lipophilic balance (HLB) value of the tri-block copolymer is 29. Exemplary tri-block copolymers can be obtained from BASF Corporation and are sold under the trade name of Pluronic™ F68.

In certain embodiments, emulsions of the present invention comprise a tri-block copolymer of poly(ethylene oxide)-poly(propylene oxide)-poly(ethylene oxide) (PEO-PPO-PEO) with an average molecular weight of 6500. In certain such embodiments, the tri-block copolymer comprises 50% PEO content with an average number of PEO units of about 74, such as 73.86, and an average number of PPO units of about 56, such as 56.03. In certain such embodiments, the hydrophilic-lipophilic balance (HLB) value of the tri-block copolymer is 15. Exemplary tri-block copolymers can be obtained from BASF Corporation and are sold under the trade name of Pluronic™ P105.

In certain embodiments, the emulsion may further comprise a lipid. In certain embodiments of emulsions of the present invention that further comprise a lipid, the lipid is DMPC. In certain embodiments of emulsions of the present invention that further comprise a lipid, the emulsion further comprises a block copolymer. In certain embodiments, the block copolymer is a tri-block copolymer which comprises poly(ethylene oxide) and poly(propylene oxide). In certain such embodiments the block copolymer is poly(ethylene oxide)-poly(propylene oxide)-poly(ethylene oxide) (PEO-PPO-PEO) tri-block copolymer with an average molecular weight of 1900, an average number of PEO units of about 22, such as 21.59, and an average number of PPO units of about 16, such as 16.38. In certain embodiments, the emulsion of the present invention further comprises DMPC and a poly(ethylene oxide)-poly(propylene oxide)-poly(ethylene oxide) (PEO-PPO-PEO) tri-block copolymer with an average molecular weight of 1900, an average number of PEO units of about 22, such as 21.59, and an average number of PPO units of about 16, such as 16.38 (e.g., Pluronic™ L35).

In certain embodiments, the emulsion may further comprise polyethylamine.

In certain embodiments, the emulsion may further comprise protamine sulfate. In certain embodiments of emulsions of the present invention that further comprise protamine sulfate, the emulsion further comprises a block copolymer. In certain embodiments, the block copolymer is a tri-block copolymer which comprises poly(ethylene oxide) and poly(propylene oxide). In certain such embodiments the block copolymer is poly(ethylene oxide)-poly(propylene oxide)-poly(ethylene oxide) (PEO-PPO-PEO) tri-block copolymer with an average molecular weight of 1900, an average number of PEO units of about 22, such as 21.59, and an average number of PPO units of about 16, such as 16.38 (e.g., Pluronic™ L35). In certain embodiments, the emulsion of the present invention further comprises protamine sulfate and a poly(ethylene oxide)-poly(propylene oxide)-poly(ethylene oxide) (PEO-PPO-PEO) tri-block copolymer with an average molecular weight of 1900, an average number of PEO units of about 22, such as 21.59, and an average number of PPO units of about 16, such as 16.38 (e.g., Pluronic™ L35).

In certain embodiments, the emulsion may further comprise an emulsifier. In certain such embodiments, the emulsifier is also a non-ionic solubiliser. In certain embodiments, the emulsifier comprises glycerol polyethylene glycol ricinoleate. In certain such embodiments, the emulsifier further comprises fatty acid esters of polyethylene glycol, free polyethylene glycols, and ethoxylated glycerol. In certain embodiments, the emulsifier is prepared by reacting castor oil and ethylene oxide in a molar ratio of 1:35. Exemplary emulsifiers can be obtained from BASF Corporation and are sold under the trade name of Cremophor® EL.

In certain embodiments, the invention contemplates any combination of the foregoing. Those skilled in the art will recognize that all specific combinations of the individual possible components of the emulsions as disclosed herein, e.g., a compound of any one of formulae 1-37, 40-41, 1a, or perfluoro-15-crown-5 ether, a block copolymer (e.g., a tri-block copolymer which comprises poly(ethylene oxide) and poly(propylene oxide), a lipid, an emulsifier comprising glycerol polyethylene glycol ricinoleate, polyethylamine, or protamine sulfate, are within the scope of the invention. As an example, an emulsion may contain one or more compound(s) of any one of formulae 1-37, 40-41, 1a, or perfluoro-15-crown-5 ether, a block copolymer (e.g., a tri-block copolymer which comprises poly(ethylene oxide) and poly(propylene oxide), a lipid, and polyethylamine and/or protamine sulfate.

In certain embodiments, the emulsion comprises a compound of formula 1, a compound of formula 16, a compound of formula 17, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1, a compound of formula 16, a compound of formula 17, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1, a compound of formula 16, a compound of formula 17, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1, a compound of formula 16, a compound of formula 17, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1, a compound of formula 16, a compound of formula 17, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1, a compound of formula 16, a compound of formula 17, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1, a compound of formula 18, a compound of formula 19, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1, a compound of formula 18, a compound of formula 19, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1, a compound of formula 18, a compound of formula 19, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1, a compound of formula 18, a compound of formula 19, a poly(ethylene oxide)-poly(propylene oxide)-poly(ethylene oxide) (PEO-PPO-PEO) tri-block copolymer with an average number of PEO units of about 153, such as 152.73, and an average number of PPO units of about 29, such as 28.97 (e.g., Pluronic™ F68), and protamine sulfate; a compound of formula 1, a compound of formula 18, a compound of formula 19, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1, a compound of formula 18, a compound of formula 19, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1, a compound of formula 40, a compound of formula 41, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1, a compound of formula 40, a compound of formula 41, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1, a compound of formula 40, a compound of formula 41, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1, a compound of formula 40, a compound of formula 41, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1, a compound of formula 40, a compound of formula 41, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1, a compound of formula 40, a compound of formula 41, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1a and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1, a compound of formula 16, a compound of formula 17, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1, a compound of formula 16, a compound of formula 17, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1, a compound of formula 16, a compound of formula 17, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1, a compound of formula 18, a compound of formula 19, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1, a compound of formula 18, a compound of formula 19, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1, a compound of formula 18, a compound of formula 19, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1, a compound of formula 40, a compound of formula 41, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1, a compound of formula 40, a compound of formula 41, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1, a compound of formula 40, a compound of formula 41, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1a, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; a compound of formula 1a, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; a compound of formula 1a, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and protamine sulfate; perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68), and polyethylamine; perfluoro-15-crown-5 ether and a poly(ethylene oxide)-poly(propylene oxide)-poly(ethylene oxide) (PEO-PPO-PEO) tri-block copolymer with an average molecular weight of 8400, an average number of PEO units of about 153, such as 152.73, and an average number of PPO units of about 29, such as 28.97 (e.g., Pluronic™ F68); a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL); a compound of formula 1a, a compound of formula 1, a poly(ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL); a compound of formula 1a, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL); a compound of formula 1a, a compound of formula 1, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL); perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL); a compound of formula 1, a compound of formula 16, a compound of formula 17, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL); a compound of formula 1, a compound of formula 18, a compound of formula 19, perfluoro-15-crown-5 ether, a poly (ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL); a compound of formula 1, a compound of formula 40, a compound of formula 41, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL); a compound of formula 1, a compound of formula 16, a compound of formula 17, a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL); a compound of formula 1, a compound of formula 18, a compound of formula 19, a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL); or a compound of formula 1, a compound of formula 40, a compound of formula 41, a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL).

In certain embodiments, the emulsion comprises a compound of formula 42, a poly(ethylene oxide)-poly(propylene oxide)-poly(ethylene oxide) (PEO-PPO-PEO) tri-block copolymer with an average molecular weight of 6500, an average number of PEO units of about 74, such as 73.86, and an average number of PPO units of about 56, such as 56.03 (e.g., Pluronic™ P105), and an emulsifier, wherein the emulsifier is a non-ionic solubiliser comprising glycerol polyethylene glycol ricinoleate (e.g., Cremophor® EL).

Emulsions of the present invention will preferably have a distribution of particle sizes that allow adequate cellular uptake. In certain embodiments, a uniform particle size may be advantageous. The desired degree of uniformity of particle size may vary depending upon the application. In certain embodiments, the emulsion has a mean particle size less than 500 nm, or less than 400 nm, or less than 300 nm, or less than 200 nm in diameter. Optionally, 25%, or 50%, or 75% or more of the particles will fall within the selected range. Particle sizes may be evaluated by, for example, light scattering techniques or by visualizing the emulsion particles using EM micrographs. In certain cell types that have a relatively small amount of cytoplasm, such as most stem cells, the emulsions have a mean particle size of less than 200 nm, or less than 100 nm, or less than 50 nm in diameter.

Emulsions for use in cells should preferably be stable at a wide range of temperatures. In certain embodiments, emulsions will be stable at body temperature (37° C. for humans) and at a storage temperature, such as 4° C. or room temperature (20-25° C.). For example, it will often be desirable to store the emulsion at a cool temperature, in the range of 2-10° C., such as 4° C., and then warm the emulsion to room temperature (e.g., 18 to 28° C., and more typically 20 to 25° C.). After labeling of cells, the emulsion will experience a temperature of about 37° C. Accordingly, a preferred emulsion will retain the desired range of particle sizes at temperatures ranging from refrigeration temperatures up to body temperature. In certain embodiments, the emulsion is stable at temperatures ranging from 4° C. to 37° C.

In certain embodiments, the emulsion has a polydispersity index ranging from 0.1 to 0.2.

The present invention provides a method for preparing an emulsion of a PFPE derivative with a block copolymer using low energy methods. In certain embodiments, the block copolymer is a tri-block copolymer which comprises poly (ethylene oxide) and poly(propylene oxide).

The present invention further provides a method for preparing an emulsion comprising low energy methods. In certain such embodiments, the low energy method comprises a thin film method.

In certain embodiments of emulsions of the present invention, the emulsion further comprises PFPE-oxide, 1a.

The present invention also provides a method for preparing a composition comprising a compound of formula 1 and a compound of formula 38:

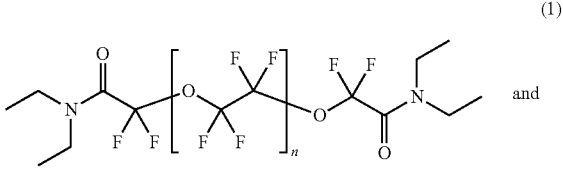

(1)

and

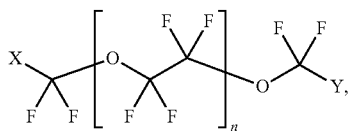

wherein n, independently for each occurrence, represents an integer from 4 to 16; and one or both of X and Y is an amide other than diethyl amide, comprising:

1) reacting perfluoropolyether methyl ester (39),

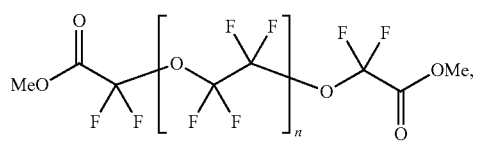

having two methyl ester end groups with a primary or secondary aliphatic amine other than diethyl amine;

2) reacting unmodified methyl ester end groups with excess diethyl amine; and 3) removing unreacted diethyl amine; and 4) optionally removing non-volatile amines by solid phase extraction and filtration using fluorous phase silica gel (FluoroFlash, Fluorous Inc.)

In certain embodiments, more than 80%, or more than 85%, or more than 90%, or more than 91%, or more than 92%, or more than 93%, or more than 94%, or more than 95% of the methyl ester end groups are converted to amides.

In certain embodiments, excess diethyl amine is removed in vacuo.

In certain embodiments, excess non volatile amine is eluted with fluorophobic solvent after loading the sample onto fluorous silica gel column FluoroFlash (Fluorous Inc.).

In certain embodiments, less than one equivalent of the amine other than diethyl amine is reacted with perfluoropolyether methyl ester 39 (e.g., less than 100 mol % of amine other than diethyl amine as compared to perfluoropolyether methyl ester 39 is reacted). In certain embodiments, less than 90 mol %, or less than 80 mol %, or less than 70 mol %, or less than 60 mol %, or less than 50 mol %, or less than 40 mol %, or less than 30 mol %, or less than 20 mol %, or less than 10 mol % of amine other than diethyl amine is reacted with perfluoropolyether methyl ester 39. In certain such embodiments, the reaction between the amine other than diethyl amine and perfluoropolyether methyl ester 39 is allowed to proceed to completion. In certain embodiments wherein any amine other than diethyl amine remains unreacted, the unreacted amine other than diethyl amine is removed by selective extraction with an organic solvent such as ethanol or THF. In certain embodiments the unreacted amine other then diethylamine is eluted from a fluorous phase column by fluorophobic solvent.

In certain embodiments, compositions prepared using the method described above are as defined above for the composition comprising a compound of formula 10 and a compound of formula 1; the composition comprising a compound of formula 12 and a compound of formula 1; the composition comprising a compound of formula 14 and a compound of formula 1; the composition comprising a compound of formula 16 and a compound of formula 1; or the composition comprising a compound of formula 18 and a compound of formula 1; or the composition comprising a compound of formula 40 and a compound of formula 1.

Detection moieties suitable for PET imaging may also be used to create dual mode imaging reagents that are detectable by nuclear magnetic resonance techniques and by PET techniques. For example, the $^{18}$F isotope is a potent label for PET detection methods. A fluorocarbon imaging reagent may comprise a mixture of $^{18}$F and $^{19}$F isotopes, thus providing a dual mode label that is suitable for MRI/MRS and PET. $^{18}$F and $^{19}$F may also be added in separate monomers to form a mixed copolymer, or $^{18}$F portions may be located at either end of a linear polyether, at the position where most other functional moieties would be added. $^{18}$F has no NMR signal and so may be added at positions that would, for example, tend to decrease NMR linewidth, simplify the NMR spectrum, or alleviate chemical shifts from resonances that adversely affect the read-out obtained by a nuclear magnetic resonance technique. In addition, molecules of the fluorocarbon imaging reagents can incorporate other radioisotopes that are effective PET probes, such as $^{11}$C, $^{15}$O, and $^{13}$N. Those skilled in the art can, in view of this specification, devise many other PET-detectable moieties that can be incorporated into or, for example, attached to an endgroup(s), of the imaging reagents of this disclosure.

The properties of an emulsion may be controlled primarily by the properties of the imaging reagent itself, the nature of surfactants and/or solvents used, and the type of processing device (e.g., sonicator, Microfluidizer, homogenizer, etc.). Methods for forming emulsions with certain PFPE molecules are extensively described in U.S. Pat. Nos. 5,330,681 and 4,990,283, herein incorporated by reference in their entirety. A continuous phase of a polyhydroxylated compound, such as polyalcohols and saccharides in concentrated aqueous solution may be effective. The following polyalcohols and saccharides have proved to be particularly effective: glycerol, xylitol, mannitol, sorbitol, glucose, fructose, saccharose, maltitol, dimer compounds of glycerol (di-glycerol or bis(2,3-di-hydroxypropyl)ether, solid water soluble polyhydroxylated compounds as sugars and glycerol condensation products as triglycerol and tetraglycerol. The dispersion in emulsion may be performed in the presence of conventional surfactants, including cationic, anionic, amphoteric and nonionic surfactants. Examples of suitable surfactants include sodium lauryl sulphate, sulphosuccinate (sulphosuccinic hemiester), coco-amphocarboxyglycinate, potassium cetyl phosphate, sodium alkyl-polyoxyethylene-ether carboxylate, potassium benzalkonium chloride, alkyl amidopropyl betaine, cetyl-stearilic ethoxylated alcohol, and sorbitanethoxylate(20)-mono-oleate Tween 20. While thermodynamic equations may be used to attempt to predict mixtures of imaging reagents that will give emulsions having the desired particle sizes and stability, it is generally accepted that actual testing of various mixtures will be most effective. The emulsification of mixtures is simple and quick, permitting rapid testing of a wide range of combinations to identify those that give rise to emulsions that are suitable for use in the methods disclosed herein.

Preferably an emulsion is designed to facilitate uptake of the imaging reagent by the subject cells. A surfactant may be designed to form stable emulsions that carry a large quantity of PFPE (e.g., PFPE amide, as in compounds or compositions of the present invention) into the aqueous phase. Additionally, it may have properties that increase the intracellular delivery of the emulsion particles in the shortest possible incubation time. Increasing the PFPE (e.g., PFPE amide, as in compounds or compositions of the present invention) intracellular loading improves sensitivity to the labeled cells. Furthermore, minimizing the culture time can be important when working with the primary cells cultures. The efficiency of intracellular uptake depends on cell type. For example macrophages and some dendritic cells will endocytose almost any particulate, whereas other cell types of interest may only be weakly phagocytic. In either case the uptake efficiency can be boosted substantially by designing the surfactant so that the surface of the emulsion particle has properties that promote cellular uptake in culture (i.e. "self-delivering" emulsion particles). The emulsion particle surface can be made to have lipophilic, or optionally cationic, properties via appropriate surfactant design. For example the surfactant can incorporate lipids, such as cationic or neutral lipids, oil-in-water emulsions, micelles, mixed micelles, or liposomes, that tend to bind to or fuse with the cell's surface, thereby enhancing emulsion particle uptake. In certain embodiments, a colloidal system for use as a delivery vehicle in vitro and in vivo is a liposome (i.e., an artificial membrane vesicle). The preparation and use of such systems is well known in the art. Suitable cationic lipids are described in the following and are herein incorporated in their entirety: Felgner et al., 1987, PNAS 84, 7413-7417; Eppstein et al., U.S. Pat. No. 4,897,355), (Rose, U.S. Pat. No. 5,279,833; Eppand et al. U.S. Pat. No. 5,283,185; Gebeyehu et al., U.S. Pat. No. 5,334,761; Nantz et al., U.S. Pat. No. 5,527,928; Bailey et al., U.S. Pat. No. 5,552,155; Jesse, U.S. Pat. No. 5,578,475). Other approaches include incorporation into the surfactant peptides (e.g. oligo-Arg9 and TAT-like peptides) that facilitate entry into cells, or antibodies that target specific cell surface molecules. Additionally, in certain embodiments, one can incorporate small cationic proteins into the surfactant, such as protamine sulfate, to enhance cellular uptake. Protamine sulfate is non-toxic to cells and has FDA approval for use in humans as a heparin antagonist. In certain embodiments, colloidal dispersion systems are used, such as macromolecule complexes, nanocapsules, microspheres, and beads. Other approaches for enhancing uptake of the emulsified fluorocarbons, such as by using additional transfection agents or by using electroporation of the cells, is described herein.

In preferred embodiments, emulsions have "self-delivering" properties without having to add uptake enhancing reagents. Said emulsions are preferably stable and have a shelf-life of a period of months or years.

It is understood that surfactants and uptake enhancing reagents are not meant to be exclusive groups and in some cases they may be overlapping.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

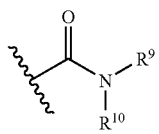

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

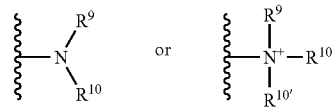

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

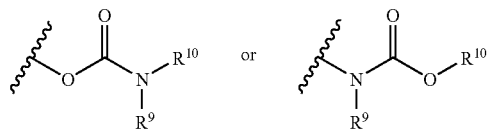

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —$OCO_2$—$R^9$, wherein $R^9$ represents a hydrocarbyl group.

The term "carboxy", as used herein, refers to a group represented by the formula —$CO_2H$.

The term "ester", as used herein, refers to a group —C(O)$OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

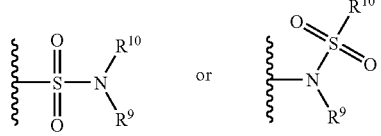

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^9$, wherein $R^9$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^9$, wherein $R^9$ represents a hydrocarbyl.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

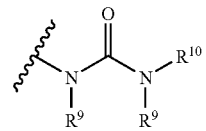

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

Certain compounds of the present invention may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Methods of preparing substantially isomerically pure compounds are known in the art. If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers. Alternatively, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Techniques for inverting or leaving unchanged a particular stereocenter, and those for resolving mixtures of stereoisomers are well known in the art, and it is well within the ability of one of skill in the art to choose an appropriate method for a particular situation. See, generally, Furniss et al. (eds.), *Vogel's Encyclopedia of Practical Organic Chemistry* 5$^{th}$ Ed., Longman Scientific and Technical Ltd., Essex, 1991, pp. 809-816; and Heller, *Acc. Chem. Res.* 23: 128 (1990).

3. Cells and Labeling

Methods described herein may be used with a wide range of cells, including both prokaryotic and eukaryotic cells, and preferably mammalian cells. Technologies for cell preparation include cell culture, cloning, nuclear transfer, genetic modification and encapsulation.

A partial list of suitable mammalian cells includes: blood cells, myoblasts, bone marrow cells, peripheral blood cells, umbilical cord blood cells, cardiomyocytes (and precursors thereof), chondrocytes (cartilage cells), dendritic cells, fetal neural tissue, fibroblasts, hepatocytes (liver cells), islet cells of pancreas, keratinocytes (skin cells) and stem cells. In certain preferred embodiments, the cells to be used are a fractionated population of immune cells. Recognized subpopulations of immune cells include the lymphocytes, such as B lymphocytes (Fc receptors, MHC class II, CD 19+, CD21+), helper T lymphocytes (CD3+, CD4+, CD8−), cytolytic T lymphocytes (CD3+, CD4−, CD8+), natural killer cells (CD16+), the mononuclear phagocytes, including monocytes, neutrophils and macrophages, and dendritic cells. Other cell types that may be of interest include eosinophils and basophils.

Cells may be autologous (i.e., derived from the same individual) or syngeneic (i.e., derived from a genetically identical individual, such as a syngeneic littermate or an identical twin), although allogeneic cells (i.e., cells derived from a genetically different individual of the same species) are also contemplated. Although less preferred, xenogeneic (i.e., derived from a different species than the recipient) cells, such as cells from transgenic pigs, may also be administered. When the donor cells are xenogeneic, it is preferred that the cells are obtained from an individual of a species within the same order, more preferably the same superfamily or family (e.g. when the recipient is a human, it is preferred that the cells are derived from a primate, more preferably a member of the superfamily Hominoidea).

Cells may, where medically and ethically appropriate, be obtained from any stage of development of the donor individual, including prenatal (e.g., embryonic or fetal), infant (e.g., from birth to approximately three years of age in humans), child (e.g. from about three years of age to about 13 years of age in humans), adolescent (e.g., from about 13 years of age to about 18 years of age in humans), young adult (e.g., from about 18 years of age to about 35 years of age in humans), adult (from about 35 years of age to about 55 years of age in humans) or elderly (e.g., from about 55 years and beyond of age in humans).

In many embodiments, cells are labeled by contacting the cells with an emulsion of the imaging reagent, such that the reagent is taken up by cells. Both phagocytic and non-phagocytic cells may be labeled by such a method. For example, as demonstrated in WO2005072780, both dendritic cells (phagocytic) and gliosarcoma cells (non-phagocytic) can be labeled by contacting the cells with an emulsion of the imaging reagent.

It certain aspects, a method of the invention may comprise labeling cells in vivo with a $^{19}F$ imaging reagent and detecting labeled cells in the subject. The cells to be labeled may be determined by specific properties of the cells such as phagocytic activity. The cells that are labeled may be controlled by the route of administration of the imaging reagent. The types of cells that are labeled may be controlled by the nature of the imaging reagent. For example, simple colloidal suspensions of imaging reagent will tend to be taken up more quickly by cells with phagocytic activity. As another example, an imaging reagent may be formulated with or covalently bound to a targeting moiety that facilitates selective targeting of the imaging reagent to a particular population of cells. In certain embodiments, fluorocarbon imaging reagent may comprise a compound of any one of formulae 1-17, 20-37, or 40-41, or Perfluoro-15-crown ether.

In certain embodiments the cells to be labeled are stem cells. Stem cell therapies are commonly used as part of an ablative regimen for treatment of cancer with high dose radiation and/or chemotherapeutic agents. Ablative regimens generally employ hematopoietic stem cells, or populations of cells containing hematopoietic stem cells, as may be obtained, for example, from peripheral blood, umbilical cord blood or bone marrow. Cells of this type, or a portion thereof, may be labeled and tracked in vivo to monitor survival and engraftment at the appropriate location. Other types of stem cells are increasingly attractive as therapeutic agents for a wide variety of disorders.

As an example, cells may be mouse embryonic stem cells, or ES cells from another model animal. The labeling of such cells may be useful in tracking the fate of such cells administered to mice, optionally as part of a preclinical research program for developing embryonic stem cell therapeutics. Examples of mouse embryonic stem cells include: the JM1 ES cell line described in M. Qiu et al., Genes Dev 9, 2523 (1995), and the ROSA line described in G. Friedrich, P. Soriano, Genes Dev 5, 1513 (1991), and mouse ES cells described in U.S. Pat. No. 6,190,910. Many other mouse ES lines are available from Jackson Laboratories (Bar Harbor, Me.). Examples of human embryonic stem cells include those available through the following suppliers: Arcos Bioscience, Inc., Foster City, Calif., CyThera, Inc., San Diego, Calif., BresaGen, Inc., Athens, Ga., ES Cell International, Melbourne, Australia, Geron Corporation, Menlo Park, Calif., Göteborg University, Göteborg, Sweden, Karolinska Institute, Stockholm, Sweden, Maria Biotech Co. Ltd.—Maria Infertility Hospital Medical Institute, Seoul, Korea, MizMedi Hospital—Seoul National University, Seoul, Korea, National Centre for Biological Sciences/Tata Institute of Fundamental Research, Bangalore, India, Pochon CHA University, Seoul, Korea, Reliance Life Sciences, Mumbai, India, ReNeuron, Surrey, United Kingdom, StemCells, Inc., Palo Alto, Calif., Technion University, Haifa, Israel, University of California, San Francisco, Calif., and Wisconsin Alumni Research Foundation, Madison, Wis. In addition, examples of embryonic stem cells are described in the following U.S. Pat. Nos. and published patent applications: 6,245,566; 6,200,806; 6,090,622; 6,331,406; 6,090,622; 5,843,780; 20020045259; 20020068045. In preferred embodiments, the human ES cells are selected from the list of approved cell lines provided by the National Institutes of Health and accessible at http://escr.nih.gov. In certain preferred embodiments, an embryonic stem cell line is selected from the group comprising: the WA09 line obtained from Dr. J. Thomson (Univ. of Wisconsin) and the UC01 and UC06 lines, both on the current NIH registry.

In certain embodiments, a stem cell for use in disclosed methods is a stem cell of neural or neuroendocrine origin, such as a stem cell from the central nervous system (see, for example U.S. Pat. Nos. 6,468,794; 6,040,180; 5,753,506; 5,766,948), neural crest (see, for example, U.S. Pat. Nos. 5,589,376; 5,824,489), the olfactory bulb or peripheral neural tissues (see, for example, Published US Patent Applications 20030003574; 20020123143; 20020016002 and Gritti et al. 2002 J Neurosci 22(2):437-45), the spinal cord (see, for example, U.S. Pat. Nos. 6,361,996, 5,851,832) or a neuroendocrine lineage, such as the adrenal gland, pituitary gland or certain portions of the gut (see, for example, U.S. Pat. No. 6,171,610 and PC12 cells as described in Kimura et al. 1994 J. Biol. Chem. 269: 18961-67). In preferred embodiments, a neural stem cell is obtained from a peripheral tissue or an easily healed tissue, thereby providing an autologous population of cells for transplant.

Hematopoietic or mesenchymal stem cells may be employed in certain disclosed methods. Recent studies suggest that bone marrow-derived hematopoietic (HSCs) and mesenchymal stem cells (MSCs), which are readily isolated, have a broader differentiation potential than previously recognized. Purified HSCs not only give rise to all cells in blood, but can also develop into cells normally derived from endoderm, like hepatocytes (Krause et al., 2001, Cell 105: 369-77; Lagasse et al., 2000 Nat Med 6: 1229-34). Similarly, HSCs from peripheral blood and from umbilical cord blood are expected to provide a useful spectrum of developmental potential. MSCs appear to be similarly multipotent, producing progeny that can, for example, express neural cell markers (Pittenger et al., 1999 Science 284: 143-7; Zhao et al., 2002 Exp Neurol 174: 11-20). Examples of hematopoietic stem cells include those described in U.S. Pat. Nos. 4,714,680; 5,061,620; 5,437,994; 5,914,108; 5,925,567; 5,763,197; 5,750,397; 5,716,827; 5,643,741; 5,061,620. Examples of mesenchymal stem cells include those described in U.S. Pat. Nos. 5,486,359; 5,827,735; 5,942,225; 5,972,703, those described in PCT publication nos. WO 00/53795; WO 00/02654; WO 98/20907, and those described in Pittenger et al. and Zhao et al., supra.

Stem cell lines are preferably derived from mammals, such as rodents (e.g. mouse or rat), primates (e.g. monkeys, chimpanzees or humans), pigs, and ruminants (e.g. cows, sheep and goats), and particularly from humans. In certain embodiments, stem cells are derived from an autologous source or an HLA-type matched source. For example, stem cells may be obtained from a subject in need of pancreatic hormone-producing cells (e.g. diabetic patients in need of insulin-producing cells) and cultured to generate autologous insulin-producing cells. Other sources of stem cells are easily obtained from a subject, such as stem cells from muscle tissue, stem cells from skin (dermis or epidermis) and stem cells from fat.

In some preferred embodiments, cells for administration to a human should be compliant with good tissue practice guidelines set by the U.S. Food and Drug Administration (FDA) or equivalent regulatory agency in another country. Methods to develop such a cell line may include donor testing, and avoidance of exposure to non-human cells and products.

Cells derived from a donor (optionally the patient is the donor) may be administered as unfractionated or fractionated cells, as dictated by the purpose of the cells to be delivered. Cells may be fractionated to enrich for certain cell types prior to administration. Methods of fractionation are well known in the art, and generally involve both positive selection (i.e., retention of cells based on a particular property) and negative selection (i.e., elimination of cells based on a particular property). As will be apparent to one of skill in the art, the particular properties (e.g., surface markers) that are used for positive and negative selection will depend on the desired population of cells. Methods used for selection/enrichment of cells may include immunoaffinity technology or density centrifugation methods. Immunoaffinity technology may take a variety of forms, as is well known in the art, but generally utilizes an antibody or antibody derivative in combination with some type of segregation technology. The segregation technology generally results in physical segregation of cells bound by the antibody and cells not bound by the antibody, although in some instances the segregation technology which kills the cells bound by the antibody may be used for negative selection.

Any suitable immunoaffinity technology may be utilized for selection/enrichment of the selected cells to be used, including fluorescence-activated cell sorting (FACS), panning, immunomagnetic separation, immunoaffinity chromatography, antibody-mediated complement fixation, immunotoxin, density gradient segregation, and the like. After processing in the immunoaffinity process, the desired cells (the cells bound by the immunoaffinity reagent in the case of positive selection, and cells not bound by the immunoaffinity reagent in the case of negative selection) are collected and either subjected to further rounds of immunoaffinity selection/enrichment, or reserved for administration to the patient.

Immunoaffinity selection/enrichment is typically carried out by incubating a preparation of cells comprising the desired cell type with an antibody or antibody-derived affinity reagent (e.g., an antibody specific for a given surface marker), then utilizing the bound affinity reagent to select either for or against the cells to which the antibody is bound. The selection process generally involves a physical separation, such as can be accomplished by directing droplets containing single cells into different containers depending on the presence or absence of bound affinity reagent (FACS), by utilizing an antibody bound (directly or indirectly) to a solid phase substrate (panning, immunoaffinity chromatography), or by utilizing a magnetic field to collect the cells which are bound to magnetic particles via the affinity reagent (immunomagnetic separation). Alternately, undesirable cells may be eliminated from the preparation using an affinity reagent which directs a cytotoxic insult to the cells bound by the affinity reagent. The cytotoxic insult may be activated by the affinity reagent (e.g., complement fixation), or may be localized to the target cells by the affinity reagent (e.g., immunotoxin, such as ricin B chain).

Although it is expected that methods disclosed herein will be frequently used for in vivo monitoring of cells, it should be noted that the methodologies are equally effective for the monitoring of cells in culture, in a tissue sample or other ex vivo cellular material. For therapeutic uses, cells may be labeled at a desired step during the preparation for administration to the patient.

A variety of methods may be used to label cells with imaging reagent. In general, cells will be placed in contact with imaging reagent such that the imaging reagent becomes associated with the cell. Conditions will often be standard cell culture conditions designed to maintain cell viability. The term "associated" is intended to encompass any manner by which the imaging reagent and cell remain in sufficiently close physical proximity for a sufficient amount of time as to allow the imaging reagent to provide useful information about the position of the cell, whether in vivo or in vitro. Imaging reagent may be located intracellularly, e.g. after phagocytosis or surfactant mediated entry into the cell. Immune cells, such as dendritic cells, macrophages and T cells are often highly phagocytic and data presented herein and in other studies demonstrate that such cells, and other phagocytic cell types, are readily labeled. Other cell types, such as stem cells may also be labeled, regardless of phagocytic activity. Imaging reagent may be inserted into a cell membrane or covalently or non-covalently bound to an extracellular component of the cell. For example, certain linear fluorocarbons described herein may be derivatized to attach one or more targeting moiety. A targeting moiety will be selected to facilitate association of the imaging reagent with the cell to be labeled. A targeting moiety may be designed to cause non-specific insertion of the fluorocarbon into a cell membrane (e.g., a hydrophobic amino acid sequence or other hydrophobic moiety such as a palmitoyl moiety or myristoyl moiety) or to facilitate non-specific entry into the cell. A targeting moiety may bind to a cell surface component, as in the case of receptor ligands. A targeting moiety may be a member of a specific binding pair, where the partner is a cell surface component. The targeting moiety may be, for example, a ligand for a receptor, or an antibody, such as a monoclonal or polyclonal antibody or any of the various polypeptide binding agents comprising a variable portion of an immunoglobulin (e.g., Fv fragment, single chain Fv (scFv) fragment, Fab' fragment, F(ab')2 fragment, single domain antibody, camelized antibody, humanized antibody, diabodies, tribodies, tetrabodies). In certain embodiments, fluorocarbon imaging reagent may comprise a compound of any one of formulae 1-17, 20-37, or 40-41, or Perfluoro-15-crown ether.

Cellular labeling with fluorocarbons emulsions can also be facilitated using transfection agents to aid in cell delivery. Often transfection agents consist of cationic lipids, cationic liposomes, poly-cations, and the like. The transfection agent is pre-mixed with the fluorocarbon emulsion labeling agent, whereby it becomes associated with, or coats, the emulsion particles. The transfection agent-treated emulsion particles are then added to the cultured cells and incubated so that the cells become labeled. Common transfection agents include Lipofectamine (Invitrogen, Inc) FuGene, DOTAP (Roche Diagnostics, Inc.), and poly-L-lysine. Small proteins can also be used as transfection agents, such as many types of protamines. Protamines, the major DNA-binding proteins in the nucleus of sperm in most vertebrates, package the DNA in a volume less than 5% of a somatic cell nucleus. Protamines are simple proteins of low molecular weight that are rich in arginine and strongly basic. Commercially available protamines come from the sperm of salmon and certain other species of fish. The term "protamine" as used herein, refers to a low molecular weight cationic, arginine-rich polypeptide. The protamine molecule typically comprises about 20 to about 200 amino acids and is generally characterized by containing at least 20%, 50% or 70% arginine. Protamines are often formulated as salts, with one or more counter ions such as sulfate, phosphate and chloride.

Data provided in this application show that protamines (e.g., protamine sulfate) are highly effective in delivering PFPE fluorocarbon emulsion particles to cultured cells. Suitable protamine sulfates can come from a variety of sources (e.g., salmon, herring, trout, etc.) and be of various grades and forms (e.g., USP, grades II, III, X, etc.), with and without histones or any recombinant derivative. Examples of other protamine solutions that may be used as transfection agents include protamine phosphate, protamine chloride, protamine sulfate-2, protamine sulfate-3, protamine sulfate-10, and protamine free base.

Data provided in this application shows self-deliverable nanoemulsions prepared with fluorocarbon imaging reagents (e.g., a compound of any one of formulae 1-17, 20-37, or 40-41) and incorporate either PEI or Protamine Sulfate, optionally with a block copolymer (Pluronic™) surfactant. Simple co-incubation of cells with certain self-deliverable nanoemulsions provides sufficient cell labeling for imaging, without the need for transfection reagents.

Cell electroporation can also be used to deliver fluorocarbon emulsion particles into cells. Electroporation has the advantage that labeling is very rapid process, and it does not require the use of transfection agents. Many methods of cell electroporation are know in the art for a wide range of cell types, and several commercially available electroporation instruments are available (e.g., BTX, Inc., Harvard Apparatus, Inc., Amaxa Biosystems, Inc., etc.). Electroporation is used to deliver nucleic acids, molecules, and small particulates into cells in vitro. Magnetoelectorporation has been shown to be effective for MRI in cell culture (Walczak P., Magn Reson Med. 2005. October; 54(4):769-74). Data presented in U.S. provisional application No. 60/792,003 demonstrated that cell electroporation is effective in delivering linear PFPE fluorocarbon emulsion particles into dendritic cells, and there is no barrier to using the same method to fluorocarbon-label many other phagocytic and non-phagocytic cell types, such as stem cells.

Where cells are to be used in a therapeutic regimen, various methods have been used to for delivery of cells including injections and use of special devices to implant cells in various organs. The present invention is not tied to any particular delivery method. Data presented herein demonstrate that labeled cells may be monitored regardless of whether the cells are delivered directly to a particular site or delivered systemically. For example, labeled DCs were successfully imaged following either a focal implantation directly into tissues or an intravenous injection, and T-cells were imaged following intraperitoneal injection. Cells may be inserted into a delivery device which facilitates introduction by injection or implantation into the subjects. Such delivery devices may include tubes, e.g., catheters, for injecting cells and fluids into the body of a recipient subject. In a preferred embodiment, the tubes additionally have a needle, e.g., a syringe, through which the cells of the disclosure can be introduced into the subject at a desired location. The cells may be prepared for delivery in a variety of different forms. For example, the cells may be suspended in a solution or gel or embedded in a support matrix when contained in such a delivery device. Cells may be mixed with a pharmaceutically acceptable carrier or diluent in which the cells of the disclosure remain viable. Pharmaceutically acceptable carriers and diluents include saline, aqueous buffer solutions, solvents and/or dispersion media. The use of such carriers and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the disclosure may be prepared by incorporating cells as described herein in a pharmaceutically acceptable carrier or diluent and, as required, other ingredients enumerated above, followed by filtered sterilization.

4. Nuclear Magnetic Resonance Techniques

As described herein, nuclear magnetic resonance techniques may be used to detect populations of labeled cells. The term "detect" is used to include any effort to ascertain the presence or absence of a labeled molecule or cell, particularly by a nuclear magnetic resonance technique. The term "detect" is also intended to include more sophisticated measurements, including quantitative measurements and two- or three-dimensional image generation. For example, MRI may be used to generate images of such cells. In many instances, the labeled cells may be administered to a living subject. Following administration of the cells, some portion of the subject, or the entire subject, may be examined by MRI to generate an MRI data set. A "data set", as the term is used herein, is intended to include raw data gathered during magnetic resonance probing of the subject material, the acquisition parameters, as well as information processed, transformed or extracted from the raw data. The raw data includes transient signals obtained by MRI/MRS, including the free-induction decays, spin-echoes, stimulated-echoes, and/or gradient echoes. Examples of processed information include two-dimensional or three-dimensional pictorial representations of the subject material. The processed information may also include magnitude images, the real and imaginary image components, as well as the associated phase map images. Another example of extracted information is a score representing the amount or concentration of imaging reagent or $^{19}F$ signal in the subject material. By using the amount of $^{19}F$ signal in the subject material, and a calibration of the mean amount of imaging reagent per cell pre-implantation, one can estimate the absolute number of cells in the subject material. The amount of $^{19}F$ signal present in a subject material can be represented or calculated in many ways; for example, the average signal-to-noise-ratio (SNR) of the $^{19}F$ signal for a region of interest (ROI) may be measured and used to calculate the abundance of labeled cells. In certain embodiments, the average intensity, or pixel- or voxel-wise summation of the $^{19}F$ signal may be used to calculate the abundance of labeled cells. This type of data may be gathered at a single region of the subject, such as, for example, the spleen or another organ of particular relevance to the labeled cells. Labeled cells may be examined in contexts other than in the subject. It may be desirable to examine labeled cells in culture. In certain embodiments, labeled cells may be applied to or generated within a tissue sample or tissue culture, and labeled cells may therefore be imaged in those contexts as well. For example, an organ, tissue or other cellular material to be transplanted may be contacted with an imaging reagent to generate labeled cells prior to implantation of such transplant in a subject.

In general, labeling agents of the disclosure are designed for use in conventional MRI detection systems. In the most common implementation of MRI, one observes the hydrogen nucleus (proton, $^1H$) in molecules of mobile water contained in subject materials. To detect labels disclosed herein, an alternate nucleus is detected, $^{19}F$. $^{19}F$ MRI has only slightly less intrinsic sensitivity compared to $^1H$; the relative sensitivity is approximately 0.83. Both have a nuclear spin of +½. The natural isotopic abundance of $^{19}F$ is 100%, which is comparable to 99.985% for $^1H$. The physical principles behind the detection and image formation are the same for both $^1H$ and $^{19}F$ MRI. The subject material is placed in a large static magnetic field. The field tends to align the magnetic moment associated with the $^1$H or $^{19}$F nuclei along the field direction. The nuclei are perturbed from equilibrium by pulsed radio-frequency (RF) radiation at the Larmor frequency, which is a characteristic frequency proportional to the magnetic field strength where nuclei resonantly absorb energy. Upon removing the RF, the nuclei induce a transient voltage in a receiver antenna; this transient voltage constitutes the nuclear magnetic resonance (NMR) signal. Spatial information is encoded in both the frequency and/or phase of the NMR signal by selective application of magnetic field gradients that are superimposed onto the large static field. The transient voltages are generally digitized, and then these signals may be processed by, for example, using a computer to yield images.

At constant magnetic field strength, the Larmor frequency of $^{19}$F is only slightly lower (~6%) compared to $^1$H. Thus, it is straightforward to adapt conventional MRI scanners, both hardware and software, to acquire $^{19}$F data. The $^{19}$F detection may be coupled with different types of magnetic resonance scans, such as MRI, MRS or other techniques. Typically, it will be desirable to obtain a $^1$H MRI image to compare against the $^{19}$F image. In a living organism or other biological tissue, the proton MRI will provide an image of the subject material and allow one to define the anatomical context of the labeled cells detected in the $^{19}$F image. In a preferred embodiment of the disclosure, data is collected for both $^{19}$F and $^1$H during the same session; the subject is not moved during these acquisitions to better ensure that the two data sets are in spatial registration. Normally, $^{19}$F and $^1$H data sets are acquired sequentially, in either order. An RF coil (i.e. antenna) can be constructed that can be electrically tuned from the $^{19}$F and $^1$H Larmor frequency. Tuning between these two frequencies can be performed manually (e.g. via an electromechanical variable capacitor or inductor), or electrically, via active electronic circuitry. Alternatively, with appropriate modifications to the hardware and/or software of the MRI instrument, both data sets can be acquired simultaneously, for example, to conserve imaging time. Simultaneous acquisition of the $^{19}$F and $^1$H data sets require an RF coil or antenna that can be electrically tuned simultaneously to the $^{19}$F and $^1$H Larmor frequency (i.e., a double-tuned coil). Alternatively the RF coil can be "broadband," with one broadly-tuned electrical resonance that covers both Larmor frequencies (i.e. $^{19}$F and $^1$H). Other imaging techniques, such as fluorescence detection may be coupled with $^{19}$F MRI. This will be particularly desirable where a fluorocarbon imaging reagent has been derivatized with a fluorescent moiety. In other embodiments, the $^{19}$F MRI scan may be combined with a PET scan in the same subject or patient by using dual-model radioactive $^{18}$F/$^{19}$F fluorocarbon labeling reagents as described herein.

MRI examination may be conducted according to any suitable methodology known in the art. Many different types of MRI pulse sequences, or the set of instructions used by the MRI apparatus to orchestrate data collection, and signal processing techniques (e.g. Fourier transform and projection reconstruction) have been developed over the years for collecting and processing image data (for example, see *Magnetic Resonance Imaging, Third Edition*, editors D. D. Stark and W. G. Bradley, Mosby, Inc., St. Louis Mo. 1999). The reagents and methods of this disclosure are not tied to any particular imaging pulse sequence or processing method of the raw NMR signals. For example, MRI methods that can be applied to this disclosure broadly encompasses spin-echo, stimulated-echo. gradient-echo, free-induction decay based imaging, and any combination thereof. Fast imaging techniques, where more than one line in k-space or large segments of k-space are acquired from each excited signal, are also highly suitable to acquire the $^{19}$F (or $^1$H) data. Examples of fast imaging techniques include fast spin-echo approaches (e.g. FSE, turbo SE, TSE, RARE, or HASTE), echo-planar imaging (EPI), combined gradient-echo and spin-echo techniques (e.g. GRASE), spiral imaging, and burst imaging. The development of new and improved pulse sequence and signal processing methods is a continuously evolving field, and persons skilled in the art can devise multiple ways to image the $^{19}$F labeled cells in their anatomical context.

As another example of a nuclear magnetic resonance technique, MRS can be used to detect the presence of fluorocarbon-labeled cells in localized tissues or organs. Normally MRS methods are implemented on a conventional MRI scanner. Often the localized volume of interest (VOI) is defined within a conventional anatomical $^1$H MRI scan. Subsequently, the magnitude of the $^{19}$F NMR signal observed within the VOI is directly related to the number of labeled cells, and/or the mean concentration of PFPE per cell present in the tissue or organ. Methods for isolating a VOI within a much larger subject are well known the art (for example, *Magnetic Resonance Imaging, Third Edition*, Chapter 9, Editors D. D. Stark and W. G. Bradley, Mosby, Inc., St. Louis Mo. 1999). Examples include using a localized RF surface coil near the VOI, surface spoiling, surface coil $B_1$-gradient methods, slice-selective Bo-gradient techniques, STEAM, PRESS, image selective in vivo spectroscopy (ISIS), and magnetic resonance spectroscopic imaging (MRSI). The development of new and improved pulse sequence and signal processing methods is continuously evolving for MRS, and persons skilled in the art can devise multiple ways to detect the $^{19}$F NMR signals emanating from the fluorocarbon labeled cells in VOIs.

In certain embodiments the disclosure provides a method of quantifying the numbers of labeled cells in vivo or in subject materials within an ROI. An ROI may include all labeled cells in a subject or labeled cells in specific organs such as the pancreas, specific tissues such as lymph nodes, or any region or of one or more voxels showing detectable MRI/MRS $^{19}$F signal. A ROI can be an otherwise undefined area beyond a particular experiment. There are a number of ways that labeled cells may be quantified in the subject materials or in vivo, as described herein.

Calibrating the mean "cellular dose" of $^{19}$F labeling agent pre-implantation of a particular cell population is often a pre-requisite for quantitative cell determinations in subject materials or the patient. It is anticipated that different cell types have different innate abilities to take up the labeling agents in vitro, and thus the cellular dose of the labeling agent will also vary. Furthermore, different cells of the same type acquired from different sources (e.g., different patients) may have different affinities for the labeling agent. Thus a cellular dose calibration may be required. This calibration may be used, initially, to modify the labeling protocol (i.e., incubation conditions, duration of time that cells are incubated with labeling fluorocarbon emulsion, concentration of fluorocarbon emulsion in culture medium during labeling, etc.) to achieve a certain range of cellular dose before labeled cells are actually used in a subject to be imaged. Alternatively, one can fix the labeling conditions and protocol and measure the mean value $^{19}$F labeled per cell, as is, for subsequent quantification in the subject to be imaged. In certain embodiments the mean number of $^{19}$F molecules (F's) per cell of a labeled cell population is measured (i.e., calibrated) in vitro prior to administration of the cells to the subject or patient. In certain embodiments the mean number of $^{19}$F molecules (F's) per cell of a labeled cell population is calibrated in a test population of cells of a particular type, not necessarily destined for a patient, but used to calibrate cellular dose of labeling agent as a consequence of a particular labeling protocol or set of conditions; optionally, the value of cellular dose is then used for future labeling and in vivo imaging experiments in the same population type of cells with the same labeling protocol.

The cellular dose of labeling agent can be assayed in vitro using a variety of quantitative techniques. For example, one can use a one-dimensional (1D) $^{19}$F NMR spectrum obtained from a cell pellet, cell suspension, or cell lysate, of a known number of labeled cells. From this spectrum, one can calculate the integrated area of the $^{19}$F spectrum or a portion thereof, originating from the labeling reagent associated with the cells. The integrated area of the $^{19}$F spectrum, denoted $S_{cells}$, is directly proportional to the total amount of $^{19}$F in the cell pellet, suspension, or lysate. To measure the absolute number of $^{19}$F nuclei, the measured $S_{cells}$ may be normalized to a $^{19}$F standard. A $^{19}$F standard can be, for example, a solution of a known volume and concentration of a fluorochemical, where one can calculate the total number of $^{19}$F nuclei in the standard, denoted $F_{stan}$. A suitable fluoro-chemical reference ideally has a simple $^{19}$F NMR spectrum, preferable with a single narrow resonance (e.g. trifluoroacetic acid or TFA) and optionally a $^{19}$F chemical shift that is significantly different than the labeling fluorocarbon. The $^{19}$F standard can be placed in the same NMR tube as the labeled cell material being measured, in a separate tube, or optionally can be measured in a separate experiment using the same NMR instrument. The integrated area of the spectrum from the $^{19}$F standard, denoted $S_{stan}$, can then be measured. Subsequently, the mean number of $^{19}$F per labeled cell, denoted $F_c$, can be calculated, for example using the formula:

$$F_c = \frac{S_{cells}}{S_{stan}} F_{stan} \frac{1}{N_{cells}}$$

where $N_{cells}$ is the number of labeled cells contained in the in vitro test sample. Quantitative NMR methods for $^{19}$F and other nuclei are well know in the art, and those skilled can devise many variations to the cellular dose calibration procedure described above. Besides $^{19}$F NMR, there are other quantitative methods that can be used to assay the cellular dose of the labeling reagent. For example, a reagent may be labeled fluorescently, luminescently, optically, or radioactively.

In order to extract accurate quantification of labeled cells from the $^{19}$F MRI/MRS data sets, additional calibrations and standards may be employed. For example, one can use a calibrated external $^{19}$F reference (i.e. phantom) during the actual $^{19}$F MRI/MRS scan of the subject material containing labeled cells. The image intensity of the calibrated phantom is used when analyzing the $^{19}$F MRI/MRS data set to proved an absolute standard for the number of $^{19}$F nuclei when examining the subject material or patient. The calibrated phantom is used to normalize the sensitivity of the particular MRI/MRS system that has been loaded with a particular subject to be imaged. The $^{19}$F reference may be, for example, one or more vessels containing a solution of a known concentration of $^{19}$F nuclei. In preferred embodiments, the solution contains a dilute concentration of the emulsified fluorocarbon labeling reagent. Optionally, the solution contains non-emulsified fluorocarbon labeling reagent, a gel, or liquid, for example that has been diluted in a suitable solvent. Optionally, the solution can be comprised of another fluoro-chemical, ideally with a simple $^{19}$F NMR spectrum, preferable with a single narrow NMR resonance (e.g. trifluoroacetic acid (TFA) or trifluoroacetamide (TFM) and other fluorinated acids, trifluorotoluene or trifluoroethanol). In preferred embodiments, the T1 and T2 values of the reference solution are similar to those of the labeling reagent. Optionally, the solution can contain perfluorocarbon-labeled cells, or lysates of the same. The non-cellular reference has the advantage of longer storage times. Optionally, the solution can take the form of a gel. The vessel containing the solution is preferably sealable, and can take a variety of geometries; preferred vessel geometries include ellipsoidal, cylindrical, spherical, and parallel piped shapes. One or more vessels containing $^{19}$F reference solution can be used during the $^{19}$F MRI/MRS of the subject material. If multiple $^{19}$F references (i.e. vessels) are used they can contain the same $^{19}$F concentration or different concentrations, and in the case of the latter, they ideally contain graded concentrations of fluorochemical. The placement of the calibrated $^{19}$F reference vessel(s) can be placed preferably externally or alongside, or optionally inside, the imaged subject or patient prior to data acquisition. In preferred embodiments, the reference is imaged using $^{19}$F MRI along with the subject in the same image field of view (FOV). Optionally, $^{19}$F MRS data is acquired in the reference either sequentially or in parallel with the subject data set. Optionally, data from the reference can be acquired using MRI/MRS acquired in a separate scan. Optionally, the external reference is not scanned along with a subject in every $^{19}$F MRI/MRS examination, but rather, values of the reference $^{19}$F signal intensity acquired using MRI/MRS is used from a scan of a comparable subject or a simulated-subject. In a given $^{19}$F MRI/MRS scan, the calibrated $^{19}$F standard may be sampled by one or more voxels. The observable $^{19}$F intensity produced by a voxel may be proportional to the concentration of the fluorochemical in the solution (or gel) and the voxel volume. Often in a $^{19}$F MRI scan the reference standard is comprised of many voxels. Often one calculates the mean intensity of one, several, or all voxels in the reference standard. Optionally, the mean image intensity is calculated over an ROI defined within the $^{19}$F image of the reference standard. Optionally, the physical geometry of the reference standard vessel contributes to defining the observed $^{19}$F signal intensity; for example, the volume compartment(s) containing the $^{19}$F reference solution is smaller than the voxel volume. In other embodiments, the calibrated external reference relies on a solution with a $^1$H signal intensity of a known number of detectable $^1$H; in this case the sensitivity of the $^{19}$F signal in the subject material is reference to a $^1$H calibrated standard. Ideally the solution or gel in the $^1$H calibrated reference (contained in a vessel as described above) yields a simple $^1$H NMR spectrum, preferable with a single narrow NMR resonance (e.g., $H_2O$, or mixtures of $H_2O-D_2O$). Other than a different nuclei, the use of the $^1$H standard reference is the same in many other respects as described above for the $^{19}$F reference. Optionally, the calibrated reference standard contains any other MRI/MRS-active nuclei. In some embodiment, the reference is an internal organ or tissue detected via $^1$H MRI/MRS, where the data may be raw or normalized. In other embodiments, the reference is a standard that is not scanned with the subject, but is calibrated by relevant factors such as the weight of the patient or the size of the body cavity.

By computationally manipulating or combining two or more key parameters from the $^{19}$F MRI/MRS data set, one can calculate the number of labeled cells present in an ROI as described herein. For example, a key set of parameters may include: (i) the cellular dose of labeling agent (i.e., $F_c$) measured in vitro; (ii) in vivo $^{19}$F MRI/MRS data set taken in the subject at one or more time points following labeled cell administration; (iii) the voxel volume; (iv) the in-plane voxel area (i.e., area of the image pixel); (v) optionally, the MRI/MRS data set from the $^{19}$F reference standard; (vi) optionally, the measured Johnson noise of the $^{19}$F MRI/MRS data in the subject material; (vii) optionally, the measured signal-to-noise ratio (SNR) of one or more voxels of the $^{19}$F MRI/MRS data set in the subject material; (viii) optionally, the measured SNR of one or more voxels of the $^{19}$F MRI/MRS data set from the reference standard; (ix) optionally, the $^{19}$F NMR relaxation times (T1, T2, and T2*) of the subject material; (x) optionally, the $^{19}$F NMR relaxation times (T1, T2, and T2*) of the reference standard (for example, see *Magnetic Resonance Imaging, Third Edition*, chapter 4, editors D. D. Stark and W. G. Bradley, Mosby, Inc., St. Louis Mo. 1999). Those skilled in the art can derive other parameters, combinations of the above set, or derivations thereof, particularly from the $^{19}$F MRI/MRS dataset, that can be used to quantify the number of labeled cells in situ. In certain embodiments the above set of key parameters can be used to derive quantitative or statistical measures of the accuracy or confidence of the measured number of labeled cells.

There are many ways to combine the key parameters (i-x, above), any subsets of these, or any of their combinations or approximations, to estimate the effective number of labeled cells seen by $^{19}F$ MRI in the subject material, denoted by $N_c$. For example, one can use an equation of the form $$N_c = \frac{[F_R]v}{I_R} \frac{1}{F_c} \sum_{i=1}^{N_{ROI}} I_c^{(i)}$$

where: $N_c$=total number of labeled cells in the ROI; $[F_R]$=concentration of $^{19}F$ in the calibrated $^{19}F$ reference solution (or gel); v=voxel volume; $I_R$=mean intensity of the calibrated $^{19}F$ reference taken with the MRI/MRS scan, averaged over one or more voxels; $F_c$=average $^{19}F$ cellular dose of the labeling agent measured in vitro; $N_{ROI}$=number of voxels in the ROI containing labeled cells; $I_c^{(i)}$=image intensity of the $i^{th}$ voxel in the ROI containing labeled cells; i=unitless index for voxels in the ROI containing labeled cells.

There are also many ways to approximate $N_c$ from the $^{19}F$ data set. For example, one could use the expression $$N_c \approx \frac{I_c^{avg}}{I_R} [F_R]v \frac{1}{F_c} N_{ROI}$$

where $I_c^{avg}$ is the average intensity of the ROI containing the labeled cells, (i.e. the average intensity of the $N_{ROI}$ voxels). As another example, one could use $$N_c \approx \frac{I_c^{avg}}{I_R} V_c \frac{1}{F_c} [F_R]$$

where $V_c$ is the total volume of the ROI containing the labeled cells. As a further example, one could use $$N_c \approx \frac{I_c^{avg}}{I_R} \frac{V_c}{V_R} \frac{1}{F_c} N_R$$

where $V_R$ is the effective volume of the reference in the $^{19}F$ MRI/MRS and $N_R$ is the number $^{19}F$ nuclei in $V_R$. Note that in all of the above formulas the various intensities (i.e., $I_R$, $I_c^{avg}$, $I_c^{(i)}$) can be normalized to the image noise, and thus the above formulas can be equivalently expressed in terms of the appropriate SNR values for the particular regions. Thus, there are many ways to estimate the number of labeled cells, $N_c$, and many similar forms of these basic expressions can be derived by basic mathematical manipulations, however, all rely on the same basic content contained within the input parameters described by (i-x). Furthermore, quantification of labeled cells in an ROI need not be expressed in terms of absolute numbers or effective cell numbers. Other quantitative indices can be derived that are indicative of the amount of cells in an ROI. For example, one can calculate the ratio $I_c^{avg}/I_R$, or the ratio of the average SNR values observed in the ROI and the reference; all of these fall within subsets of the above expressions and/or the parameters.

It is noted that the above analysis of cell numbers and related indices assume that the $^{19}F$ NMR relaxation times (i.e., particularly T1 and/or T2) of the fluorocarbon label is approximately the same as material in the calibrated $^{19}F$ reference standard. In the case that the relaxation times are not comparable, one of skill in the art can readily correct for this by employing the known MRI intensity equations of the particular imaging protocol being used, expressed in terms of T1 and T2.

Optionally, the $^{19}F$ MRI data set of the subject material can undergo post-processing before the actual cell quantification calculation is performed (as described above). For example, post-processing algorithms may include "de-noising" the $^{19}F$ data set. This can be accomplished by, for example, by thresholding the image to cut off low-intensity noise; this involves resealing the image intensity so that low values are set to zero. In magnitude MRI images, random Johnson noise is often apparent and uniformly distributed across the image FOV. It is well know in the art that one can threshold out the low-level image intensity so that regions known to contain no true signal (i.e. devoid of $^{19}F$ and/or $^1H$ nuclei) appear to have a null or very near-null intensity. This process can be performed in an ad-hoc fashion (i.e. "manually" or by visual inspection), or by using a computer algorithm. In other embodiments, de-noising of the data set can be achieved by using other algorithms, for example using wavelet analysis, and many methods are known in the art for image de-noising. The following references are incorporated in their entirety herein: Khare, A., et al., INTERNATIONAL JOURNAL OF WAVELETS MULTIRESOLUTION AND INFORMATION PROCESSING, 3 (4): 477-496 December 2005; Cruz-Enriquez, H., et al., IMAGE ANALYSIS AND RECOGNITION, 3656: 247-254 2005; Awate, S P., et al., INFORMATION PROCESSING IN MEDICAL IMAGING, PROCEEDINGS, 3565: 677-688 2005; Ganesan, R., et al., IIE TRANSACTIONS, 36 (9): 787-806 September 2004; Scheunders, P., IEEE TRANSACTIONS ON IMAGE PROCESSING, 13 (4): 475-483 April 2004; Ghugre, N R., MAGNETIC RESONANCE IMAGING, 21 (8): 913-921 OCT 2003; Bao, P., et al., IEEE TRANSACTIONS ON MEDICAL IMAGING, 22 (9): 1089-1099 September 2003; Wu, Z Q., et al., ELECTRONICS LETTERS, 39 (7): 603-605 Apr. 3, 2003; LaConte, S M., et al., MAGNETIC RESONANCE IN MEDICINE, 44 (5): 746-757 November 2000; Laine, A F., ANNUAL REVIEW OF BIOMEDICAL ENGINEERING, 2: 511-550 2000; Zaroubi, S., et al., MAGNETIC RESONANCE IMAGING, 18 (1): 59-68 January 2000; Nowak, R D., IEEE TRANSACTIONS ON IMAGE PROCESSING, 8 (10): 1408-1419 October 1999; and Healy, D M., et al., ANNALS OF BIOMEDICAL ENGINEERING, 23 (5): 637-665 September-October 1995.

Other types of post-processing algorithms are know in the art that can be applied to the $^{19}F$ MRI data set before or after quantification, such as zero-filling (A Handbook of Nuclear Magnetic Resonance, $2^{nd}$ Edition, Ray Freeman, Addison Wesley Longman Press 1997) and various image interpolation, de-noising, and image smoothing algorithms (for example, see The Image Processing Handbook, $3^{rd}$ Edition, John C. Russ, CRC Press/IEEE Press).

In certain embodiments the above set of key parameters (i-x) can be used to derive quantitative or statistical measures of the accuracy or confidence of the measured number of labeled cells or related indices. $^{19}F$ MRI/MRS data sets are often subject to SNR limitations within ROI, and thus it is often useful to calculate a metric of the confidence or accuracy of the measurement. Many methods are known in the art for the statistical analysis of MRI and other biomedical-type images. The claimed embodiment is understood to encompass these known methods.

5. Computer Methods

Figure 53:
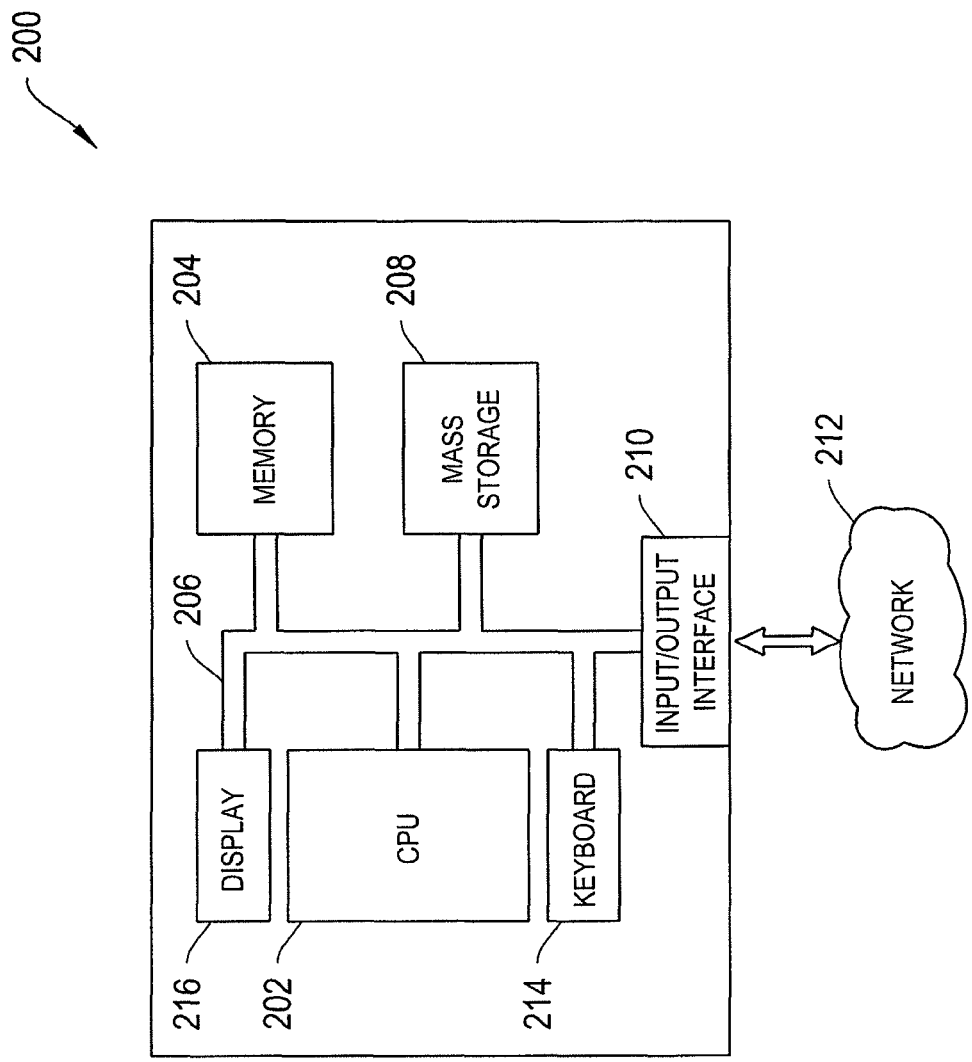
FIG. 53. A functional block diagram of a general purpose computer system 200 for performing the functions of the computer 104 according to an illustrative embodiment of the invention.

Methods for quantifying labeled cells will typically be conducted with the aid of a computer, which may operate software designed for the purpose of such quantification. Such software may be a stand-alone program or it may be incorporated into other software, such as MRI image processing software. FIG. 53 shows a functional block diagram of general purpose computer system 200 for performing the functions of the computer according to an illustrative embodiment of the disclosure. The exemplary computer system 200 includes a central processing unit (CPU) 202, a memory 204, and an interconnect bus 206. The CPU 202 may include a single microprocessor or a plurality of microprocessors for configuring computer system 200 as a multi-processor system. The memory 204 illustratively includes a main memory and a read only memory. The computer 200 also includes the mass storage device 208 having, for example, various disk drives, tape drives, etc. The main memory 204 also includes dynamic random access memory (DRAM) and high-speed cache memory. In operation, the main memory 204 stores at least portions of instructions and data for execution by the CPU 202.

The mass storage 208 may include one or more magnetic disk or tape drives or optical disk drives, for storing data and instructions for use by the CPU 202. At least one component of the mass storage system 208, preferably in the form of a disk drive or tape drive, stores the database used for processing the cell quantification of the disclosure. The mass storage system 208 may also include one or more drives for various portable media, such as a floppy disk, a compact disc read only memory (CD-ROM), or an integrated circuit non-volatile memory adapter (i.e. PC-MCIA adapter) to input and output data and code to and from the computer system 200.

The computer system 200 may also include one or more input/output interfaces for communications, shown by way of example, as interface 210 for data communications via the network 212. The data interface 210 may be a modem, an Ethernet card or any other suitable data communications device. To provide the functions of a computer, the data interface 210 may provide a relatively high-speed link to a network 212, such as an intranet, internet, or the Internet, either directly or through another external interface. The communication link to the network 212 may be, for example, optical, wired, or wireless (e.g., via satellite or cellular network). Alternatively, the computer system 200 may include a mainframe or other type of host computer system capable of Web-based communications via the network 212.

The computer system 200 also includes suitable input/output ports or uses the interconnect bus 206 for interconnection with a local display 216 and keyboard 214 or the like serving as a local user interface for programming and/or data retrieval purposes. Alternatively, server operations personnel may interact with the system 200 for controlling and/or programming the system from remote terminal devices via the network 212.

The computer system 200 may run a variety of application programs and stores associated data in a database of mass storage system 208. One or more such applications may enable the receipt and delivery of messages to enable operation as a server, for implementing server functions relating to quantification.

The components contained in the computer system 200 are those typically found in general purpose computer systems used as servers, workstations, personal computers, network terminals, and the like. In fact, these components are intended to represent a broad category of such computer components that are well known in the art. Certain aspects of the disclosure may relate to the software elements, such as the executable code and database for the server functions of the quantification system.

The disclosure will be more readily understood by reference to the following examples, which are included merely for purposes of illustration of certain aspects and embodiments of the present application, and are not intended to limit the disclosure.

EXAMPLES

Data presented in WO2005072780 demonstrated that immune cells and other cell types cells could readily be labeled with a fluorocarbon imaging reagent ex vivo, and that labeled cells could be detected in vivo. Data presented in U.S. provisional application No. 60/792,003 demonstrated the further feasibility of the disclosed methods is presented, including data demonstrating the in vivo quantification of labeled cells. The exemplary embodiment of the disclosure develops novel imaging reagents and emulsions and evaluates their efficacy in tissue culture.

1. Imaging Reagent Preparation

Simple, very efficient and scalable synthetic methods are presented for PFPE derivatization and nanoemulsion preparations. PFPE ester 39 proved to be a versatile starting material for synthesis of a variety of nanoparticles, including dual fluorescent-19F MRI reagents, self deliverable PFPE nanoparticles and nanoparticles with highly efficient uptake in both phagocytic and non-phagocytic cell types. Emulsions that promote cellular uptake and emulsions that would promote serum stability are presented. The emulsions produced were highly stable at storage temperatures (4 and 25° C.) and body temperature (37° C.). Simple changes in the emulsification process and simple chemical modifications of PFPE end groups allow fine tuning of nanoparticle properties towards specific applications.

Examples of chemical modifications of PFPE end groups to variety of amides that can serve as both emulsion stabilizers or conjugation sites are presented.

Figure 45:
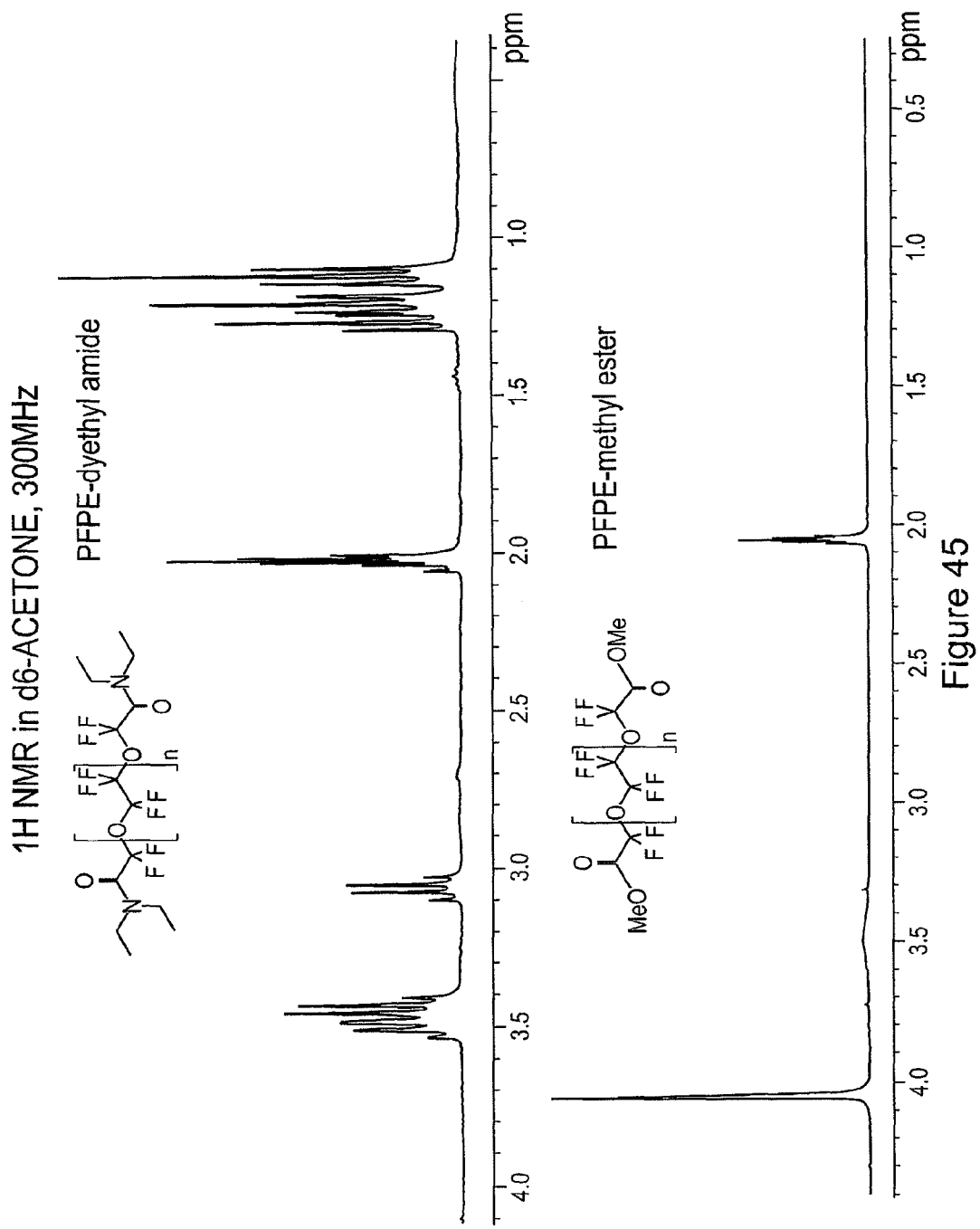
FIG. 45. $^1$H NMR of PFPE amide 1 and starting material PFPE ester 39. The disappearance of methyl group peak (4.1 ppm) serves as an indicator for the PFPE ester to PFPE amide conversion and was used for monitoring coupling reactions.
Figure 46:
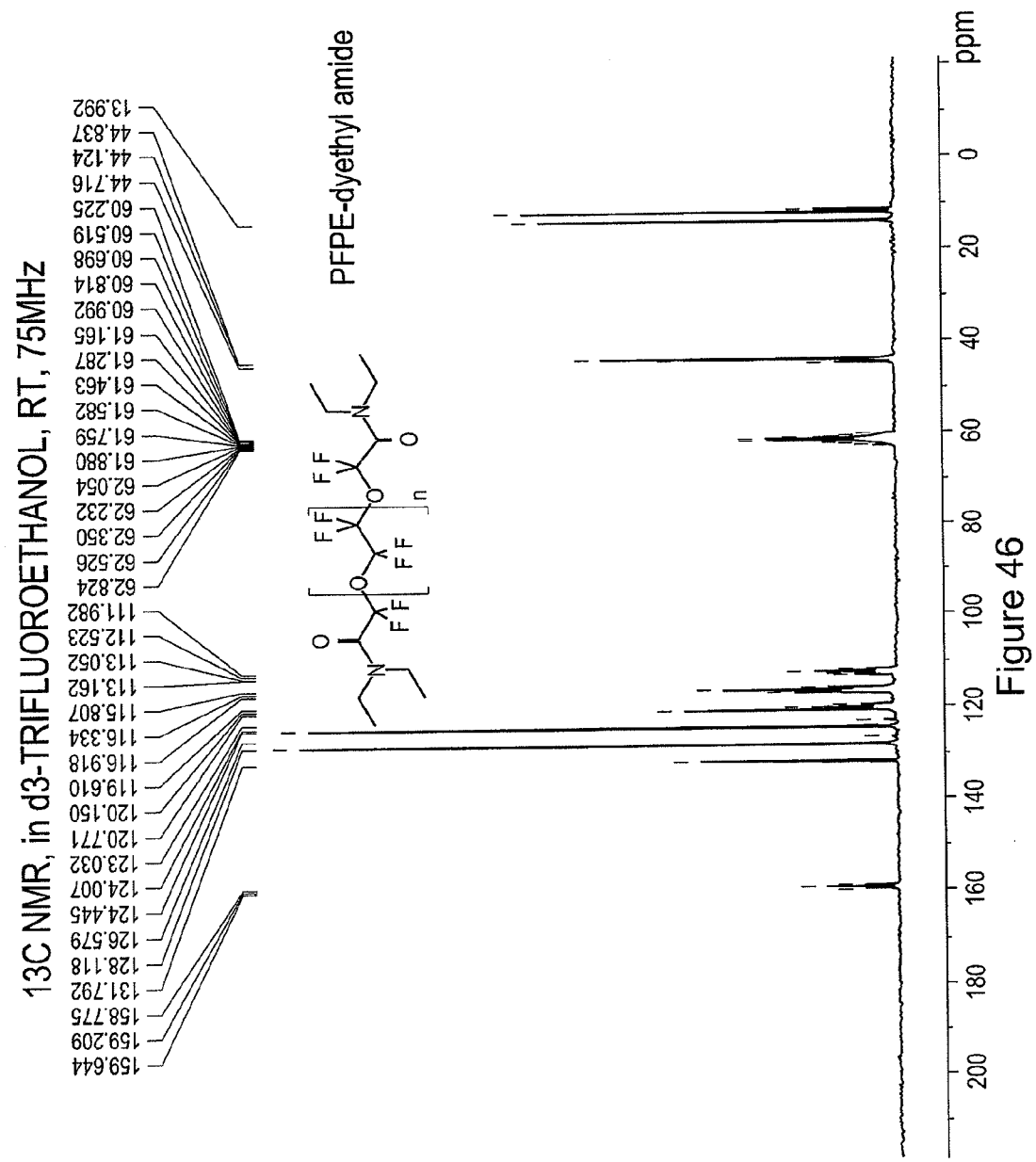
FIG. 46. $^{13}$C NMR of PFPE amide 1 in d$_3$-trifluoroethanol solvent that completely solubilizes PFPE.
Figure 47:
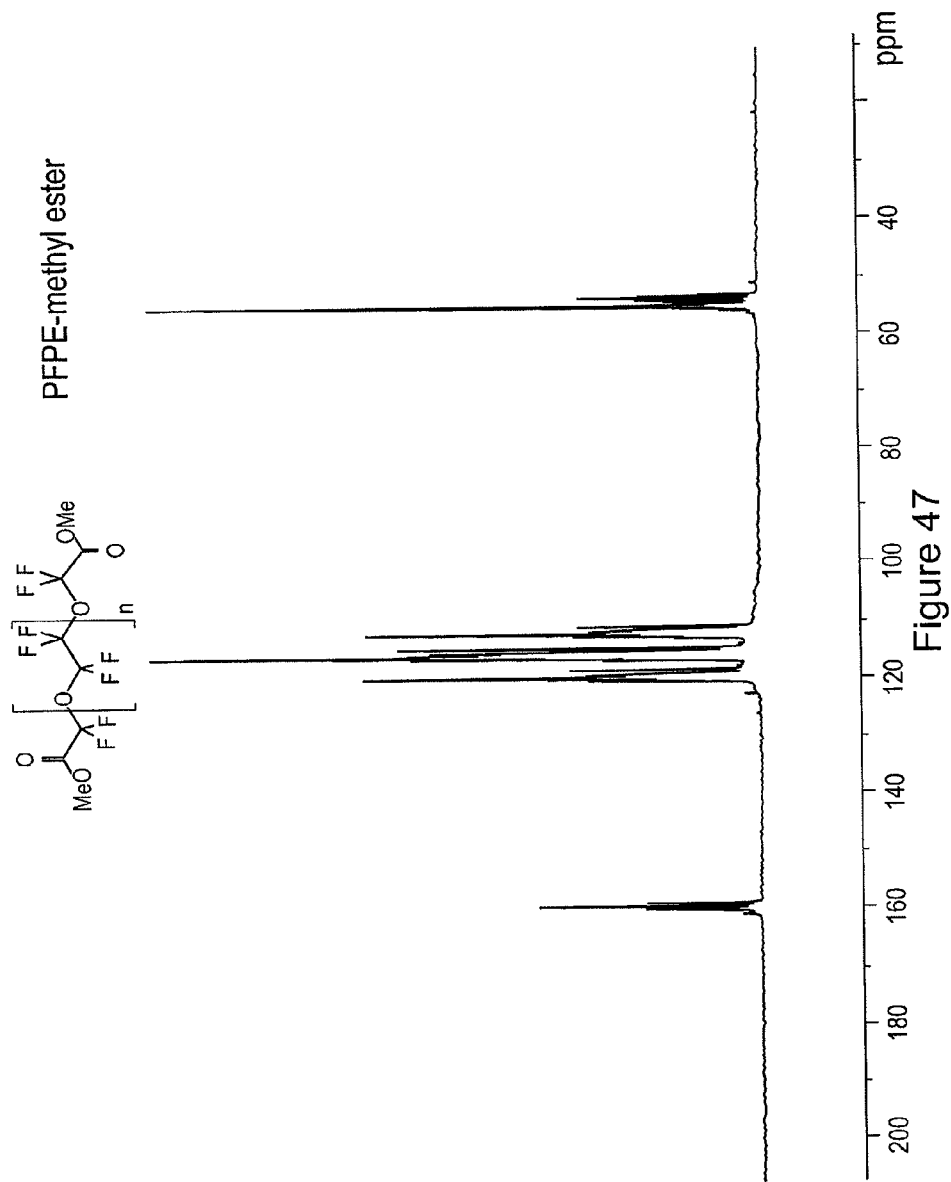
FIG. 47. $^{13}$C NMR of PFPE ester 39.

Synthesis of Symmetrical PFPE Diamides:

In general, PFPE methyl ester oil (39) was mixed with excess amine, either neat liquid or a solution of the amine in an appropriate solvent, as specified in Scheme 1, under inert atmosphere (argon or nitrogen) at room temperature. The reaction was allowed to stir 1-3 days, depending on the amine reactivity, to allow complete conversion. When amine was added as a solid, trifluorotoluene or trifluoroethanol was used as solvent and the temperature was increased to 40, 50, 60 or 70° C. depending on the amine reactivity (Scheme 2). Reaction progress was followed by 1H NMR monitoring the disappearance of the methyl ester peak (FIG. 45). After reaction completion, high vacuum was employed to remove resulting methanol and the excess unreacted amine. When non-volatile amines were used, an acidic aqueous wash was used to extract excess amine, and the desired PFPE amide was extracted with appropriate solvent. A recent patented procedure (U.S. Pat. No. 7,038,068 B2) describing purification of linear PFPEs by selective organic solvent extractions, was used for PFPE amide derivative purification. When organic solvent extraction was not enough, adsorption to fluorous phase silica gel (FluoroFlash, Fluorous Inc.) and elution of the purified product with methanol followed by trifluoroethanol or perfluorohexanes was used. Structures of the PFPE amide derivatives were confirmed by 1H, 13C, 19F NMR and MALDI-TOF mass spectrometry. Compounds 1, 2, and 6 were prepared according to this general procedure, as is shown in Scheme 1, wherein n, independently for each occurrence, represents an integer from 4 to 16.

Scheme 1:

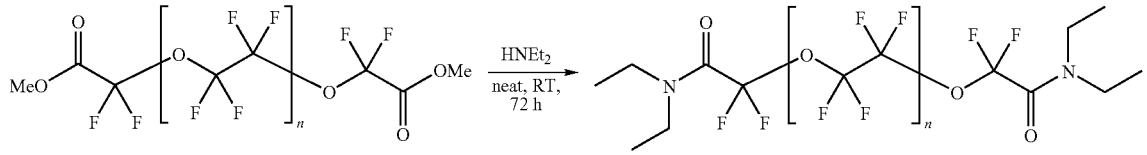

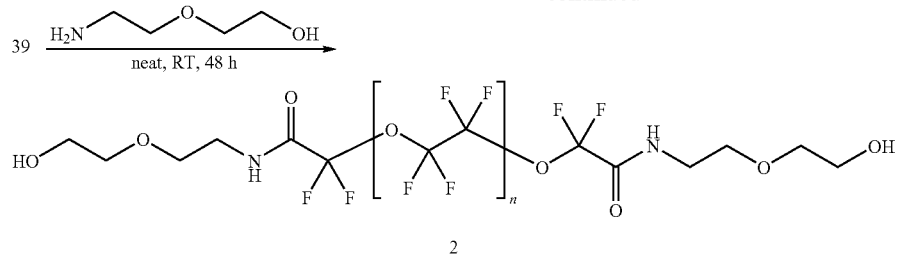

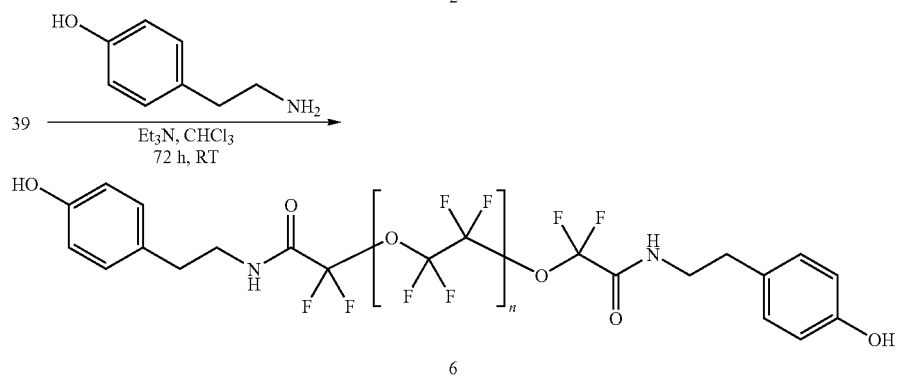

General Experimental Procedures

All reactions were performed in flame dried round bottom flasks under a nitrogen or argon atmosphere unless indicated otherwise. All reagents and solvents were purchased from Aldrich, Acros, TCI or Lancaster Synthesis and used without further purification. THF and DMF were purchased anhydrous grade and used without further purification. 1H and $^{13}$C NMR spectra were obtained on a Bruker Avance 300 at 300 and 75 MHz in CDCl$_3$ unless otherwise noted. Chemical shifts were reported in parts per million (ppm) using the residual solvent signal as an internal standard. $^1$H NMR spectra are tabulated as follows: chemical shift, multiplicity (s=singlet, d=doublet, t=triplet, q=quartet, qn=quintet, m=multiplet, b=broad), number of protons and coupling constant(s). $^{13}$C NMR spectra were acquired using a proton decoupled pulse sequence with a pulse sequence delay of 5 sec. $^{19}$F NMR was obtained on Bruker Avance 500 at 470 MHz in water or acetone. Chemical shifts were reported as parts per million (ppm) using Trifluoroacetic acid as an internal standard with $^{19}$F chemical shift at −76.0 ppm. Low resolution and high resolution mass spectra (MS and HRMS, respectively) were obtained in positive ion mode by matrix-assisted laser desorption ionization (MALDI) using a pentafluorobenzoic acid matrix (Marie, A.; Alves, S.; Fournier, F.; Tabet, J. C. Analytical Chemistry (2003), 75, 1294-1299) and an Applied Biosystems 4700 MALDI-TOF/TOF-MS.

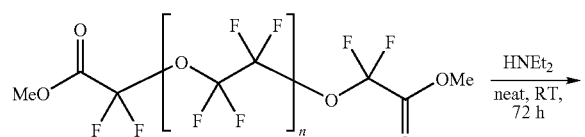

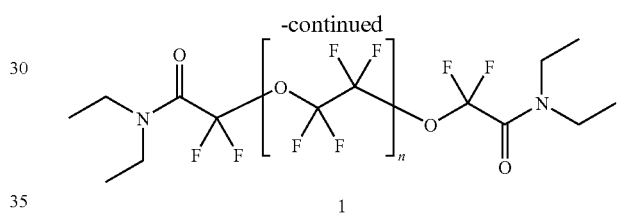

Figure 50:
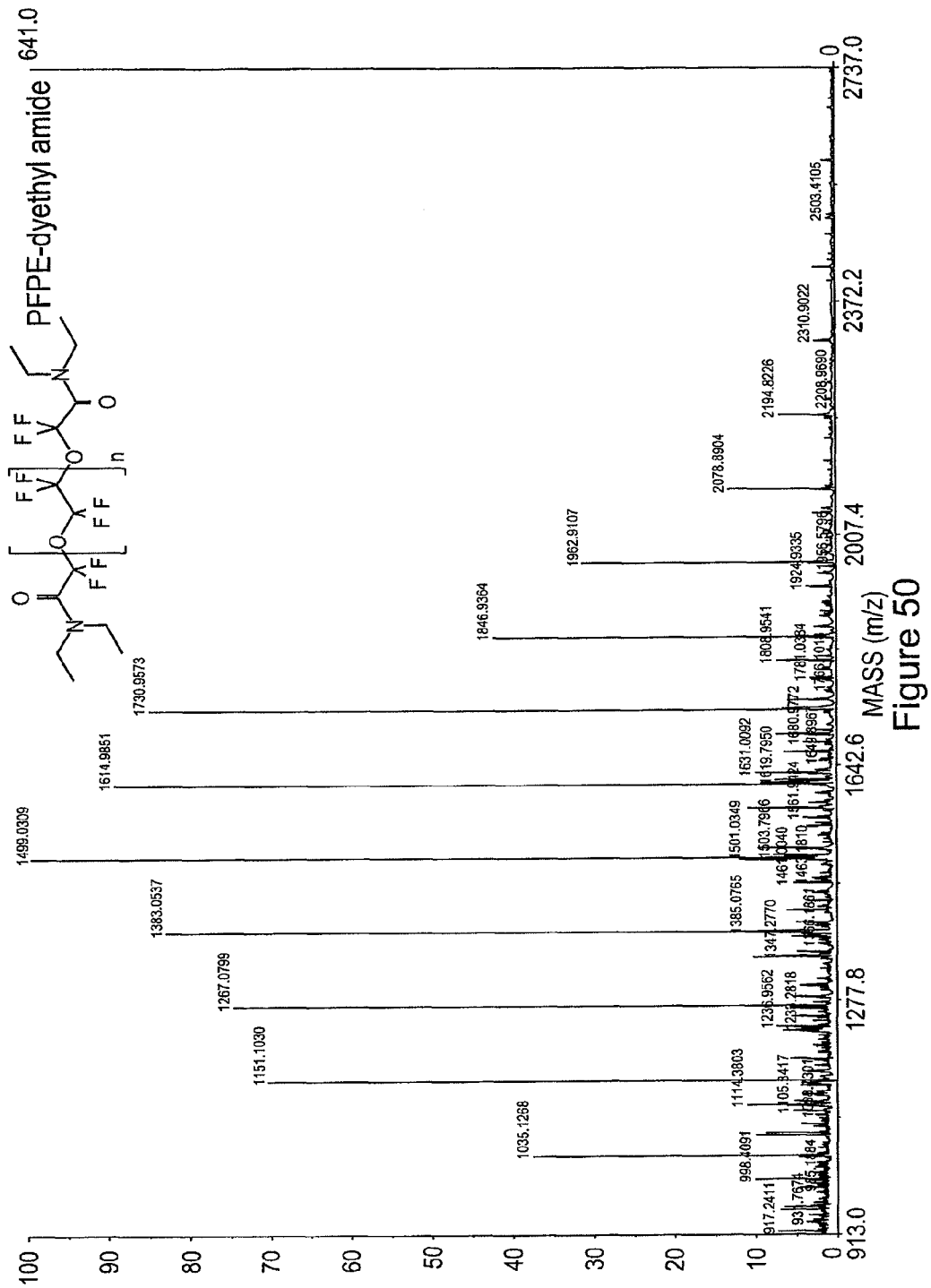
FIG. 50. MALDI-TOF mass spectrometry analysis of PFPE amide 1.
Figure 51:
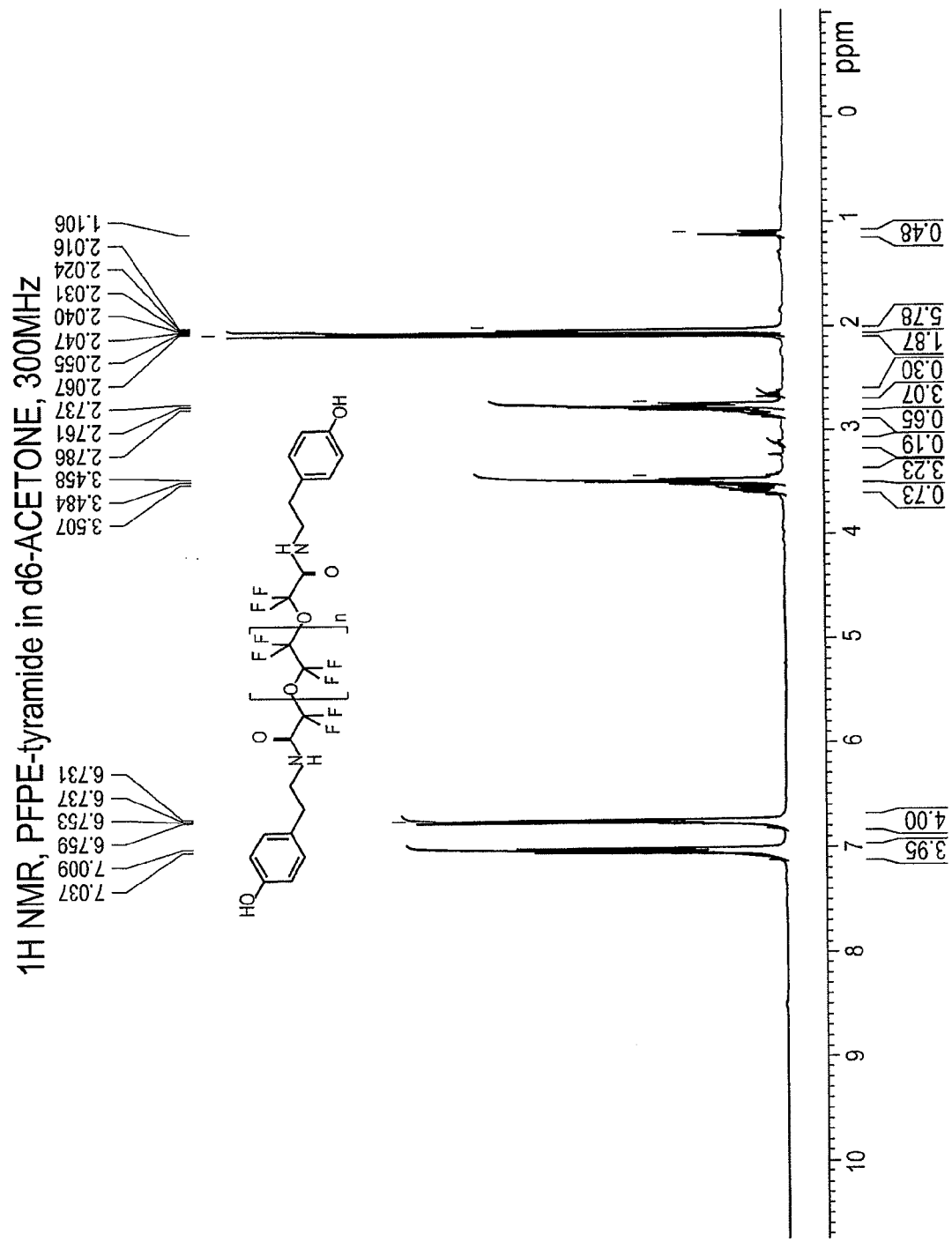
FIG. 51. $^1$H NMR of PFPE-tyramide purified on FluoroFlash by selective fluorophobic solvent elution.

Perfluoropolyether diethyl amide (1). General Procedure A, PFPE coupling to amines with low boiling point: A literature procedure was used with extensive modifications (Piacenti, F.; Camaiti, M. Journal of Fluorine Chemistry (1994), 68, 227-235). Perfluoropolyether methyl ester 39 (81.0 g, 50 mL, 46.3 mmol, Ave MW=1750) and diethylamine (81.3 g, 115 mL, 1.1 mol), were mixed in a round bottom flask (500 mL) under an argon atmosphere, and stirred at room temperature for 72 h. The excess amine and methanol formed during the reaction were removed by vacuum. The resulting brown oil was washed with THF (200 mL) and the oil and THF phase separated. The lower phase was collected and the residual solvent was removed by vacuum which afforded purified perfluoropolyether diethylamide 1 (73.1 g, 45 mL, 39.5 mmol, 85%) as a yellow to orange clear oil: $^1$H NMR (300 MHz, d$_6$-acetone) δ CH$_2$ 3.57-3.42 (4H, m), CH$_2$ 2.85-2.75 (4H, m), CH$_3$ 1.27-1.90 (6H, m), CH$_3$ 1.22-1.1 (6H, m); $^{13}$C NMR (75 MHz, d$_3$-trifluoroethanol) δ C=O 159.2 (t, J$_{C-F}$=32 Hz), OCF$_2$ 120.2 (t, J$_{C-F}$=48 Hz), OCF$_2$CF$_2$ 116.3 (t, J$_{C-F}$=44 Hz), CF$_2$O 112.5 (t, J$_{C-F}$=48 Hz), CH$_2$ 44.1, CH$_2$ 43.8, CH$_3$ 14.0, CH$_3$ 12.1; $^{19}$F (500 MHz, referenced TFA −76.0) OCF$_3$ −58.4, OCF$_2$NEt$_2$ −74.4, (CF$_2$CF$_2$O) −91.1; MS (MALDI-TOF, positive ion) (CF$_2$CF$_2$O)$_{16}$ 2194.9022 [M+Na]$^+$, (CF$_2$CF$_2$O)$_{15}$ 2078.8904 [M+Na]$^+$, (CF$_2$CF$_2$O)$_{14}$ 1962.9107 [M+Na]$^+$, (CF$_2$CF$_2$O)$_{13}$ 1846.9364 [M+Na]$^+$, (CF$_2$CF$_2$O)$_{12}$ 1730.9573 [M+Na]$^+$, (CF$_2$CF$_2$O)$_{11}$ 1614.9851 [M+Na]$^+$, (CF$_2$CF$_2$O)$_{10}$ 1499.0309 [M+Na]$^+$, (CF$_2$CF$_2$O)$_9$ 1499.0309 [M+Na]$^+$, (CF$_2$CF$_2$O)$_8$ 1383.0537 [M+Na]$^+$, (CF$_2$CF$_2$O)$_7$ 1267.0799 [M+Na]$^+$, (CF$_2$CF$_2$O)$_6$ 1151.1030 [M+Na]$^+$, (CF$_2$CF$_2$O)$_5$ 1035.1268 [M+Na]$^+$. Only the main monomer repeats are shown. Mass spectrometry data shows a distribution of PFPE linear molecules with different lengths, (FIG. 50).

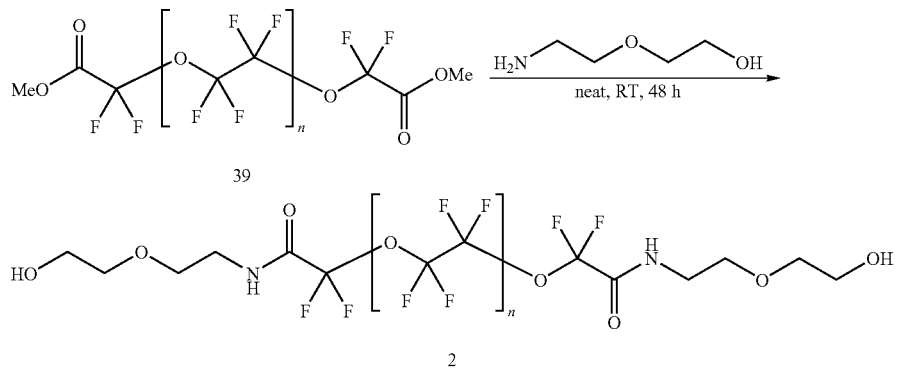

Perfluoropolyether O-(2-Hydroxyethyl)ethanolamide (2). General procedure A was used with some modifications. 2-(2-Aminoethoxy)ethanol (2.2 g, 20.9 mmol) was mixed with triethylamine (4.2 mL, 30 mmol) at room temperature in a round bottom flask (100 mL) under an argon atmosphere. Perfluoropolyether methyl ester 39 (17.5 g, 10.8 mL, 10 mmol, Ave MW=1750) was added. The reaction mixture turns brown and clear immediately while its temperature rises to 40° C. The reaction mixture is allowed to cool to room temperature and stirring continued for 48 h. The excess triethylamine and methanol, formed during the reaction, were removed by vacuum. The crude reaction product was loaded on the Fluoro Flash short column (20 g) and washed with 50 mL of acetonitrile. Elution with methanol (100 mL) and concentration in vacuo afforded perfluoropolyether O-(2-Hydroxyethyl)ethanolamide 2 (11.1 g, 5.9 mmol, 59%) with average MW 1895, as a dark yellow oil. $^1$H NMR (300 MHz, $d_6$-acetone) δ NH 8.55 (2H, singlet), $OCH_2$ 3.62 (8H, t, $J_{H-H}$=5.1 Hz), $CH_2N$ 3.53 (8H, t, $J_{H-H}$=4.8 Hz), OH 3.30 (2H, singlet); $^{19}$F (470 MHz, referenced TFA −76.0) $OCF_2CONHCH_2$ −78.8, $(CF_2CF_2O)$ −89.5.

removed by vacuum. Previously reported fluorous solid phase extraction method was followed with some modifications (Zhang, W.; Curran, D. Tetrahedron (2006), 62, 11837-11865). Fluorous silica gel adsorbs perfluoropolyether and allows easy elution of all non fluorinated organic compounds. The purification procedure was as follows. The crude reaction product was dissolved in acetone and loaded onto Fluoro Flash™ short column (10 g) packed wet with acetonitrile/water (95:5 v/v). The crude PFPE oil in acetone was loaded by gravity and then the Fluoro Flash column washed with acetonitrile/water (8:2 v/v) mixture (50 mL) followed by methanol (200 mL) and methanol/trifluoroethanol (1:1 v/v) (100 mL). Fluorophilic methanol fractions were collected, and the residual solvent was removed by vacuum which afforded purified perfluoropolyether tyramide 6 (4.8 g, 2.5 mmol, 86.2%) with average MW 1950 as a yellowish waxy solid: $^1$H NMR (300 MHz, $d_6$-acetone) δ $CH(C_6H_6)$ 7.02 (4H, d, $J_{H-H}$=4.2 Hz), $CH(C_6H_6)$ 6.75 (4H, d, $J_{H-H}$=4.2 Hz), $CH_2$ 3.48 (4H, t, $J_{H-H}$=7.8 Hz), $CH_2$ 2.76 (4H, t, $J_{H-H}$=7.5 Hz); $^{19}$F

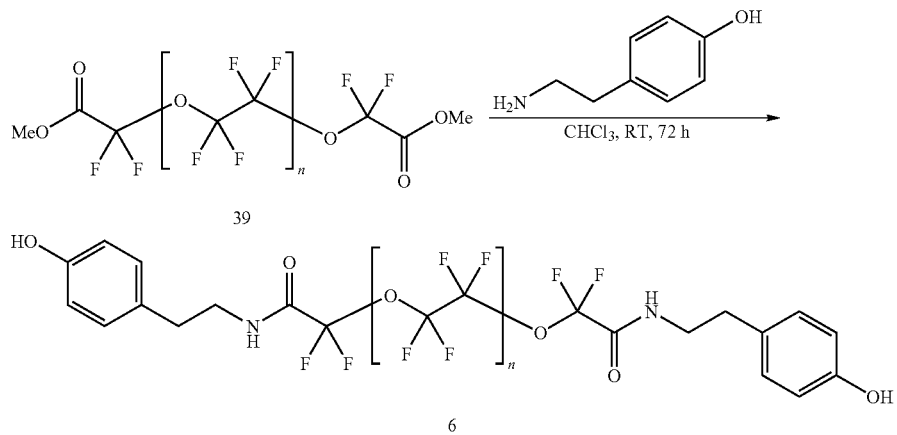

Perfluoropolyether tyramide (6). General Procedure B, PFPE coupling to amines as solids and high boiling point liquids. 4-(2-Aminoethyl)phenol (0.8 g, 6.0 mmol) was dissolved in chloroform (25 mL) in a round bottom flask (100 mL) and triethylamine (0.9 g, 1.2 mL, 8.6 mmol) was added under an argon atmosphere at room temperature while stirring. Perfluoropolyether methyl ester 39 (5.0 g, 3.1 mL, 2.9 mmol, Ave MW=1750) was added at once and the reaction mixture was stirred at room temperature for 72 h. The excess triethylamine and methanol formed during the reaction were (470 MHz, referenced TFA −76.0, $d_6$-acetone) $OCF_3$ −56.4, $OCF_2CONCH_2$ −78.9, $(CF_2CF_2O)$ −89.4.

$^{19}$F NMR Analysis

Figure 48:
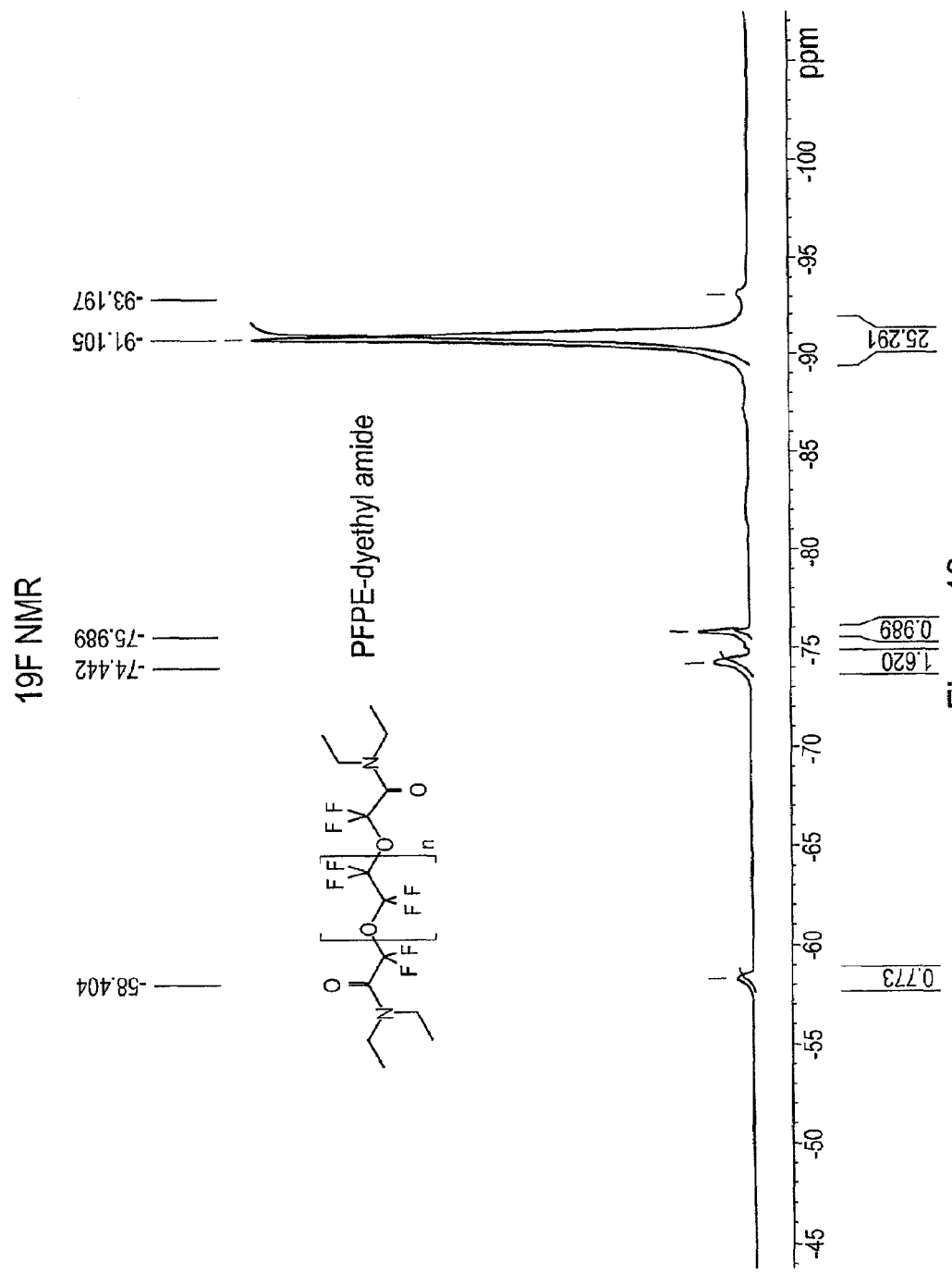
FIG. 48. $^{19}$F NMR spectrum of PFPE amide 1. The diagnostic peak for the preterminal CF2 group is at −74.4 ppm, where the TFA reference is set to −76 ppm.
Figure 49:
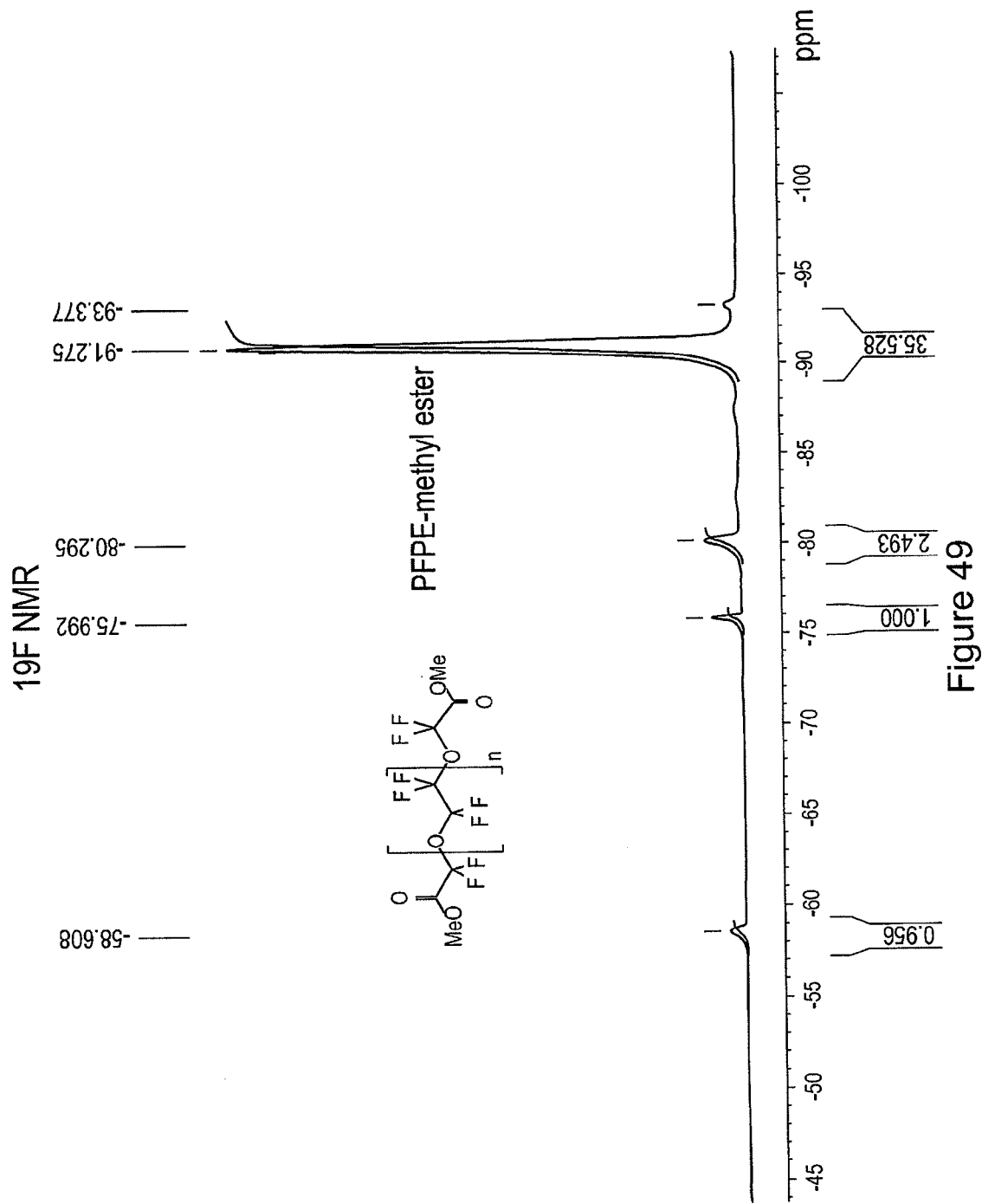
FIG. 49. $^{19}$F NMR spectrum of PFPE ester. The diagnostic peak for the preterminal CF2 group is at −80.3 ppm. The chemical shift of this peak was used as an indicator for amine coupling and amide synthesis.
Figure 52:
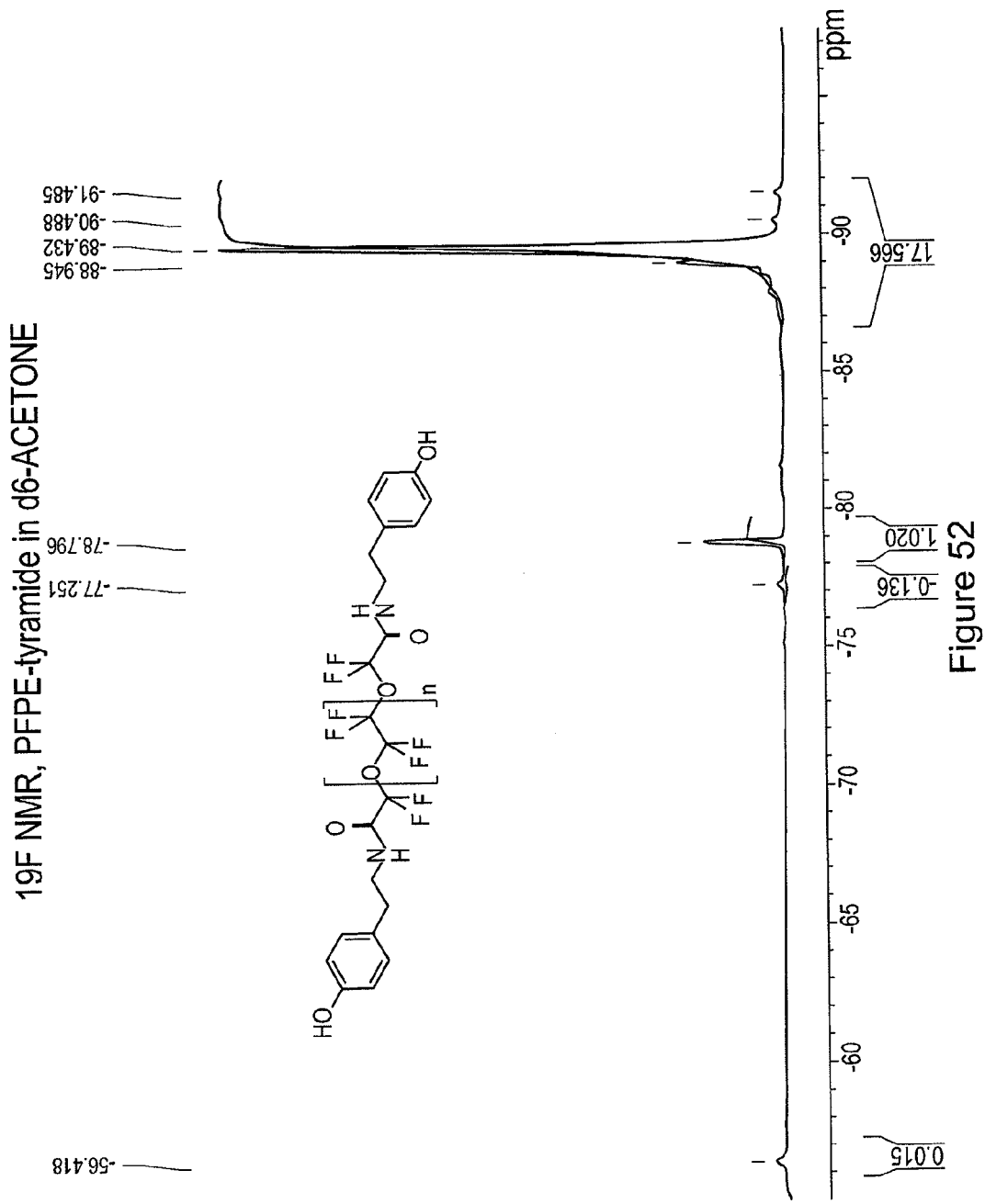
FIG. 52. $^{19}$F NMR of PFPE-tyramide. The diagnostic peak is at −78.8 ppm for the preterminal CF2 group.

The $^{19}$F NMR spectra can be used to unambiguously distinguish PFPE ester from PFPE amides. The $CF_2COOMe$ preterminal in PFPE ester (39) has a chemical shift of −80.3 ppm (FIG. 49). In the PFPE-diethyl amide (1), the $CF_2CON$ preterminal has chemical shift of −74.4 ppm (FIG. 48), and in the PFPE-tyramide conjugate where the end group has a secondary amide, the $CF_2CON$ preterminal has chemical shift of −77.8 ppm (FIG. 52).

In the case of the BODIPy-TR PFPE conjugate (compounds 16 and 17), the most diagnostic peak was the $^{19}$F on the dye at −127.7 ppm for $CF_2$. These results indicate the usefulness of $^{19}$F NMR in the analysis of PFPE modifications, PFPE emulsion products, and the PFPE uptake evaluation in target cells.

Similarly, compounds 7 and 8 were prepared according to the reactions in Scheme 2, wherein n, independently for each occurrence, represents an integer from 4 to 16.

amine of a PEG moiety and the coupling was allowed sufficient time to complete, usually 1-3 days at room temperature. The rest of free, unmodified ester end groups were converted to diethyl amide in the final step, and after vacuum removal of the excess diethyl amine and methanol, the end product contained defined molar ratios of PEG coupled to PFPE blended with PFPE diethyl amide (1). The ratio of two different modifications of PFPE end groups were easily confirmed by 1H and 13C NMR. Any uncoupled primary amine was removed Scheme 2:

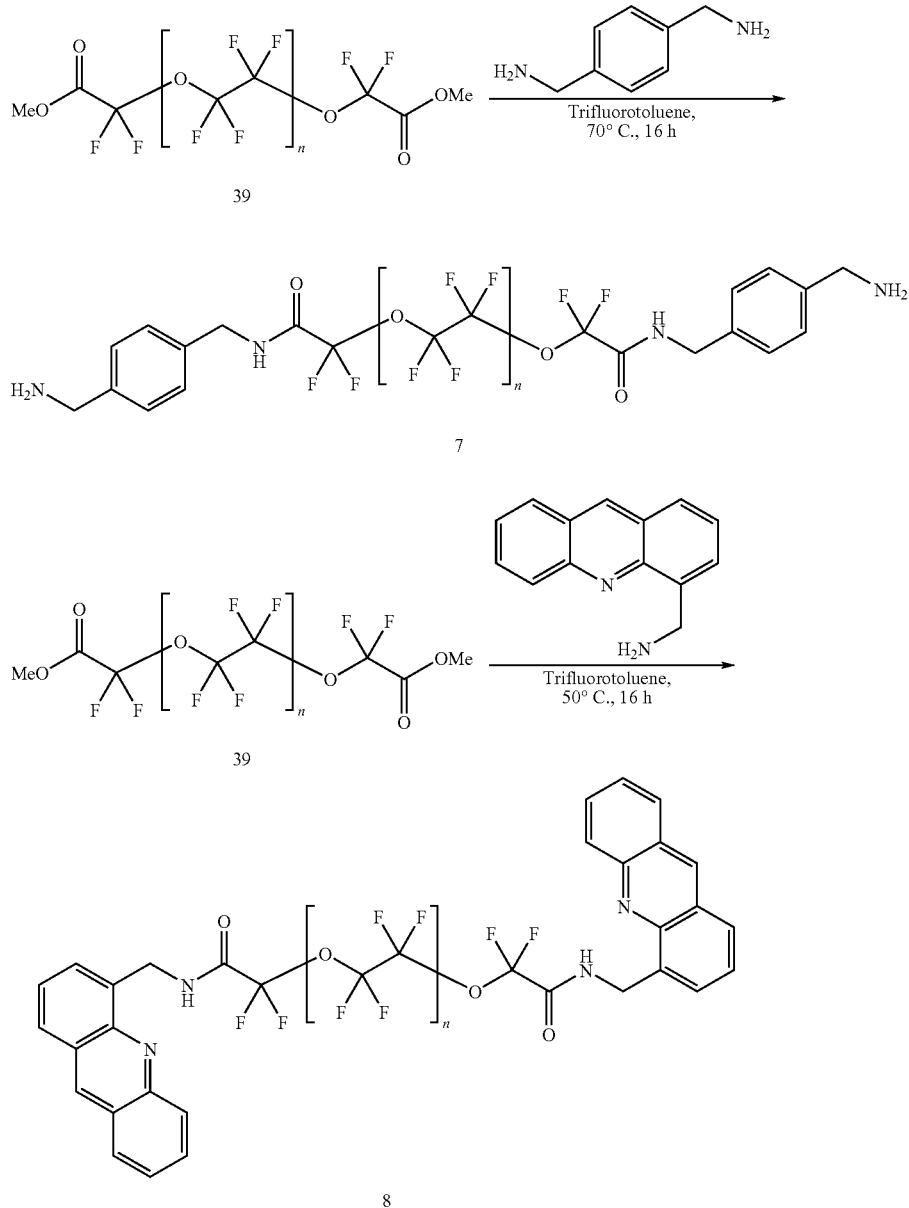

Synthesis of Compositions:

Compositions comprising a compound of formula 1 and a compound of formula 10; a compound of formula 1 and a compound of formula 12; and a compound of formula 1 and a compound of formula 14 were prepared according to the reactions shown in Scheme 3, wherein n, independently for each occurrence, represents an integer from 4 to 16. In general, PFPE methyl ester (39) was first reacted with a primary by selective organic solvent extraction, usually ethanol or THF. The composition comprising a compound of formula 10 and a compound of formula 1 was produced in a molar ratio of 1:2. The composition comprising a compound of formula 12 and a compound of formula 1 was produced in a molar ratio of 1:4. The composition comprising a compound of formula 14 and a compound of formula 1 was produced in a molar ratio of 1:10.

Scheme 3:

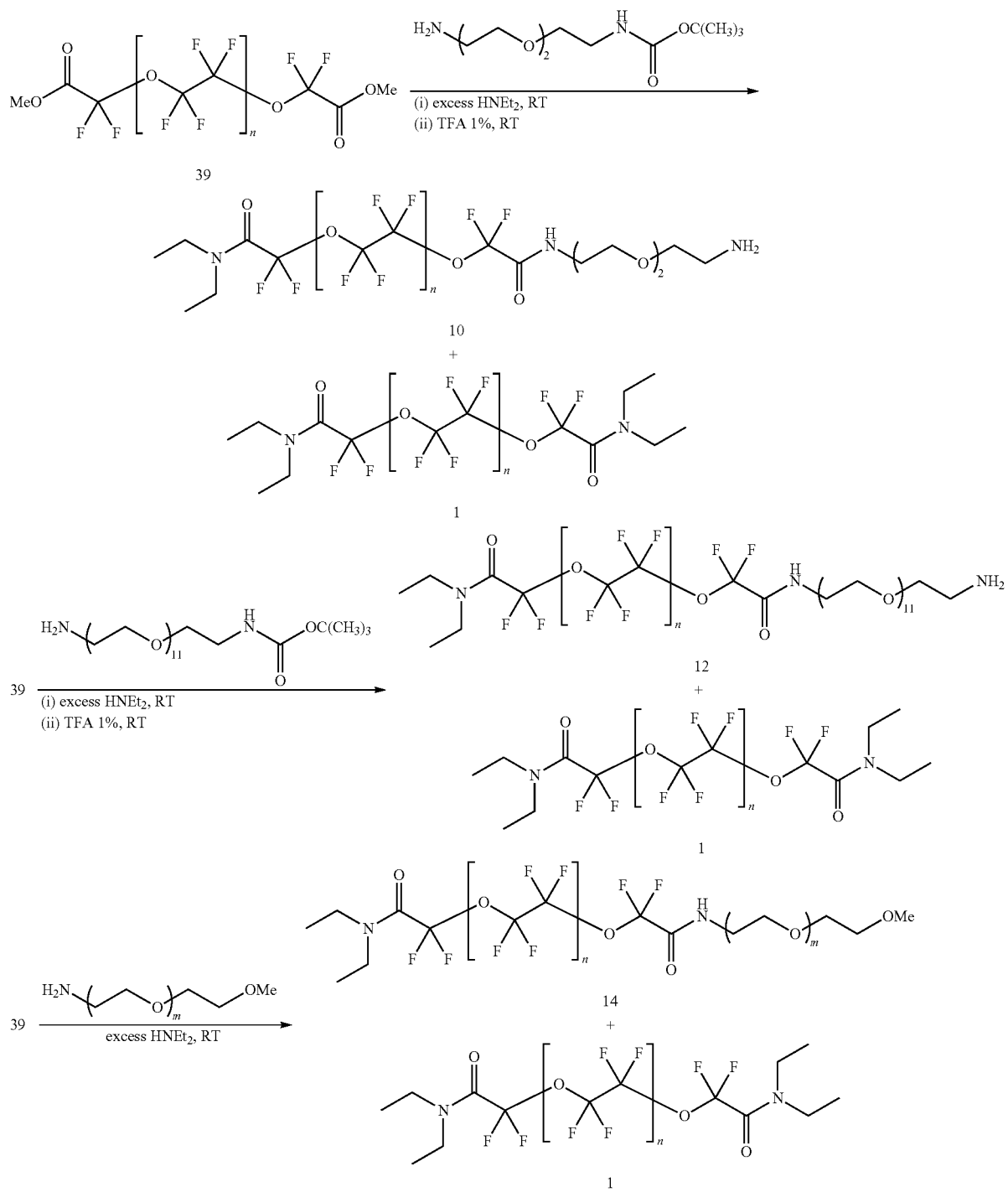

Compositions comprising a compound of formula 1 and a compound of formula 16; and a compound of formula 1 and a compound of formula 18 were prepared according to the reactions shown in Scheme 4, wherein n, independently for each occurrence, represents an integer from 4 to 16.

Fluorescent "Blended" PFPE Amides (FBPAs).

General procedure. The fluorescent dyes (FITC, BODIPy-TR and Alexa647) were purchased from Molecular Probes, Eugene, Oreg. as mono-conjugates to 1,5-diaminopentane (cadaverine), where the unmodified primary amine allows direct coupling to PFPE ester 39. Our synthetic approach for fluorescent PFPEs relies on the highly efficient initial coupling of the primary amine of the fluorescent dye conjugate to PFPE ester 39, as described in the model reaction above, Scheme 3, wherein complete conversion (>99%) is observed by $^1$H NMR after 48 h at rt. The final product is FBPA, a perfectly blended mixture of PFPE derivatives comprised of dye di-conjugate (e.g., compound 17, 19, or 41), dye mono-conjugate (e.g., compound 16, 18, or 40) and PFPE amide 1 (Scheme 4).

Briefly, fluorescent dye (FITC, BODIPy-TR or Alexa647) cadaverine conjugate was added at 0.5 to 2.0 mol % to a solution of PFPE ester 1 in trifluoroethanol or perfluorohexanes. The reaction was allowed to proceed at room temperature under inert atmosphere for up to 48 h. The remaining free, unmodified PFPE ester 39 end groups were converted to diethyl amide in the final step, and the excess unreacted diethyl amine and the side product methanol were removed by vacuum. Since the fluorescent dye was conjugated directly to only a portion of PFPE end groups thereby forming a secondary amide, while the remainder of PFPE end groups were capped with tertiary amide, fluorescence and UV/VIS absorbance measurements of labeled PFPE were used for coupling efficiency estimates. Any uncoupled primary amine was removed by selective organic solvent extraction, usually ethanol, or eluted by fluorophobic solvent (e.g., acetonitrile/water, 4:1) from the fluorous phase silica gel.

PFPE ester 39 is fully soluble only in trifluoroethanol, trifluorotoluene and perfluorohexanes. Trifluoroethanol was the only solvent that solubilizes both the dye and the PFPE oil. BODIPy-TR cadaverine was added at low concentration (5 mg dye/1 mL of PFPE oil) and allowed to react for 48 h at r.t. in trifluoroethanol or perfluorohexanes.

Scheme 4

(a)

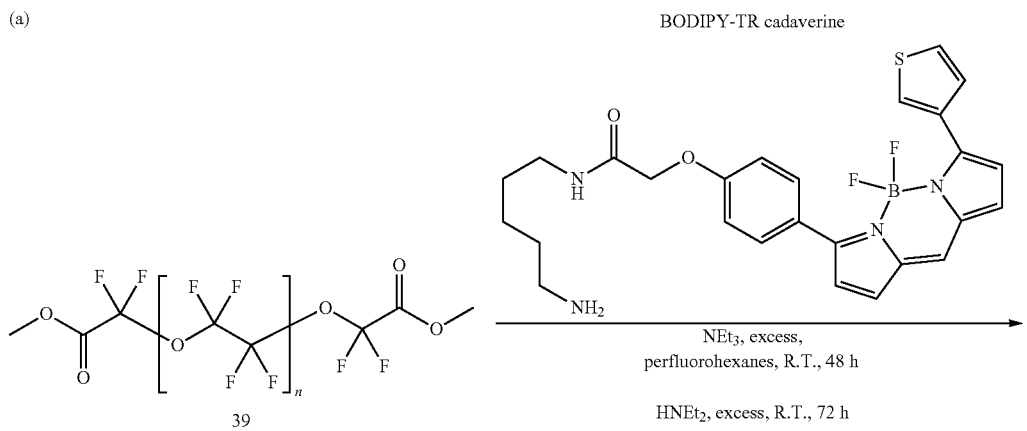

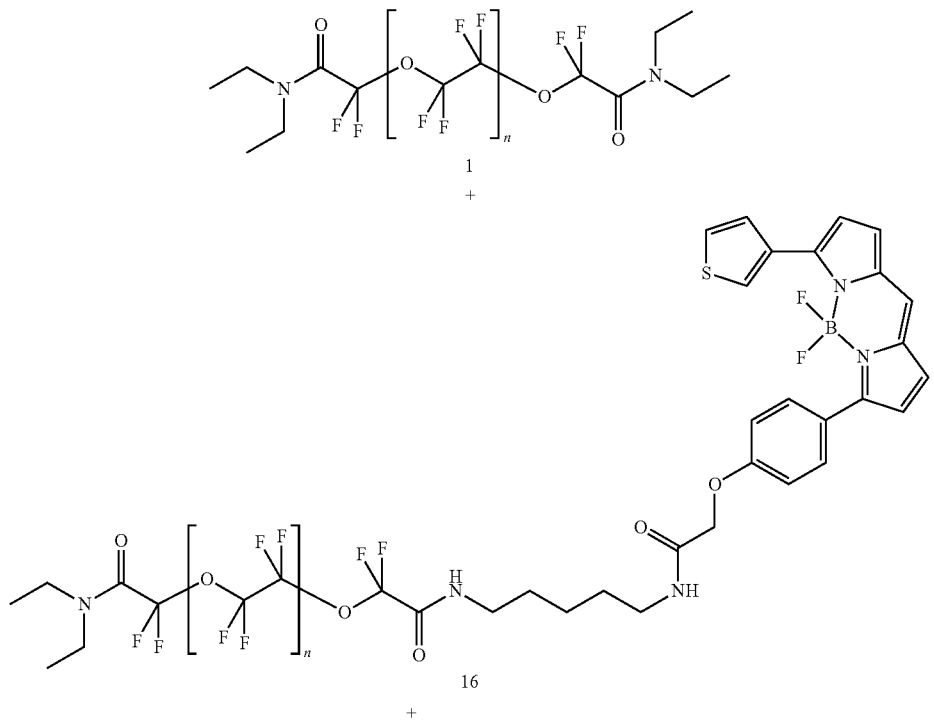

-continued
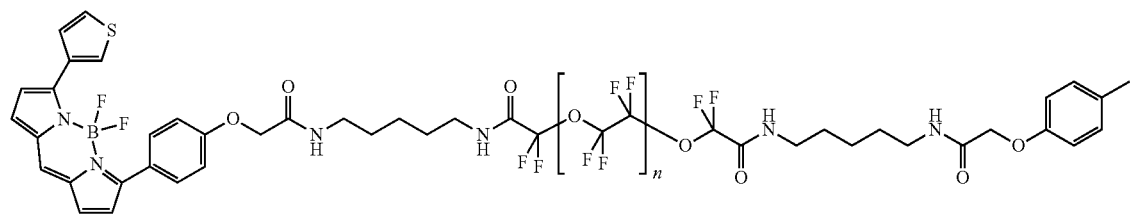
17
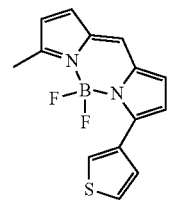
(b)
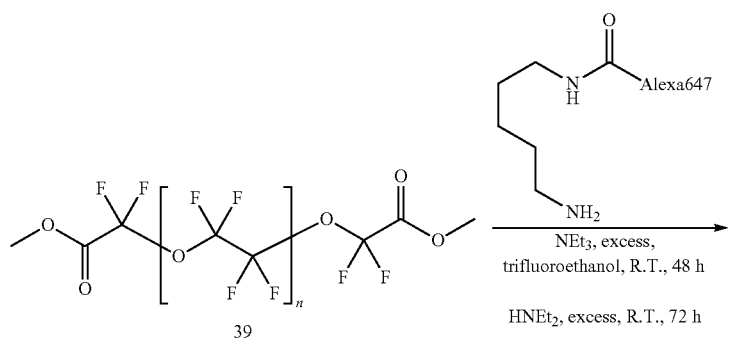
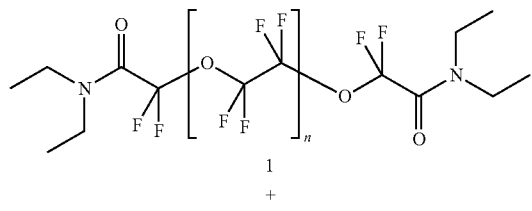
1
+
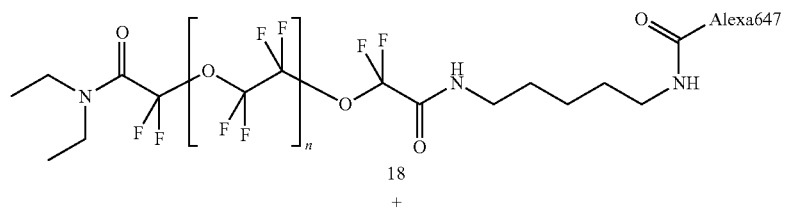
18
+
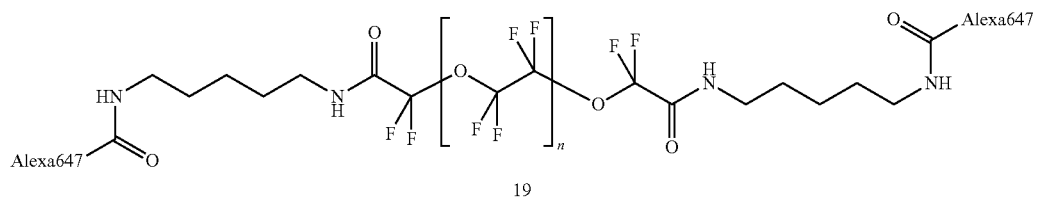
19

(c)
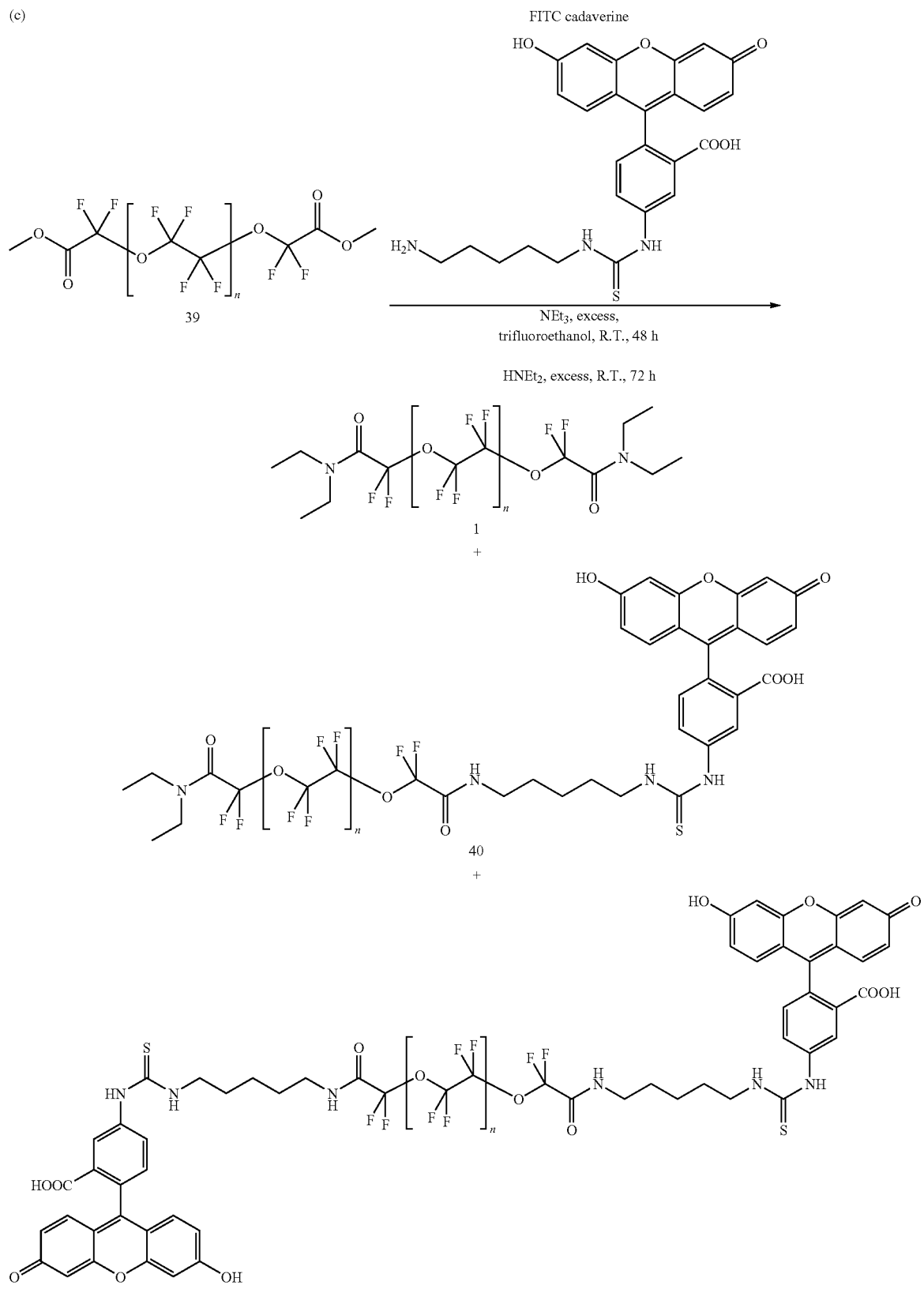

Figure 59:
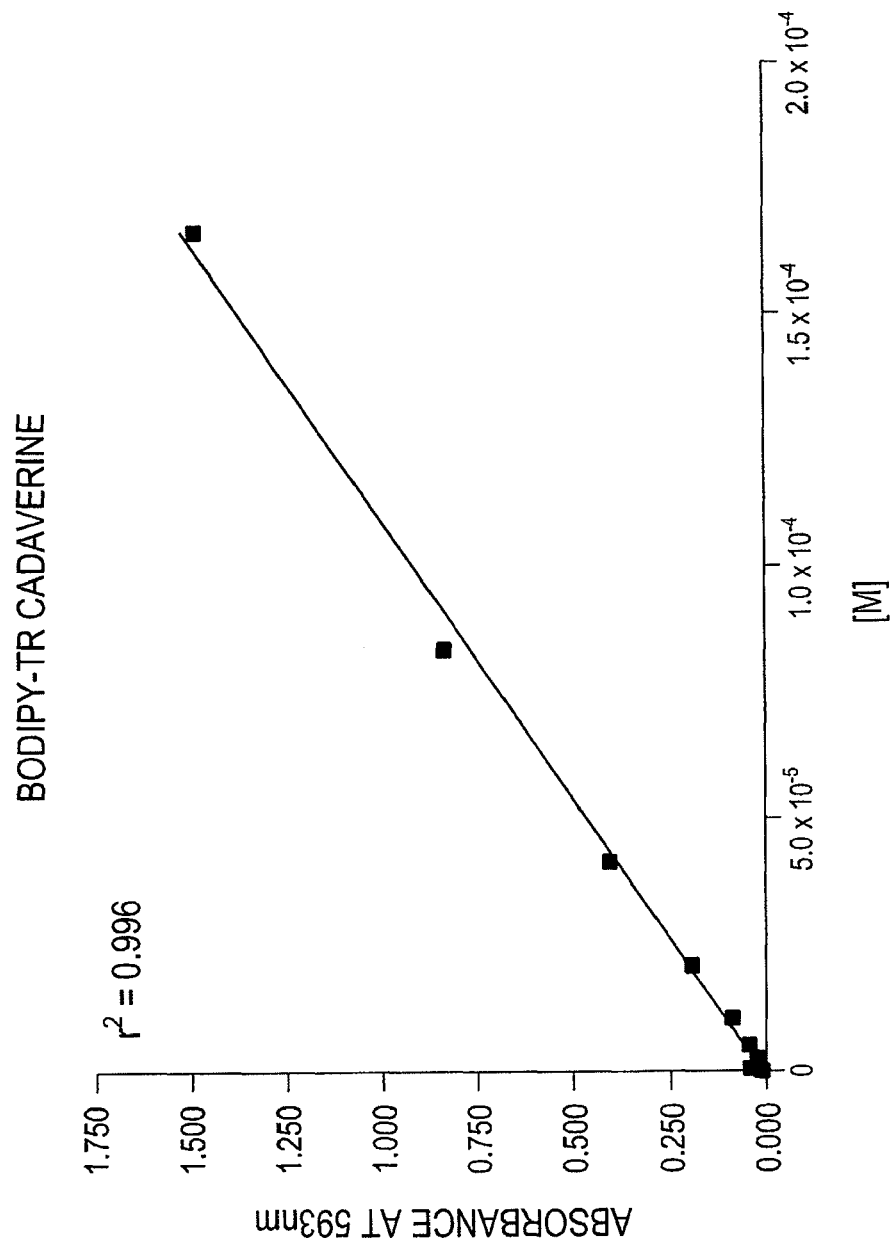
FIG. 59. BODIPy-TR Cadaverine concentration versus absorbance calibration curve. The absorbance was measured at a fixed absorption wavelength 593 nm, which was experimentally determined as the absorbance maxima in trifluoroethanol. Data represents the average of three independent measurements (mean±SD).

BODIPy-TR PFPE amide (FBPA composed of PFPE amide 1, 16 and 17). A flame dried round bottom flask (50 mL) was charged with perfluoropolyether methyl ester 39 (3.96 mL, 3.67 mmol) under an argon atmosphere. BODIPy-TR cadaverine (0.02 g, 0.04 mmol) was added to PFPE oil as a solid and, after extensive stirring, perfluorohexane solvent was added (3.00 mL) followed by triethylamine (1.50 mL, 10.8 mmol). (Alternatively, trifluoroethanol can be used as a solvent for the fluorescent conjugate such that the BODIPy-TR Cadaverine is added as solution in trifluoroethanol. This approach is used on large scale.) The reaction mixture was allowed to stir at r.t. for 48 h protected from light. Diethylamine (9.50 mL, 91.8 mmol) was added to convert all unreacted ester end groups into tertiary amide, and the reaction continued for 72 h at r.t. The excess diethyl amine and methanol were removed by vacuum, and the final dark blue oil was further purified as follows. The product was subjected to ethanol wash (10 mL), and then purified by fluorous solid phase filtration. A FluoroFlash column was packed wet in acetonitrile/water (95:5 v/v). Product was loaded on the column using negative pressure. The column was washed with acetonitrile (100 mL), and the fluorophobic fractions combined, concentrated to dryness in vacuo and redissolved in trifluoroethanol (20 mL). The column was then washed with THF (100 mL) followed by trifluoroethanol (50 mL), and the fluorophilic fractions combined, concentrated to dryness and the residue dissolved in trifluoroethanol (20 mL). These solutions were used for spectrophotometric measurements. BODIPy-TR cadaverine was dissolved in trifluoroethanol, and a standard curve was constructed by measuring absorbance at 593 nm. The BODIPy-TR concentrations in the fluorophilic and fluorophobic fractions were estimated from the standard curve. BODIPy-TR coupling yield was 46.8%, and the final concentration of the fluorescent dye in neat oil was 4.6 mM. The FBPA oil was stored in the dark at r.t. until used for nanoemulsion preparations. The absorbance standard curve is shown in FIG. 59.

Due to low concentration of the dye in FBPA, $^1$H and $^{13}$C NMR analysis did not produce useful data. The fluorous phase extractions were performed to remove any uncoupled organic dye from the highly fluorinated PFPE oil at the final step of the FBPA preparations. Fluorous phase solid extractions and UV spectrophotometry were used to confirm the conjugation and to calculate coupling yield.

FITC PFPE amide (FBPA composed of PFPE amide 1, 40 and 41). A flame dried round bottom flask (50 mL) was charged with perfluoropolyether methyl ester 39 (1.62 mL, 1.5 mmol) under an argon atmosphere. FITC-TR cadaverine (0.01 g, 0.015 mmol, 1 mol %) was dissolved in trifluoroethanol (2.0 mL) and added to PFPE oil, followed by triethylamine (0.84 mL, 6.0 mmol). The reaction mixture was allowed to stir at r.t. for 48 h protected from light. Diethylamine (1.24 mL, 12.0 mmol) was added to convert all unreacted ester end groups of PFPE into tertiary amide, and the reaction continued for 72 h at r.t. The excess diethyl amine and methanol were removed by vacuum, and the final dark yellow oil was washed once with ethanol, concentrated in vacuo and used for fluorescent nanoemulsion preparations without further purifications.

Alexa647 PFPE amide (FBPA composed of PFPE amide 1, 18 and 19). A flame dried glass vial (2.5 mL) flushed with argon, was charged with perfluoropolyether methyl ester 39 (0.086 mL, 0.08 mmol). Alexa647-TR cadaverine (0.002 g, 0.002 mmol, 2.5 mol %) was dissolved in trifluoroethanol (2.0 mL) and added to PFPE oil, followed by triethylamine (0.04 mL, 0.29 mmol). The reaction mixture was allowed to shake on a mechanical shaker at 80 rpm at r.t. for 48 h protected from light. Diethylamine (0.08, 0.77 mmol) was added to convert all unreacted ester end groups of PFPE into tertiary amide, and the reaction was allowed to proceed for 72 h at r.t. The excess diethyl amine and methanol were removed by vacuum, and the final dark yellow oil was washed with ethanol, concentrated in vacuo, and used for fluorescent nanoemulsion preparations without further purifications.

The FBPA was used for fluorescent PFPE nanoemulsion preparations by microfluidization on large scale (25 mL). PFPE amides demonstrated stability and held the fluorescent dye in the PFPE oil phase during microfluidization. Fluorescence measurements showed the BODIPy-TR dye spectrum did not change after coupling to PFPE. Using the same approach, PFPE methyl ester 39 was labeled with highly fluorescent AlexaFluor 647 dye, to allow prolonged fluorescent imaging of labeled cells in vivo. AlexaFluor labeled cadaverine was directly coupled to PFPE methyl ester 39 at 2.5 mol % and the rest of ester end groups were converted to diethyl amide by treatment with excess diethylamine. Labeling was performed at room temperature in trifluoroethanol After the fluorescent dye was coupled, fluorescence and UV/VIS absorbance measurements of labeled PFPE were used for coupling efficiency estimates, (FIG. 43A-B). Following the same approach, the PFPE ester 39 was coupled to FITC dye via cadaverine linker at 2 mol %, while the rest of ester end groups were converted to tertiary amides with excess diethylamine (Scheme 4). In all cases the resulting product is fluorescent "blended" PFPE amide (FBPA). These oils were named "blended" because of the specific nature of fluorinated oils to stay together as its own phase. These fluorescent oils behaved as unique oil phase in all emulsion preparation experiments.

We have also explored how well PFPE oxide 1a and PFPE amide 1 blend together. We have found that PFPE oils blend at any given ratio and we used the blended PFPE oils (PFPE amide 1 and PFPE oxide 1a) for nanoemulsion preparations by microfluidization. We also successfully blended FBPA oils with PFPE oxide 1a in order to prepare highly stable fluorescent nanoemulsion on large scale. The "blended" PFPE oil approach can be and was applied to all PFPE derivatives and it was successful in most emulsion preparations. The PFPE derivatives tended to form a unique oil phase that was not mixing readily with either water or oil and rather stayed as a separate phase. This was mostly true for those "blended" oils that contained fluorescent dyes, or were made by mixing PFPE amide 1 and PFPE oxide 1a at different ratios.

By definition "blended" PFPE oil contains PFPE derivative 1 mixed with PFPE oxide 1a at volume ratios from 1/100-1/1. In most emulsions we used 1/9 ratio v/v. If the PFPE amide is actually FBPA, it was also blended with PFPE oxide 1a at volume ratio 1/10. These blends were used for fluorescent nanoemulsion preparations described in detail below.

The amino-reactive dye Cy5 may be used to couple to an imaging reagent. In such instances the composition comprising a compound of formula 10 and a compound of formula 1 may be used, as shown in Scheme 5, wherein n, independently for each occurrence, represents an integer from 4 to 16.

Scheme 5:

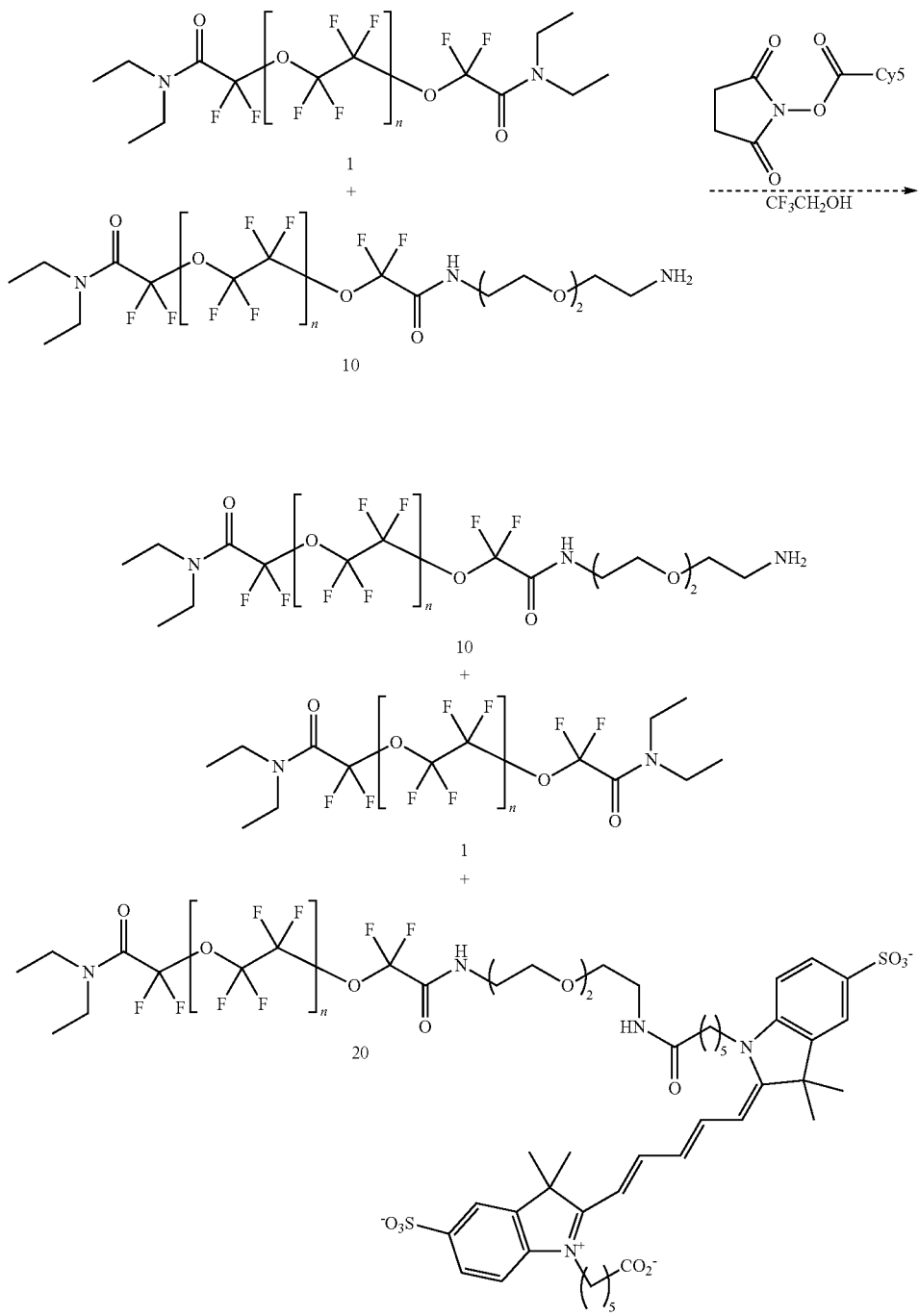

In general, any amino-reactive dye can be coupled onto an imaging reagent set forth above that contains an amine functionality. For example, compounds 27, 30, 33, or 36 may be prepared according to the proposed reactions in Scheme 6, wherein n, independently for each occurrence, represents an integer from 4 to 16. Furthermore, any of these compounds can be further blended with PFPE oxide 1a and/or PFPE amide 1 to form new FBPA blends, as described above. This takes advantage of the fact that PFPE derivatives tend to mix better with PFPE derivatives than with water or organic oils. Any of these fluorescent and non-fluorescent PFPE derivatives can be blended with each other in any combination, providing diverse set of PFPE oils available for nanoemulsion preparation and further fine tuning of final nanoemulsion MRI reagent properties.

Scheme 6:
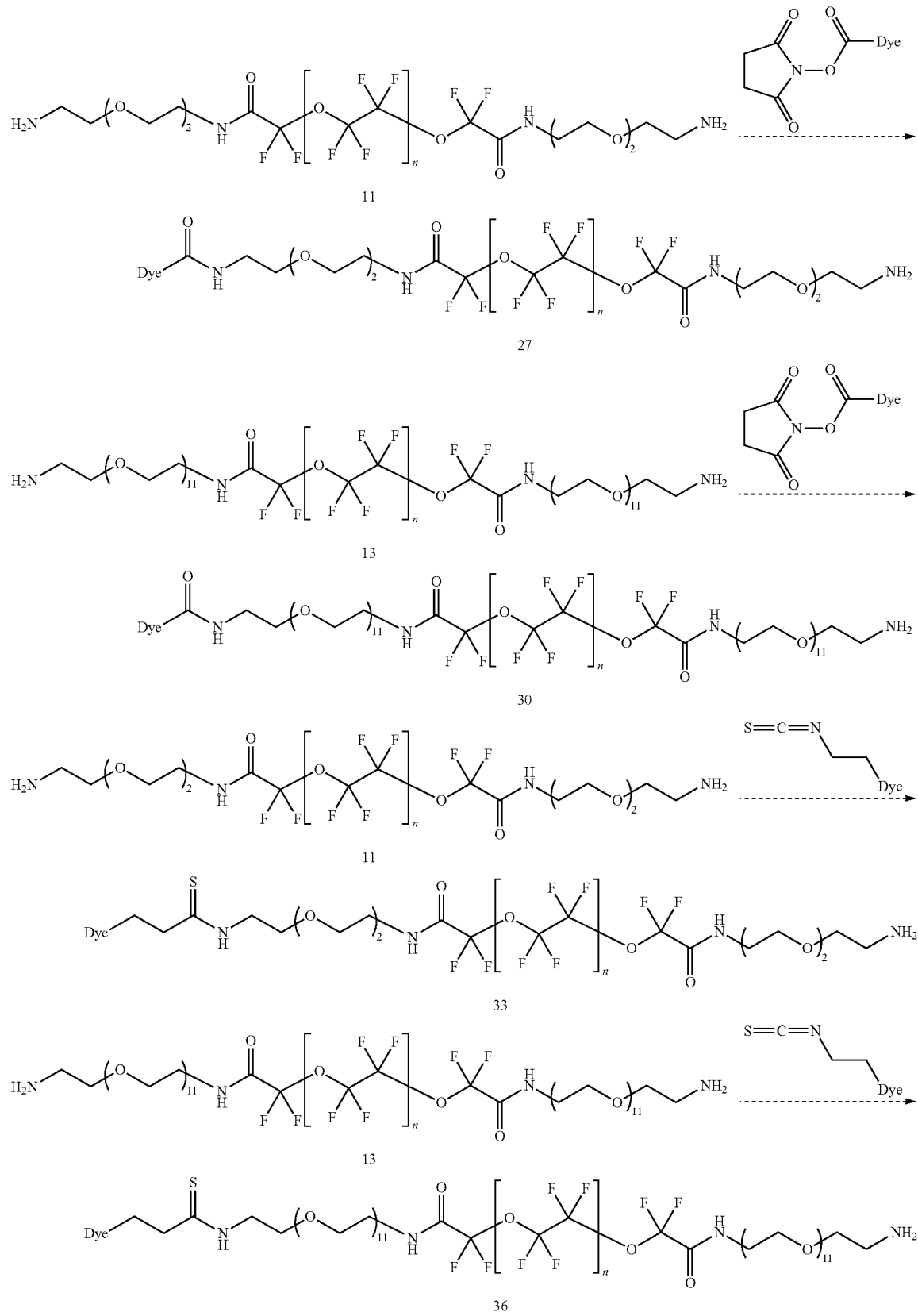

Due to the low concentration of dyes used for labeling PFPE modified oils, $^{19}$F NMR and MS data were not sufficient indicators for the coupling yield. We could not observe presence of the dye that was usually 1 mol % or less by NMR or MS analysis. Alternative analytical approaches were used. A combination of spectrophotometric analysis and fluorescence was used to determine the dye coupling to the PFPE. In the case of the highly fluorescent Alexa647 dye, extremely low concentrations (0.05 mol %) were sufficient to give adequate fluorescent tagging of target cells labeled with PFPE emulsions. In the case of BODIPy-TR label, 0.5 mol % was sufficient. For each dye, standard curves were constructed in trifluoroethanol to avoid solubility differences between PFPE, PFPE conjugates, and the free dye. Fluorescently labeled PFPEs were purified by solvent extraction or FluoroFlash filtration to remove unreacted dye. Then, fluorescent PFPE oil was dissolved in trifluoroethanol and both UV/VIS absorbance and fluorescence were measured. Concentration of the dye was estimated from the constructed standard curves by two independent methods, including fluorescence and UV/VIS absorbance (FIG. 43A-B). It is known in the art that fluorescent dyes can change their fluorescent properties upon conjugation to macromolecules. Therefore, the absorbance and emission spectra were obtained for fluorescently labeled PFPE, compounds of formula 10 and formula 1, and compounds of formula 16 and formula 1; Fluorescence emission spectra of Alexa 647 was unaffected by the conjugation to PFPE (FIG. 43C-D). Examples of analytical data, including HPLC, $^1$H, $^{13}$C, $^{19}$F NMR and MALDI-TOF of selected PFPE derivatives, are presented in FIGS. 41-52.

Alternative Channel MRI Reagent (Compound 42):

Compound 42 was prepared according to Scheme 7 and the following procedure:

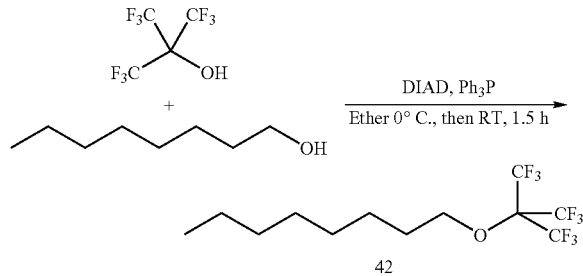

The following procedure was modified from Jiang et al (36). To a solution of 1-octanol in anhydrous ether (5.25 g, 40.35 mmol) was added triphenylphosphine (11.11 g, 42.37 mmol) and the mixture stirred at room temperature for 15 minutes until the powder completely dissolved. The reaction mixture was then placed on an ice bath (0° C.) and diisopropylazodicarboxylate (8.71 mL, 44.38 mmol) was added dropwise. The addition was performed under argon atmosphere. During the addition the solution changed color to pale yellow and yellow precipitate formed. After the addition was complete, the reaction mixture was stirred for an additional 30 minutes on the ice batch and then perfluoro-tert-butanol (10.00 g, 42.37 mmol) was added in one portion and the resulting mixture was stirred for 1.5 h at room temperature. The crude reaction mixture was filtered over short SiO$_2$ column to remove triphenylphosphine oxide precipitate. The filtrate was concentrated, redissolved in a small amount of ether and loaded on a SiO$_2$ column. The product was eluted with perfluorohexanes/ether (1:1 v/v) mixture and concentrated in vacuo. Removal of the unreacted perfluoro-tert-butanol under vacuum gave the product 42 as a clear colorless oil (8.36 g, 59.5%). $^1$H NMR (300 MHz, d$_6$-acetone) δ 4.12 (t, 2H, J=6.2 Hz), 1.79 (dt, 2H, J=6.6, 6.3 Hz), 1.46-1.30 (m, 10H); $^{19}$F NMR (477 MHz, neat) δ −71.39 (s, 9F); $^{13}$C NMR (75.6 MHz, neat) δ 120.5 (q, J=289.9 Hz), 70.3, 31.5, 25.1, 22.3; MS (ESI) m/z 388.5 (M++K, 40).

2. Emulsion Preparation

PFPE is a lipophobic and hydrophobic polymer, which presents challenges for emulsification. On the other hand, there is a clear advantage to these properties. PFPE oils readily mix with each other at any given ratio providing a unique fluorinated phase for nanoemulsion preparation. Blended PFPE oils are readily accessible through simple vortexing of diverse PFPE derivatives (e.g., the FBPAs described above). The blended oils may then be used for variety of emulsion preparations and in general behave as a single PFPE oil phase.

A variety of emulsification methods were extensively explored. Sonication and microfluidization processing techniques were tested, as well as low energy methods, such as thin film and vortexing. In all emulsion preparations, PFPE derivatives remained chemically unchanged. Lipids, block copolymers (e.g., Pluronics™) and polyamines were used as excipients for PFPE emulsification.

In all of the experiments using sonication, a Sonifier Cell Disruptor (Misonix Inc., Farmingdale, N.Y.) was used at 20 watts output power and at 20 kHz. The tip of the probe is immersed into a small volume of liquid, usually 0.1-0.5 mL in an Eppendorf tube. Unless noted differently, all emulsifications were performed at room temperature.

In all of the described experiments using microfluidization, a M-110S Laboratory Microfluidizer Processor (Microfluidics, Inc., Newton, Mass.) was used at 40-60 psi working pressure with sample volumes in the range 10-40 mL, not excluding higher volumes (up to 100 mL). Microfluidization, homogenization, and the like can also be used for production of large batches of emulsion product exceeding 1 L.

Specific Examples of Emulsion Formulations

PFPE Amide/F68 Emulsion

Pluronic™ F68 was dissolved in aqueous buffer (HBSS, Hyclone) at 150 mg/mL. PFPE amide 1 was added at 152 mg/mL, and the mixture (250 μL) was placed in an 1.5 mL Eppendorf vial and sonicated (at 20 W and 20 kHz) at room temperature for 30 seconds. The emulsion was then diluted 1:3 in 1×HBSS and the particle size was measured by dynamic light scattering in Malvern Zetasizer Nano within 1 h. The molar ratio of PFPE amide 1 to F68 was 4.6:1. The polydispersity (PDI) was 0.12 to 0.19 and the average particle size 200 nm. The critical micellar concentrations (CMC) for the PFPE amide 1 and F68 was estimated by plotting the light scattering intensity and average diameter and looking for the curve intersection, as shown in FIG. 1.

PFPE/L35 Emulsion:

PFPE amide 1 (24 μL, 36.5 mg, 0.02 mmol) and Pluronic™ L35 (54 μL, 57.4 mg, 0.03 mmol) were mixed in an 1.5 mL Eppendorf tube and sonicated neat for 10 s. Deionized water (122 μL) was then added and the mixture was sonicated until it turned clear (10-15 s). Emulsions prepared as above were stable at high concentrations for about 2-3 hours. If the emulsion was diluted 10-fold in water, the particle size and PDI remained constant for at least 3-5 days.

Figure 2:
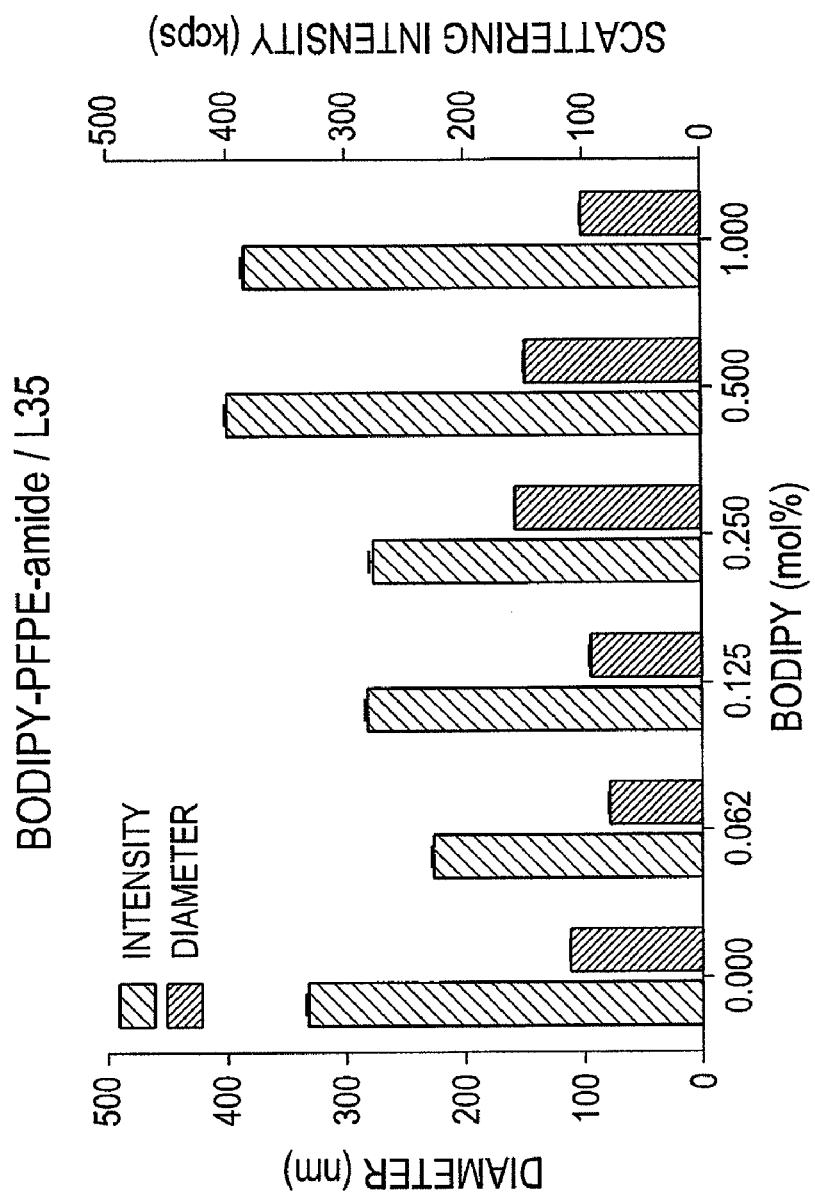
FIG. 2. Effect of neutral lipophilic fluorescent dye on PFPE amide 1 emulsification. The composition containing BODIPy-PFPE amide 16 and PFPE amide 1 emulsified with L35 in water by sonication. Lipophilic dye does not significantly affect the particle size and polydispersity of PFPE emulsion. Data represents average of three independent measurements (mean±SD).

Dual Fluorescent/MRI Nanoemulsion Label—Pilot Version Prepared by Sonication:

The first fluorescent nanoemulsion was prepared with BODIPy-TR PFPE amide by sonication. The composition containing PFPE-BODIPy amide 16 and PFPE amide 1 (1 mol % dye) was diluted in pure PFPE amide 1 at various concentrations. For a given mixture dye concentration, the PFPE/BODIPy (24 μL) was sonicated with L35 (54 μL) and water (122 μL). The presence of BODIPy-TR, a lipophilic neutral dye, in PFPE-amide oil 1 had little effect on particle size and emulsification of PFPE amide 1, as shown in FIG. 2. The particle diameter was 114.1±31.4 nm and the PDI varied from 0.1 to 0.4.

Figure 3:
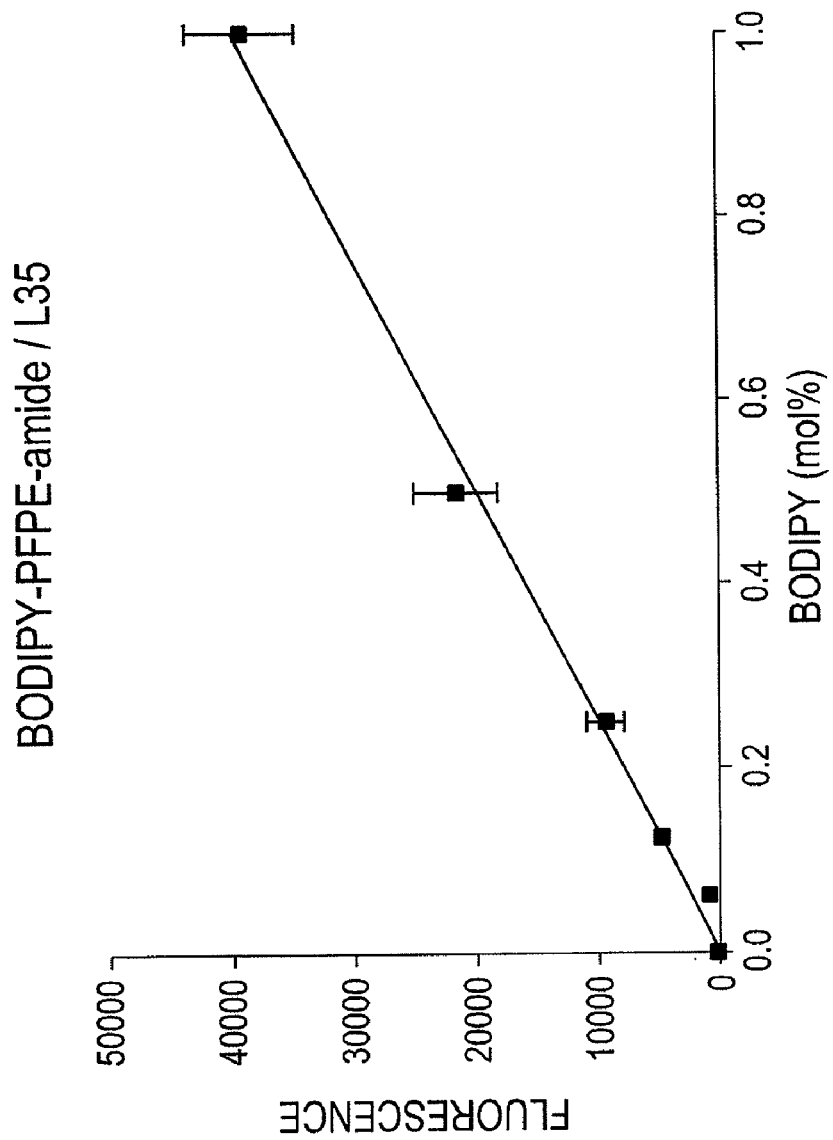
FIG. 3. Fluorescence intensity of BODIPy labeled PFPE amide oil. The composition containing BODIPy-PFPE amide 16 and PFPE amide 1 emulsified in water with L35. Data represents an average fluorescence intensity measured in triplicate (mean±SD).

BODIPy-PFPE amide 16/L35 emulsions with increasing BODIPy-TR dye concentrations (0-1 mol %) were diluted in water 10 times. The fluorescence intensity was measured in a black, flat bottom 96-well plate on TECAN plate reader using 580 nm excitation and 630 nm emission, as shown in FIG. 3.

The presence of lipophilic fluorescent dye had virtually no effect on emulsification of PFPE amide 1 with L35 by sonication. The particle size and PDI were comparable, and this result indicated that uptake may not change. This is important because tissue culture protocols that are developed for labeling cells can be used for both fluorescent and non-fluorescent versions of the PFPE nanoparticles. Furthermore it is anticipated that the fluorescent analogs could be used for in vitro measurements of the key parameter Fc as part of the cell labeling protocol development or validation. Thus, the mean cell loading, measured by Fc, could be evaluated using low-cost fluorimeters, rather than expensive $^{19}$F NMR instrumentation, and the Fc result could be used for subsequent in vivo experiments using the non-fluorescent versions of the PFPE.

A nanoemulsion with Alexa647-PFPE amide was prepared following the same procedure as above. Alexa647 PFPE amide was diluted in PFPE amide to obtain final dye concentration at 0.05 mol % to PFPE, which was then emulsified with L35. The average emulsion particle diameter was determined to be 122±17 nm.

Figure 4:
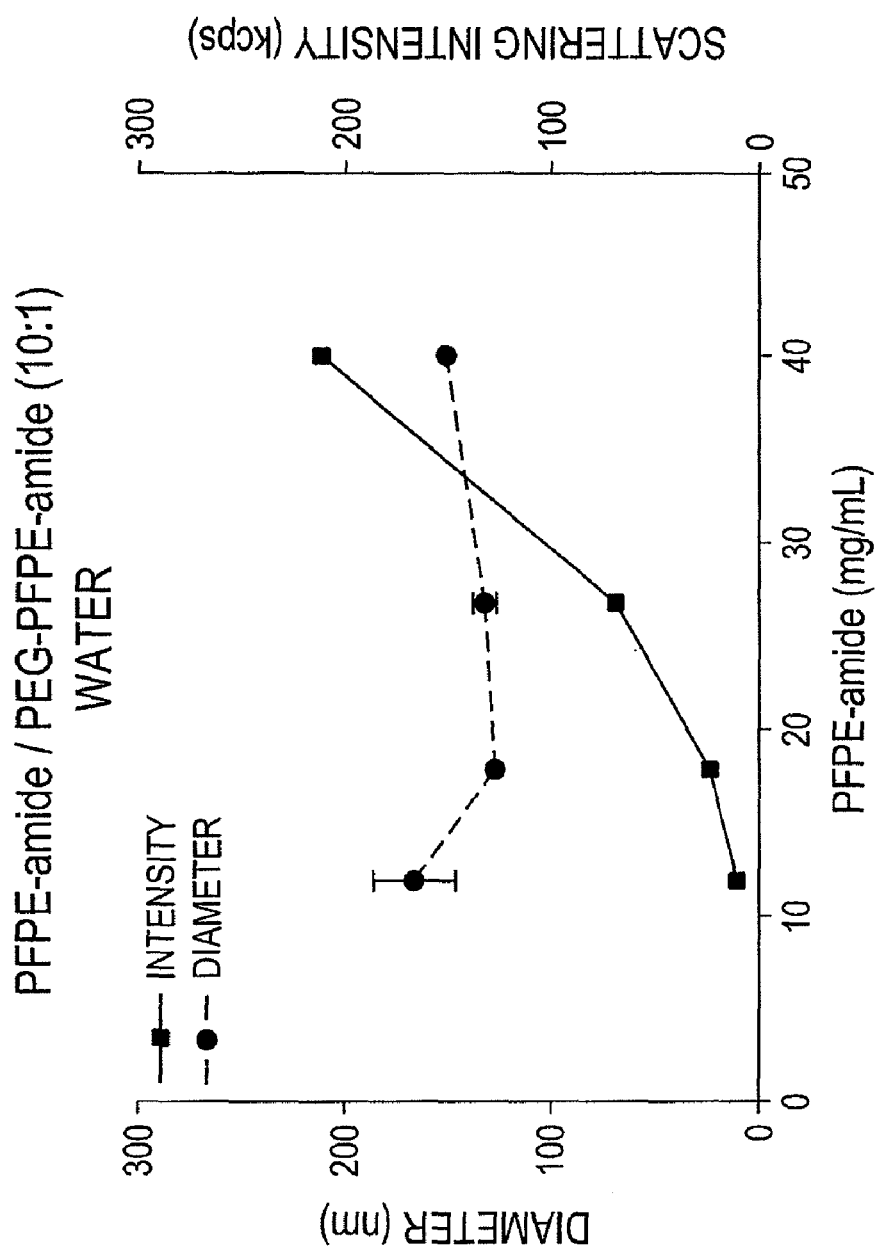
FIG. 4. The composition comprising PEG-PFPE amide 14 and PFPE amide 1 emulsified by sonication in water without additional emulsifiers or surfactants. Particle size was measured by DLS. The data represents an average of two independent measurements mean±SD.
Figure 5:
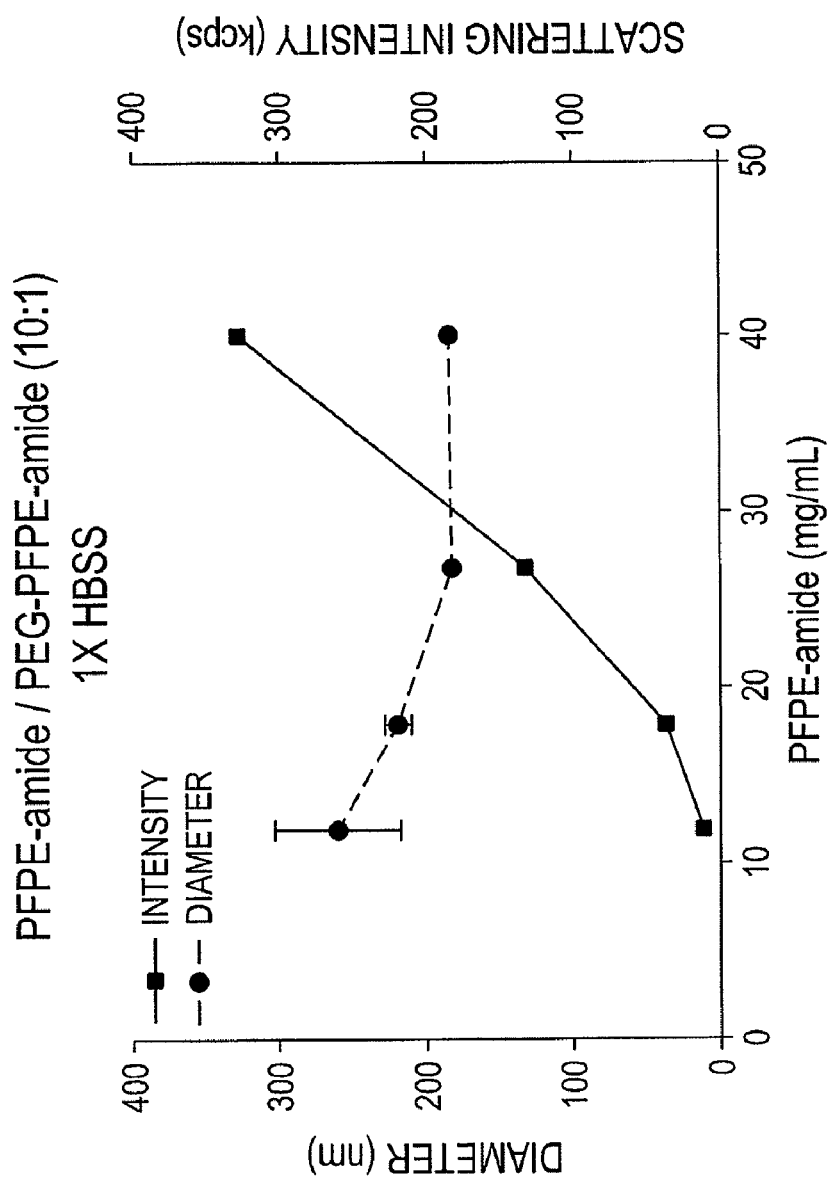
FIG. 5. The composition comprising PEG-PFPE amide 14 and PFPE amide 1 emulsified by sonication in 1×HBSS without additional emulsifiers or surfactants. Particle size was measured by DLS. The data represents an average of two independent measurements (mean±SD).

Composition of PEG-PFPE-Amide 14 and PFPE Amide 1:

The composition comprising PEG-PFPE amide 14 and PFPE amide 1 (25 μL) was sonicated in 1 mL of water (as shown in FIG. 4) or 1×HBSS (as shown in FIG. 5) for 30 seconds. The emulsion dilutions were then tested using DLS. Particle size of PEG-PFPE amide 14 in water was 144±17.8 nm with PDI ranging from 0.2 to 0.3. The critical micellar concentration in water 33.5 mg/mL was estimated by plotting scattering light intensity and particle size (FIG. 4). Particle size increased to 211±36.4 nm, with PDI ranging form 0.15 to 0.40, when PEG-PFPE was emulsified in 1×HBSS buffer. The CMC in 1×HBSS was estimated to be 30.1 mg/mL, as shown in FIG. 5.

Figure 6:
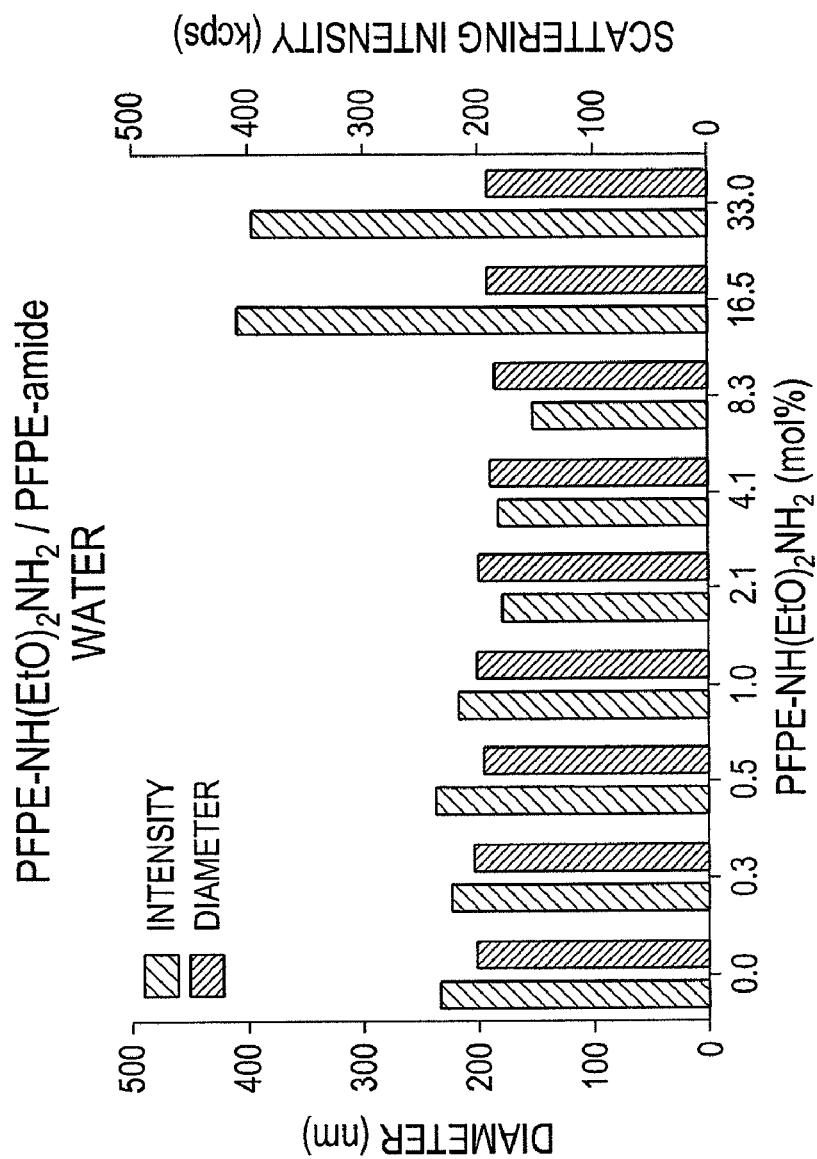
FIG. 6. Particle size measurements of the emulsification of the composition comprising PEG-PFPE amide 10 and PFPE amide 1 with different mol % of 10 in water, without additional emulsifiers or surfactants.
Figure 7:
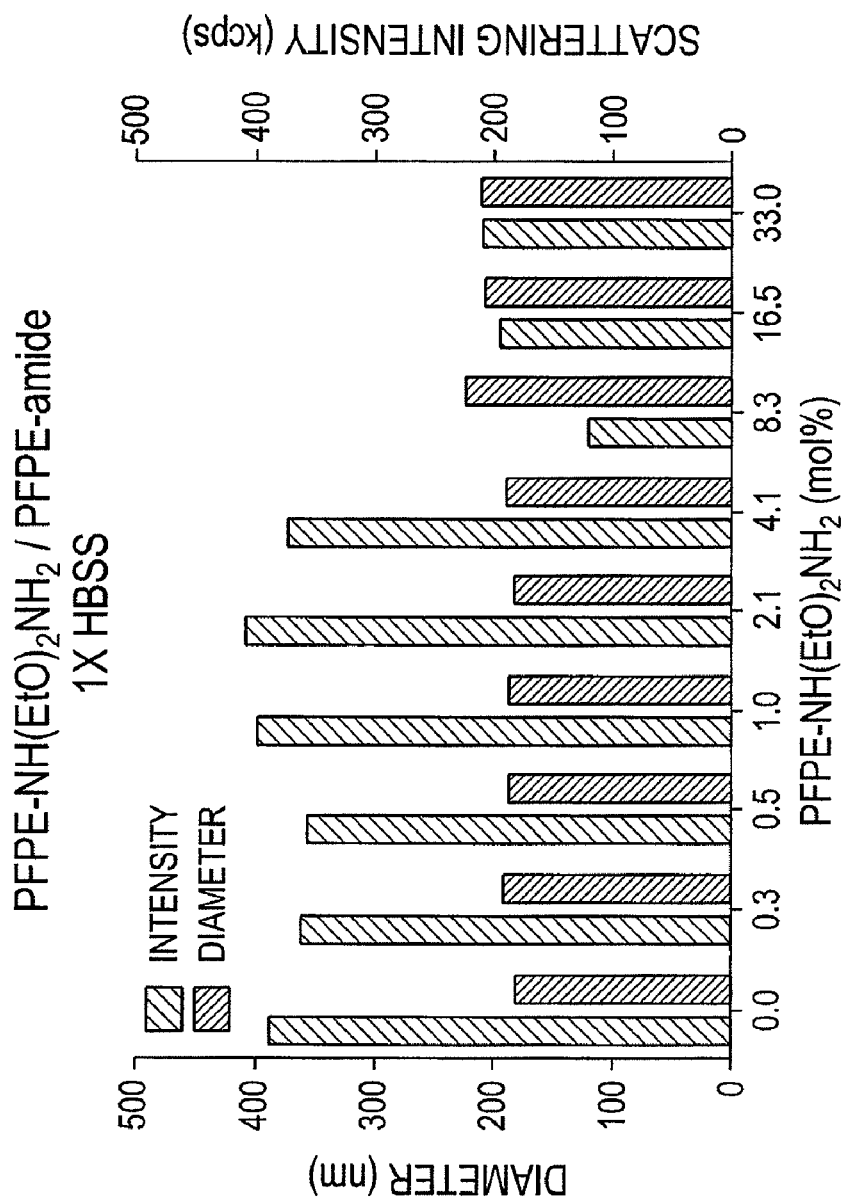
FIG. 7. Particle size measurements of the emulsification of the composition comprising PEG-PFPE amide 10 and PFPE amide 1 with different mol % of 10 in 1×HBSS without additional emulsifiers or surfactants.

Composition of PEG-PFPE-Amide 10 and PFPE Amide 1:

Different concentrations of the composition of PEG-PFPE-amide 10 and PFPE amide 1 were prepared by carefully diluting a composition of 33 mol % PEG-PFPE-amide 10 in PFPE amide 1. A total of 9 oil samples were prepared with decreasing concentrations of PEG-PFPE-amide 10, from 33 to 0 mol %. Each oil (25 μL) was sonicated in 125 μL of water or 1×HBSS for 10 sec, then diluted to 750 μL with external phase and sonicated for 30 sec, at the same power setting. The emulsions were then tested for particle size and zeta potential and stored at room temperature. FIGS. 6 and 7 shows the particle size and scattering intensity for all samples. When water was used as medium, the average particle size was 195.4±4.5 nm with PDI=0.1-0.3, as shown in FIG. 6. When 1×HBSS was used, particle size was unchanged, 193±14.5 nm with PDI=0.1-0.3, as shown in FIG. 7.

In both media, the amount of PEG-PFPE amide 10 in PFPE amide 1 had no effect on the particle size or polydispersity. Emulsions with less then 5 mol % PEG-PFPE amide 10 remained stable for at least four days at room temperature. These stable emulsions kept the same particle size, scattering intensity and polydispersity, as measured by DLS measurements. The same stability was observed both in water and HBSS buffer. Covalent conjugation of a very short PEG of only two ethylene oxide units can serve two purposes. First, it can serve as a linker for attachment of targeting agents and dyes. Second, it aids in emulsification by acting as both an emulsifier and a steric stabilizer of formed droplets.

Figure 8:
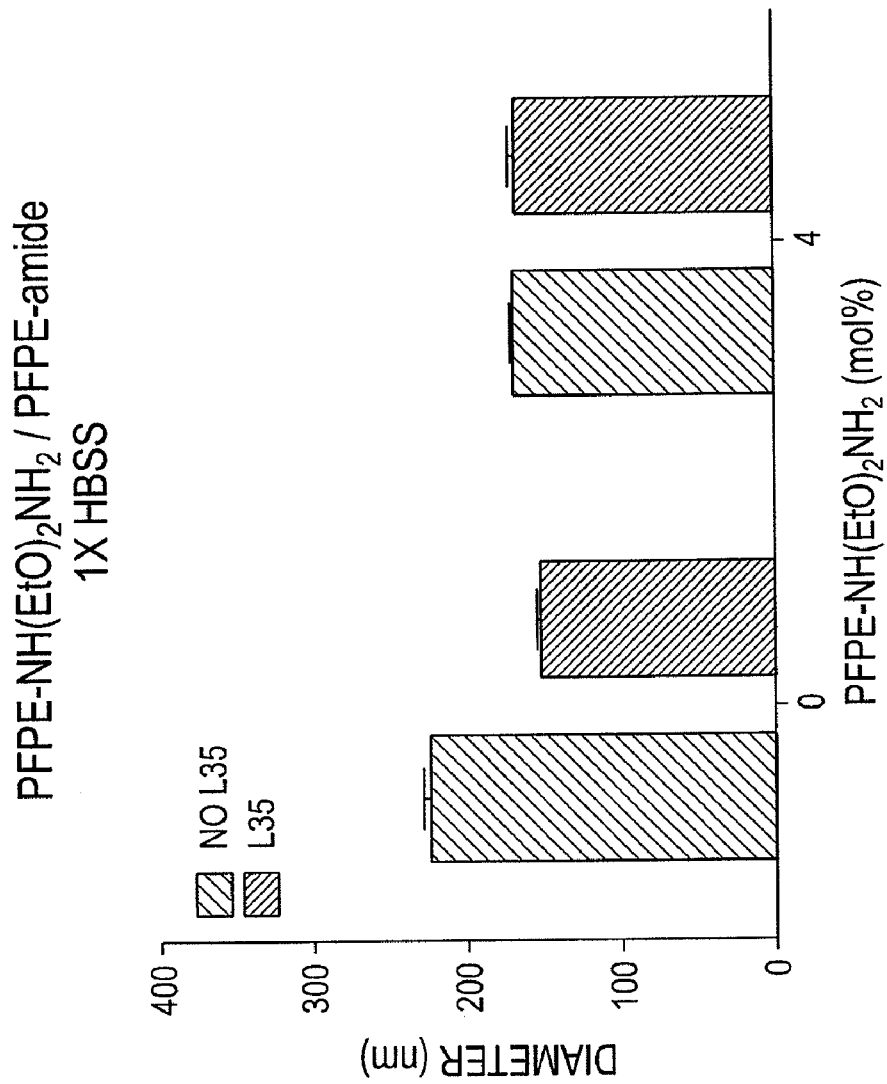
FIG. 8. Effect of PEG-PFPE-amide 10 on PFPE amide 1 emulsification using Pluronic™ L35. Emulsion was prepared by sonication.

Composition of PEG-PFPE-Amide 10 and PFPE Amide 1/L35:

The composition of PEG-PFPE-amide 10 and PFPE amide 1, with 4 mol % of 10, was compared to PFPE amide 1 alone when emulsified by sonication with L35 in a mol ratio 1:1, in 1×HBSS, following the same procedure as described above for the same composition. Data is presented in FIG. 8.

When L35 was used as emulsifier, the presence of PEG-PFPE-amide 10 on PFPE amide 1 did not have significant effect on particle size. However, emulsification of PFPE amide 1 with L35 gave significantly lower particle size then PFPE amide 1 sonicated in 1×HBSS alone. These findings indicate that the presence of hydrophilic groups surrounding the PFPE amide emulsion droplet promotes the emulsion stability.

Emulsification with Lipids:

Cationic lipids CTAB, DDAB, and a neutral lipid DMPC were used alone or with Pluronic™ L35 to emulsify PFPE amide 1. These lipids are expected to improve particle uptake by promoting cell membrane adherence. Lipids with positive charge are known to promote cell-particle interactions due to the negative charge of the cell membrane.

The addition of lipids required modification to the sonication methods. Lipids as solids were first dissolved in an appropriate organic solvent (e.g., chloroform or acetone), mixed with PFPE amide 1, and dried into a thin film using a stream of argon gas. The film was then vortexed with aqueous media (water or 1×HBSS buffer), heated to 50-70° C. for 15 minutes, and vortexed again while cooling to room temperature. Emulsions were then sonicated to decrease the particle size and PDI.

Figure 9:
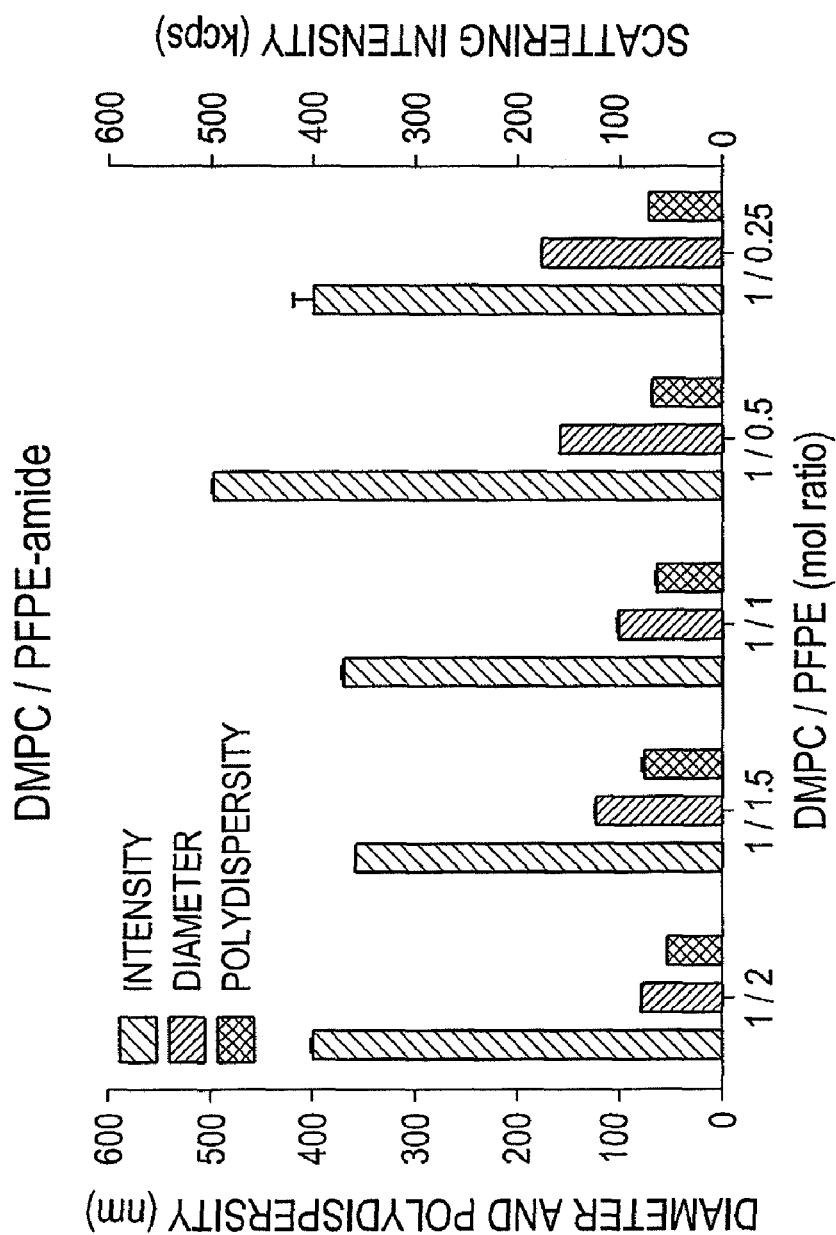
FIG. 9. Particle size and polydispersity index (PDI) were measured for PFPE amide 1 emulsified with a neutral lipid, DMPC, in various ratios using combination of thin-film and sonication methods. Data represents an average of two measurements (mean±SD).
Figure 10:
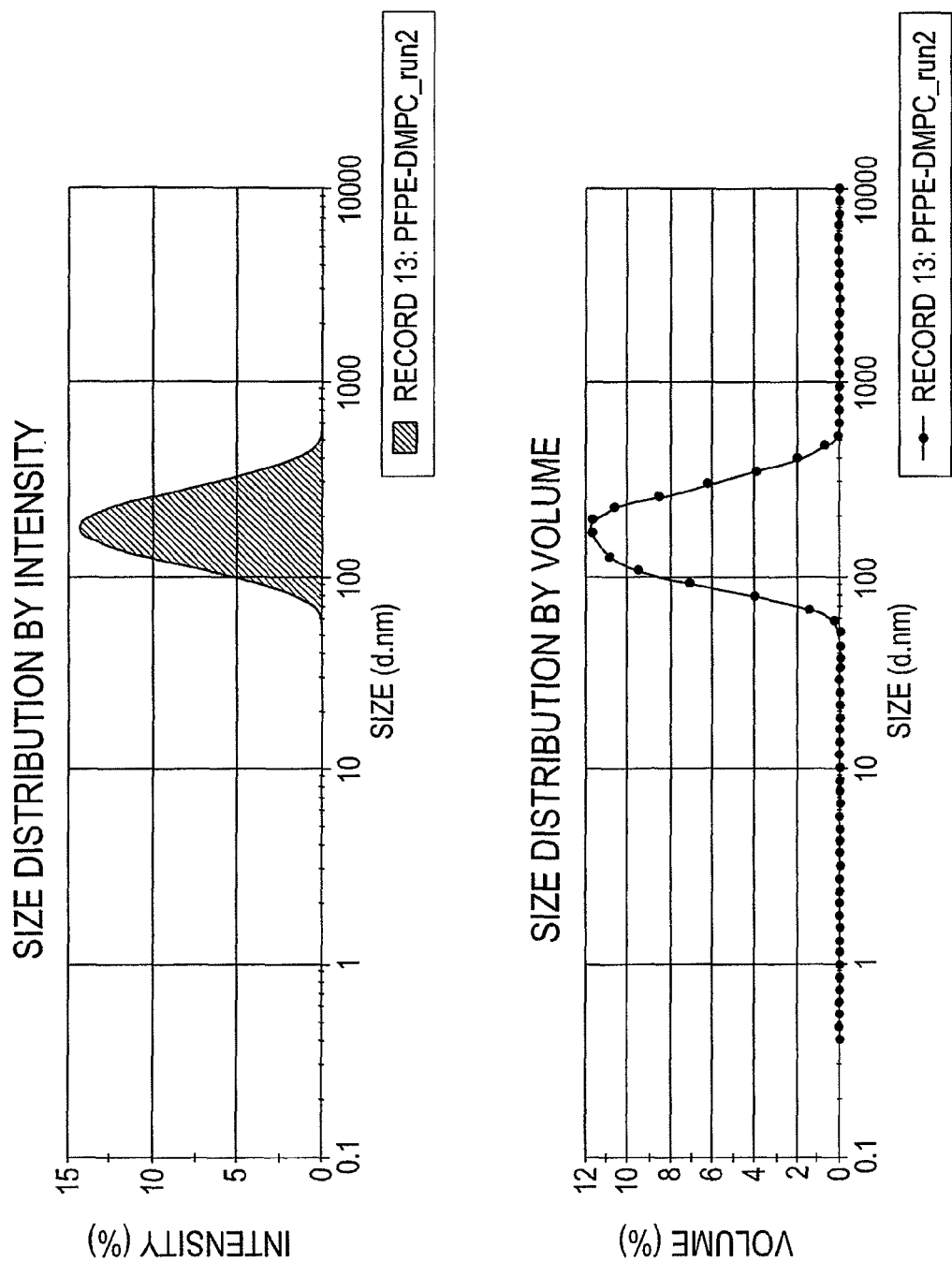
FIG. 10. Size and volume distribution of PFPE amide 1 emulsified with neutral lipid DMPC in 1×HBSS. The particle size was determined to be 159 nm with PDI=0.182 following an average of two independent measurements. Measurements performed on Zetasizer Nano (Malvern, UK).

DMPC/PFPE Amide 1 Emulsion:

PFPE amide 1 solution (152 mg/mL) in trifluoroethanol (200 μL) and DMPC solution in chloroform (200 μL), containing decreasing concentrations from 112 to 0 mg/mL, were mixed by vortexing and dried into a thin film using argon stream. The film was dried under vacuum for 30 minutes at room temperature to remove residual organic solvent. The film was mixed with water (400 μL) and sonicated 3 times for 15 seconds, diluted with 500 μL of water, and sonicated again two times for 30 seconds. Molar ratios of PFPE amide 1 to DMPC were 1:2, 1:1.5, 1:1, 1:0.5 and 1:0.25, as shown in FIG. 9. All emulsions were clear and they were kept at room temperature for 24 hours before DLS measurements. As the amount of lipid was decreased, the particle size increased and the polydispersity decreased. An optimal particle size (158.5±1.0 nm) and PDI (0.17-0.19) was achieved at a molar ratio 1:0.5 PFPE amide 1 to DMPC, as is shown in FIG. 10.

Figure 11:
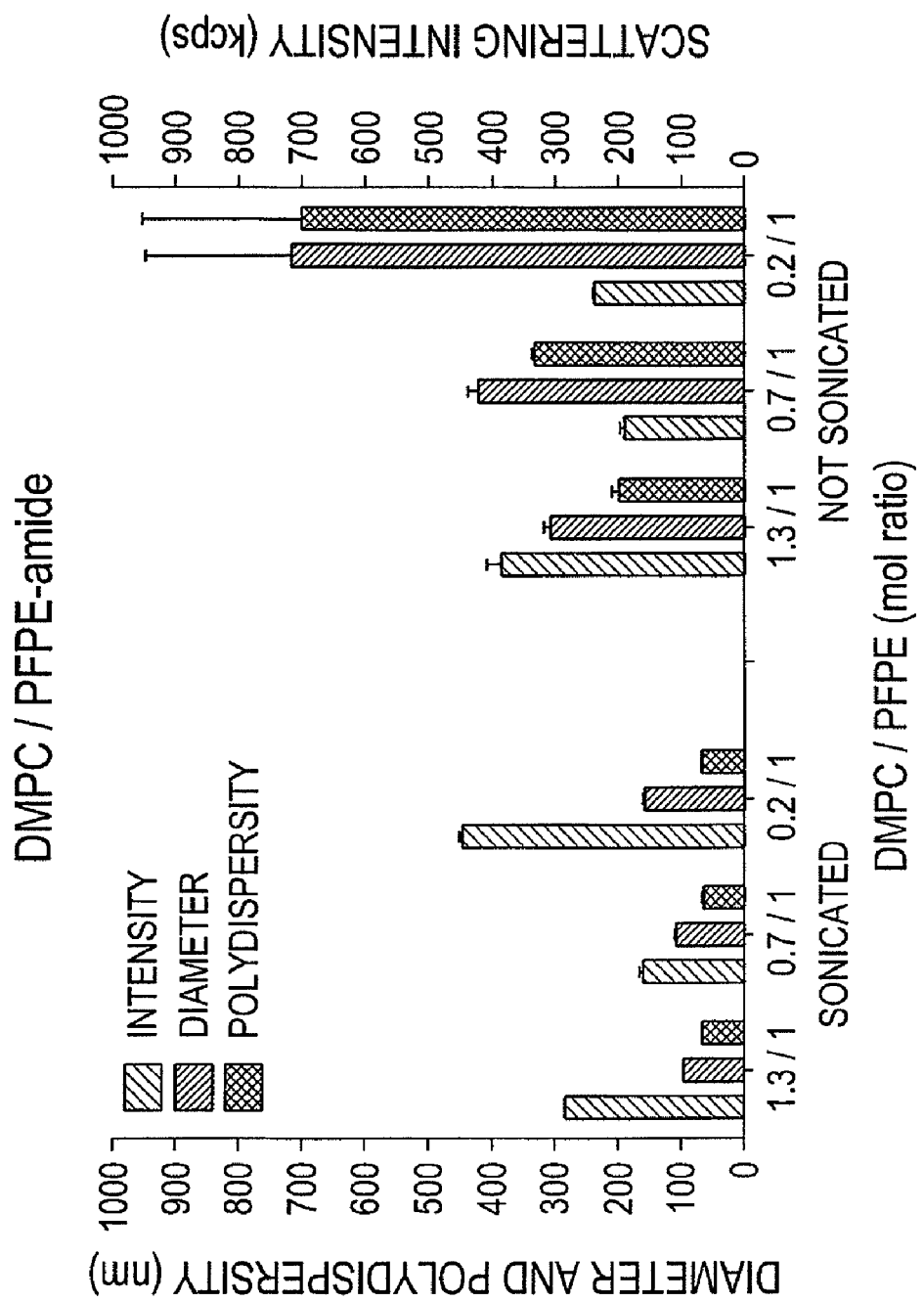
FIG. 11. Comparing particle size and PDI for low and high energy emulsification process for lipid based PFPE amide 1 emulsions. Sonication significantly decreased emulsion droplet size. Data represents an average of two measurements (mean±SD). Measurements performed on Zetasizer Nano (Malvern, UK).

To test the effect of high-energy emulsification on the PFPE amide 1/lipid mixtures, the same procedure as above was used, and all emulsions were split in half. One half was sonicated and the other half was not. The particle size decreased significantly when sonication was used, as shown in FIG. 11.

Figure 14:
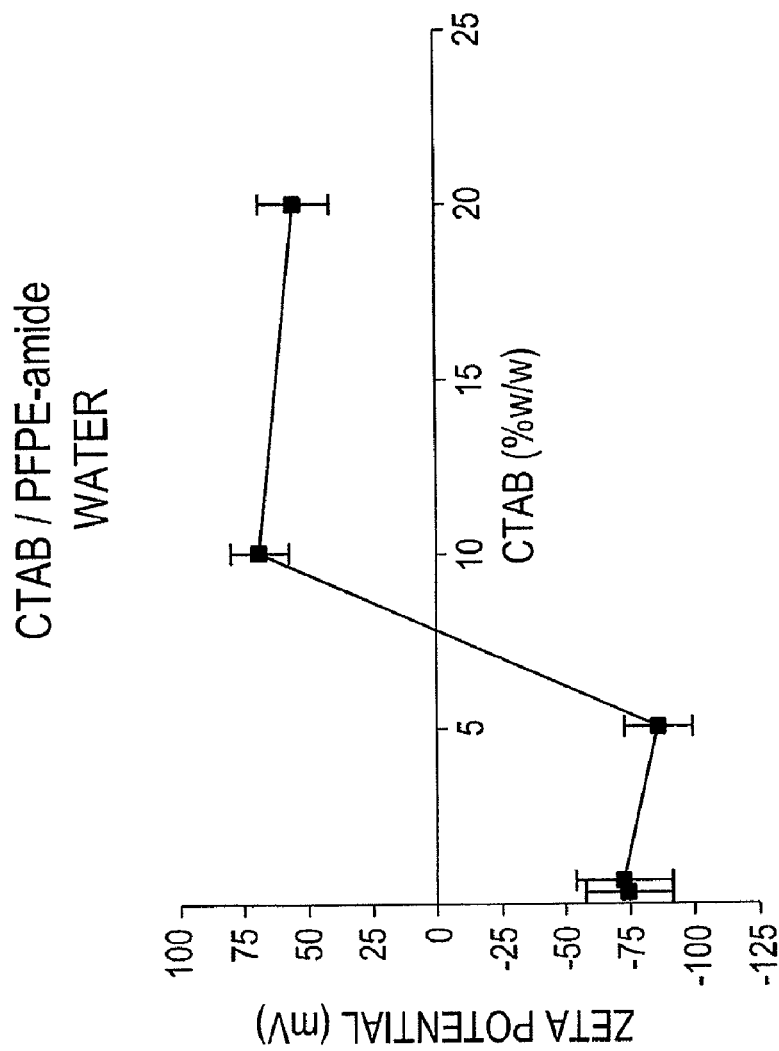
FIG. 14. Reversal of zeta potential sign by addition of cationic lipid to PFPE amide 1 emulsion. Data represents an average of two measurements (mean±SD). Measurements performed on Zetasizer Nano (Malvern, UK).

Introducing a neutral lipid did not change the intrinsically negative zeta potential of the PFPE amide 1 emulsified in water. The zeta potential was also negative when PFPE amide 1 was emulsified with neutral Pluronics™ in water or 1×HBSS. The neutral lipid DMPC was used as a model to test feasibility of mixing PFPE amide 1 with lipids. Cationic lipids (CTAB or DDAB) were then introduced to investigate reversal of the negative zeta potential of PFPE amide 1 particles made with Pluronics™, as shown in FIG. 14.

Figure 12:
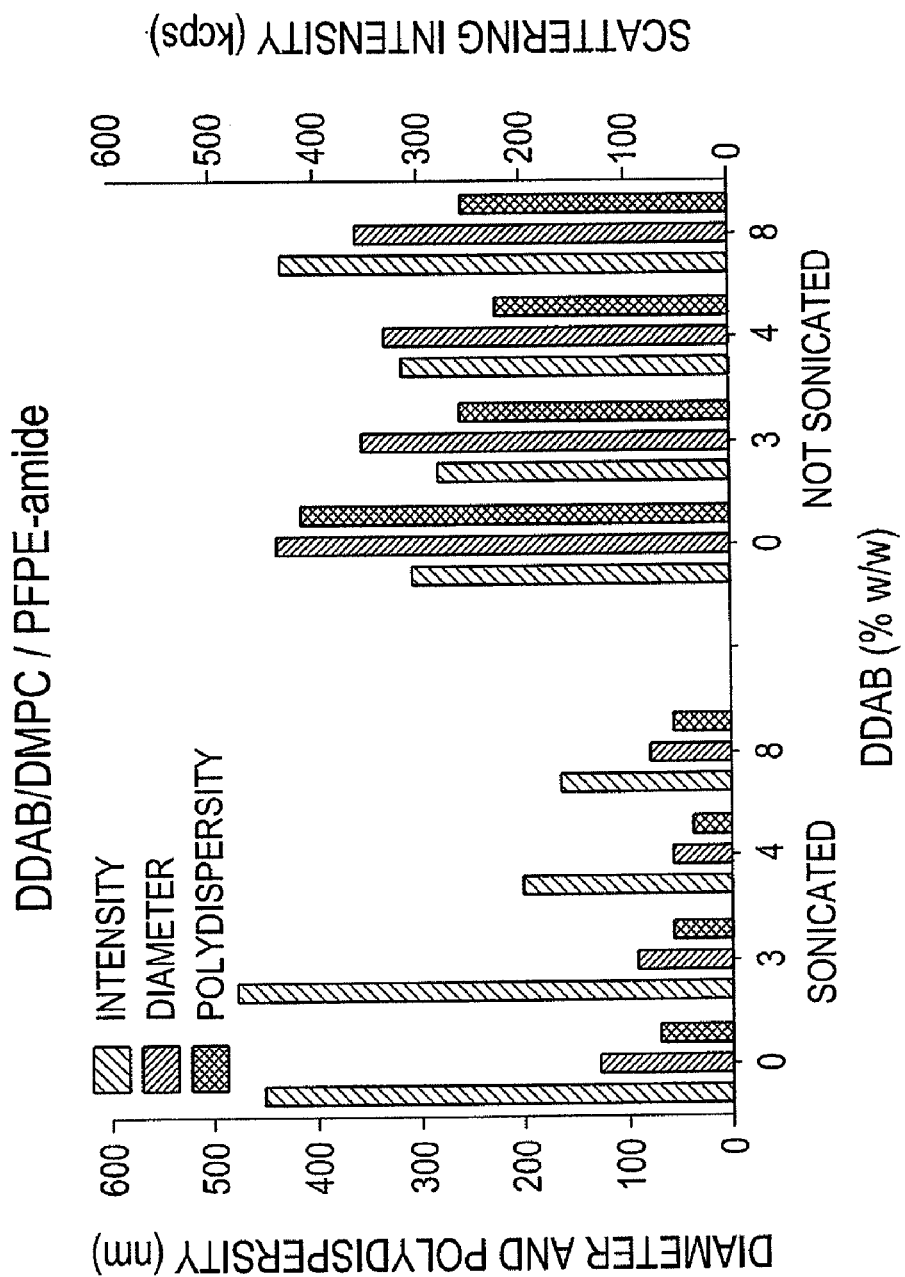
FIG. 12. Characterization of a DDAB/DMPC/PFPE amide 1 emulsion. Sonication decreased emulsion droplet size and PDI. Data represents an average of two measurements (mean±SD). Measurements performed on Zetasizer Nano (Malvern, UK).

DMPC/DDAB/PFPE Amide 1:

In a round bottom glass tube, DMPC (18 mg), DDAB (0-8 mg) and PFPE amide 1 (76 mg) were dissolved in trifluoroethanol (400 μL), vortexed and dried into a thin film using a stream of argon gas. The film was then further dried for 15 minutes under vacuum. Water (1 mL) was added while vortexing vigorously, and the emulsion was heated for 15 minutes at 60° C. Each emulsion was divided in two 0.5 mL portions, and one was sonicated for 30 seconds at room temperature, and the other was left untreated at room temperature. All samples were diluted by ⅓ with water prior to DLS measurements. The DLS measurements showed a clear need for sonication in this system to decrease particle size and polydispersity. Brief sonication (<20 sec) gave a dramatic reduction in particle size and polydispersity. The particle size was the smallest with 4% DDAB, as shown in FIG. 12. When introducing lipids to PFPE emulsions, due to the high lipophobicity of PFPE, high energy emulsification methods were needed. Lipophobicity of PFPE also explains why stability of lipid-containing emulsions was lower then in emulsions made with Pluronics™ alone.

Figure 13:
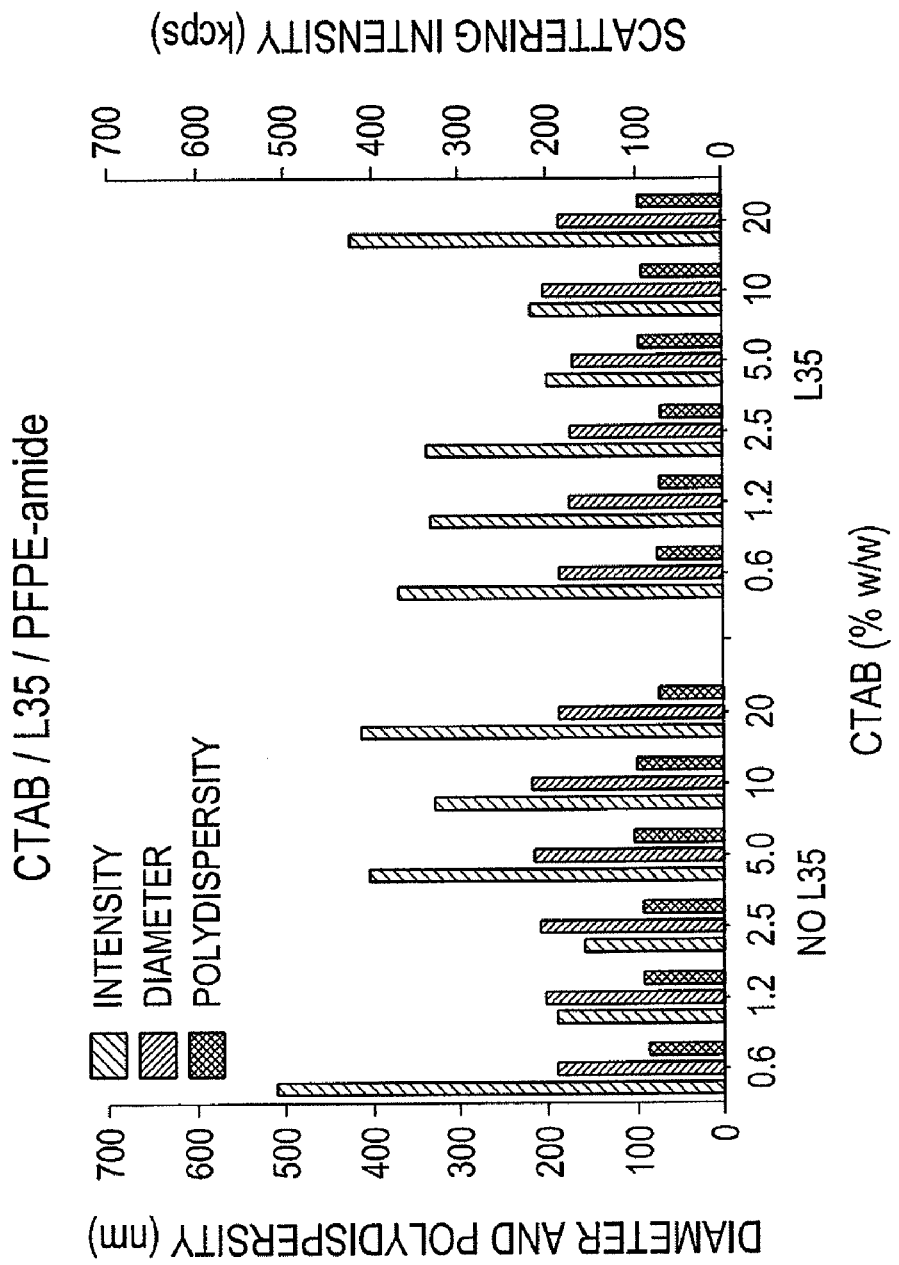
FIG. 13. Dynamic light scattering study of the effects of different amounts of cationic lipid (CTAB) on PFPE amide 1 emulsification, alone and in combination with Pluronics™. No significant change in size and PDI with increasing concentration of CTAB.

CTAB/PFPE Amide 1:

CTAB and PFPE-amide 1 were dissolved in trifluoroethanol (300 μL) in a round bottom glass tube. Argon gas was blown into the tube through a pipette tip until a homogenous off-white film was formed. The tube was connected to vacuum for at least 30 minutes. Water medium or 1×HBSS were added (1 mL/sample) while vortexing vigorously and then the tube was placed in a water bath at 60° C. for 15 minutes. Each sample was then sonicated for 30 sec to homogenize the particles. The DLS measurements showed no change in particle size with increasing amounts of CTAB. There was also no change in size when L35 was used as co-emulsifier, as shown in FIG. 13. However, the zeta potential did increase with CTAB addition, as shown in FIG. 14. The percentages shown are with respect to the dry material weight.

PFPE Amide 1/Polyethylamine Emulsion by Sonication:

Polyethylenimine (PEI) is a polyamine transfection agent known to help DNA, RNA and proteins enter into cells. Low molecular weight PEI (e.g., 430 or 800) was utilized as both a coemulsifier and a means to introduce primary amino groups to facilitate cellular uptake of the nanoparticles. The goal was to introduce a sufficient number of free amino groups and to keep the particle size and PDI as low as possible. PEI also serves as a surfactant due to large number of hydrophilic groups (i.e., primary amino groups).

Figure 15:
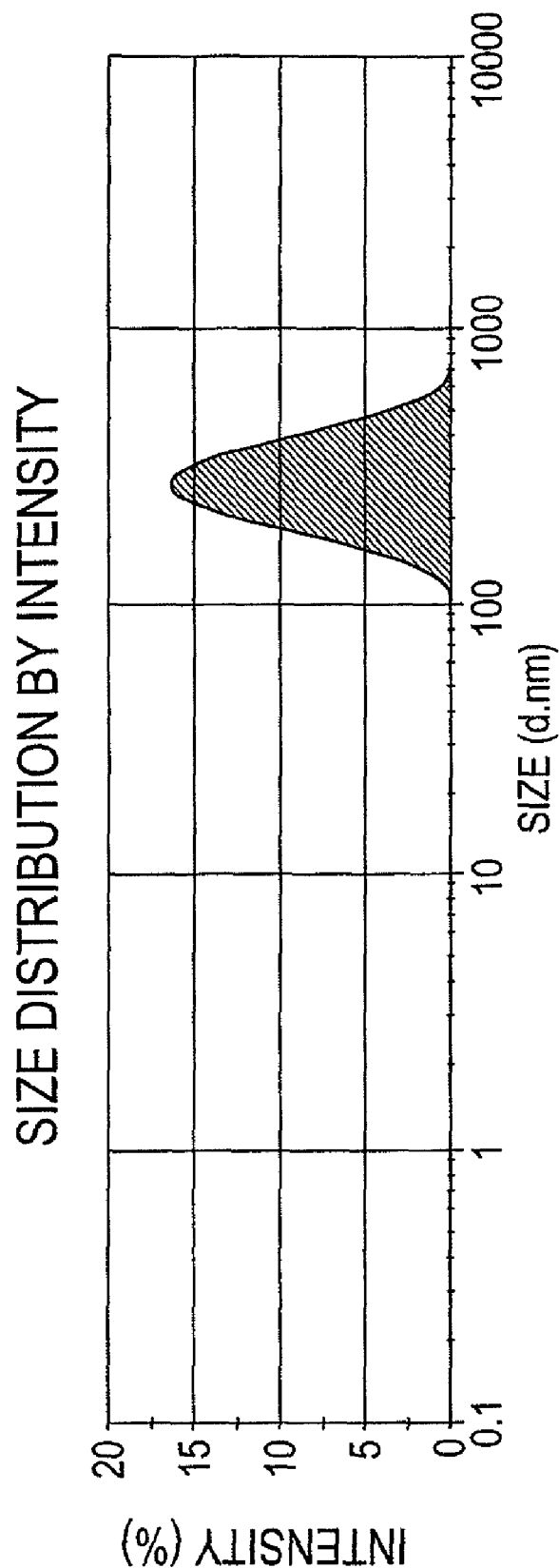
FIG. 15. Size distribution by light scattering intensity distribution of PFPE amide 1/PEI emulsion in water. Presence of PEI did not affect the size or PDI.

The primary amines in polyethylamine (PEI, average MW=800) interact with highly reactive PFPE methyl ester 39 end groups. 5% of PFPE methyl ester 39 mixed with PFPE amide 1 was used for emulsification with PEI. PEI was dissolved in absolute ethanol (100 mg/mL). PFPE methyl ester 39/PFPE amide 1, 5:95 v:v (50 μL), was vortexed with water (450 μL) and PEI ethanol solution (100 μL), placed on a rotovap at 40° C. to remove ethanol under vacuum, and then sonicated two-times for 10 sec. The solution was diluted four-times to measure particle size by DLS, as shown in FIG. 15. This was the first PFPE/PEI emulsion ever prepared and PFPE was never before combined with polyethylenimines. Highly hydrophilic PEI serves as an emulsifier and gives needed amino groups for uptake.

Figure 16:
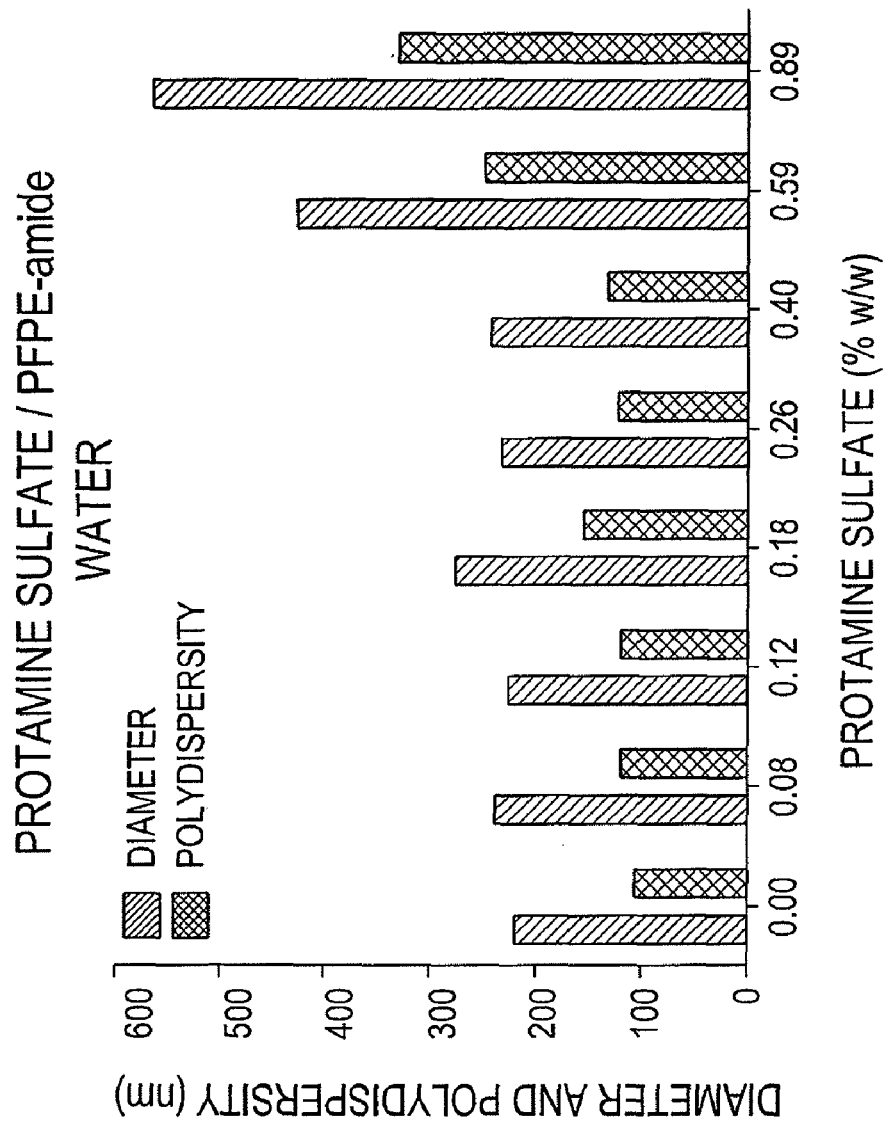
FIG. 16. Particle size and PDI measurements of protamine sulfate/PFPE amide 1 nanoparticles prepared by sonication. Increasing amounts of Protamine Sulfate increased both size and PDI.
Figure 17:
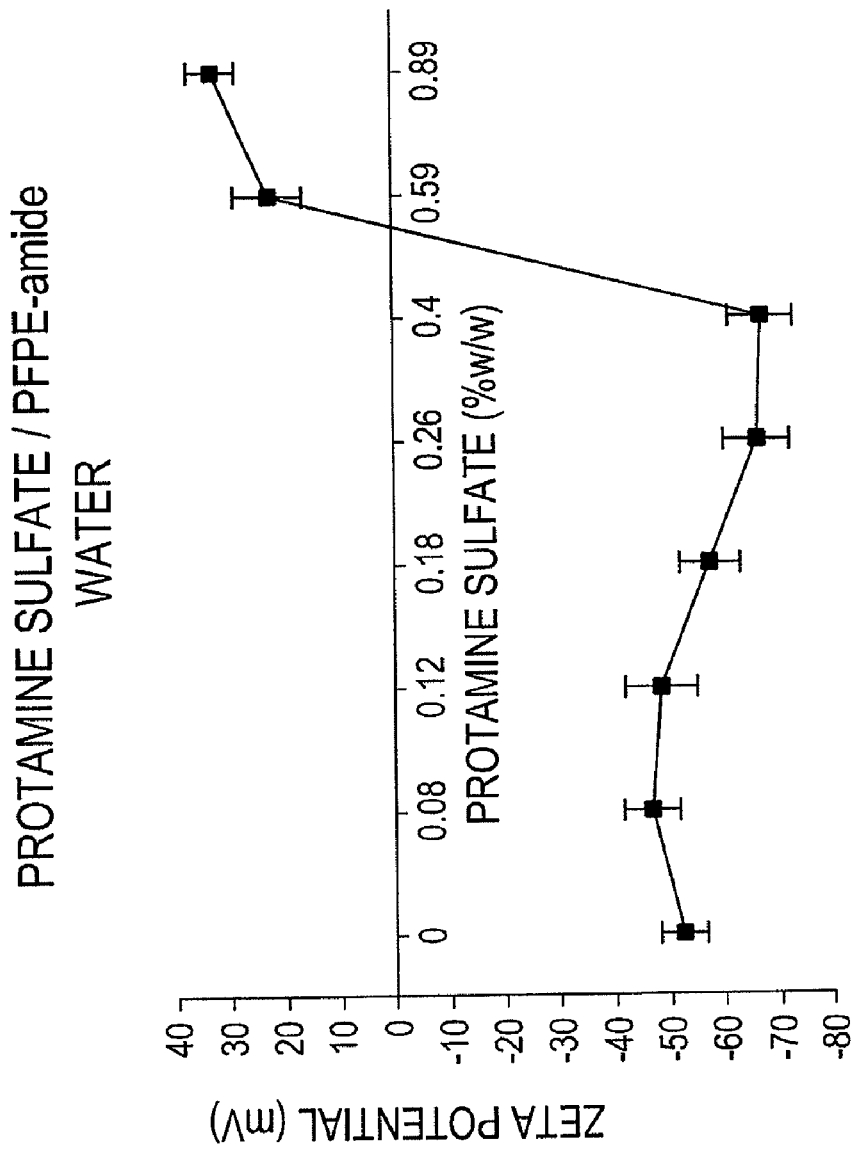
FIG. 17. Protamine Sulfate/PFPE amide 1 zeta potential measurement. When Protamine Sulfate reached 0.5% w/w, the particle size increased and the zeta potential changed its sign to positive. Data represents an average of two measurements (mean±SE). Measurements performed on Zetasizer Nano (Malvern, UK).

PFPE Amide 1/Protamine Sulfate Nanoparticles by Sonication:

Protamine sulfate is a common transfection reagent, and it is highly biocompatible. Protamine sulfate is FDA approved for human use and clinically used as an antagonist to heparin. Its low toxicity makes it a desirable delivery reagent for DNA and RNA. Nanoparticles of PFPE amide 1 formulated with protamine sulfate were designed to promote cellular uptake. For each test emulsion of PFPE amide 1 with protamine sulfate, PFPE amide 1 (50 μL) was sonicated for 10 sec in 300 μL of deionized water. Protamine sulfate (salmine sulfate, USP) solution in water (300 μL, 0 to 20 mg/mL) was added and vortexed vigorously for 20 sec. The emulsions were sonicated for 10 sec and diluted ⅓ in water for DLS measurements. Increasing amounts (% w/w) of protamine sulfate led to an increase in particle size and zeta potential, as shown in FIGS. 16 and 17.

Figure 18:
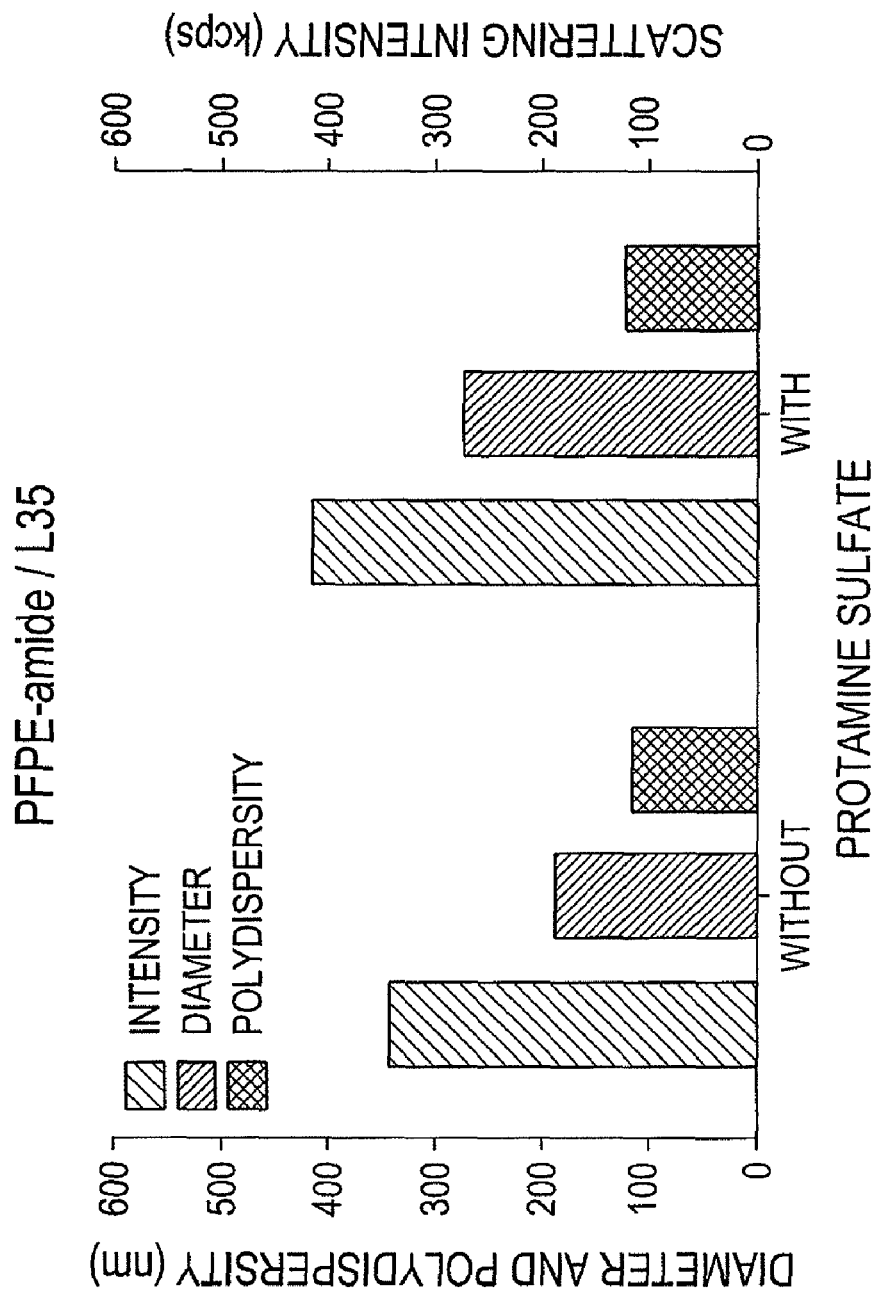
FIG. 18. Dynamic light scattering (DLS) measurements of PFPE amide 1/L35 emulsion coated with protamine sulfate for improved cellular delivery. Presence of protamine sulfate slightly increased particle size of coated particles.
Figure 35A:
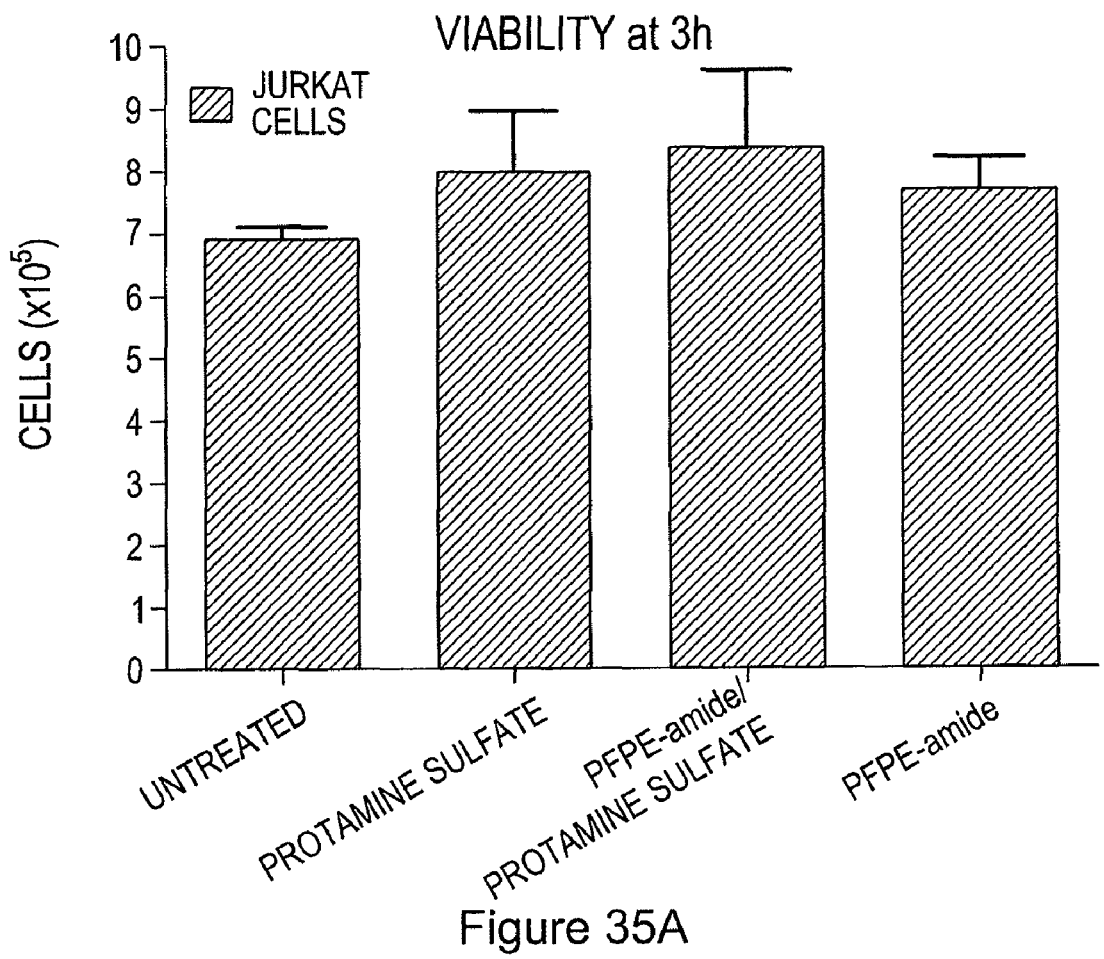
FIGS. 35A-35B. Jurkat cells labeling with PFPE/L35 emulsion with and without protamine sulfate. A) Cell numbers were estimated from Cell Titer Glo luminescence-cell number correlation curve. B) Fluorine content estimated from 19F NMR spectra for Jurkat cell suspensions. A dramatic increase in uptake for the protamine sulfate coated nanoemulsion droplets was observed. Data represents the average of two independent measurements (mean±SD).
Figure 35B:
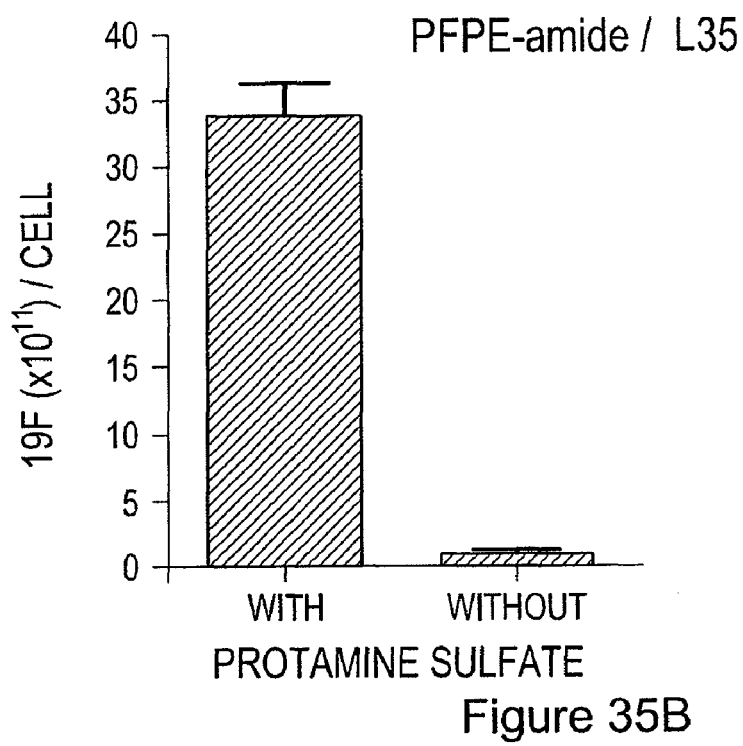
Figure 36:
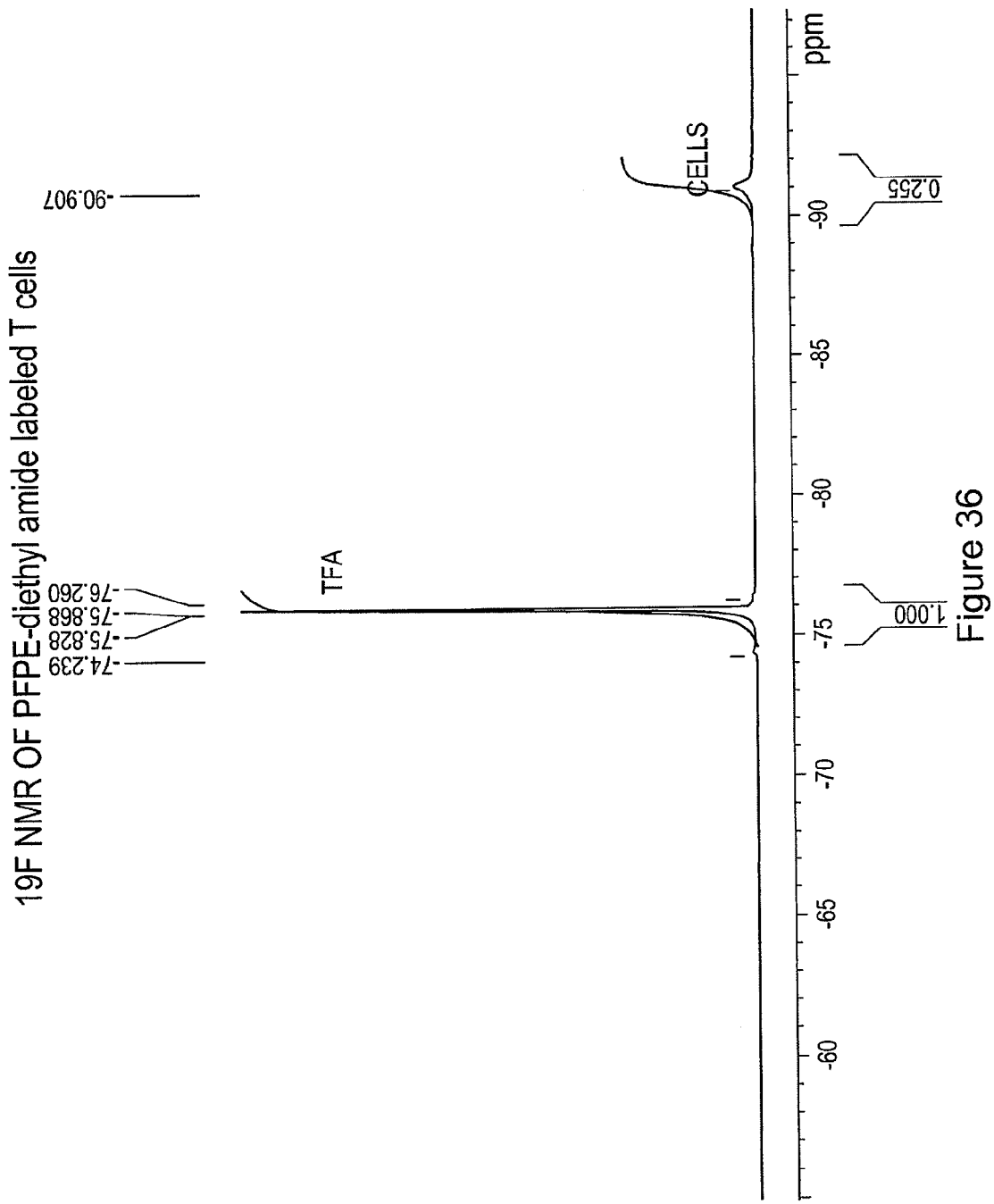
FIG. 36. 19F NMR spectrum of PFPE amide/L35 labeled T cell pellet. TFA was used as a reference.

Protamine Sulfate Coated PFPE Amide 1/L35 Emulsion:

PFPE amide 1 was emulsified with L35 using sonication, in molar ratio 1:1, as described above, and diluted in serum free media containing low concentration of protamine sulfate (10 μg/mL). The mixture was incubated at room temperature for 30 min. The emulsion was analyzed by DLS without further dilution, as shown in FIG. 18. Coating PFPE amide 1/L35 emulsion droplets with protamine sulfate increased the droplet size and PDI by 30%. This increase in size had no detrimental effects on cellular uptake of PFPE/L35 particles, as discussed below. Coating the PFPE amide 1/L35 nanoemulsion droplets with protamine sulfate increased uptake in jurkat cells several fold (FIG. 35B) without having any negative effects on the cell viability (FIG. 35A).

These initial experiments with incorporating protamine sulfate into the PFPE nanoemulsions served as the basis for the design of highly stable and very efficient PFPE/F68/Protamine Sulfate emulsions. In this new emulsion the protamine sulfate was incorporated into the nanoparticles at low amount (0.01-1% w/w) by microfluidization.

Microfluidization Emulsification Examples

Sonication methods are effective on small scale, resulting in small size particles (<200 nm) and low PDI (0.1-0.3) in most cases. However this method cannot be used for large scale preparations. Our goal was to prepare batches of stable emulsions for repeated cell labeling and MRI imaging. Presented studies indicate a clear need for high energy methods. Microfluidization utilizes high shear forces to decrease the droplet size of the prepared emulsions and exhibited a decreased PDI.

Microfluidization of PFPE Amide 1/F68:

Pluronic™ F68 is a nontoxic and FDA approved emulsifier. It has been approved in presence of egg yolk lecithin for emulsification of perfluorocarbons in blood substitutes preparations. F68 has a high molecular weight (8400) and provides greater stability to PFPE nanoemulsions compared to L35. F68 is used as an emulsifier for most of the examples presented below using microfluidization, and in some cases in combination with sonication.

Figure 19:
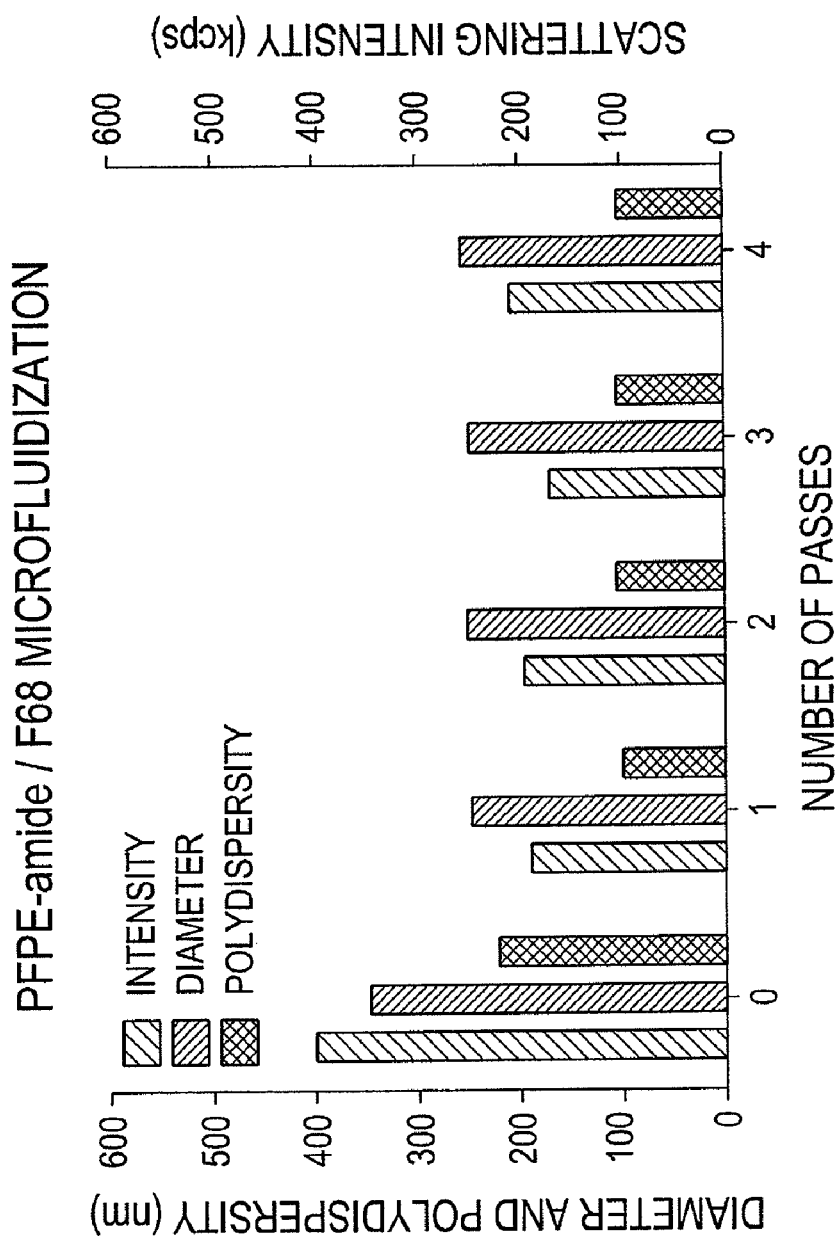
FIG. 19. Particle size and PDI measurements after microfluidization of PFPE amide 1/F68 emulsion in 1×HBSS. Increased number of passes decreased particle size and PDI.
Figure 20:
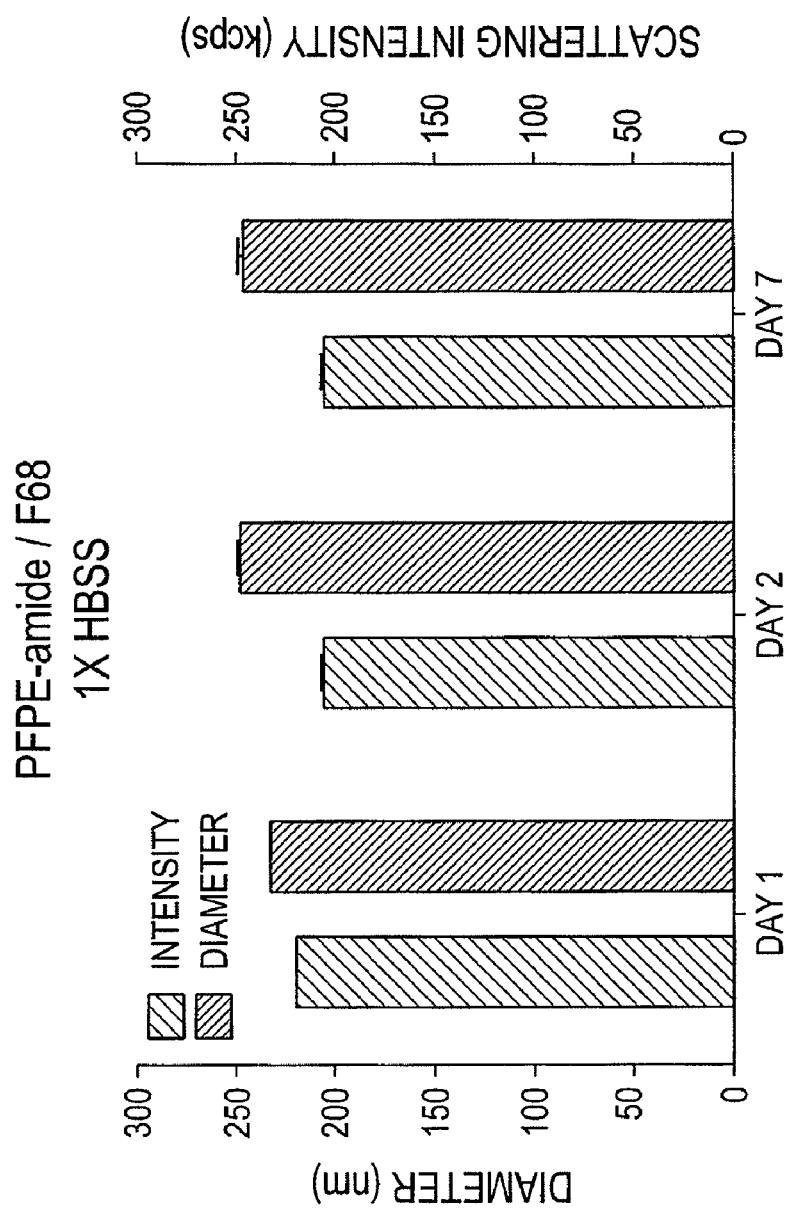
FIG. 20. Stability of PFPE amide 1/F68 microfluidized emulsion in 1×HBSS evaluated by DLS measurements over time. Data represents an average of two independent measurements (mean±SD).
Figure 21:
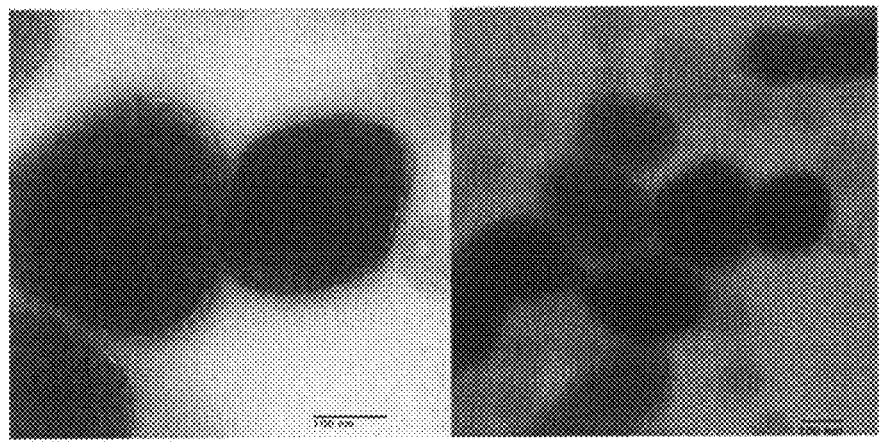
FIG. 21. Electron microscopy (EM) measurements, magnification 150× and 70× respectively, showed well defined droplets with average size 200 nm of a PFPE amide 1/F68 microfluidized emulsion.

PFPE amide 1 (1 mL) was mixed by vortexing with F68 solution in 1×HBSS buffer (67 mg/mL, 4 mL), followed by three periods of sonication each lasting for one minute, where the mix was cooled on ice between the periods for 30 sec. The emulsion was then diluted to 20 mL with 1×HBSS and passed through a microfluidizer (M-110S Microfluidics, Inc. Newton, Mass.) at 40 psi working air pressure. Initial sonication produced large particles (~345 nm) and large PDI (0.4) due to low energy transfer efficiency from the tip of sonicator through the large volume (4 mL) of the pre-emulsion. The first pass through the microfluidizer had the most dramatic effect, decreasing particle size by 100 nm, and decreasing the PDI three-fold. Further passages did not have a significant effect on particle size, and PDI stayed constant, as is shown in FIG. 19. PFPE amide 1/F68 emulsion was monitored by DLS for one week. It showed no changes in particle size and PDI over this period, as is shown in FIG. 20. Particle size of PFPE amide 1/F68 microfluidized emulsion was confirmed by electron microscopy (EM), as is shown in FIG. 21.

Microfluidization of PFPE Amide 1/L35 and PFPE Amide 1/L64:

PFPE amide 1 (637 μL), L35 (9 μL) or L64 (13.8 μL) were mixed by vortexing with 13.2 mL of 1×HBSS and passed through a microfluidizer 2 times at 40 psi working pressure. The emulsions were vortexed again, sealed in containers and stored at room temperature for four days prior the first DLS measurements.

Figure 22:
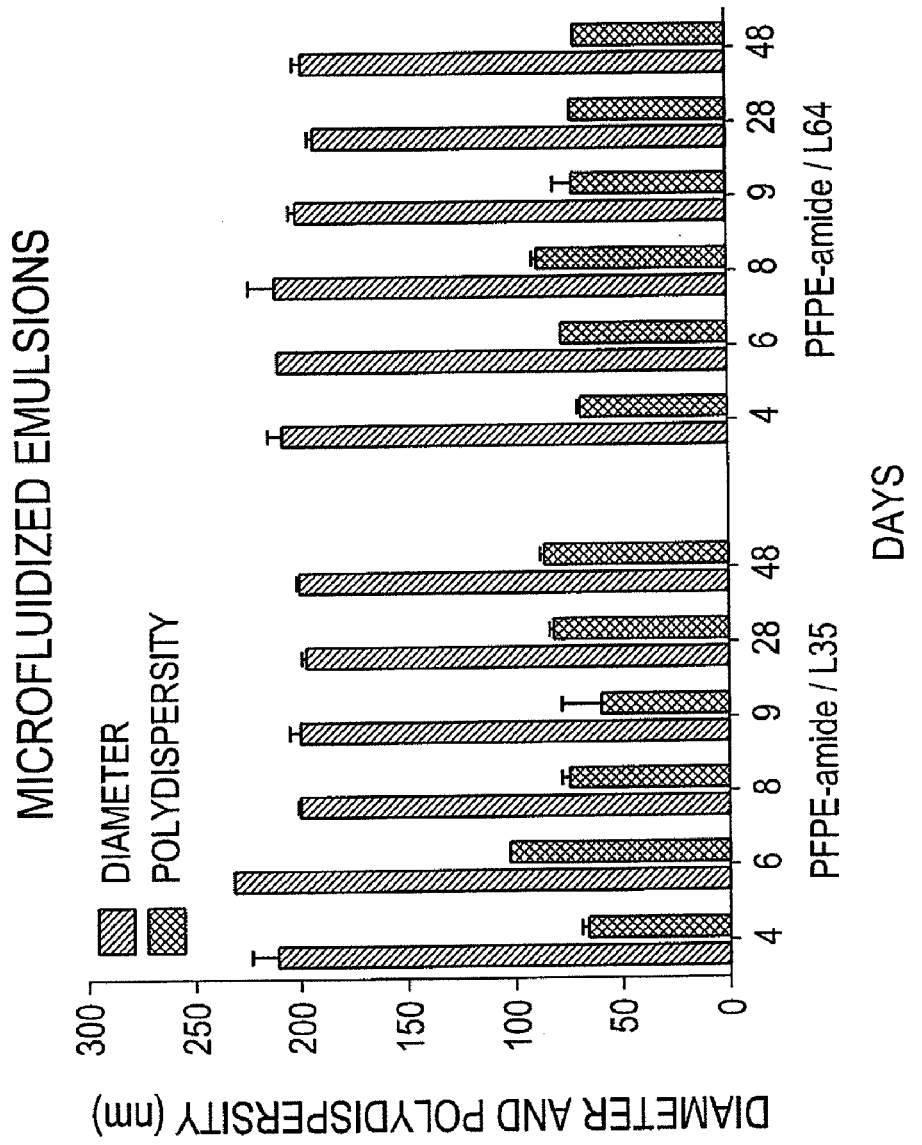
FIG. 22. Stability of microfluidized emulsions containing PFPE amide 1/L35 and PFPE amide 1/L64 prepared in water and stored at room temperature. Data represents an average of two independent measurements (mean±SD). Emulsions were stable for 7 weeks as shown by no changes in size and PDI over time.

The emulsion sedimented slowly but homogenized quickly by simple shaking. No oil separation was observed during the follow-up. Particle size and PDI stayed constant over six weeks of testing, as is shown in FIG. 22. When the PFPE amide 1 without Pluronics™ was microfluidized, the emulsion had the same particle size, but it degraded and oil drops formed in only two days. It was clear that a small amount of Pluronics™ was necessary to keep the droplets of PFPE amide 1 from coalescing. The molar ratio of PFPE amide 1 to Pluronics™ was 100:1.

Microfluidization of PFPE Amide 1/F68 with PEI

Figure 23A:
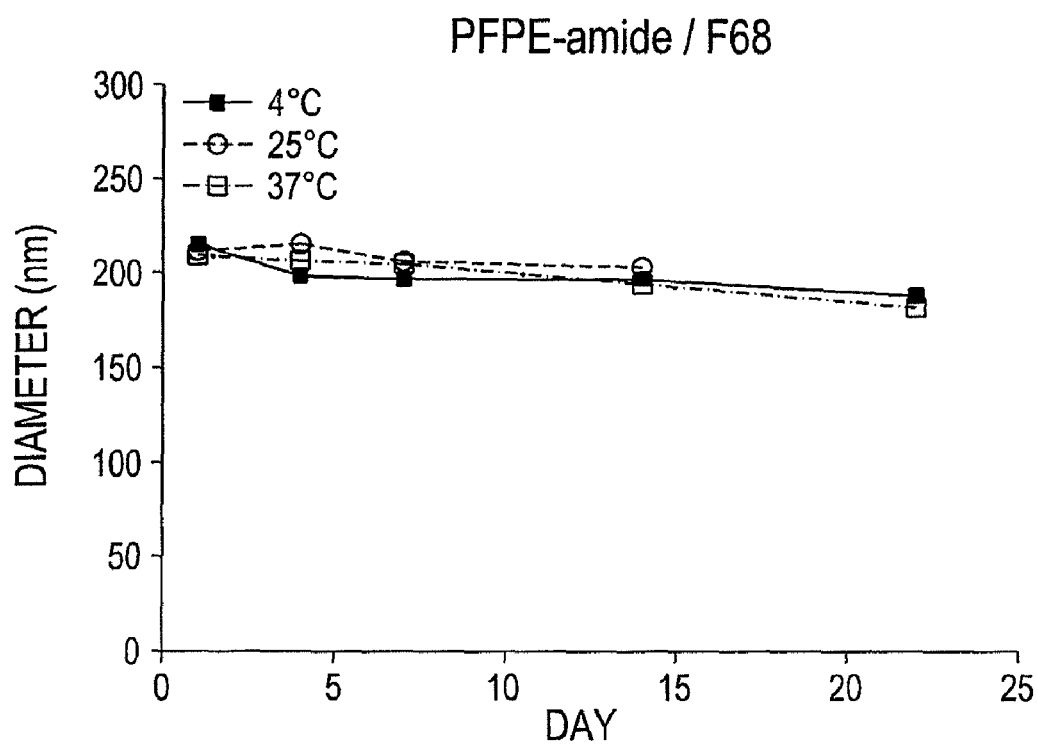
FIG. 23. Stability of PFPE amide 1/F68 emulsions microfluidized with/without PEI (low MW) in water. All emulsions were stored at the original concentration and diluted 10 times in water prior to each measurement. Data represents particle size presented as diameter measured by DLS over time after storage at different temperatures.
Figure 23B:
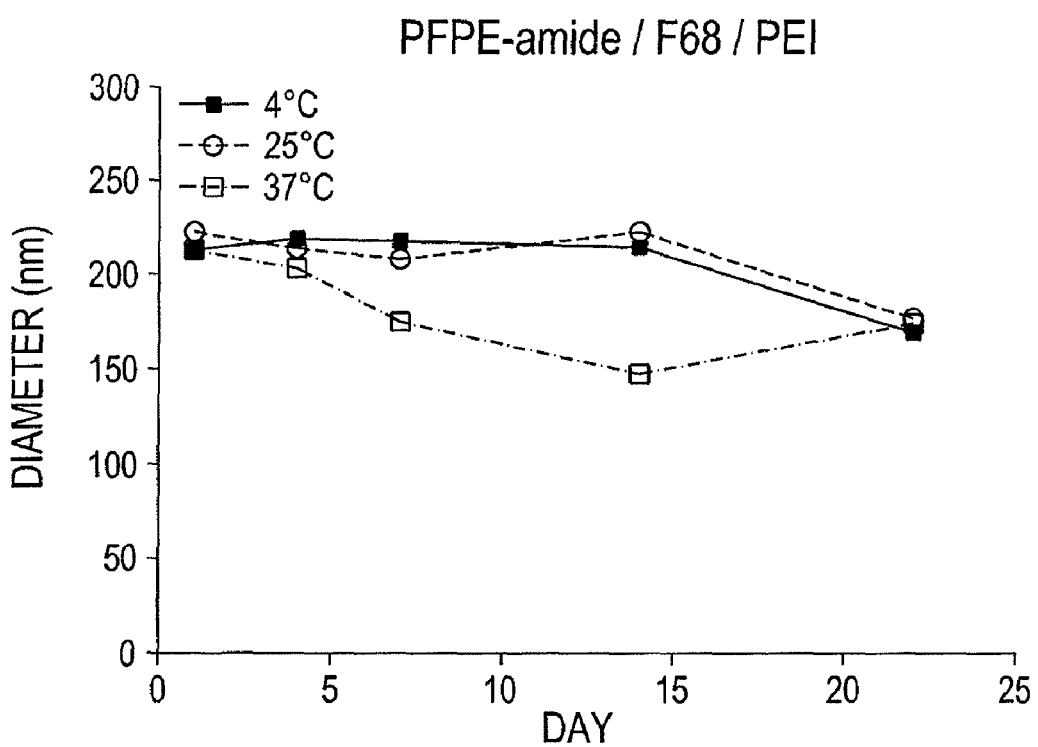
Figure 41:
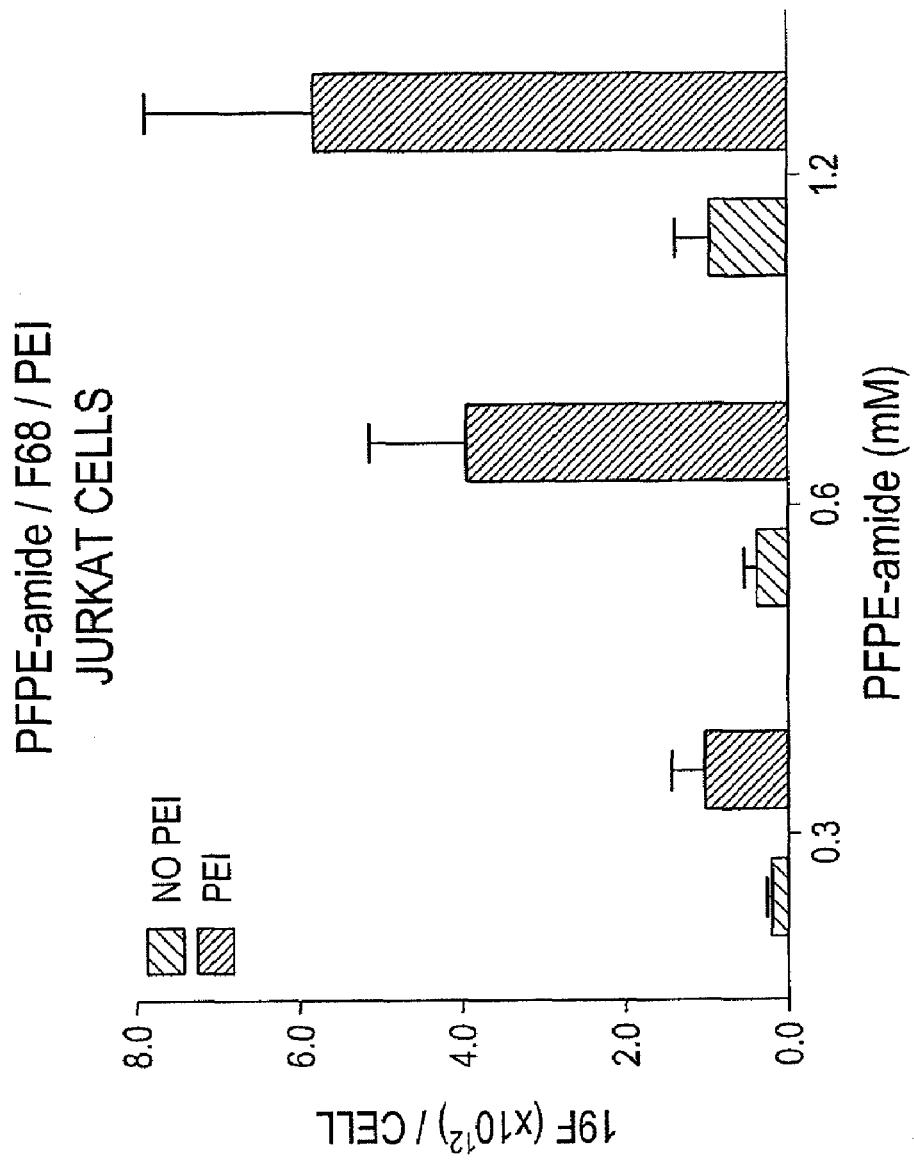
FIG. 41. Jurkat cells labeled with PFPE-oxide/F68 emulsions with and without PEI. Uptake was increased by PEI several fold. The data represents an average of triplicate experiments (mean±SD).

Polyethylenimine (PEI, MW~430) was not coupled directly to PFPE, but incorporated into the emulsion during processing to coat the particles with primary and secondary amine groups that are known to promote cellular uptake. PFPE diethyl amide 1 (10% w/w) was emulsified with F68 in water by microfluidization. PFPE-diethyl amide 1 (1.52 g, 1 mL) and F68 solution (0.68 mL, 100 mg/mL in water) were mixed, vortexed in water (6.7 mL) and then processed using an Ultraturax device (Tekmar, Cincinnati, Ohio) for 5 min at room temperature. PEI (Mn~430) solution (0.52 mL, 100 mg/mL in water) and 6.7 mL of water were added, and the emulsion was vortexed on high for 2 min. The pre-emulsion was passed through the microfluidizer while the processing chamber was chilled on ice. The processing included two sequential passes at a 50 psi working pressure. A control emulsion (PFPE-diethyl amide/F68) was prepared the same way without the PEI solution. Particle size was 200 nm on average and the PDI ranged form 0.1-0.2. The presence of PEI did not affect the particle size. Stability was tested at 4, 25 and 37° C. for three weeks using DLS measurements. The PFPE/F68 emulsion was stable at 37° C. for at least two weeks and the PFPE/F68/PEI emulsion was stable for at least three weeks (FIG. 23); these data represent sequential measurements of particle size at different temperatures. The emulsions were stored at the original concentration and diluted 10-fold prior to each DLS measurement. No significant changes in PDI were observed. These two emulsions were compared in uptake experiments using Jurkat cells, and a significant increase in uptake was observed when PEI was present, as shown in FIG. 41.

PFPE-Oxide/F68/PEI

Figure 24A:
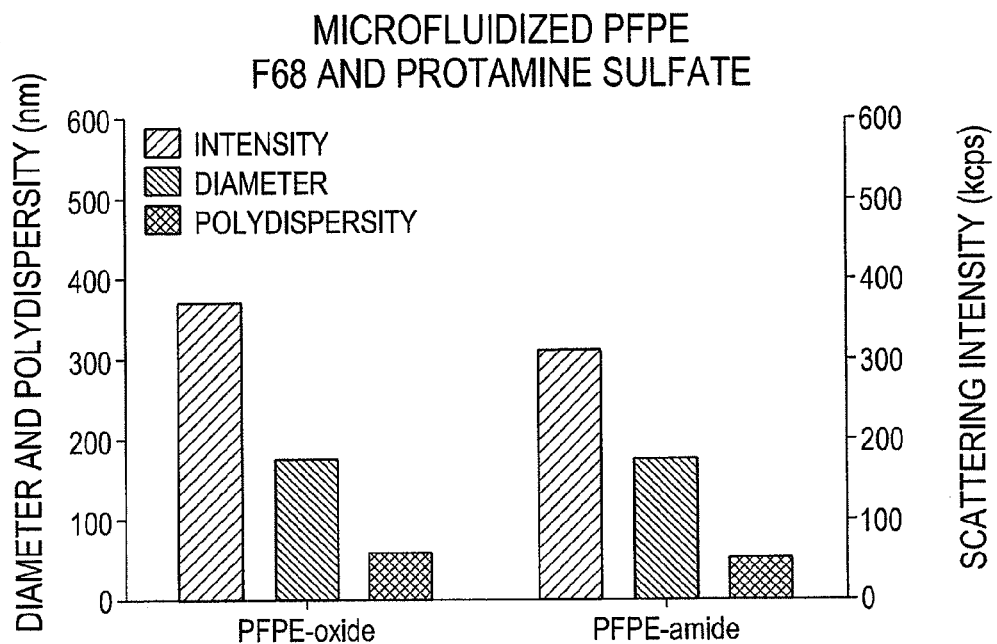
FIG. 24. A) DLS comparison of PFPE-oxide/F68 emulsion to PFPE amide 1/F68 after microfluidization. Both compounds emulsify the same way and show identical particle size and PDI. B) Long term stability (250 days) of PFPE-oxide/F68/PEI emulsion at three different temperatures 4, 25 and 37° C. Data represents the measured Z average (i.e., diameter in nm units) over time.

PFPE-oxide (1a) is an analogue of PFPE that has no hydrocarbon end groups and has lower average molecular weight (MW~1300). PFPE-oxide is a mixture of polymers custom synthesized by direct fluorination of PEG-OH (Exfluor, Roundrock, Tex.), and its main peak at −91.6 ppm corresponds to 36 fluorine spins. PFPE-oxide emulsifies similarly to PFPE-diethyl amide using microfluidization with F68, as shown in FIG. 24A. Therefore, PFPE-oxide can replace PFPE diethyl amide in cell labeling applications where further conjugation of PFPE to targeting agents or fluorescent dyes is not required. Furthermore, PFPE-oxide 1a has very similar physical properties to PFPE amide 1, and was used blended with PFPE amide 1 and FBPA (fluorescent blended PFPE amides) in the preparation of novel blended PFPE oil nanoemulsions. The PFPE blending capabilities opened new avenue for nanoemulsion preparations and resulted in highly stable fluorescent and non fluorescent PFPE nanoemulsions.

Figure 24B:
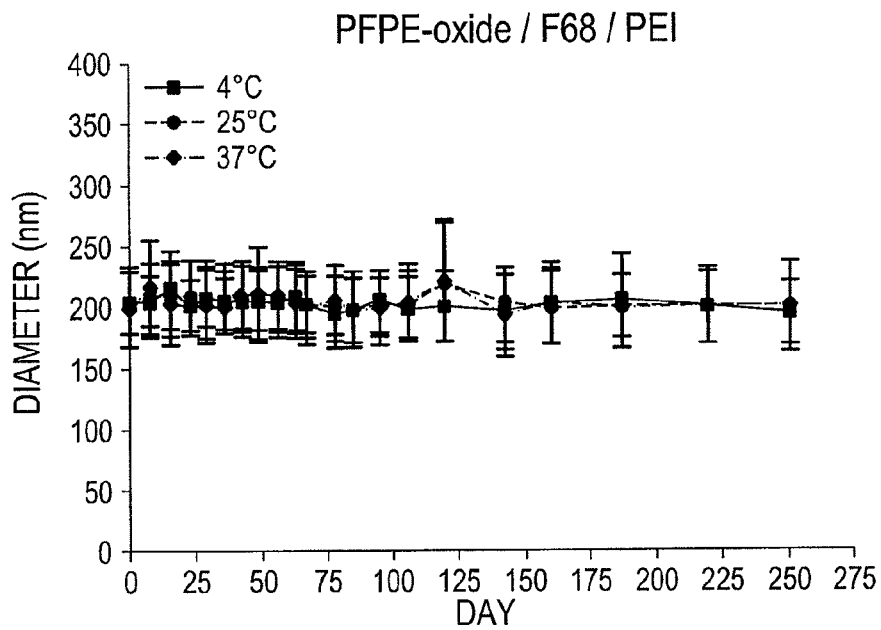
Figure 42:
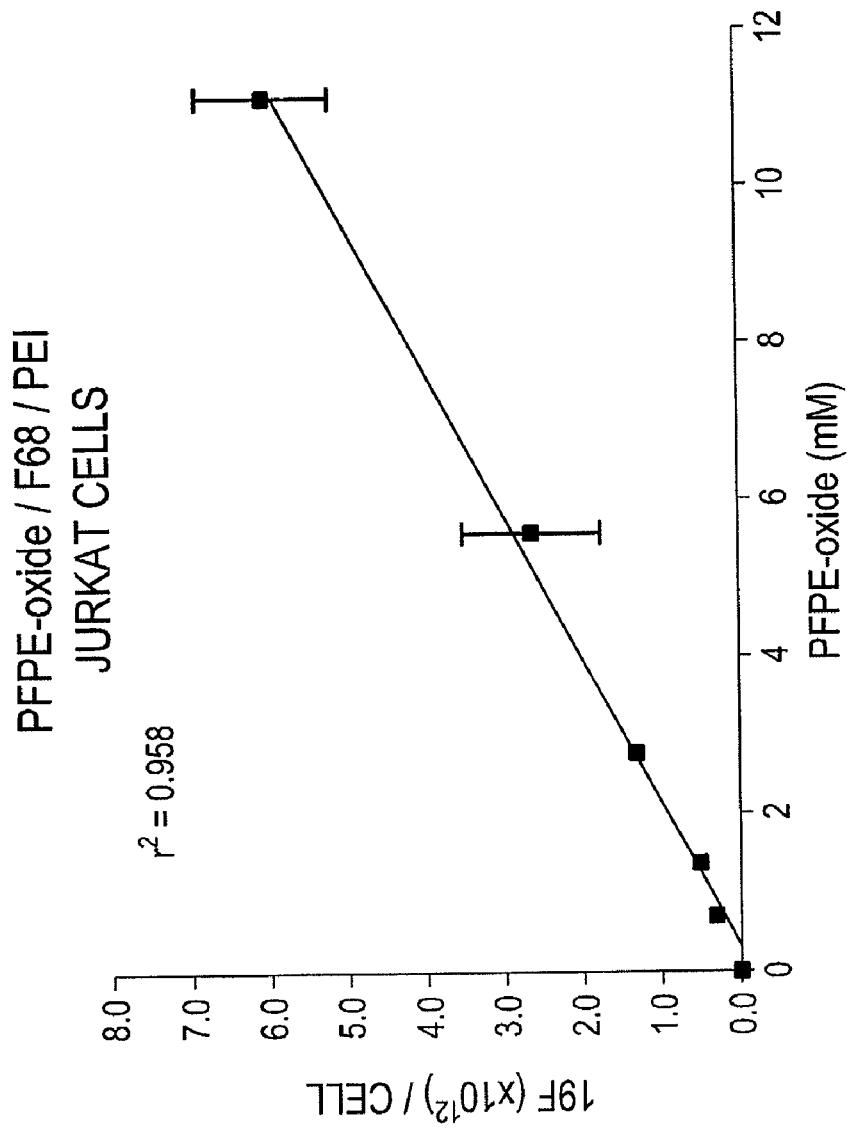
FIG. 42. Dose dependent uptake of PFPE-oxide/F68/PEI emulsion in non-phagocytic cells (Jurkat cells) labeled in suspension. Data represents the average of triplicate experiments (mean±SD).

PFPE-oxide (1.7 g, 1 mL), F68 (68 mg) and PEI (52 mg) were emulsified in water (14 mL) by passage through a microfluidizer twice under 50 psi pressure. A second emulsion was prepared in the using 1 mL of PFPE-diethyl amide, and both emulsions were compared by DLS measurements. Particle size, PDI and counts were virtually identical (FIG. 24A). The PFPE-oxide/F68/PEI emulsion showed excellent stability. It was monitored over a 250 days period by DLS to evaluate its stability at three different temperatures, 4, 25 and 37° C. The PFPE-oxide emulsion showed no change in particle size at all three temperatures over this time course, as shown in FIG. 24B. The PFPE-oxide/F68/PEI is a highly stable emulsion with a very low PDI (<0.1). This emulsion gave a reproducible, dose-dependent uptake in Jurkat cells, as shown in FIG. 42.

Figure 25:
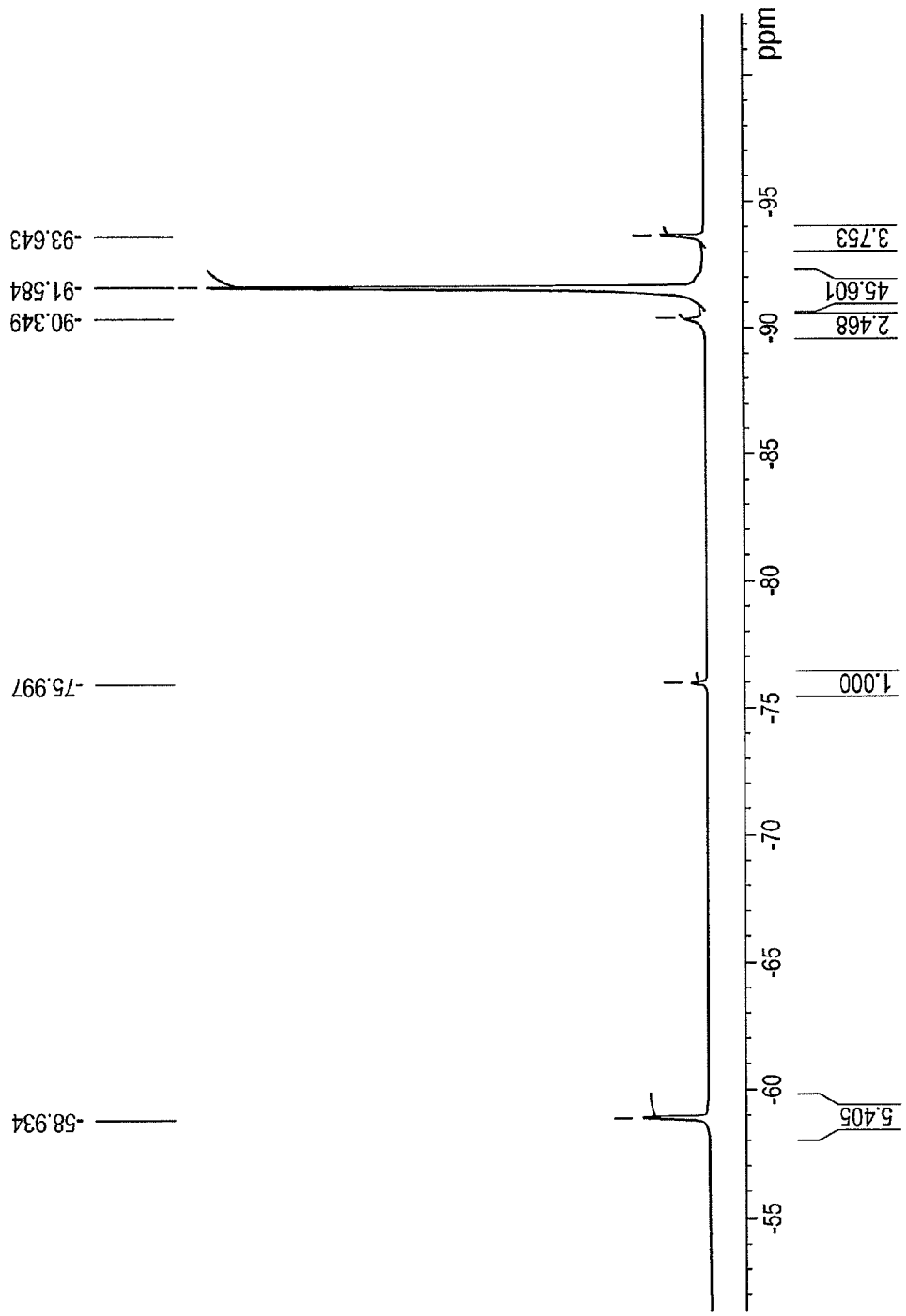
FIG. 25. $^{19}$F NMR of PFPE-oxide/F68/PEI emulsion. The main PFPE-oxide peak at −91.6 ppm has the same chemical shift as in PFPE-amide 1 emulsions. Additional identifying peaks for PFPE oxide 1a are at −58.951 and −93.641 ppm. Spectra were obtained at 470 MHz. TFA ($CF_3COOH$) (0.1% v/v) is an internal reference at −76.00 ppm.

The $^{19}$F NMR spectra of the PFPE diethyl amide and the PFPE-oxide emulsions were compared (FIG. 25). The main PFPE peaks of these two materials are at the same chemical shift (−91.0 ppm), and thus the PFPE oxide 1a can be used for $^{19}$F MRI imaging interchangeably with the PFPE-diethyl amide.

Nanoemulsions with Protamine Sulfate by Microfluidization PFPE Amide 1/F68/Protamine Sulfate:

PEI provides much improved uptake in cells and can be incorporated directly into the nanoemulsion during the emulsification process by either sonication or microfluidization. However this polyamine is not FDA approved for human applications. Therefore, Protamine sulfate was introduced in the preparation of highly stable nanoemulsions by microfluidization. Protamine sulfate is added to the surfactant (F68) and PFPE mixture in the pre-emulsion as an aqueous solution, and incorporated into the nanoemulsion droplets during microfluidization processing. The ratio of protamine sulfate to PFPE can vary from 0.01%-1% w/w. This amount of PFPE provides significant uptake increase without changing the sign of zeta potential to positive.

PFPE amide and PFPE oxide (1a) were emulsified by microfluidization with protamine sulfate. The goal was to prepare protamine coated particles during the processing and avoid the extra step of coating the emulsion particles with this material prior to its use for cell labeling. PFPE amide 1 (3.4 g, 2 mL) was mixed by vortexing with F68 (1.36 mL, 100 mg/mL in water) and protamine sulfate (0.5 mL, 20 mg/mL in water, 0.06% w/w to PFPE). Water was added (5 mL) and the vortexing was repeated for 1 min. The remaining water (15 mL) was added and the emulsion was vortexed again for 30 sec prior to microfluidization. The emulsion was microfluidized using 20-40 pulses at 80-100 psi working air pressure (corresponding to 12000-16000 psi liquid pressure) while the processing chamber was chilled on ice. Each pulse accounts for one pass through a processing chamber.

Figure 54:
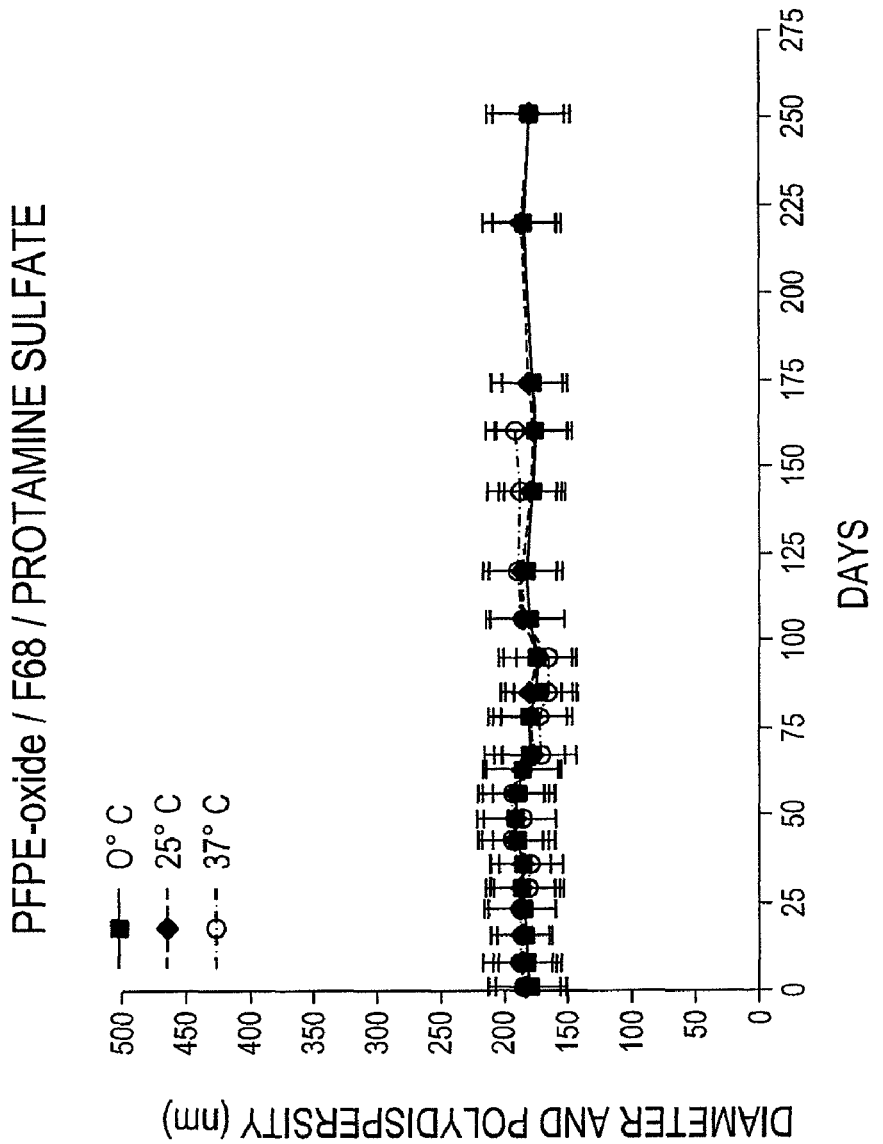
FIG. 54. A) Long term stability (250 days) at three different temperatures of PFPE-oxide/F68 and B) PFPE-oxide/F68/protamine sulfate nanoemulsion prepared by microfluidization. Measurements were made by DLS. The nanoemulsion with protamine sulfate shows greater stability at higher temperatures (25 and 37° C.). At low temperature (4° C.) both emulsions remained stable for 250 days.

PFPE Oxide (1a)/F68 with/without Protamine Sulfate:

Two PFPE-oxide emulsions were prepared, with and without protamine sulfate. The emulsions were prepared in a similar manner as described above for PFPE amide. PFPE oxide 1a (4 mL) was added to a 50 mL tube along with F68 solution (2.72 mL) and the mixture vortexed on highest speed for 1 minute. Protamine Sulfate solution (1 mL) was then added and the mixture vortexed again on highest speed for 1 minute. If no protamine sulfate was added, 1 mL of deionized water was added at this step. Next, 12 mL of water was added and the solution was vortexed again on highest speed for 1 minute. The emulsion was then transferred into the sampling chamber of the Microfluidizer, pressed with the plunger, and the plunger was held tight while pulsing exactly 40 times at the air pressure of 80-90 psi. At pulse number 40 the product was released. At this small scale there was dead volume in the lines and processing chamber. 5 mL of water was added and the left over product was slowly flushed out. The volume was adjusted with 25 mL water at the end if necessary. This method was used for the 100 mL scale, where four 25 mL batches were combined at the end. The batches were filtered immediately through Syringe Filter with a 0.2 um PTFE membrane from Pall Life Sciences without pretreatment. The shelf life for PFPE-oxide/F68 nanoemulsion and PFPE-oxide/F68/Protamine Sulfate nanoemulsion is shown in FIG. 54. Data represents the diameter and polydispersity measured by DLS at three different temperatures, as previously described, over 250 days. Both emulsions remained stable at 4° C. The PFPE-oxide/F68 emulsion began to break down at higher temperature much sooner then PFPE-oxide/F68/Protamine Sulfate, FIGS. 54A and 54B respectively.

Figure 55:
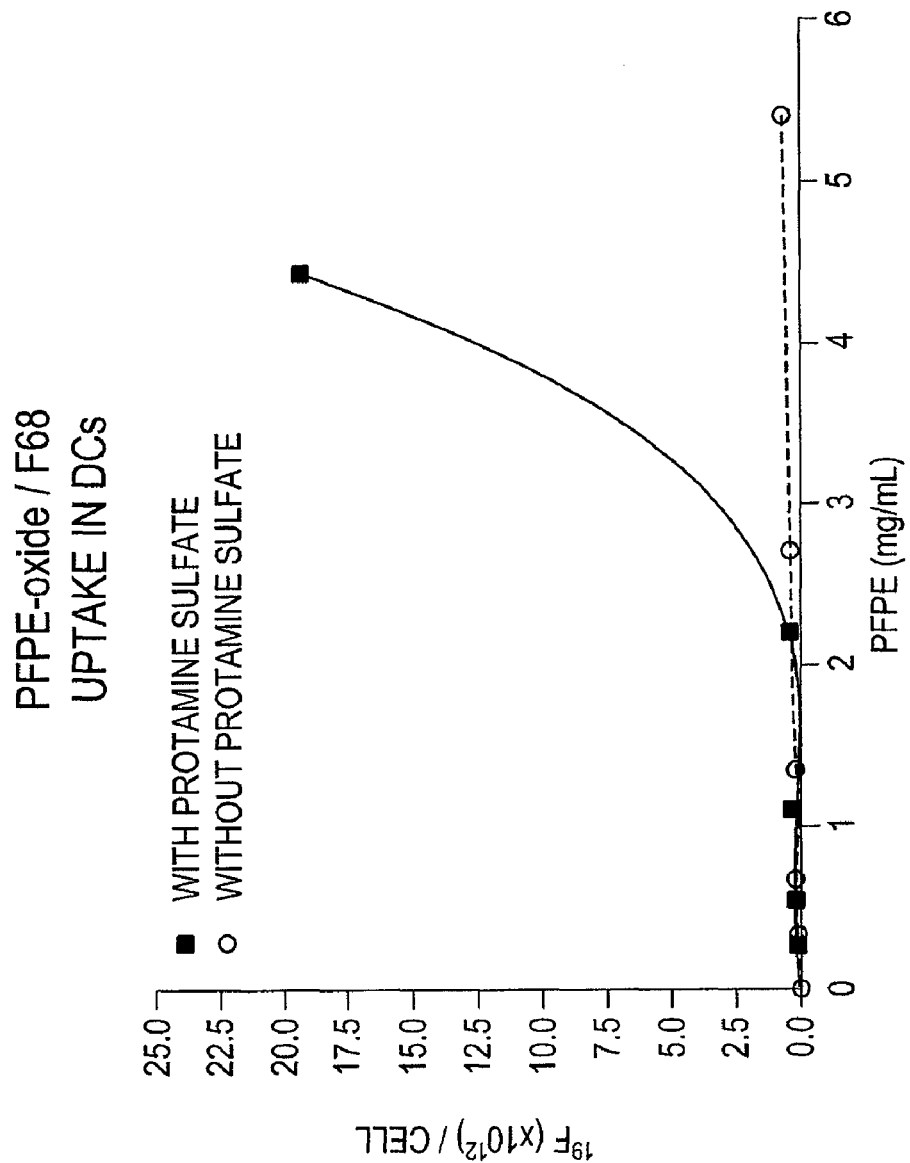
FIG. 55. Uptake dose curves of PFPE-oxide/F68 emulsions with/without protamine sulfate in DCs. Data represents the average of two independent measurements (mean±SD). A dramatic increase in uptake (e.g., almost one order of magnitude) was observed for the PFPE oxide 1a nanoemulsion with incorporated protamine sulfate.

PFPE oxide 1a emulsion with protamine sulfate showed a significant increase in uptake in DCs as compared to the PFPE oxide 1a/F68 emulsion without protamine sulfate, FIG. 55.

Figure 26:
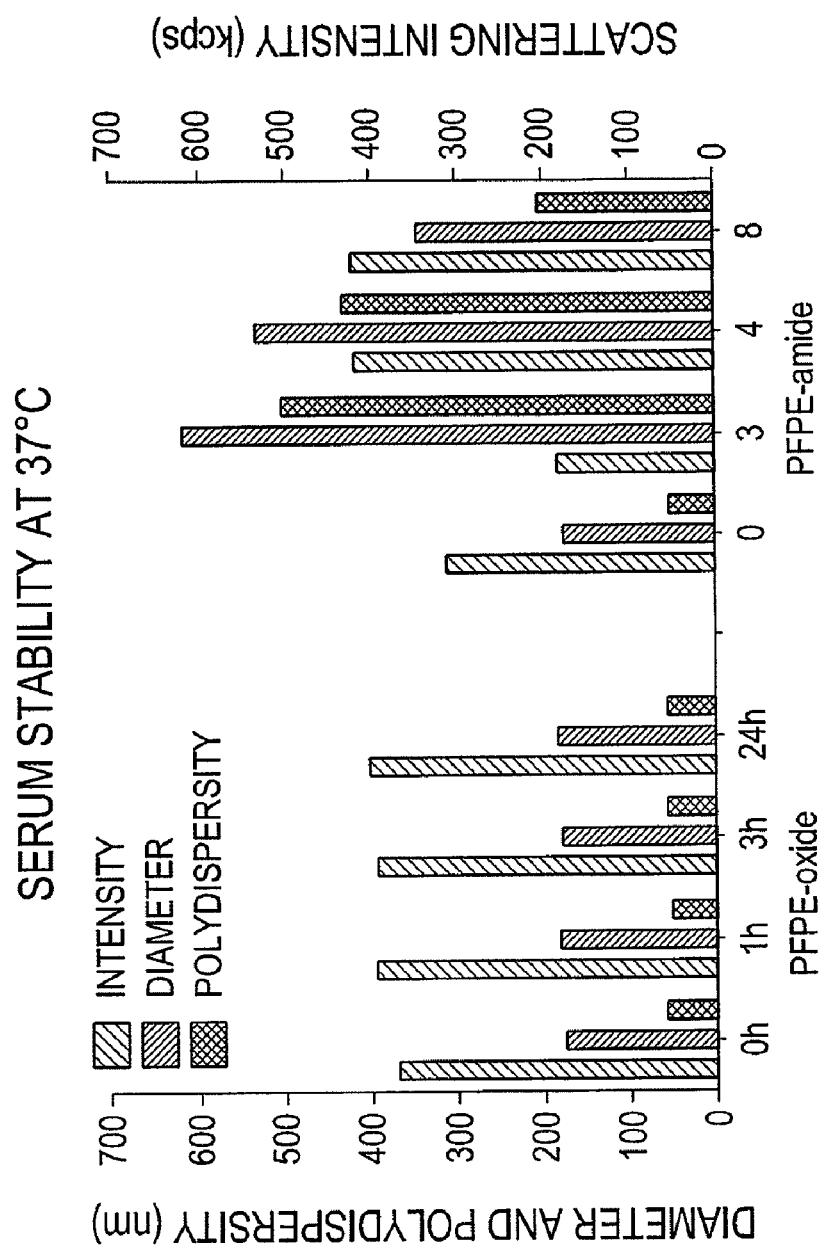
FIG. 26. Stability of PFPE emulsions in presence of serum at 37° C. in cell culture media. Emulsions were prepared by microfluidization. The data represents DLS measurements in cell culture media, at the cell labeling concentrations and at different time points, measured without further dilution.

Serum Stability Testing:

All large scale preparations of emulsions for in vivo work should ideally undergo stability tests in presence of nutrients, culture media and relevant serum content. These tests are crucial for the development of non-toxic and stable emulsions that give reproducible and reliable cell labeling in vitro. Emulsions were tested by DLS measurements in the presence of serum and cellular media nutrients at 37° C. Emulsions were mixed with cell culture media containing 10% FBS at the cell labeling concentration and incubated at 37° C. for 1, 3 and 24 h. After each time point emulsions were tested by DLS. In presence of serum, PFPE oxide 1a emulsion was far more stable then PFPE amide 1 emulsion even though the particle size and PDI were initially the same, as shown in FIG. 26.

Nanoemulsions from "Blended" PFPE Oils by Microfluidization at High Processing Pressure All the emulsion preparations described below use two or three PFPE derivatives (PFPE amides, PEG PFPE amides or FBPAs), blended further with PFPE oxide 1a. The addition of PFPE oxide 1a achieves better serum and in vivo stability. This all relies on the fact that PFPE mixes best with itself and forms its own fluorocarbon oil phase. It is also important that PFPEs are close in specific gravity, which range from 1.5-1.7 g/mL.

Blended PFPE oil emulsification was tested first by blending PFPE amide 1 and PFPE oxide 1a into one fluorinated oil phase that was then used for nanoemulsion preparation by microfluidization.

The FBPAs with FITC, BODIPy-TR and Alexa647 dyes, described above, were also blended with PFPE oxide 1a and used for fluorescent nanoemulsion preparation by microfluidization.

PFPE oils, FBPA or PFPE amide and PFPE oxide 1a were first blended together by continuous vortexing on the highest speed for 5 minutes, followed by mixing with F68 and PEI (or protamine sulfate) water solutions and then microfluidized. High mechanical energy applied within the interaction chamber of the microfluidizer disperses PFPE hydrophobic oil in water and results in monodisperse nanoemulsions. Non-fluorescent PFPE nanoemulsions were prepared by mixing PFPE oxide 1a and PFPE amide 1 at a ratio 9/1 v/v. Fluorescent nanoemulsions were prepared from PFPE oxide 1a and FBPA at 9/1 v/v ratio. All nanoemulsions were filter-sterilized (PTFE filter, pore size 0.22 μm) and stored at 4° C. until use for cell labeling. A Microfluidizer® M110S (Microfluidics, Inc., Newton, Mass.) operating at a liquid pressure of approximately 15000-20000 psi (80-100 psi working air pressure) was used for "blended" PFPE oils nanoemulsion preparations. PFPE oils (FBPA or PFPE amide 1 and PFPE oxide 1a) were mixed first with a concentrated solution of F68 in water (100 mg/mL) by vortexing on high speed for 2 minutes and then mixed with polyethylenimine (PEI) solution in water (100 mg/mL) by vortexing for 2 minutes. The mixture was diluted to 25 mL with water followed by microfluidization. After 20-40 pulses, the final nanoemulsion product was drained into a collection container and sat at r.t. for 20 minutes, followed by sterilization using a PTFE (0.2 μm) filter. The emulsion was stored at 4° C. until use.

Figure 56:
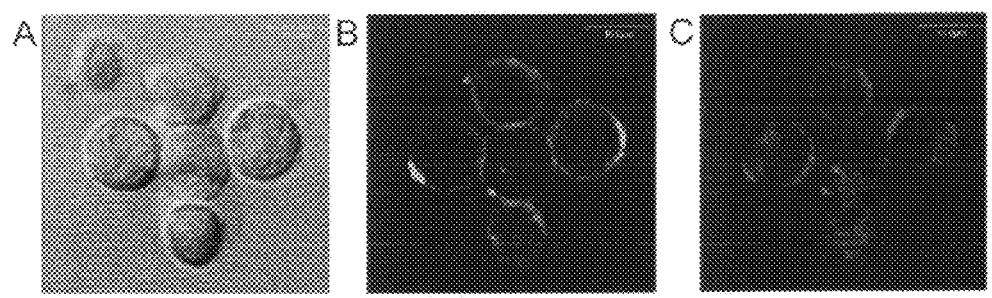
FIG. 56. Activated primary T cells labeled with BODIPy-PFPE amide 16 and PFPE amide 1 blended with PFPE oxide 1a and emulsified with F68 and PEI in water by microfluidization. A) DIC image; B) cell surface stained with CD4-FITC (green) antibody; C) BODIPy-PFPE nanoemulsion (red).
Figure 57:
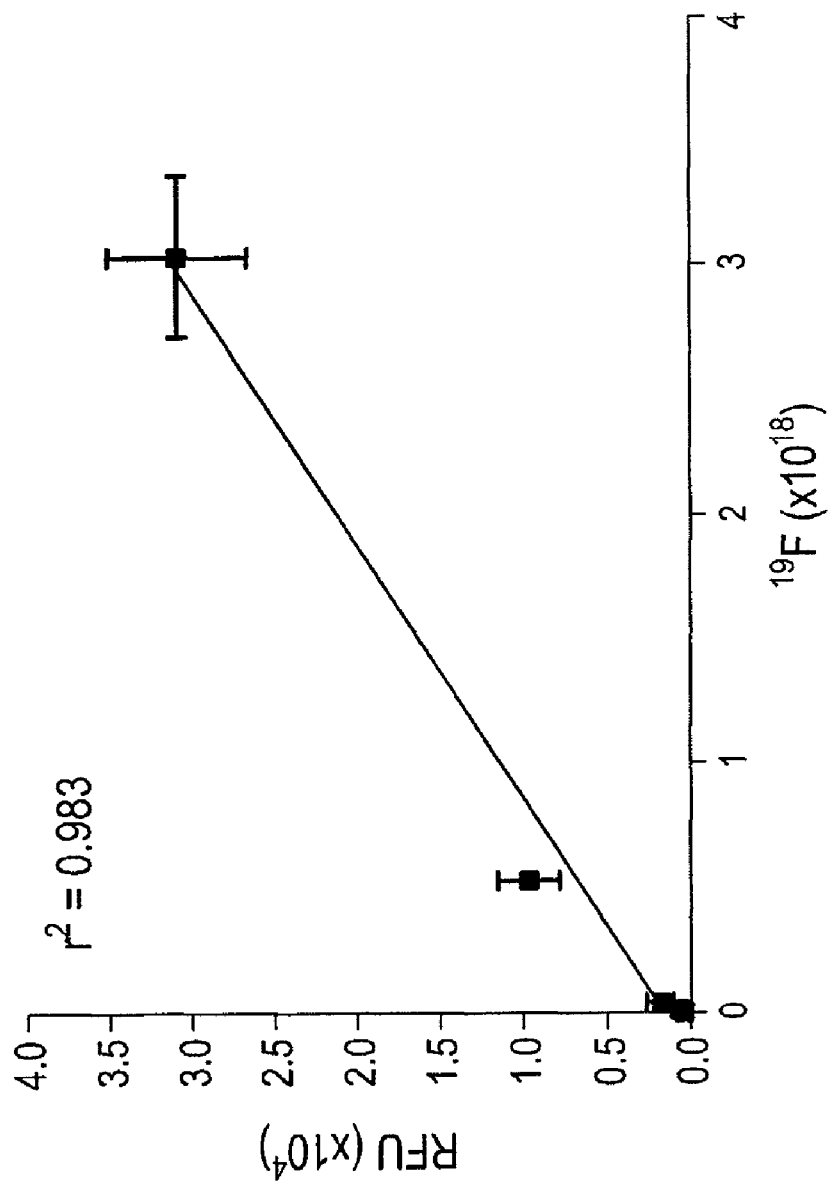
FIG. 57. Correlation between the $^{19}$F NMR and fluorescence in non-phagocytic Jurkat cells labeled with blended BODIPy-TR PFPE amide/PFPE oxide 1a nanoemulsion following 3 h co-incubation. Data represents the average of duplicate experiments (mean±SD). Data demonstrates utility of the dual fluorescent-19F label.
Figure 58:
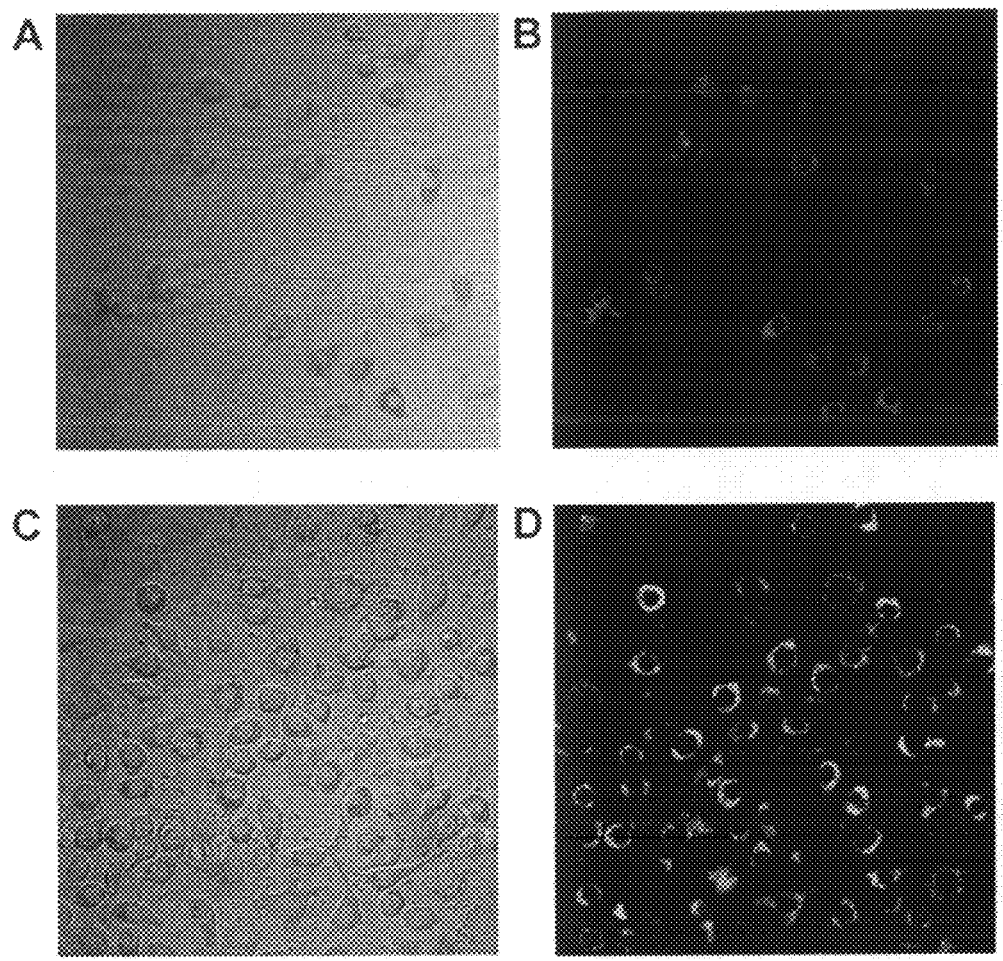
FIG. 58. Fluorescent images of DCs labeled with blended nanoemulsion. The BODIPy-TR PFPE blended nanoemulsion is shown where A) shows a DIC image and B) shows BODIPy-TR PFPE (red). The FITC PFPE blended nanoemulsion is also shown where C) is the DIC image and D) shows FITC PFPE (green).

Fluorescent blended PFPE nanoemulsion BODIPy-TR PFPE amide/PFPE oxide 1a/F68/PEI was used to label primary T cells. FIG. 56 shows confocal microscopy of labeled T cells. FITC PFPE amide/PFPE oxide 1a/F68/PEI nanoemulsion was also used for cell labeling. FIG. 58 shows labeled DCs where green fluorescence indicates cytoplasmic localization of the FITC PFPE nanoemulsion. In addition, BODIPy-TR PFPE labeled jurkat cells demonstrate linear correlation between fluorescence and 19F NMR signal, FIG. 57.

BODIPy-TR PFPE Nanoemulsion Preparation:

BODIPy-TR PFPE amide oil (0.20 mL) and PFPE oxide 1a (1.80 mL) were mixed first by vortexing on high for 5 minutes to achieve a final concentration of BODIPy-TR dye in the blended PFPE oil of 0.46 mM. The fluorescently labeled PFPE oil was then mixed with F68 solution (1.36 mL, 100 mg/mL) in water and vortexed for 2 minutes. To this mixture PEI solution (1.04 mL, 100 mg/mL) in water was added, and vortexing was repeated for 2 minutes at the highest speed. Water was added to a final volume of 25 mL; after brief vortexing, the mixture was loaded into the sample chamber of the microfluidizer. The final emulsion was drained after 20 pulses. The prepared nanoemulsion was stored at 4° C. until use.

Alexa647 PFPE and FITC PFPE Nanoemulsions Preparations:

Following the same procedure Alexa647 PFPE amide and FITC PFPE amide were used for fluorescent nanoemulsion preparations. In each case the same volume of FBPA (0.2 mL) was mixed by vortexing with PFPE oxide 1a (1.8 mL) while the rest of processing was done the same way as for BODIPy-TR PFPE amide, described above.

PFPE Amide 1/PFPE Oxide 1a Nanoemulsion Preparations:

Following the same procedure as above PFPE amide 1 and PFPE oxide 1a were blended together by vortexing and then used for emulsion preparation by microfluidization.

All "blended" PFPE oil nanoemulsions, fluorescent and non fluorescent were stability tested at three temperatures (4, 25 and 37° C.) by monitoring nanoemulsion droplet diameter (Z average) and polydispersity (PDI) over time by dynamic light scattering (DLS) measurements. The particle size was lowest for PFPE amide 1/PFPE oxide 1a blended nanoemulsion, only 140 nm, while the fluorescent versions regardless of the dye (FITC, BODIPy-TR or Alexa647) showed the average droplet size 160-190 nm. All emulsions were successfully sterile filtered and remained stable for at least 3 months at 37° C. and at least 6 months at 4 and 25° C. Serum stability was unaffected by the presence of PFPE amide 1 and FBPA in the blended PFPE oils used for these emulsion preparations and virtually the same as serum stability of emulsions prepared with PFPE oxide 1a alone.

Blended PFPE Oils Nanoemulsions Prepared by Microfluidization with Linear PFPE Oils and Perfluoro-15-Crown 5 Ether Blended Together As described above, blending PFPE oils has many advantages. PFPE amide 1, FBPA and PFPE oxide 1a readily blend with each other and behave as a discreet fluorinated oil phase in nanoemulsion preparations. These emulsions are highly stable and have low average droplet size and PDI. Perfluoro-15-crown 5 ether is a highly chemically stable and biologically inert macrocycle with 20 equivalent fluorine nuclei giving single resonance that overlaps with the $CF_2CF_2O$ repeat resonance of the linear PFPE main peak, at $-91.5$ to $-92.0$ ppm. This clear oil with quite similar density to linear PFPE oxide 1a, slightly lower viscosity. Nanoemulsions that are made by blending linear PFPE derivatives (e.g., FBPAs and PFPE amides) with perfluoro-15-crown 5 ether, which cannot be further chemically modified and conjugated, were investigated. This approach provides access to fluorescent perfluoro-15-crown 5 ether emulsions. In certain embodiments, the majority of the nanoemulsion droplet comprises crown ether as compared to linear PFPE derivative (e.g., the nanoemulsion droplet comprises 75%-95% crown ether as compared to linear PFPE derivative).

General Procedure for Blended Linear PFPE and Crown Ether Nanoemulsions:

Linear PFPE oils, FBPA or PFPE amide or PFPE oxide 1a are first blended together with perfluoro-15-crown-5 ether by continuous vortexing on the highest speed for 5 minutes, followed by mixing with F68 and PEI (or protamine sulfate) water solutions and then microfluidized. Due to high hydrophobicity and lipophobicity the linear and macrocyclic PFPE stay together as one fluorocarbon phase. The ratio of linear to crown PFPE is (99:1 to 75:25). The linear PFPE introduces functionality (fluorescence dye) to PFPE crown ether in this blended oil that would otherwise be impossible. The same approach can be used to introduce fluorescent dyes to perfluoro-15-crown-5 ether nanoemulsions prepared with lipids, cremaphor oils or other types of ionic and non-ionic surfactants.

The preparation of blended oils is easily scalable following the same methodology as described above for FBPA emulsions.

Example of nanoemulsion prepared with blended PFPE amide 1 and Perfluoro-15-crown ether. PFPE amide 1 oil (0.20 mL, 1.25% w/w) and Perfluoro-15-crown-5 ether (1.80 mL, 12.75% w/w) were mixed first by vortexing on high for 5 minutes to achieve homogenous blending of two oils. The blended oil was then mixed with F68 solution (1.36 mL, 100 mg/mL) in water and vortexed for 2 minutes. To this mixture Protamine Sulfate solution in water (0.53 mL, 18.75 mg/mL) was added, and vortexing was repeated for 2 minutes at the highest speed. Water was added to a final volume of 25 mL; after brief vortexing, the mixture was loaded into the sample chamber of the microfluidizer. The emulsion was microfluidized at 80 psi working air pressure. The final emulsion was drained after 30 pulses. The prepared nanoemulsion was sterilized by filtration through a nylon filter and stored at 4° C. until use. The particle size for this emulsion was 160 nm. The emulsion remained stable at 37° C. for 3 h in presence of serum containing media. The uptake in non-phagocitic cells of this emulsion was the same as for PFPE oxide 1a/F68/Protamine Sulfate nanoemulsion reported earlier in this text.

Low Energy Emulsification Examples

Previous examples showed the need for high energy when PFPE amide 1 or PFPE oxide (1a) is emulsified in aqueous media in presence of lipids or Pluronics™. In these examples we show that simple PFPE end group modifications allow for PFPE emulsification without sonication or microfluidization. The goal was to develop PFPE derivatives that promote self-emulsification in the presence or absence of emulsifiers, by introducing either lipophilic or hydrophilic moieties onto the PFPE end groups. Low energy emulsification methods can be easily utilized for larger scale production and decrease the emulsification processing cost. Two such PFPE derivatives are shown bellow.

Figure 27:
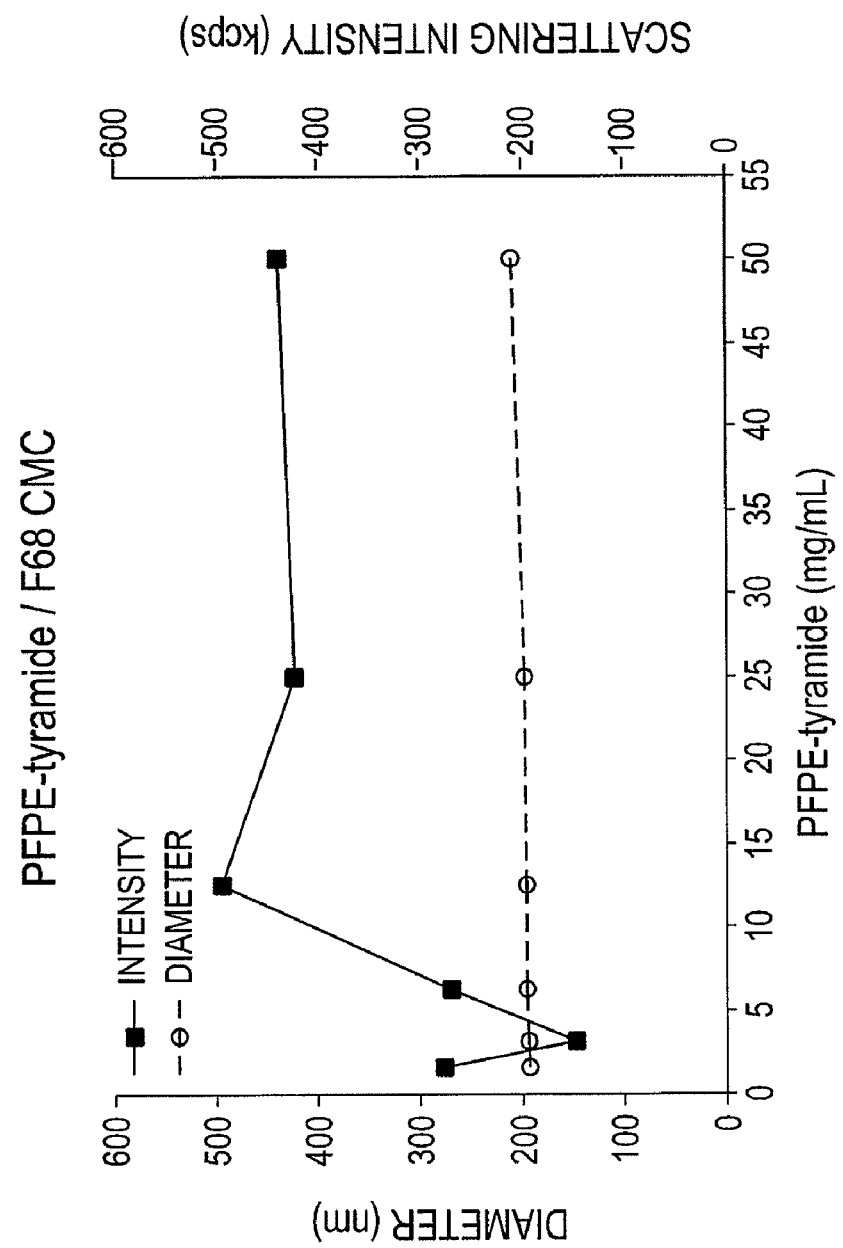
FIG. 27. Measurements of light scattering intensity and particle size as a function of concentration of PFPE-tyramide 6/F68 emulsion prepared by thin film method and heating in water. Data represents average of three independent measurements (mean±SD). The SD is too small to be visible at the presented graph scale.
Figure 28:
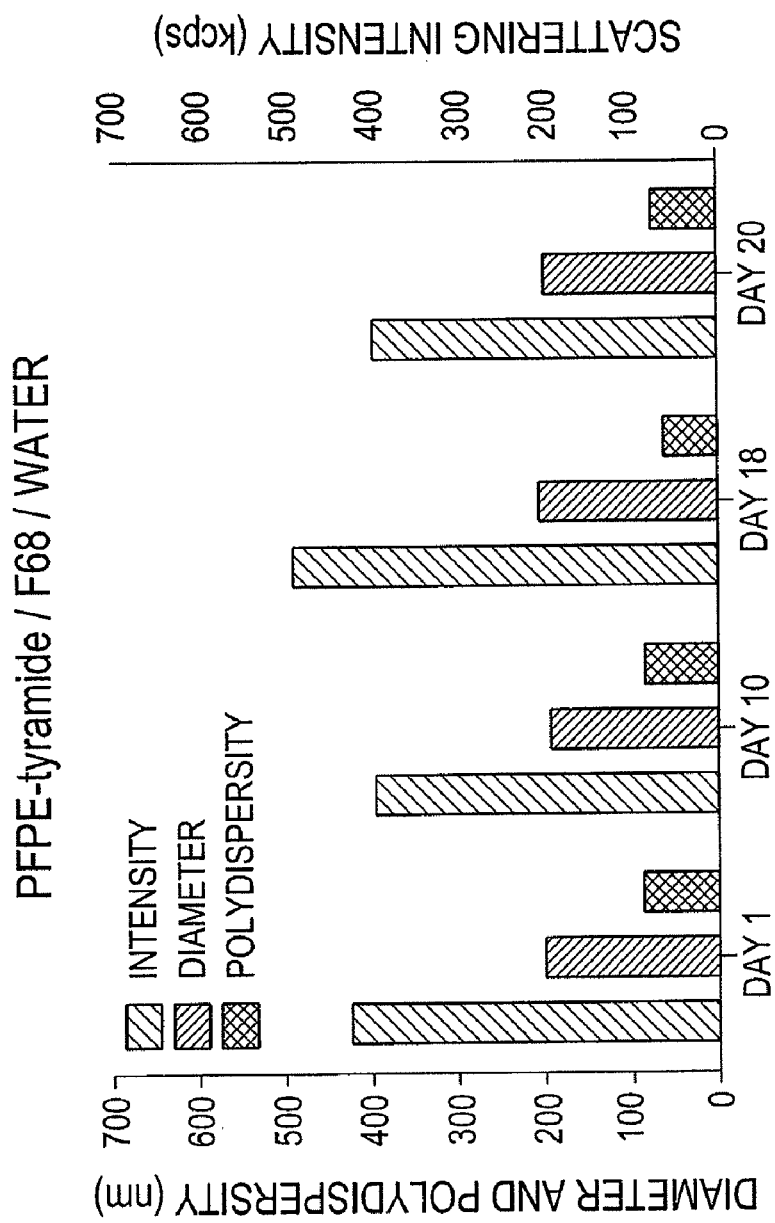
FIG. 28. Stability of PFPE-tyramide 6/F68 emulsion in water. The emulsion was stored at room temperature and diluted 10 times in water prior to each measurement. Data represents an average of two measurements (mean±SD).

PFPE-Tyramide 6/F68 Emulsion by a Thin Film Method:

PFPE-tyramide 6 (50 mg) and F68 (8.5 mg) were dissolved in trifluoroethanol (0.5 mL) and vortexed. The solution was dried into a thin film in a round bottom glass tube and placed on vacuum for 15 minutes. The film was vortexed with 1 mL of water and heated at 60° C. for 15 minutes, then cooled to room temperature while vortexing on high. Serial dilutions were made ranging form 1/1 to 1/32 in water and DLS were measurements performed. The critical micell concentration (CMC) was estimated to be 4.5 mg for PFPE tyramide 6 in this system, by plotting the light scattering intensity and particle size as a function of concentration of PFPE tyramide 6 (FIG. 27). The mole ratio of PFPE-tyramide 6/F68 was 24:1. This emulsion was monitored by DLS for three weeks to test stability. The emulsion was kept at room temperature and protected from light and air. The particle size and PDI stayed constant over the three week period, as shown in FIG. 28.

Figure 29:
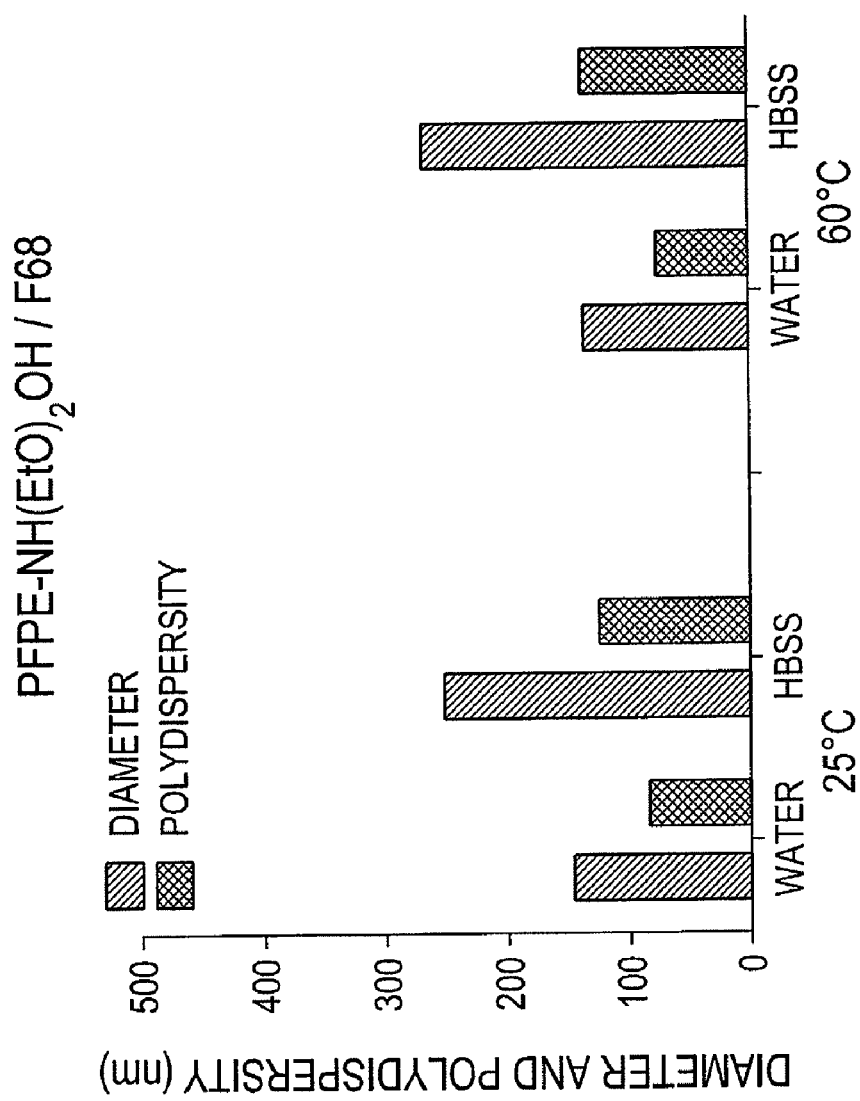
FIG. 29. DLS Measurements for PFPE (2-hydroxyl)ethyloxyethyl amide 2/F68 emulsion prepared by thin film method in water and 1×HBSS at two different temperatures. Emulsion droplets were significantly smaller in water.
Figure 30:
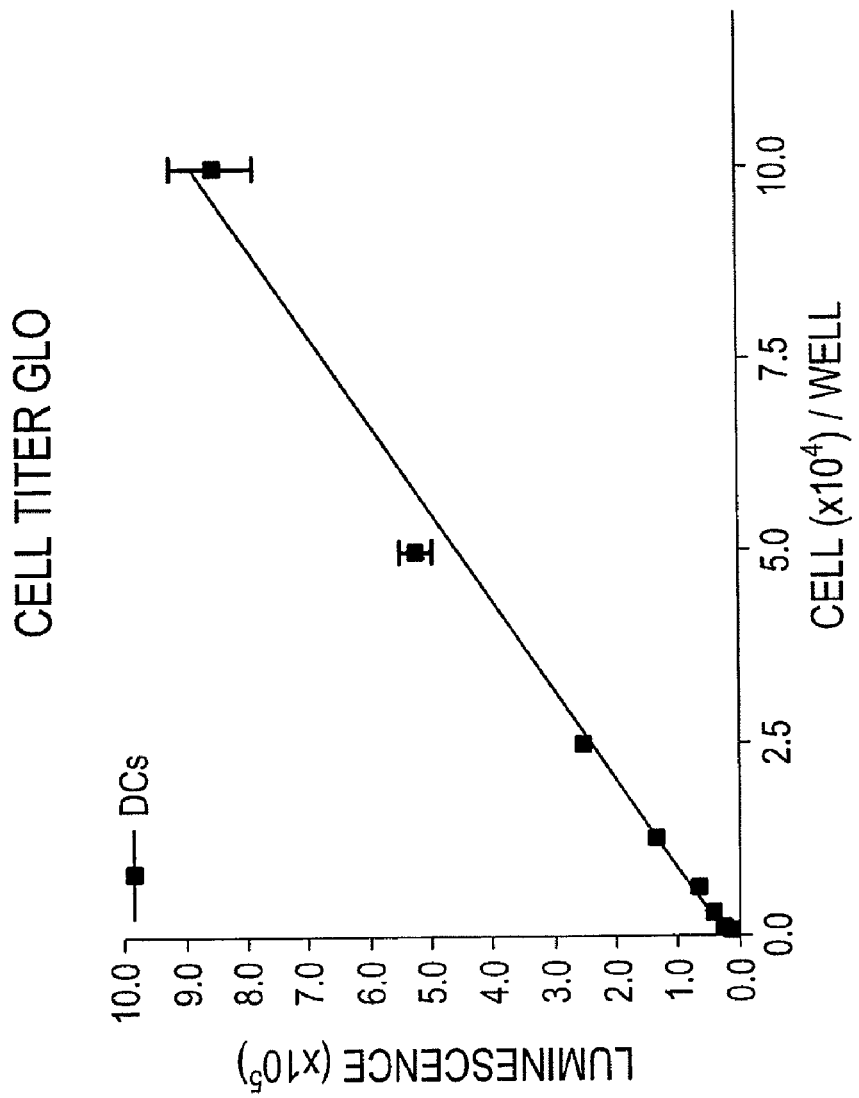
FIG. 30. Cell Titer Glo assay (Promega) versus cell number. This figure shows representative luminescence correlation curve for estimating cell number and viability following PFPE labeling of dendritic cells (DCs). Data represents the average of measurements done in triplicate (mean±SD).
Figure 31:
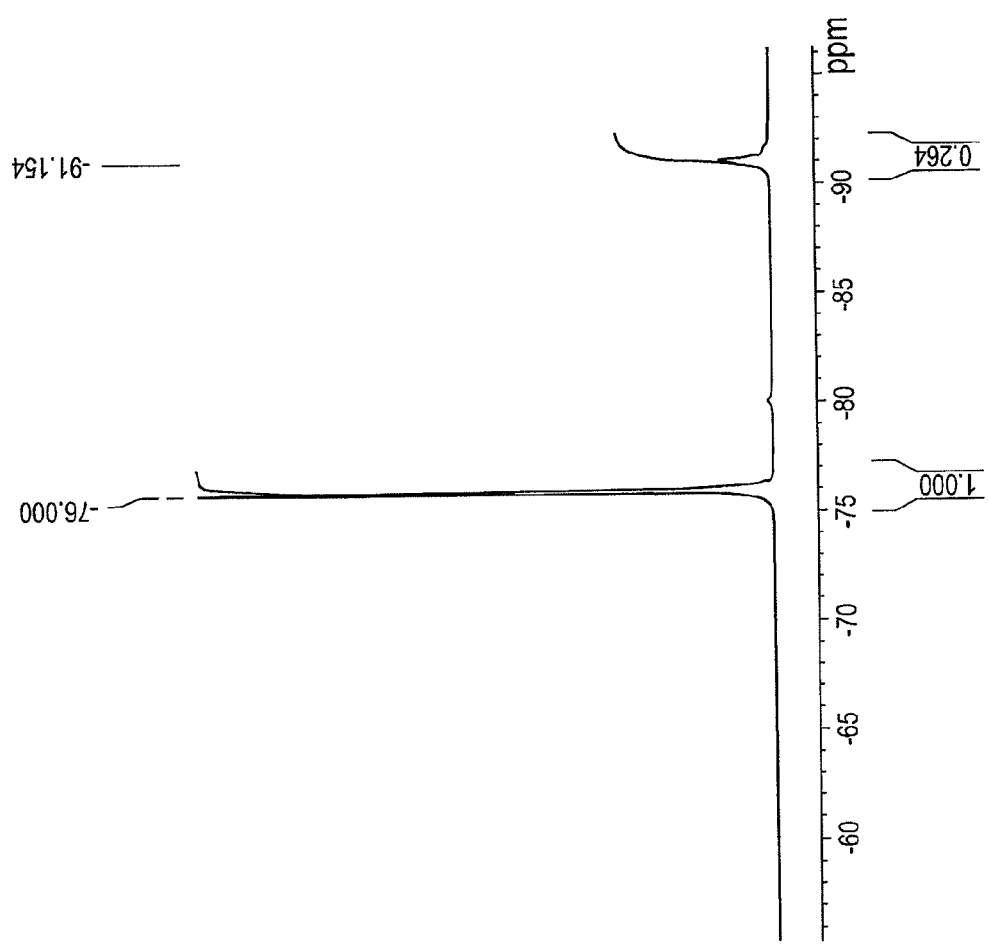
FIG. 31. $^{19}$F NMR spectrum of PFPE amide 1/L35 emulsion labeled DCs. Cells were labeled for 3 h, washed, trypsinized and resuspended in 1×PBS. TFA was used as a reference for signal quantification.

PFPE (2-hydroxyl)ethyloxyethyl Amide 2/F68 Emulsion:

PFPE (2-hydroxyl)ethyloxyethyl amide 2 was investigated as an alternative to the PFPE-tyramide derivative. The presence of 2-hydroxyl)ethyloxyethyl amide end group was to promote PFPE self-emulsification under low energy conditions. It was found that this derivative emulsifies readily in water in presence of Pluronics™ at low temperature. PFPE amide derivative 2 (50 mg) and F68 (8.5 mg) were dissolved in trifluoroethanol and dried to a thin film by a stream of argon gas. Water or 1×HBSS (1 mL) was added while vortexing. The emulsion was then split in two parts, where one part was incubated at 60° C. for 15 minutes and the other part was left at room temperature. The effects of buffer and temperature on emulsification with F68 were investigated by DLS measurements. The PFPE amide derivative 2 could not form an emulsion without F68 by the applied methods. Temperature had no effect on particle size or PDI, as shown in FIG. 29. However, the presence of salts in the 1×HBSS buffer increased the particle size. This example illustrates that the structure and composition effects the emulsification properties of PFPE by low energy emulsification methods. Factors that affect PFPE emulsification include, for example, the nature of the PFPE end groups (i.e., lipophilic or hydrophilic), the emulsifier, the external phase, and the presence of salts in the buffer.

Overall, simple and effective chemical modifications were developed to provide multifaceted MRI/MRS cell labeling reagents. PFPE is shown to be a versatile starting material for a variety of nanoparticles, including dual fluorescent-19F MRI/MRS reagents, self delivering PFPE nanoparticles, and nanoparticles with highly efficient uptake in both phagocytic and non-phagocytic cell types. PFPE-PEG derivatives can be used for direct injection experiments, where cellular uptake is not desired and prolonged circulation stability is necessary. PFPE-PEI and PFPE-protamine sulfate and the like can be used for efficient cellular labeling. Microfluidization is a very effective method for PFPE nanoparticle preparations, allowing for large scale production (>1 L) of emulsions. The emulsions produced were highly stable at typical storage temperatures (4 and 25° C.) and body temperature (37° C.). Simple changes in the emulsification process and simple chemical modifications of PFPE end groups allow fine tuning of nanoparticle properties towards specific cell types and applications.

Figure 60A:
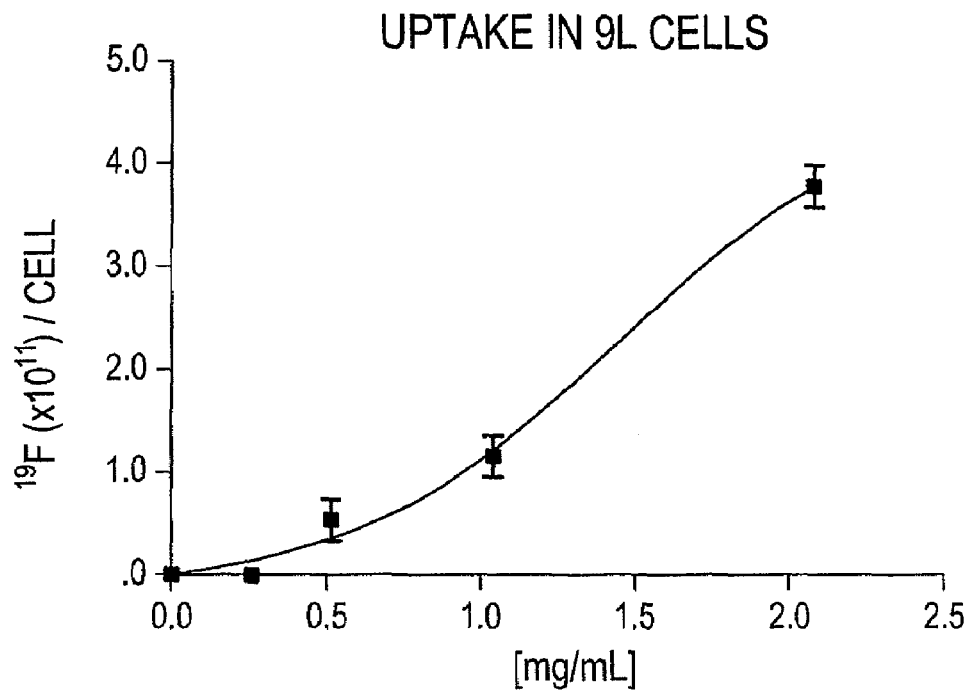
FIG. 60. 9 L cells incubated with FITC PFPE amide/Perfluoro-15-crown-5 nanoemulsion prepared with F68 and Protamine Sulfate by microfluidization. The cells were exposed to increasing concentrations of the nanoemulsion for 3 h. A) Cell numbers were estimated from Cell Titer Glo luminescence-cell number correlation curve. B) Fluorine content estimated from 19F NMR spectra for 9 L cell suspensions. Data represents the average of two independent measurements (mean±SD).
Figure 60B:
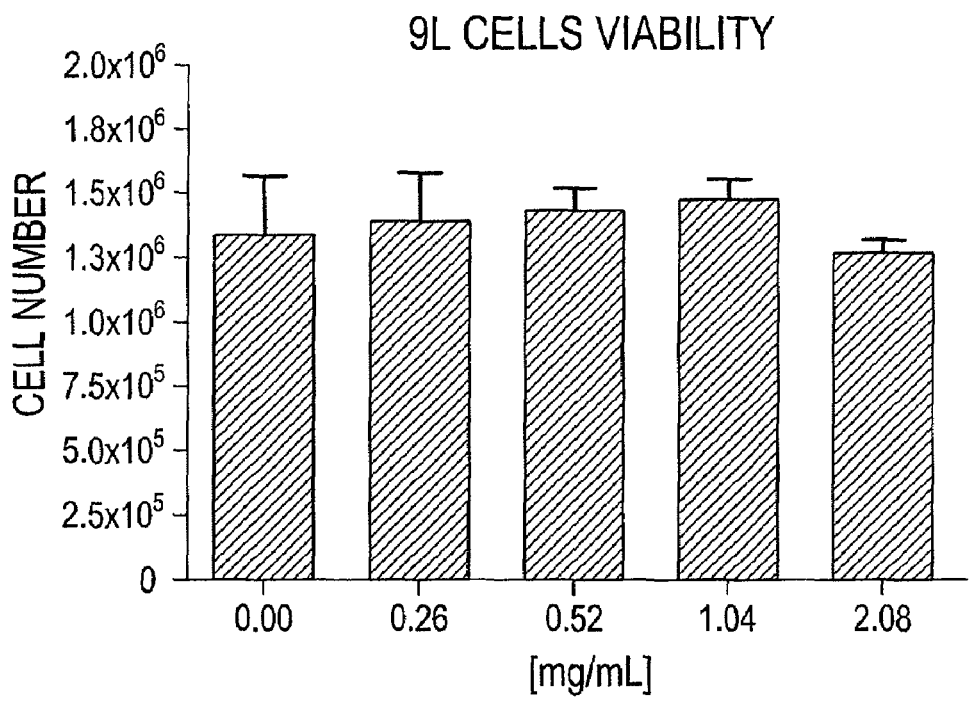

Example of Nanoemulsion Prepared with Blended FBPA (FITC or BODIPy-TR PFPE Amide) and Perfluoro-15-crown ether:

FBPA (FITC PFPE amide or BODIPy-TR PFPE amide) oil (0.20 mL, 1.25% w/w) and Perfluoro-15-crown-5 ether (1.80 mL, 12.75% w/w) were mixed first by vortexing on high for 5 minutes to achieve homogenous blending of the two oils. The blended oil was then mixed with F68 solution (1.36 mL, 100 mg/mL) in water and vortexed for 2 minutes. To this mixture Protamine Sulfate solution in water (0.53 mL, 18.75 mg/mL) was added, and vortexing was repeated for 2 minutes at the highest speed. Water was added to a final volume of 25 mL; after brief vortexing, the mixture was loaded into the sample chamber of the microfluidizer. The emulsion was microfluidized at 80 psi working air pressure. The final emulsion was drained after 30 pulses. The prepared nanoemulsion was sterilized by filtration through a nylon filter and stored at 4° C. until use. The particle size for this emulsion was 165 nm and PDI 0.06. The emulsion remained stable at 37° C. for 3 h in the presence of serum containing media. The emulsion remained stable at 37° C. storage temperature for 5 months, without change in size or PDI. Labeling efficiency of non-phagocytic cells (9 L, rat glioma cell line) was the same as for PFPE oxide 1a/F68/Protamine Sulfate nanoemulsion above. Labeling of non-phagocytic 9 L cells is shown in FIG. 60.

Formulations Prepared with Mixed Micelle and PFPE by Microfluidization

The following emulsions were designed to specifically label macrophages and other phagocytic immune cells both in vitro and in vivo. The enriched PEG containing nanoemulsion droplet surface prevented the nanoemulsion uptake in cells lacking phagocytic ability. The PEG enriched surface was introduced by two surfactants, well known in the art, pluronic P105 and Cremophor EL. The mixed micelle solution was prepared with P105 and Cremophor EL first, and PFPE blended oils incorporated into the micelle by high shear forces during microfluidization. The resulting emulsions showed high stability and very specific labeling activity towards RAW 264.1 macrophage cell line in vitro.

Example of Nanoemulsion Prepared with Blended FBPA (BODIPy-TR PFPE amide) or PFPE Amide 1 and Perfluoro-15-Crown Ether with PEG Enriched Surface:

Mixed micelle solution was prepared first in sterile saline solution with P105 pluronic and Cremophor EL at 2/3 w/w ratio. Pluronic P105 (4 g) was dissolved in 100 mL of normal sterile saline solution (0.9% NaCl) by stirring slowly at room temperature to a final concentration of 4% w/v. Cremophor EL (6 g) was dissolved in 100 mL of normal sterile saline solution by stirring at room temperature to a final concentration of 6% w/v. The two solutions were mixed at room temperature in 1/1 v/v ratio in a round bottom flask, placed in a water batch preheated to 45° C., and incubated while slowly rotating for 15 minutes. The solution was then chilled on ice for 5-10 minutes. The prepared mixed micelle solution contained micelle particles with average size of 12.3 nm and PDI 0.17. This mixed micelle solution was used for preparing PFPE nanoemulsions as follows.

Figure 61:
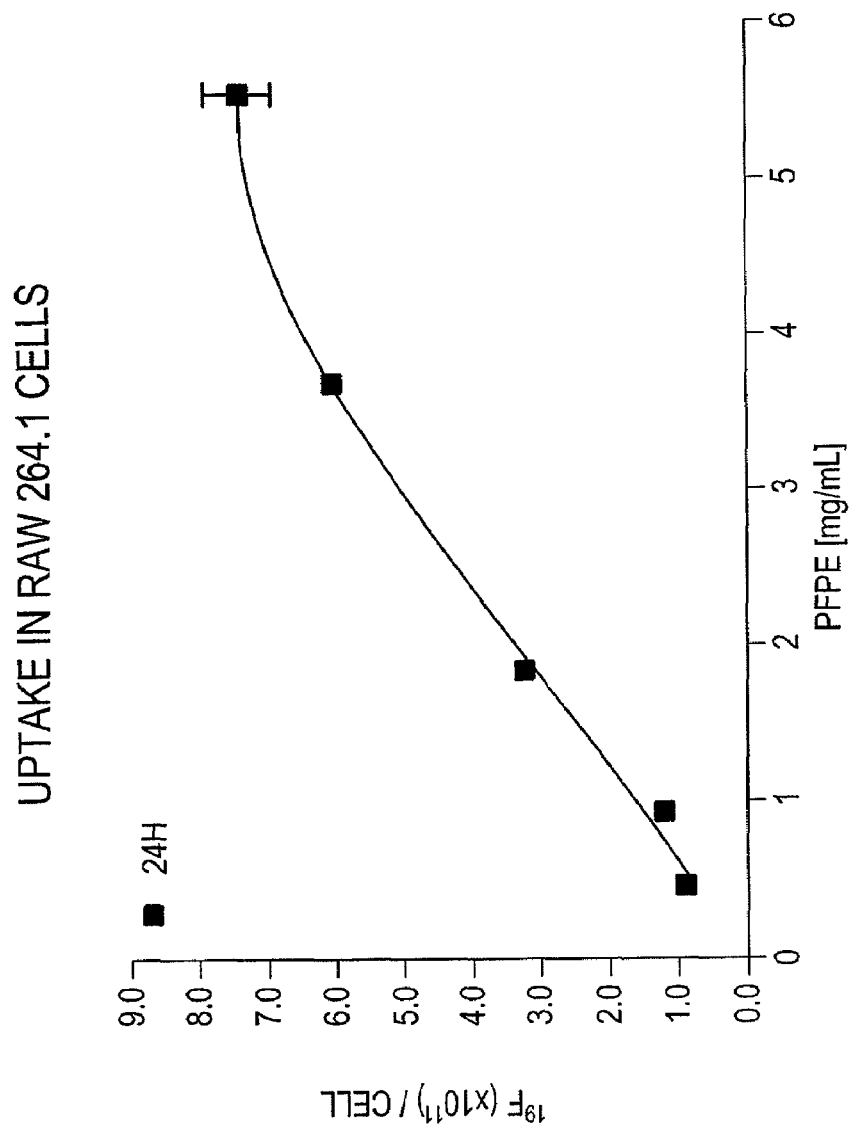
FIG. 61. RAW cells incubated with BODIPy-TR PFPE amide/Perfluoro-15-crown-5 nanoemulsion prepared with P105/Cremophor EL mixed micelle. The cells were exposed to increasing concentrations of the nanoemulsion for 24 h and cell loading was measured by $^{19}$F NMR. The data (cell loading, $^{19}$F/cell) represents an average of duplicate measurements (mean±SD).
Figure 62:
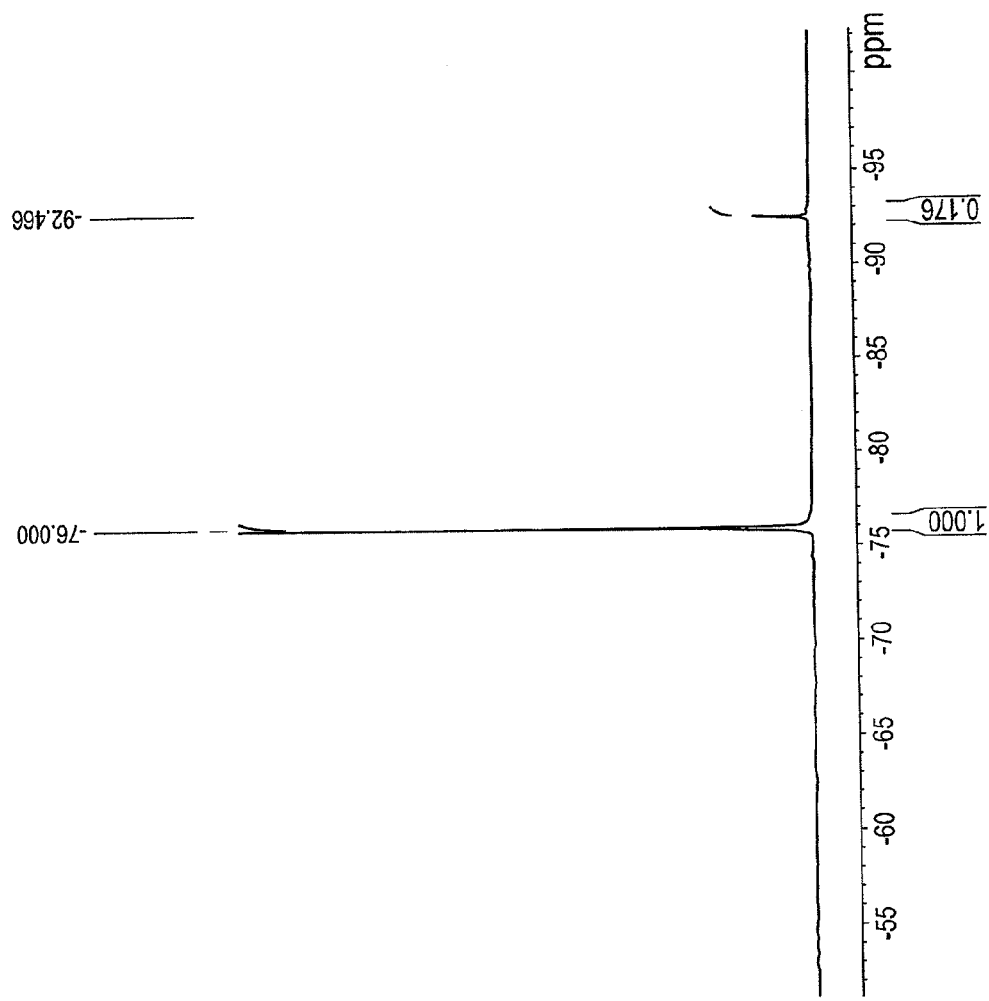
FIG. 62. 19F NMR spectrum of RAW 264.1 cells labeled with BODIPy-TR PFPE amide 1/Perfluoro-15-crown ether/P105/Cremophor EL nanoemulsion. Cells were incubated with the nanoemulsion for 24 h, washed, scrapped and resuspended in 1×PBS. TFA (−76.00 ppm) was used as a reference for signal quantification. Labeled cells are shown at −92.47 ppm in the spectrum.

PFPE amide 1 or FBPA (BODIPy-TR PFPE amide) oil (0.20 mL, 1.25% w/w) and Perfluoro-15-crown-5 ether (1.80 mL, 12.75% w/w) were mixed first by vortexing on high for 5 minutes to achieve homogenous blending of two oils. The blended oil was then mixed with 11.5 mL of mixed micelle solution by vortexing on high speed for 2-3 minutes. Saline solution was added (11.5 mL); after brief vortexing, the mixture was loaded into the sample chamber of the microfluidizer. The emulsion was microfluidized at 80 psi working air pressure while the processing chamber was chilled on ice/water bath. The final emulsion was drained after 20 pulses and stored at 4° C. until use. The average droplet size was 130-150 nm and PDI 0.05-0.1. The emulsions were stable at 37° C. for up to 24 h in presence of serum containing media. Shelf life stability tests showed the size and PDI remain unchanged for 3 months at 4° C. storage temperature. The emulsions were used to label RAW 264.1 cells (rat macrophage derived cell line) in vitro by 24 h co-incubation with cell viability at 80% or higher. The dose dependent labeling of RAW 264.1 cells with BODIPy-TR PFPE amide P105/Cremophor EL emulsion is shown in FIG. 61. Fluorine NMR spectrum of labeled RAW cells is shown in FIG. 62.

The two presented examples of PFPE/P105/Cremophor EL emulsions did not label non-phagocytic cells, and specifically labeled macrophages (data not shown). This was due to high density of PEG monomers on the particle surface that sterically hindered the cell membrane and nanoemulsion droplet interaction. Due to this steric hinderance, the cell labeling of macrophages takes 24 h, which is longer then in earlier presented examples.

Example of Nanoemulsion Prepared with Compound 42:

Mixed micelle solution was prepared as follows: Pluronic P105 (5 g) was dissolved in 100 mL water by stirring slowly at room temperature for a final concentration of 5% w/v. Cremophor EL (5 g) was dissolved in 100 mL water by stirring at room temperature for a final concentration of 5% w/v. The two solutions were mixed at room temperature in 1/1 v/v ratio in a round bottom flask, placed in a water bath preheated to 45° C., and incubated while slowly rotating for 20 minutes. The solution was then chilled on ice for 5-15 minutes, and stored at room temperature until use. The final concentration of mixed micelle solution was 5% w/v, where 2.5% w/v was P105 and 2.5% w/v was Cremophor EL, present in 1/1 w/w ratio. The mixed micelle solution was used for compound 42 nanoemulsion preparations by sonication.

All nanoemulsions were prepared by sonication during which compound 42 was loaded into the core of mixed micelle. The amount of surfactants necessary for optimal cell labeling was optimized. A series of nanoemulsions were prepared as shown in Table 1. Briefly, compound 42, which is a clear colorless oil heavier then water, was added to the sonication tube first, followed by varied amounts of micelle solution and water, vortexed briefly and then sonicated at room temperature. The amount of fluorocarbon was kept constant at 22.3%, while the amounts of Cremophor EL and pluronic P105 were varied from 4% w/v, as in emulsion A1, to 1% in emulsion A4. As shown in Table 1, as the amount of surfactant increased the droplet size of the nanoemulsions decreased.

TABLE 1

Nanoemulsion compositions prepared with mixed micelle solution and compound 42

| Nanoemulsion | P105/Cremophor EL Mixed micelle Solution (µL) | Cremophor EL and P105 (% w/v) | Comp. 42 (µL) | Water (µL) | Size (nm) | PDI | Zeta Potential (mV) |
|---|---|---|---|---|---|---|---|
| A1 | 400 | 4 | 100 | 0 | 131.1 | 0.13 | −3.15 |
| A2 | 300 | 3 | 100 | 100 | 145.3 | 0.12 | −2.23 |
| A3 | 200 | 2 | 100 | 200 | 160.2 | 0.14 | −3.82 |
| A4 | 100 | 1 | 100 | 300 | 182.5 | 0.17 | −3.33 |
|  | 500 | 0 | 0 | 0 | 14.1 | 0.11 | −6.65 |

3. Cell Labeling Experiments with Fluorescent and Non-Fluorescent PFPE Nanoemulsions Cell labeling using the nanoemulsions was demonstrated in both phagocytic cells, using a fetal-skin derived mouse DC line, and in non-phagocytic cells, including primary T cells and Jurkat cells. In all cell types studied, suitable levels of emulsion uptake for in vivo MRI (i.e., >$10^{11}$) were achieved in a modest 3 hour incubation period. Intracellular localization of the nanoparticles was visualized using fluorescence microscopy. Cellular uptake of nanoemulsion droplets was quantified using fluorescence measurements and by $^{19}$F NMR spectroscopy of lysed cell pellets. Uptake was tested by $^{19}$F NMR, where the PFPE labeled cells show a major peak at −91.58 ppm; the −76.00 ppm peak is from TFA reference added to lysed cell pellet. The integrated areas under these two peaks can be used to calculate the mean $^{19}$F/cell (see Experimental), often ranging from $10^{11}$-$10^{13}$. The same approach was used for evaluating uptake in all cell types tested.

Cell Number and Viability:

Cell viability after PFPE labeling may depend on a variety of factors, for example these may include: the PFPE derivative used, the surfactants used for emulsion preparation, the presence of lipids, the particle size, the serum stability of the emulsion and the washing efficiency. In vitro assays for cell number and viability of fluorocarbon-labeled cells are widely known in the art.

In the examples given below, cellular number was estimated using the commercial assay Cell Titer Glo (Promega). The assay implementation is easy and highly reproducible. A correlation curve was constructed for each labeling experiment at the day of experiment using the same cell culture. When testing the viability post-labeling, a small sample (50 µL) was taken from labeled cell suspension and mixed with Cell Titer Glo reagent in triplicate. Luminescence was measured within 10 minutes and the viable cell number was estimated from a linear correlation curve prepared on the day of experiment.

Toxicity and serum instability are often key screening criteria for newly developed PFPE formulations, in addition to good DLS profiles (i.e., small particle size and low PDI). The PFPE/CTAB/L35 emulsion was an example where high toxicity stopped further development. The toxicity came from CTAB primarily, even at the lowest dose, where cells detached post-labeling within one hour. The emulsion dose that was safe was too low to provide useful labeling.

PFPE/L35 and PFPE/F68 combinations were examples of useful formulations for cell labeling. Pluronics™ L35 and F68 were non-toxic when administered to cells alone. Various PFPE derivatives were tested for efficiency of cell labeling with L35 or F68 Pluronics™ with and without polyamines, PEI or protamine sulfate.

Figure 37:
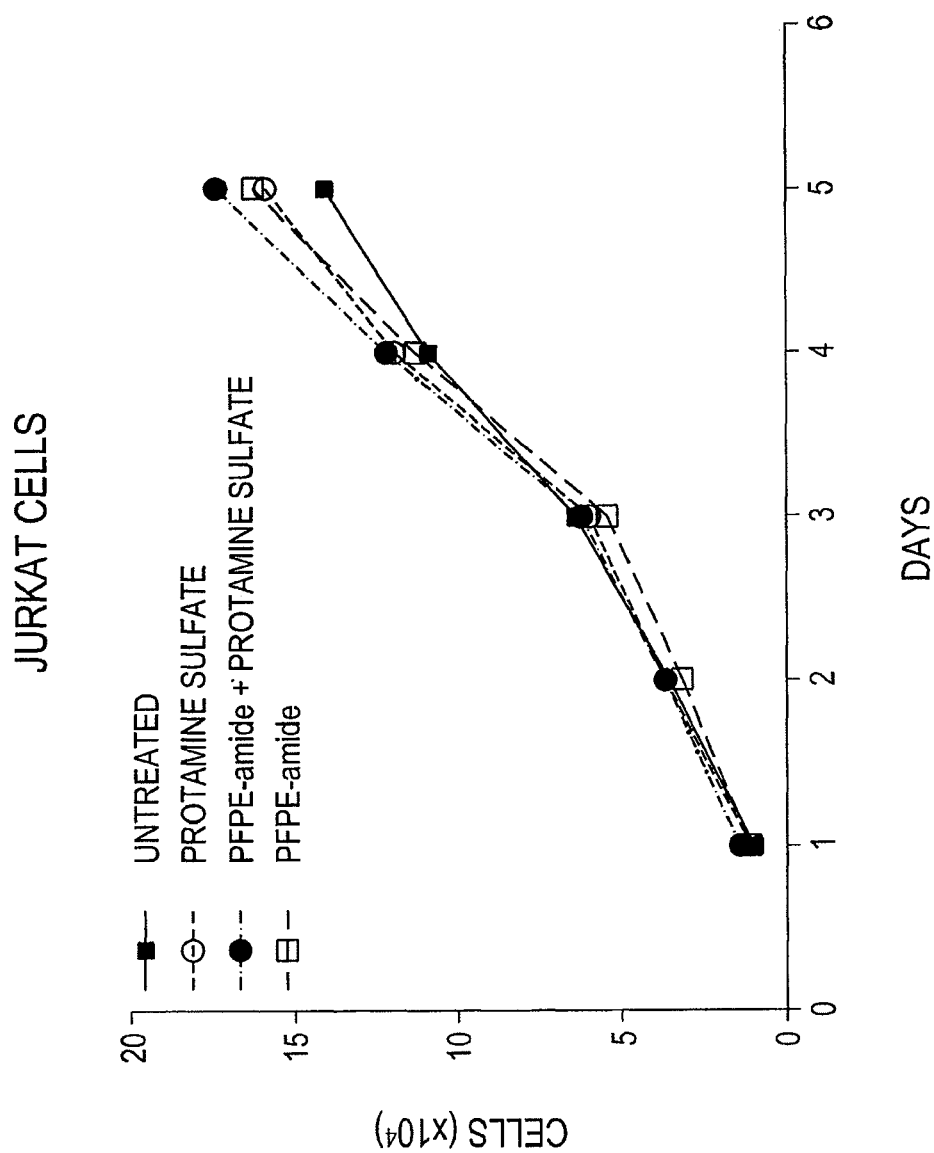
FIG. 37. Long term viability of PFPE labeled Jurkat Cells. Labeled cells were cultured in 96-well plates and viability was tested by Cell Titer Glo at each time point. Data represents the average of triplicate experiments (mean±SD).
Figure 38:
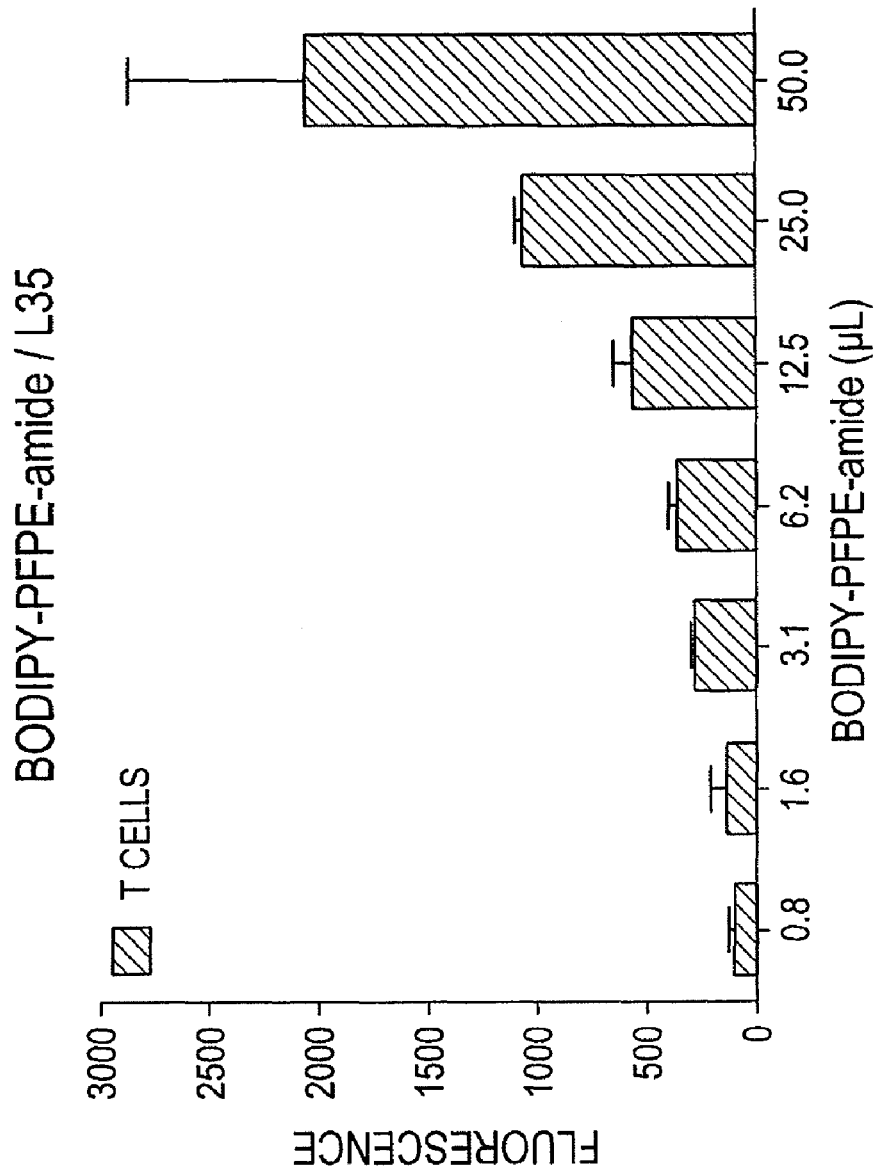
FIG. 38. BODIPy-PFPE amide 16 and PFPE amide 1 emulsified with L35 in water by sonication and used for T cell labeling. PFPE-BODIPy/L35 emulsion uptake in T cells was measured by the fluorescent signal of covalently bound BODIPy-TR dye. These quantitative fluorescence measurements demonstrate a dose dependent uptake.

PFPE labeled cells were tested for long term viability in vitro by replating labeled cells in 96 well plates at the same density as untreated controls and following them over five days by testing their viability by Cell Titer Glo each day. Growth curves were constructed. Labeled and non-labeled cells had the same growth profile, confirming that the PFPE label was non-toxic. FIG. 37 shows growth of Jurkat cells labeled with several different PFPE formulations measured by Cell Titer Glo and performed in triplicate.

3.1. PFPE Labeling of Attached Cells

Labeling mouse dendritic cells was performed according to published methods with minor modifications[35]. Dendritic cells were plated in 6-well plates, $1-2 \times 10^6$/well, and allowed to attach overnight. A PFPE diethyl amide 1/L35 emulsion was mixed with 0.3 mL of serum free media, incubated for 30 min at room temperature, and then added to the cells. After a 3 h incubation at 37° C., the cell labeling medium was removed and cells were washed three times with 1×PBS, detached by trypsinization, washed, and resuspended in 0.5 mL of complete media containing 10% FBS. A portion of the cell suspension (1/10) was used for cell number estimates by Cell Titer Glo. The cells were pelleted\ and resuspended in 0.1 mL of media for $^{19}$F NMR measurements to assess the cell loading.

PFPE Uptake Measurement by $^{19}$F NMR:

When dendritic cells were used, the cell suspension (0.1 mL) was mixed with 100 ul of 1% TFA solution in glycerol as a calibrated $^{19}$F reference. The two solutions were mixed well and transferred into a 5 mm NMR tube. Cell uptake was calculated from the relative areas under the peak at −91.5 ppm (PFPE main peak) and the TFA internal standard peak at −76 ppm. Cellular uptake (i.e., the parameter Fc) was calculated as the mean number of fluorine atoms per single viable cell.

Figure 32A:
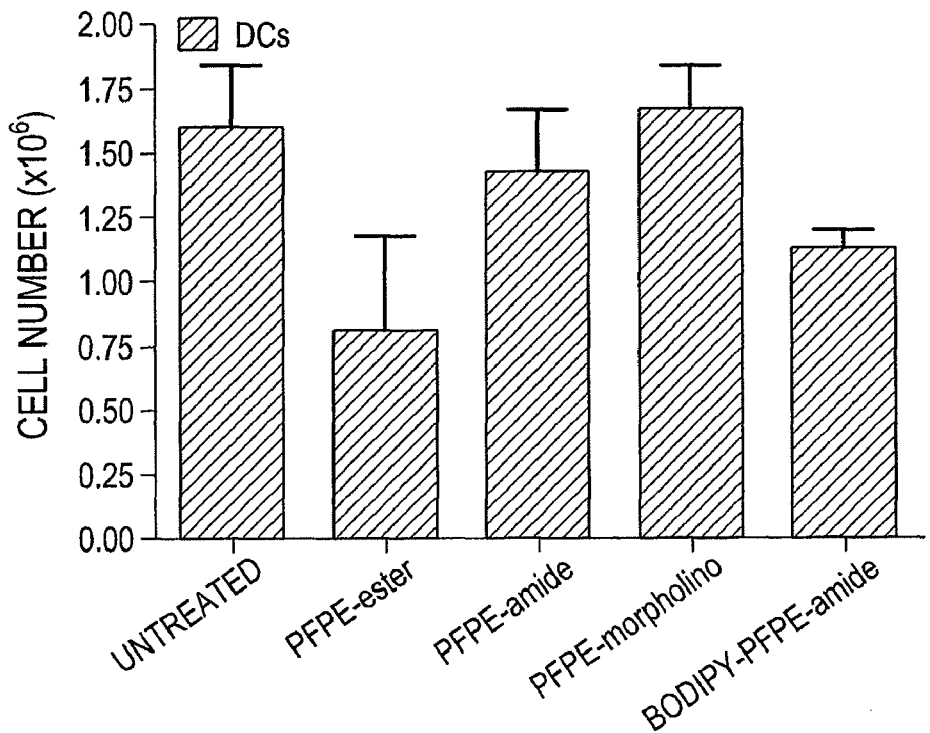
FIGS. 32A-32B. Labeling DCs with different PFPE derivatives emulsified with L35 by sonication. A) Cell number estimated from Cell Titer Glo luminescence-cell number correlation curve. Data represents the average of two independent labeling tests (mean±SD). B) Fluorine content estimated from 19F NMR spectra for DC cell suspensions. Data represents the average of two independent measurements (mean±SD).
Figure 32B:
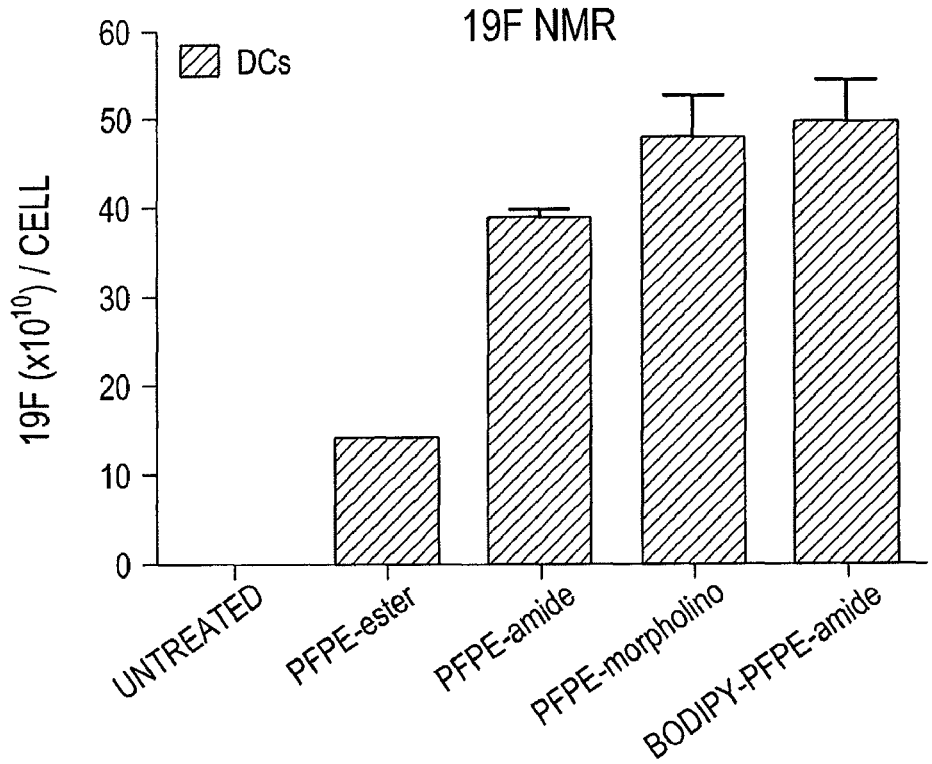

Uptake of PFPE/Pluronic™ Emulsions:

Examples of how different PFPE derivatives affect cell uptake when formulated the same way with L35 is shown in FIG. 32B. For example, modification of PFPE ester to non-hydrolizable amides (morpholino or diethylamide) clearly improved both cellular uptake and was less toxic then the PFPE-ester/L35 emulsion.

Figure 33A:
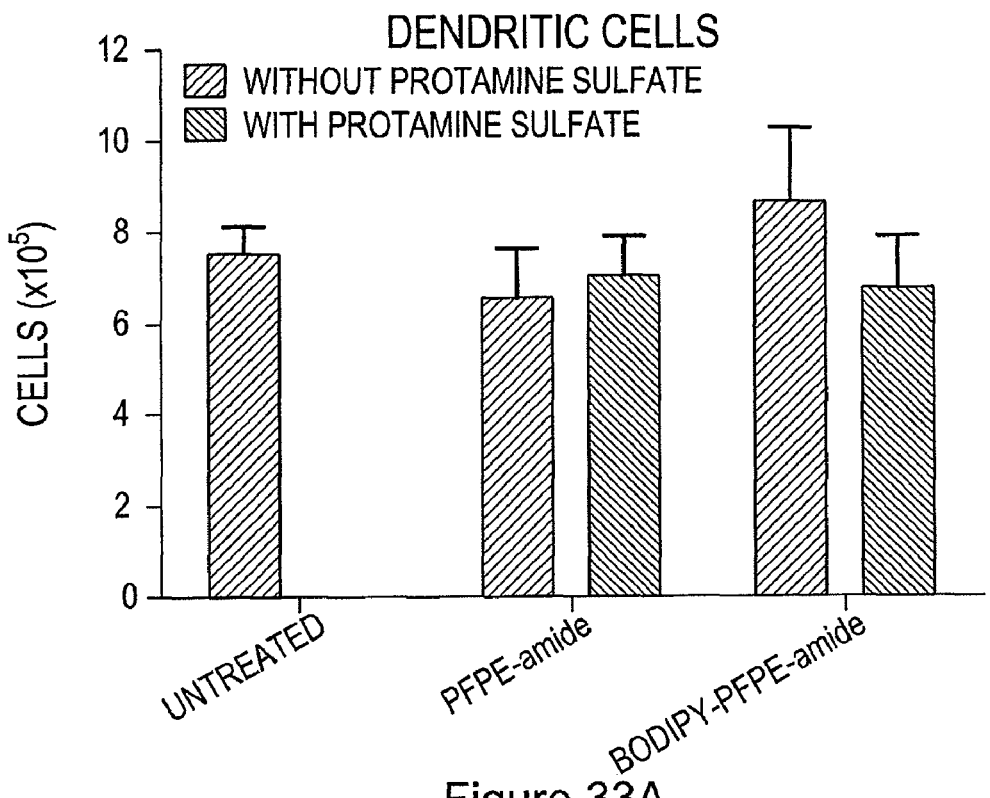
FIGS. 33A-33B. Labeling DCs with PFPE derivatives emulsified with L35 by sonication and coated with protamine sulfate prior cell labeling. A) Cell number estimated from Cell Titer Glo luminescence-cell number correlation curve. Data represents the average of two independent labeling tests (mean±SD). B) Fluorine content estimated from 19F NMR spectra for DC cell suspensions. Data represents the average of two independent measurements (mean±SD).
Figure 33B:
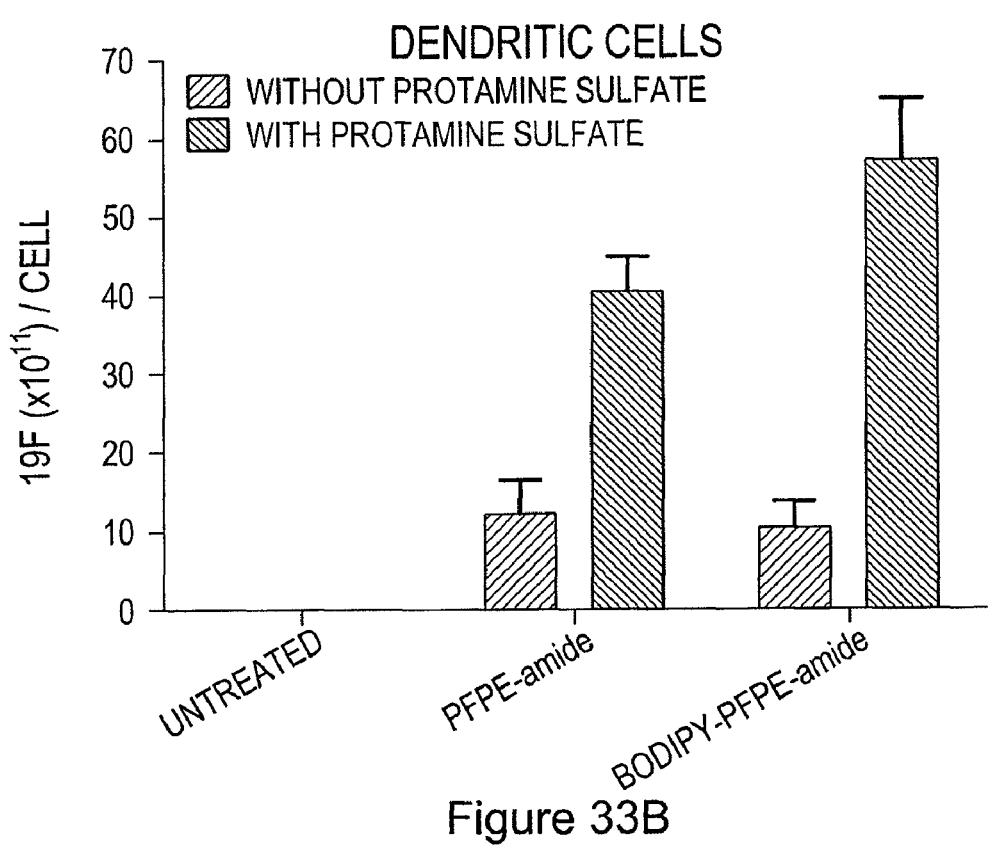

Uptake of PFPE Facilitated by Protamine Sulfate in Phagocytic Cells:

To further improve uptake in dendritic cells we used protamine sulfate. Protamine sulfate solution was mixed with prepared emulsion diluted in serum free media. After a 30 min. incubation at room temperature, the cells were treated with this mixture for three hours. When protamine sulfate was added to diluted emulsions, the emulsion particle size increased slightly (FIG. 18), but the presence of the positively charged amino groups on the droplet surface facilitated cellular uptake. Both PFPE amide/L35 and BODIPy-PFPE amide/L35 emulsion uptake was improved several fold when protamine sulfate was used, as shown in FIG. 33. Cell viability was excellent and no morphological change in labeled versus non-labeled cells was observed by light microscopy.

Figure 34A:
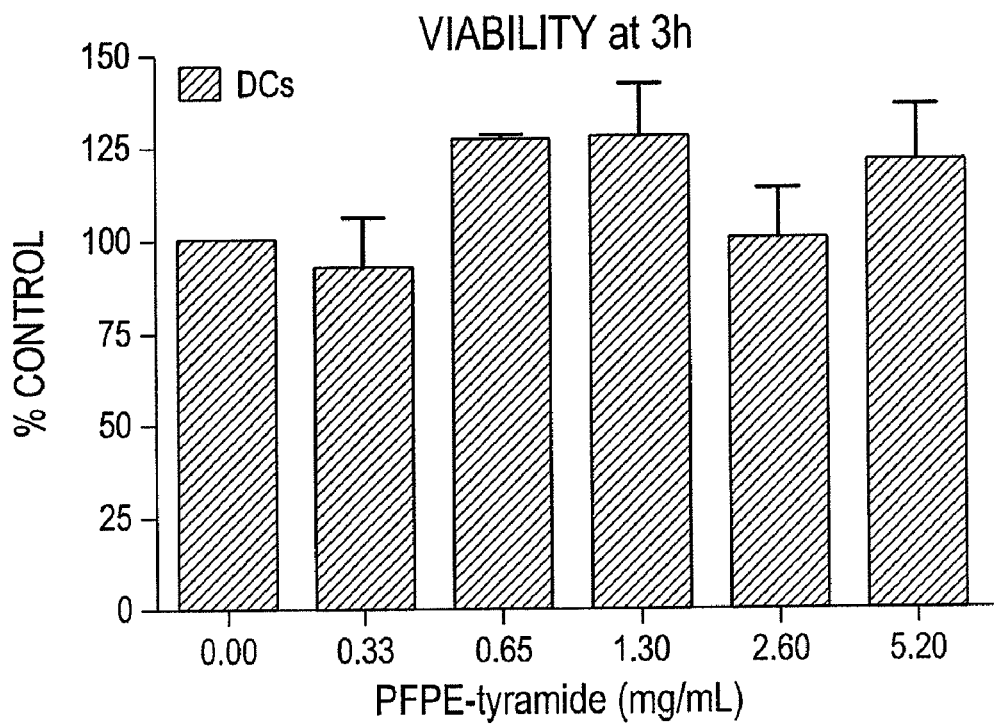
FIGS. 34A-34B. PFPE-tyramide/F68 emulsion uptake in dendritic cells. Tyramine conjugated to PFPE promotes cellular uptake and decreases cellular toxicity. A) Cellular viability estimated from Cell Titer Glo luminescence measurements. B) The 19F uptake measurement shows a linear correlation to the emulsion dose. Data represents the average of two independent measurements.
Figure 34B:
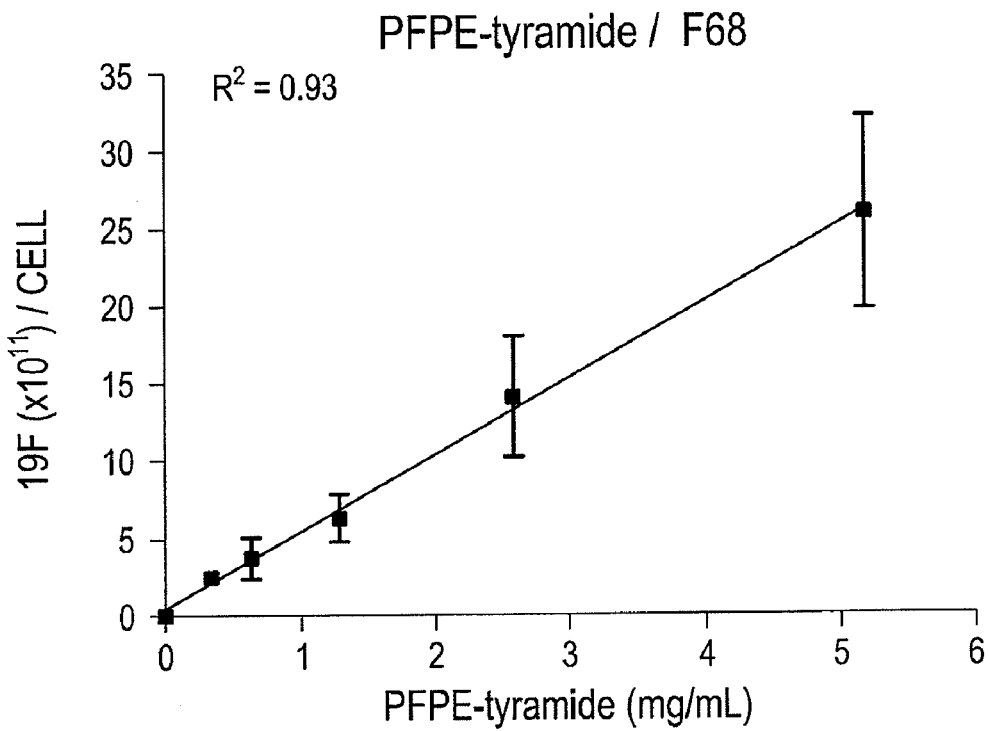

PFPE-Tyramide Facilitated Uptake:

PFPE-tyramide is a novel PFPE derivative designed to promote cellular uptake. PFPE-tyramide emulsifies easily with F68 using the low energy methods described above. PFPE tyramide was non-toxic over various doses and the $^{19}$F NMR-measured uptake showed a linear dose dependence ($R^2$=0.93), as shown in FIG. 34. Uptake was comparable to the cell labeling experiments that were facilitated with protamine sulfate. This is the first PFPE derivative designed to be self-deliverable into target cells by PFPE-conjugation to a small molecule. PFPE-tyramide also serves as a platform for many additional conjugation formulations where PFPE can be targeted to specific cell types in culture or in the body by small molecules and peptides and shows the feasibility of PFPE targeting.

4. PFPE Labeling of Cells in Suspension

PFPE amide 1 and PFPE oxide 1a emulsions were used to label cells in suspension. These emulsions showed a dose dependent labeling as measured by $^{19}$F NMR. For example, most immune cells when cultured in vitro grow in suspension. For successful cell labeling in suspension particle polydispersity is critical. Cells are mixed with emulsion droplets, and when the size and PDI are small, the mixing is homogenous which facilitates uniform cellular labeling. PFPE amide 1 and PFPE oxide 1a emulsions prepared by microfluidization satisfied these criteria.

Jurkat Cells:

Jurkat cells (ATCC, Manassas, Va.) were used as a model cell line to evaluate fluorocarbon labeling of cells in suspension. These cells were maintained according to the ATCC protocol. The suspended cells were labeled at $1-2 \times 10^6$ cells/mL in 1 mL of 20% FBS media by mixing with an emulsion dilution prepared in serum free media. After a 3 h incubation at 37° C., the cells were spun down at 1200 rpm and washed twice with media. The cells are resuspended in 0.5 mL of media. A portion of the cell suspension (1/9) was used for cell number estimates by Cell Titer Glo. The cell suspension was then spin down, and resuspended in 0.2 mL of trypsin solution in PBS, incubated at room temperature for 2 h and used for $^{19}$F NMR measurements. The lysed cell suspension (0.2 mL) was mixed with the reference TFA solution (0.2% v/v) in PBS in a 5 mm NMR tube.

Uptake of PFPE Amide 1, PFPE Oxide 1a and Blended PFPE Nanoemulsions Facilitated by Polyethylenimine (PEI) in Non-Phagocytic Cells:

To further improve uptake in non-phagocytic cells, PEI was used in PFPE microfluidized emulsion preparations. Small amounts of PEI added to the emulsion was not enough to reverse the zeta potential from negative to positive; the zeta potential was −26 mV in presence of PEI. The value of zeta potential is not predictive of the cell uptake capacity of the emulsion; however, the presence of primary amines on the PFPE emulsion droplet surface does significantly enhance cell uptake. A significant effect of PEI on PFPE uptake was observed in Jurkat cells, as shown in FIG. 41. PFPE-PEI emulsions showed a linear correlation between $^{19}$F/cell and labeling dose of emulsion in medium with an excellent viability profile (FIG. 42).

Primary T-Cells:

Primary T cells were isolated from the mouse spleen as described in WO2005072780. Cells were activated by IL-2 for 3 days prior to fluorocarbon labeling. T cells were labeled in suspension, washed three times with PBS, and resuspended for $^{19}$F NMR measurements. Viability was assessed by Cell Titer Glo, using a correlation curve constructed with non-labeled T cells. The viability of PFPE labeled T cells at the time of labeling was >60%. When labeled cells were plated and followed over 48 h, the viability was comparable to that of the un-labeled control cells.

5.1. Correlating Fluorescence to $^{19}$F NMR Signal in BODIPy-PFPE Amide/L35 Labeled Cells Introducing BODIPy-TR dye had several advantages over hydrophilic Cy dyes. The most important was the ease of coupling to PFPE. BODIPy-TR with primary amine handle is commercially available (e.g., from Molecular Probes, Eugene, Oreg.) as BODIPy-TR cadaverine. Coupling of this amine to PFPE was easy and highly efficient. BODIPy-TR dye was chosen for its chemical stability and fluorescent properties that allow simultaneous labeling with FITC or Rhodamine labeled antibodies, allowing phenotypic confirmation of cellular type and function.

The improved BODIPy-PFPE label was successfully used for T cell and DC labeling. Blended BODIPy-PFPE amide 16, PFPE amide 1 and PFPE oxide 1a, emulsified by microfluidization with F68 and PEI show clear intracellular localization in both DCs and T cells after 3 h incubation, FIGS. 56 and 57, respectively.

5.2. Correlating Fluorescence to $^{19}$F NMR Signal in BODIPy-PFPE "Blended" Oil Nanoemulsion Labeled Jurkat Cells Jurkat cells labeled with BODIPy-PFPE blended nanoemulsion showed a linear correlation between the fluorescence signal and the $^{19}$F NMR-measured uptake. This clearly shows that fluorescence measurements of cells labeled with PFPE conjugated to fluorescent dye can be used to estimate uptake without expensive NMR measurements, or serve as a second independent technique to confirm the NMR measurements. Uptake measured by fluorescence and NMR were consistent and comparable (FIG. 58).

Figure 39:
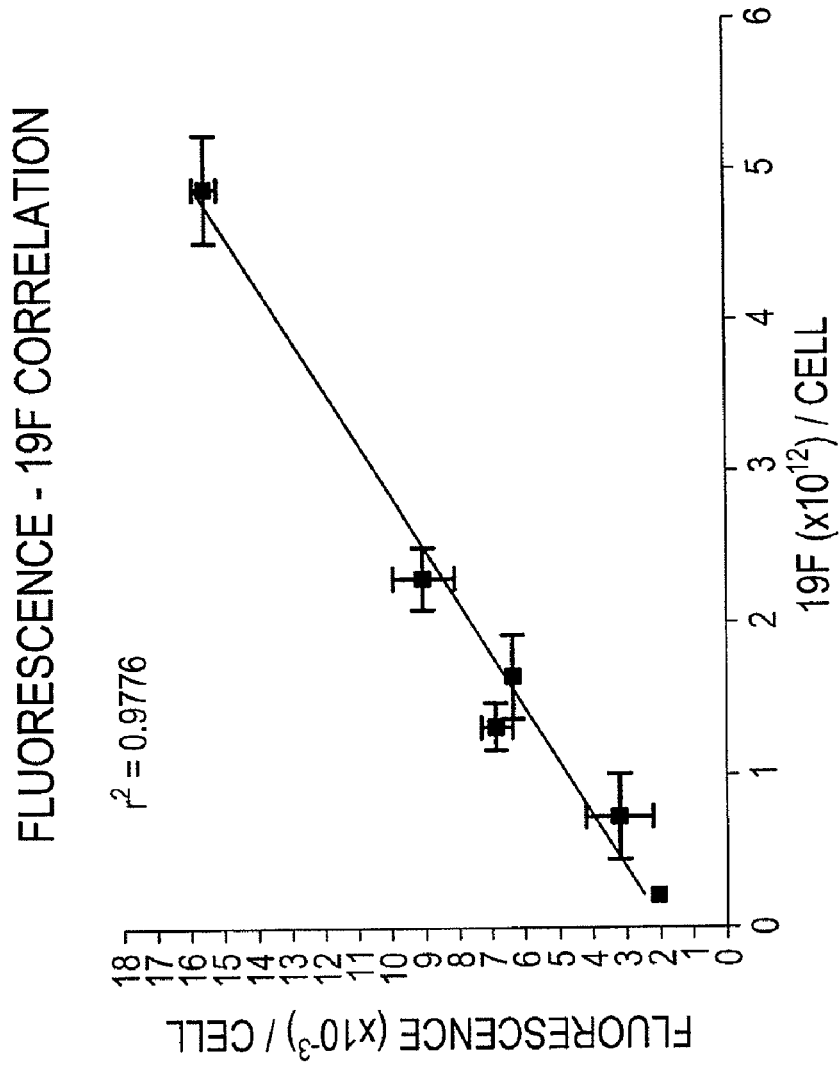
FIG. 39. Correlation between fluorescence signal and the $^{19}$F NMR signal from T cells labeled with PFPE-BODIPy/L35 emulsion. Data represents the average of duplicate experiments (mean±SD). Data demonstrates utility of the dual fluorescent-19F label.
Figure 40:
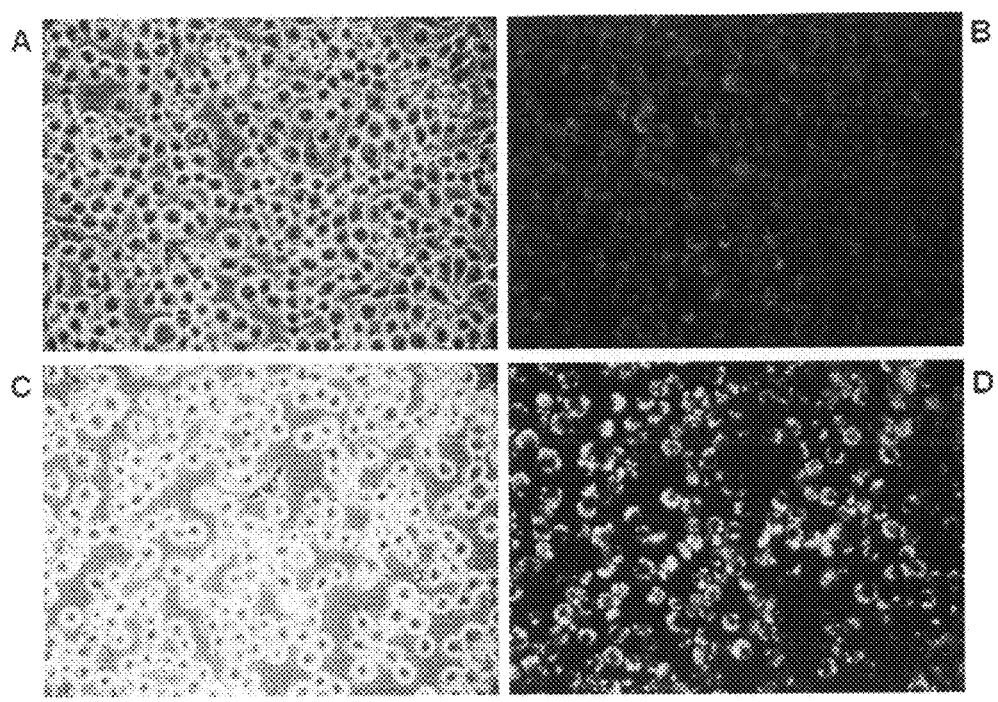
FIGS. 40A-40D. Fluorescent images of DCs labeled with BODIPy-PFPE/L35 emulsion (A is untreated, B is labeled) and BODIPy-PFPE/L35 coated with protamine sulfate (C is untreated, D is labeled).

In order to correlate fluorescence and $^{19}$F NMR signal, it was assumed that there was a linear correlation between fluorescence intensity to cell number labeled with BODIPy-PFPE. Fluorescence signal and NMR signal were normalized by the viable cell number. Correlation was linear with $R^2=0.9776$ (FIGS. 39 and 58A). Fluorescence microscopy confirmed efficient and uniform dendritic cell labeling with both FITC PFPE blended nanoemulsion (FIG. 56A-B) and BODIPy-PFPE blended nanoemulsion (FIG. 56C-D). Also, a high-level of uniform labeling was observed when the BODIPy-PFPE amide/L35 emulsion was combined with protamine sulfate (FIG. 40). In both cases, the nanoemulsion localizes in the cytoplasm and no emulsion droplets were observed outside the cells or on the cell surface.

6. Uptake of Nanoemulsion Prepared with Compound 42

Figure 63A:
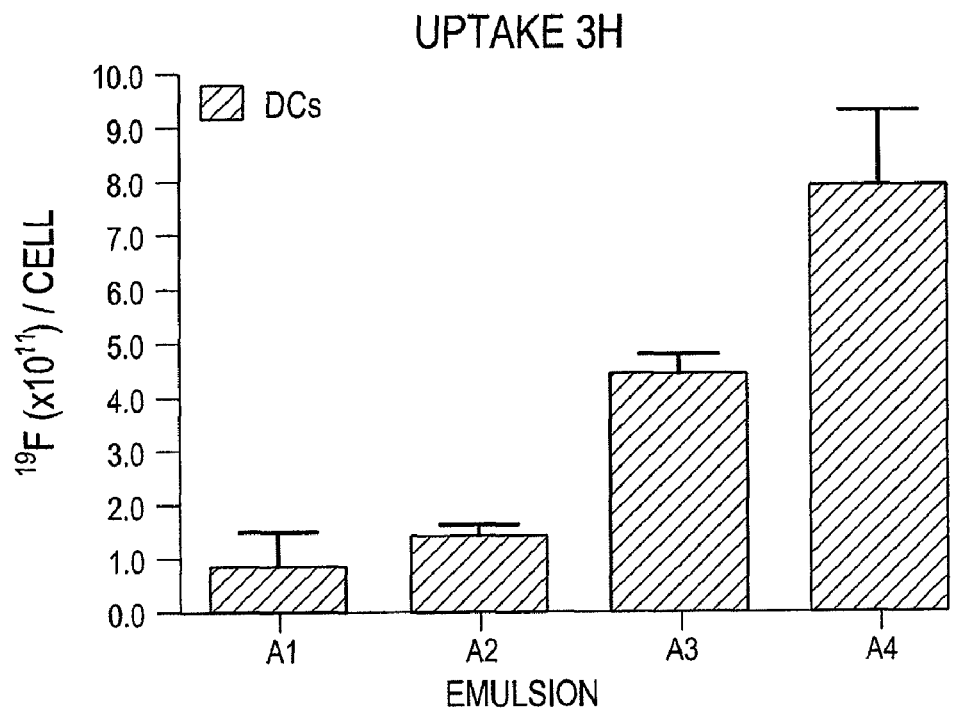
FIG. 63. Effect surfactant amount on CF$_3$ nanoemulsion uptake in DCs. A) Uptake in DCs measured by 19F NMR; B) Cell viability upon 3 h exposure to different nanoemulsions. Data represents the average of two independent measurements (mean±SD).
Figure 63B:
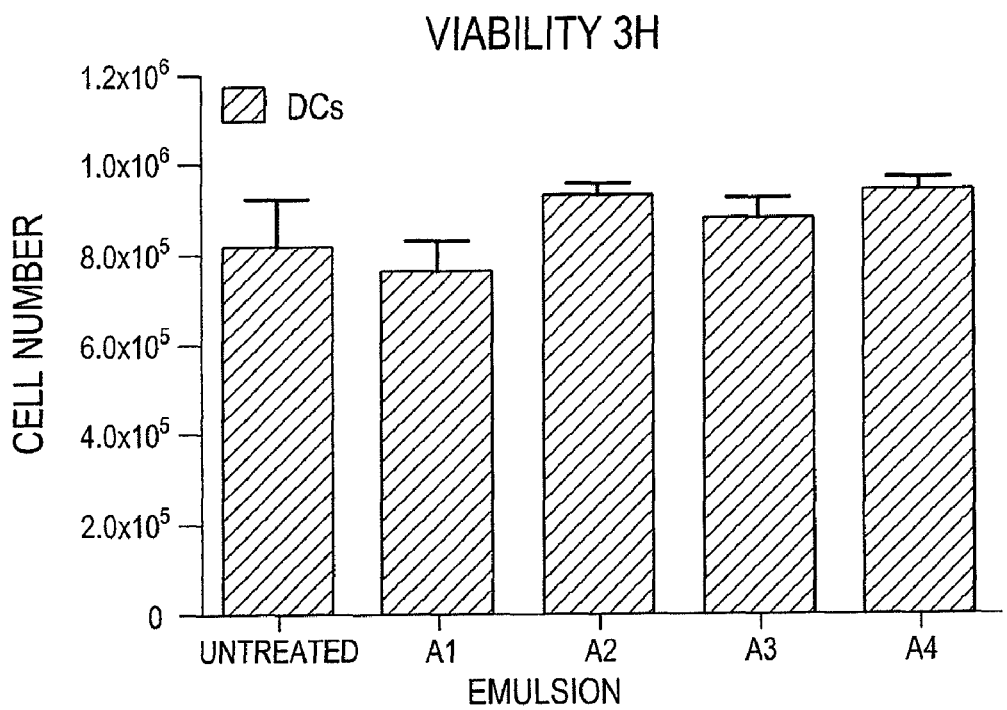
Figure 64:
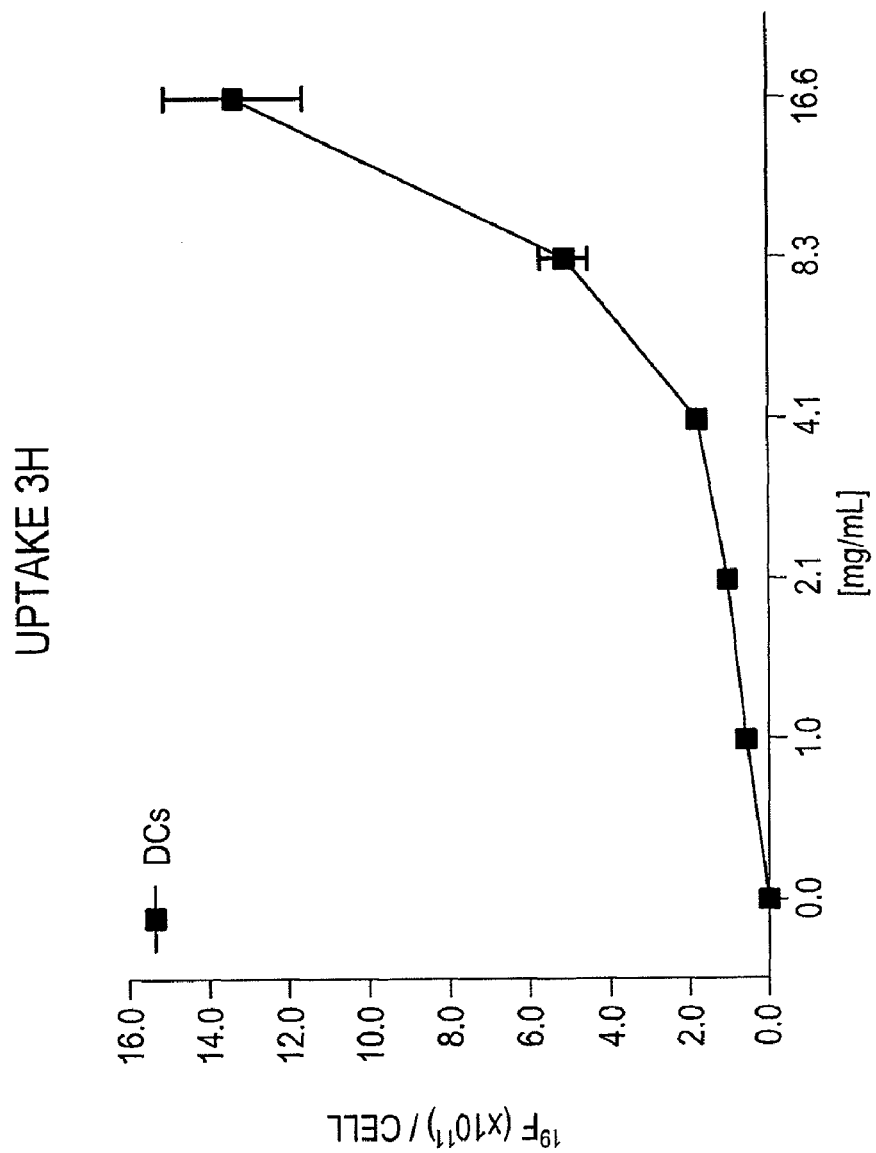
FIG. 64. Dose dependent uptake of nanoemulsion A4 in DCs upon 3 h incubation. Uptake was measured by $^{19}$F NMR. Data represents the average of 4 independent measurements (mean±SD).

Emulsions of compound 42 (see Table 1) were tested for cellular uptake in dendritic cells (FIG. 63) The increase in amount of surfactant decreased the cell uptake upon a 3 hour incubation, as measured by $^{19}$F NMR. The cell viability was unchanged upon exposure to all tested compound 42 nanoemulsions. Nanoemulsion A4 was examined for dose dependent uptake in DCs (FIG. 64).

Figure 65:
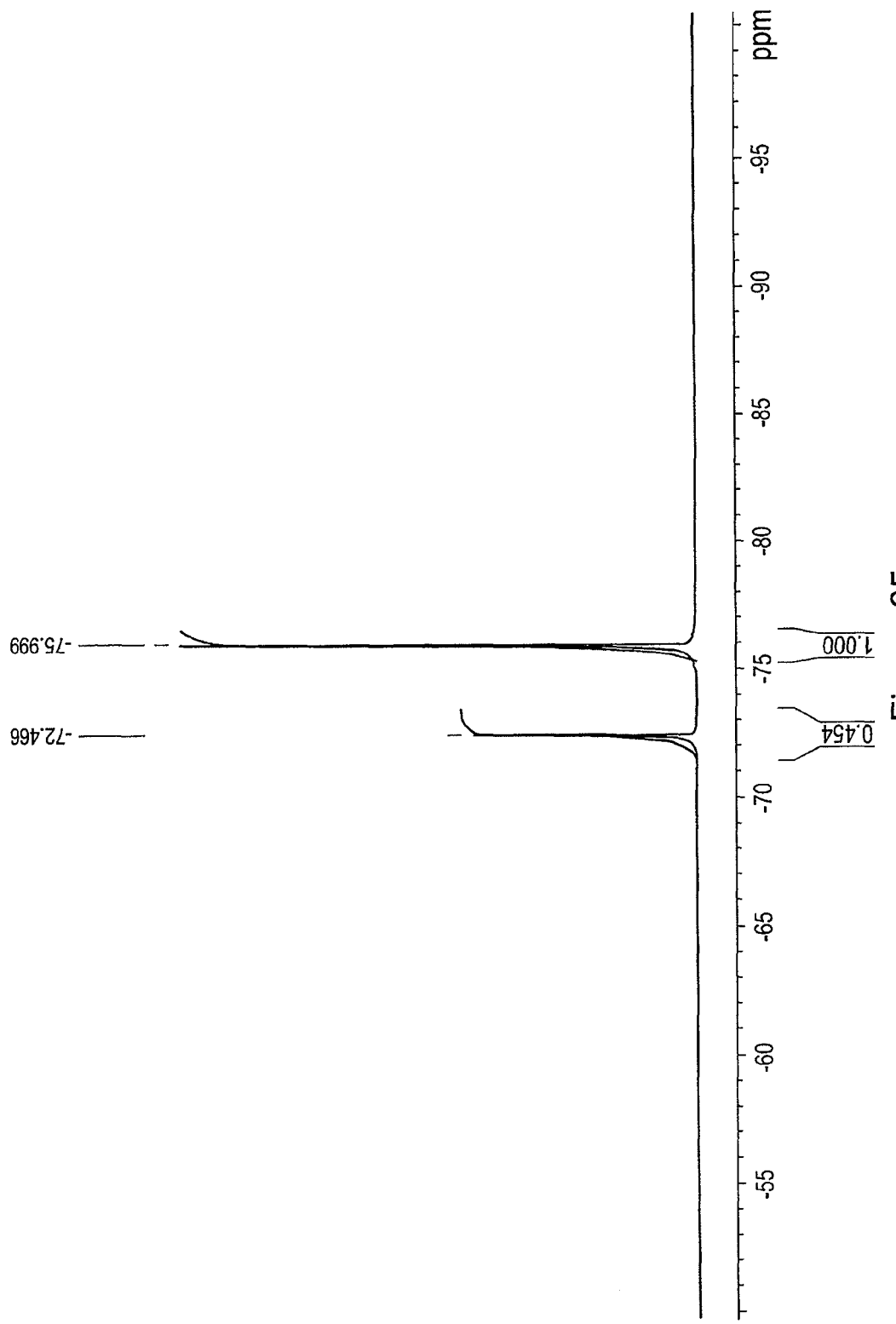
FIG. 65. $^{19}$F NMR spectrum of nanoemulsion A4 labeled DCs. Labeled cells are represented with the peak at −72.5 ppm, while TFA serves as a reference at −76.0 ppm.

Nanoemulsion A4 was also used to label bone marrow derived immature mouse DCs. These cells were incubated with nanoemulsion A4 for 4 hours, washed and the $^{19}$F NMR spectrum of labeled cells was analyzed (FIG. 65). Labeled cells showed resonance at −72.5 ppm, which is widely separated from the main peak of PFPE (−91.6 ppm).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

1. Feili-Hariri, M., et al., *Immunotherapy of NOD mice with bone marrow-derived dendritic cells*. Diabetes, 1999. 48: p. 2300-2308.
2. Pluchino, S., et al., *Injection of adult neurospheres induces recovery in a chronic model of multiple sclerosis*. Nature, 2003. 422(6933): p. 688-694.
3. Yeh, T. C., et al., *In-vivo dynamic MRI tracking of rat T-cells labeled with superparamagnetic iron-oxide particles*. Magn Reson Med, 1995. 33: p. 200-208.
4. Schulze, E., et al., *Cellular uptake and trafficking of a prototypical magnetic iron oxide label in vitro*. Invest Radiol, 1995. 30(10): p. 604-10.
5. Moore, A., R. Weissleder, and A. Bogdanov, *Uptake of dextran-coated monocrystalline iron oxides in tumor cells and macrophages*. JMRI-Journal of Magnetic Resonance Imaging, 1997. 7(6): p. 1140-1145.
6. Weissleder, R., et al., *Magnetically labeled cells can be detected by MR imaging*. JMRI-Journal of Magnetic Resonance Imaging, 1997. 7(1): p. 258-263.
7. Schoepf, U., et al., *Intracellular magnetic labeling of lymphocytes for in vivo trafficking studies*. Biotechniques, 1998. 24(4): p. 642-+.
8. Ye, Q., et al., *In vivo detection of acute rat renal allograft rejection by MRI with USPIO particles*. Kidney International, 2002. 61(3): p. 1124-1135.
9. Dousset, V., et al., *In vivo macrophage activity imaging in the central nervous system detected by magnetic resonance*. Magnetic Resonance in Medicine, 1999. 41(2): p. 329-333.
10. Josephson, L., et al., *High-fficiency intracellular magnetic labeling with novel superparamagnetic-tat peptide conjugates*. Bioconjugate Chemistry, 1999. 10(2): p. 186-191.
11. Dodd, C. H., et al., *Normal T-cell response and in vivo magnetic resonance imaging of T cells loaded with HIV transactivator-peptide-derived superparamagnetic nanoparticles*. Journal of Immunological Methods, 2001. 256(1-2): p. 89-105.
12. Ahrens, E. T., et al., *Receptor-mediated endocytosis of iron-oxide particles provides efficient labeling of dendritic cells for in vivo MR imaging*. Magn. Reson. Med., 2003. 46(6): p. 1006-1013.
13. Hoehn, M., et al., *Monitoring of implanted stem cell migration in vivo: A highly resolved in vivo magnetic resonance imaging investigation of experimental stroke in rat*. Proceedings of the National Academy of Sciences of the United States of America, 2002. 99(25): p. 16267-16272.
14. Lewin, M., et al., *Tat peptide-derivatized magnetic nanoparticles allow in vivo tracking and recovery of progenitor cells*. Nature Biotechnology, 2000. 18(4): p. 410-414.
15. Kanno, S., et al., *Macrophage accumulation associated with rat cardiac allograft rejection detected by magnetic resonance imaging with ultrasmall superparamagnetic iron oxide particles*. Circulation, 2001. 104(8): p. 934-938.
16. Fishman, J. E., et al., *Oxygen-sensitive 19F NMR imaging of the vascular system in vivo*. Magn Reson Imaging, 1987. 5(4): p. 279-85.
17. Eidelberg, D., et al., *19FNMR imaging of blood oxygenation in the brain*. Magn Reson Med, 1988. 6(3): p. 344-52.
18. Dardzinski, B. J. and C. H. Sotak, *Rapid tissue oxygen tension mapping using 19F inversion-recovery echo-planar imaging of perfluoro-15-crown-5-ether*. Magn Reson Med, 1994. 32(1): p. 88-97.
19. Noth, U., et al., *In-vivo measurement of partial oxygen-pressure in large vessels and in the reticuloendothelial system using fast 19F-MRI*. Magn Reson Med, 1995. 34(5): p. 738-745.
20. Lutz, J., et al., *Measurement of oxygen tensions in the abdominal cavity and in the skeletal muscle using 19F-MRI of neat PFC droplets*. Oxygen Transport to Tissue Xix, 1997. 428: p. 569-572.
21. Duong, T. Q. and S. G. Kim, *In vivo MR measurements of regional arterial and venous blood volume fractions in intact rat brain*. Magn. Reson. Med., 2000. 43(3): p. 393-402.
22. McGoron, A. J., et al., *Perfluorocarbon distribution to liver, lung and spleen of emulsions of perfluorotributylamine (FTBA) in pigs and rats and perfluorooctyl bromide (PFOB) in rats and dogs by F-19 NMR-spectroscopy*. Artificial Cells Blood Substitutes and Immobilization Biotechnology, 1994. 22(4): p. 1243-1250.
23. Noth, U., et al., *Perfluoro-15-crown-5-ether labelled macrophages in adoptive transfer experimental allergic encephalomyelitis*. Artificial Cells Blood Substitutes and Immobilization Biotechnology, 1997. 25(3): p. 243-254.

24. Girolomoni, G., et al., *Establishment of a cell-line with features of early dendritic cell precursors from fetal mouse skin*. European Journal of Immunology, 1995. 25(8): p. 2163-2169.
25. WO2005072780
26. Arbab, A. S., et al., Blood, 2004. August 15; 104(4):1217-23.
27. Floris S., et al., Brain. 127 (2004), pp. 616-27.
28. U.S. Pat. No. 5,958,371
29. US patent application 20020192688
30. Tonelli, et al. J. Fluorine Chem. 95 (1999), pp. 51-70.
31. Tonelli, et al. J Polym Sci Part A: Polym Chem 40 (2002), pp. 4266-4280,
32. Tonelli et al. Perfluoropolyether functional oligomers: unusual reactivity in organic chemistry, Journal of Fluorine Chemistry, Volume 118, Issues 1-2, 1 Dec. 2002, Pages 107-121
33. Piacenti and Camaiti, Synthesis and characterization of fluorinated polyetheric amides, Journal of Fluorine Chemistry, 68 (1994), pp. 227-235
34. Ahrens E T et al. *In vivo imaging platform for tracking immunotherapeutic cells*. Nat. Biotechnol. 23 (2005), pp. 983-987
35. Wei Shang and Dennis P. Curran. *Synthetic applications of fluorous solid-phase extractions (F-SPE)* Tetrahedron 62 (2006), pp. 11837-11865
36. Jiang Z-X, Yu Y B. The design and synthesis of highly branched and spherically symmetric fluorinated oils and amphiles. Tetrahedron 2007; 63(19):3982-8.

EQUIVALENTS

While specific embodiments of the subject inventions are explicitly disclosed herein, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

We claim:

1. A compound of any one of formulae 1, 2, 6-7, or 10-15:

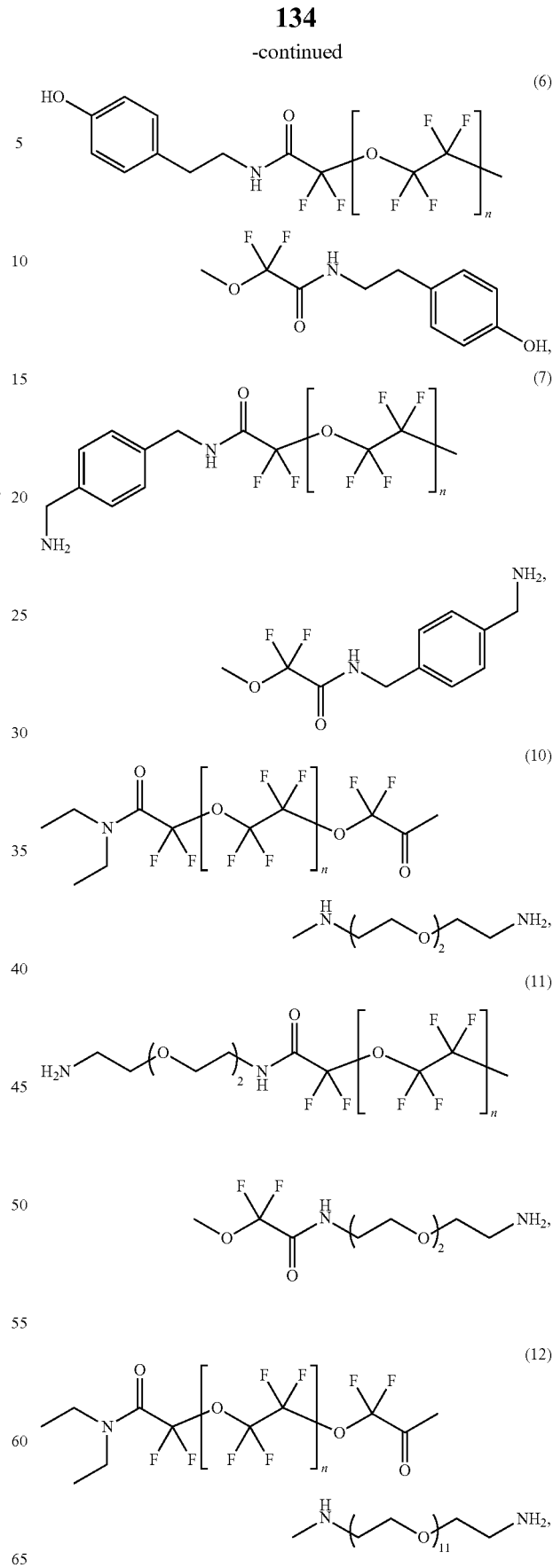

(13)

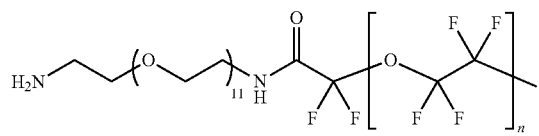

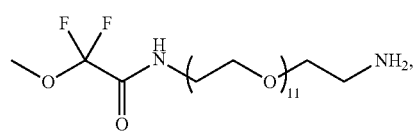

(14)

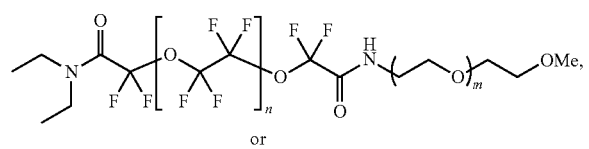

or (15)

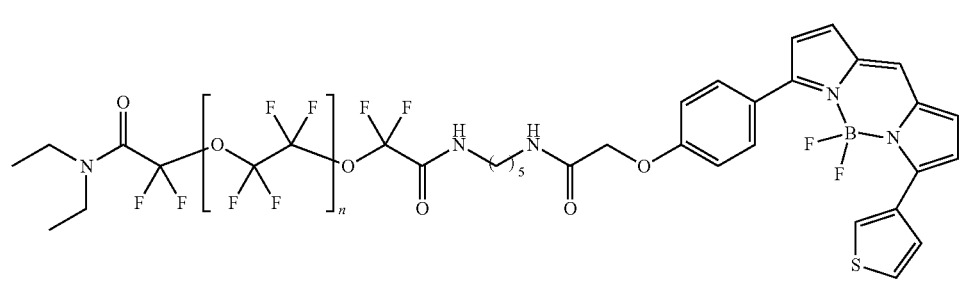

wherein
n, independently for each occurrence, represents an integer from 4 to 16.

2. A composition comprising
a compound of formula 10 and a compound of formula 1, wherein each of said compounds is as defined in claim 1;
a compound of formula 12, which compound is as defined in claim 1 and a compound of formula 1;
compound of formula 14, which compound is as defined in claim 1 and a compound of formula 1;
a compound of formula 16:

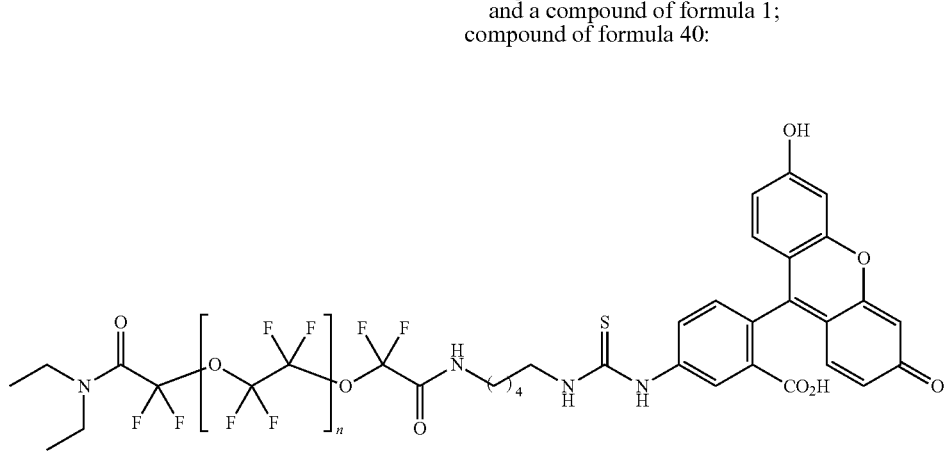

wherein
n, independently for each occurrence, represents an integer from 4 to 16
and a compound of formula 1;
compound of formula 40:

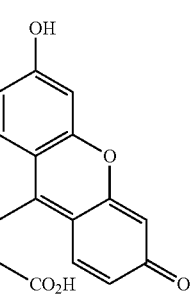

wherein
n, independently for each occurrence, represents an integer from 4 to 16
and a compound of formula 1;
a compound of formula 10 and a compound of formula 20:

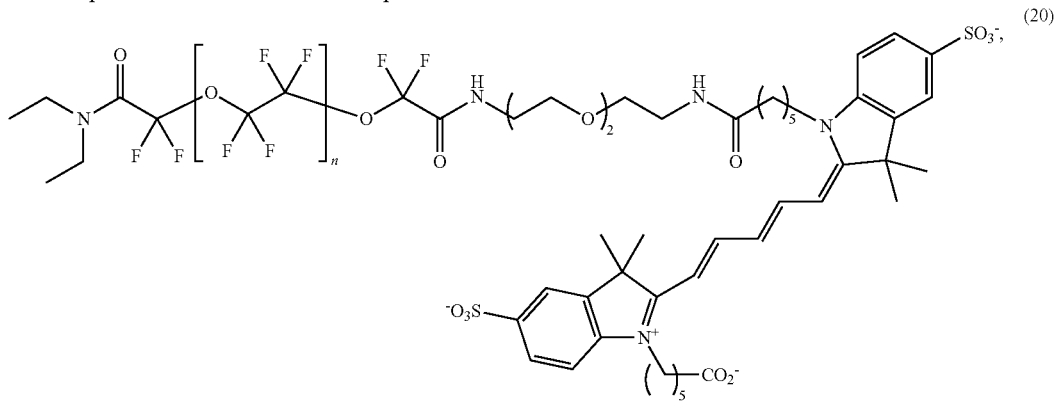

wherein
n, independently for each occurrence, represents an integer from 4 to 16;
a compound of formula 10, a compound of formula 20, and a compound of formula 1;
a compound of formula 11, which compound is as defined in claim 1 and a compound of formula 21:

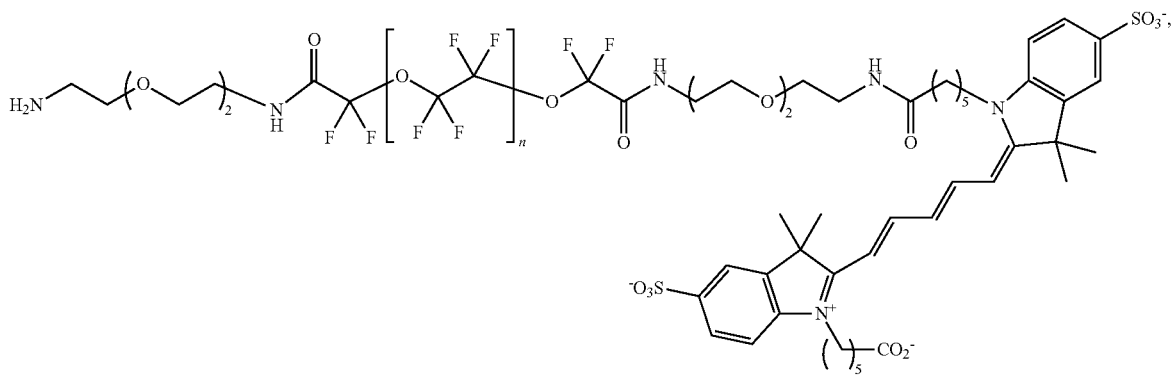

wherein
n, independently for each occurrence, represents an integer from 4 to 16;
a compound of formula 11 and a compound of formula 22:

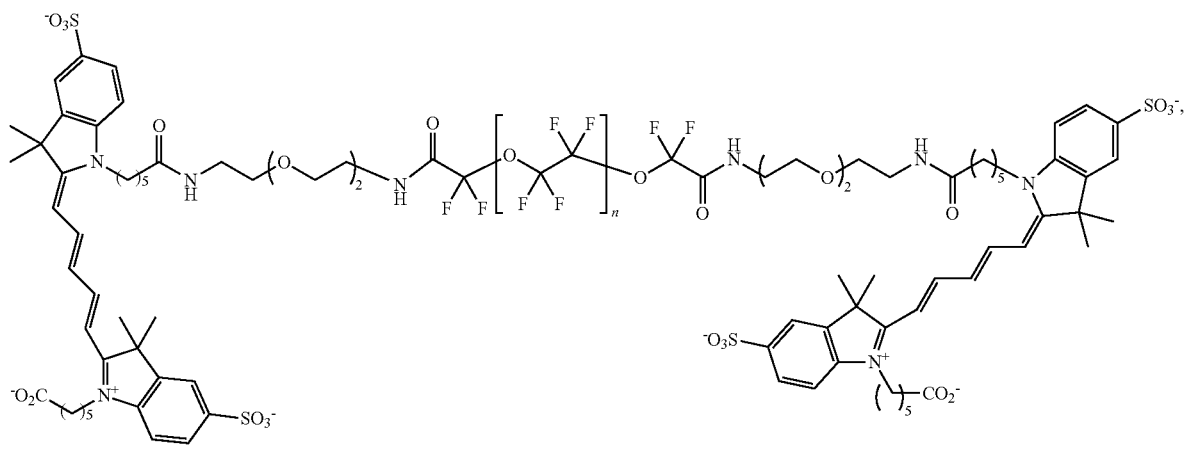

wherein
n, independently for each occurrence, represents an integer from 4 to 16;
a compound of formula 12 and a compound of formula 23:

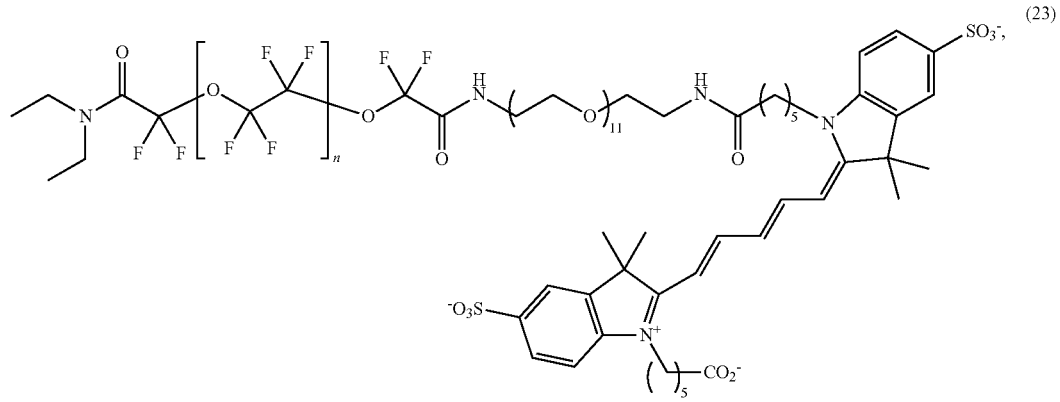

wherein
n, independently for each occurrence, represents an integer from 4 to 16:
compound of formula 12, a compound of formula 23, and a compound of formula 1;
compound of formula 13, which compound is as defined in claim 1 and a compound of formula 24:

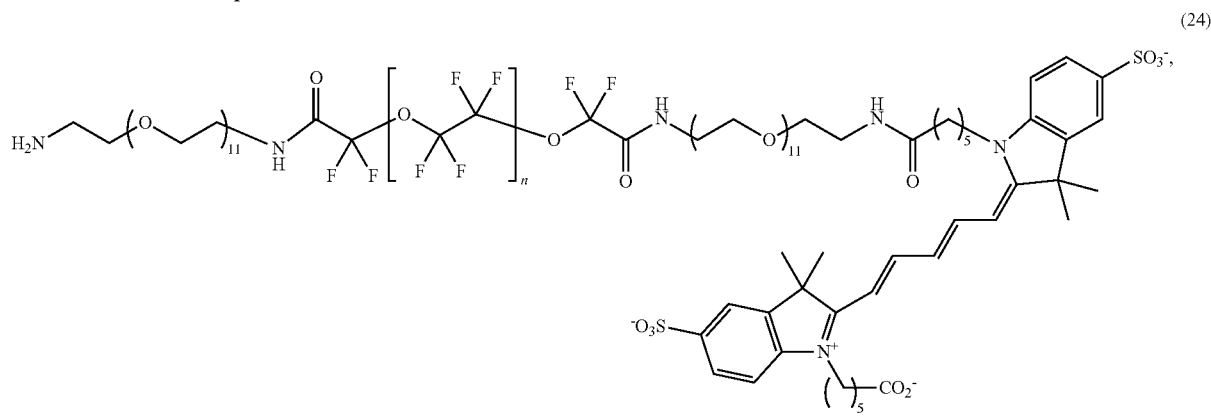

wherein
n, independently for each occurrence, represents an integer from 4 to 16;
compound of formula 13 and a compound of formula 25:

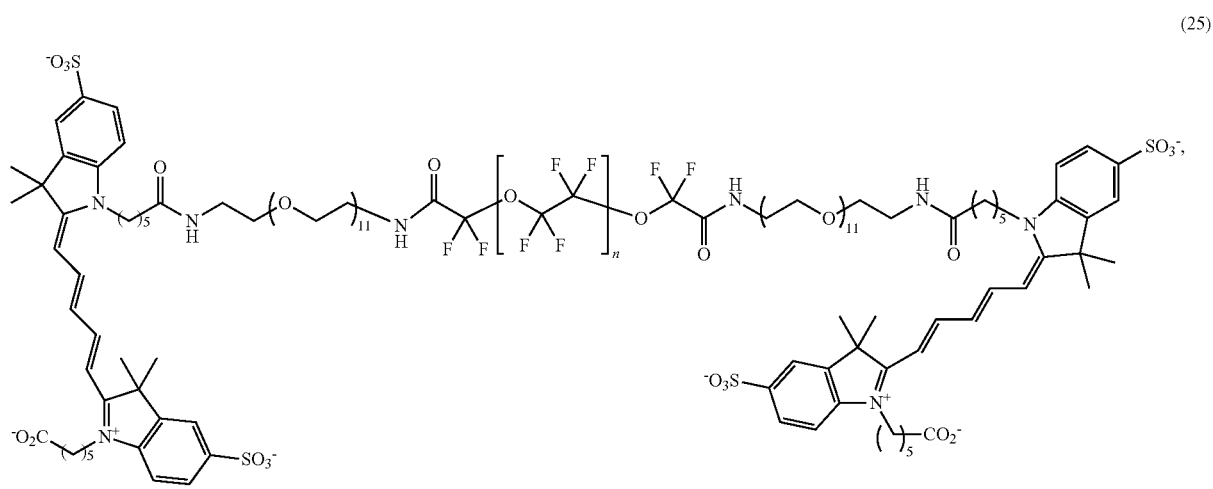

wherein
n, independently for each occurrence, represents an integer from 4 to 16;
compound of formula 10 and a compound of formula 26:

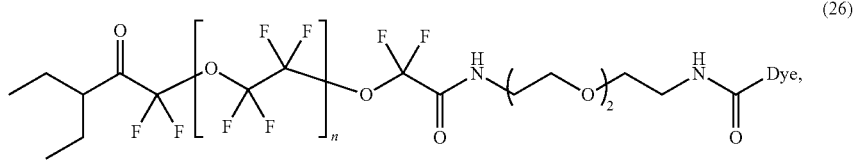

wherein
n, independently for each occurrence, represents an integer from 4 to 16; and
Dye represents a fluorescent detection moiety;
compound of formula 10, a compound of formula 26, and a compound of formula 1;
a compound of formula 11 and a compound of formula 27:

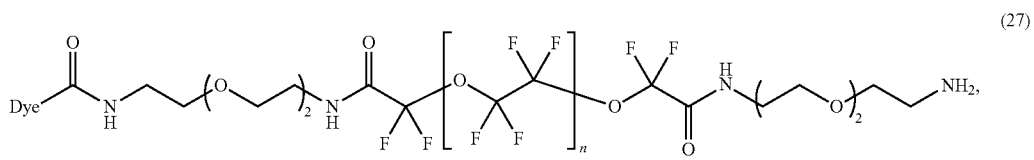

wherein
n, independently for each occurrence, represents an integer from 4 to 16; and
Dye represents a fluorescent detection moiety;
compound of formula 11 and a compound of formula 28:

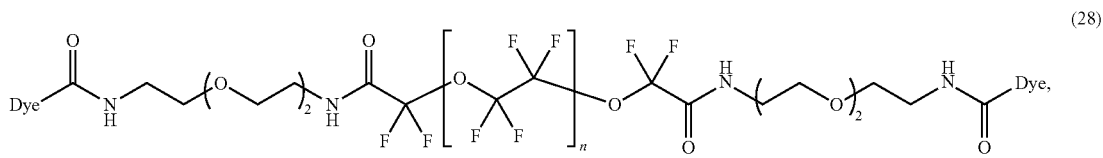

wherein
n, independently for each occurrence, represents an integer from 4 to 16; and
Dye represents a fluorescent detection moiety;
a compound of formula 12 and a compound of formula 29:

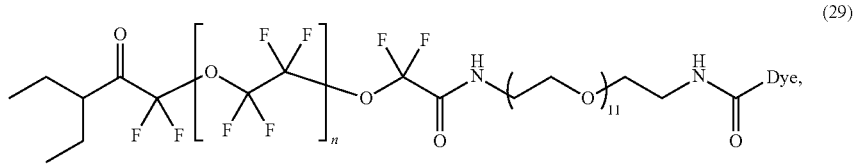

wherein
n, independently for each occurrence, represents an integer from 4 to 16; and
Dye represents a fluorescent detection moiety;
compound of formula 12, a compound of formula 29, and a compound of formula 1;

a compound of formula 13 and a compound of formula 30:

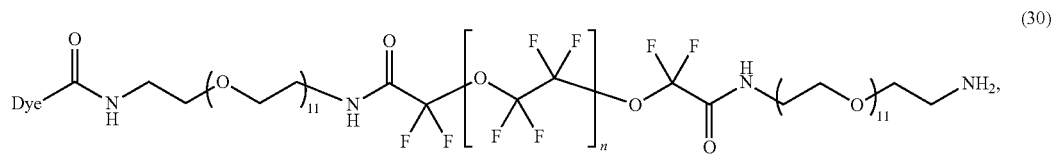
(30)

wherein
n, independently for each occurrence, represents an integer from 4 to 16; and
Dye represents a fluorescent detection moiety;
a compound of formula 13 and a compound of formula 31:

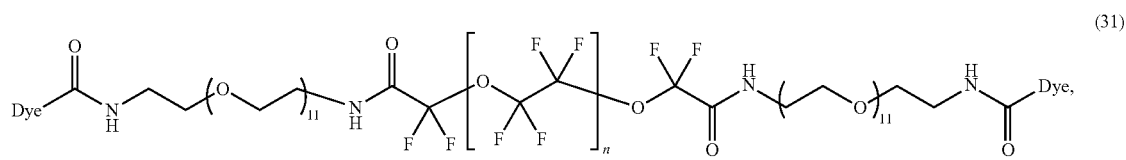
(31)

wherein
n, independently for each occurrence, represents an integer from 4 to 16; and
Dye represents a fluorescent detection moiety;
a compound of formula 10 and a compound of formula 32:

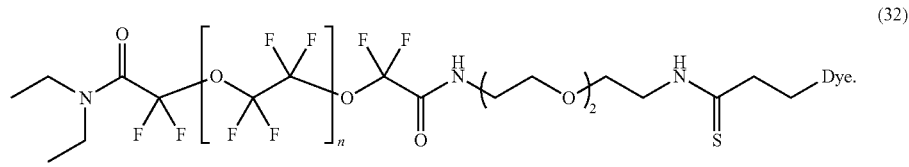
(32)

wherein
n, independently for each occurrence, represents an integer from 4 to 16; and
Dye, independently for each occurrence, represents a fluorescent detection moiety;
a compound of formula 10, a compound of formula 32, and a compound of formula 1;
compound of formula 11 and a compound of formula 33:

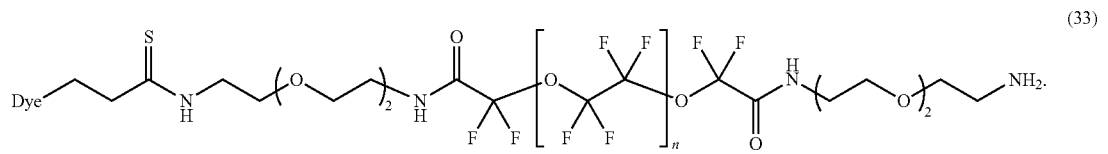
(33)

wherein
n, independently for each occurrence, represents an integer from 4 to 16; and
Dye, independently for each occurrence, represents a fluorescent detection moiety;

compound of formula 11 and a compound of formula 34:

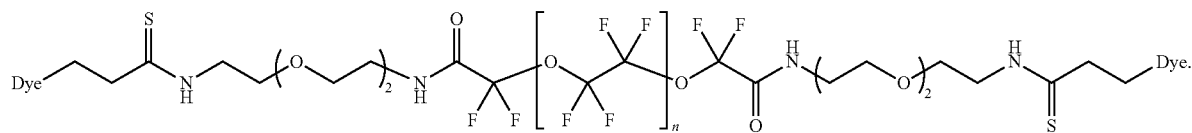

(34)

wherein
n, independently for each occurrence, represents an integer from 4 to 16; and
Dye, independently for each occurrence, represents a fluorescent detection moiety;

compound of formula 12 and a compound of formula 35:

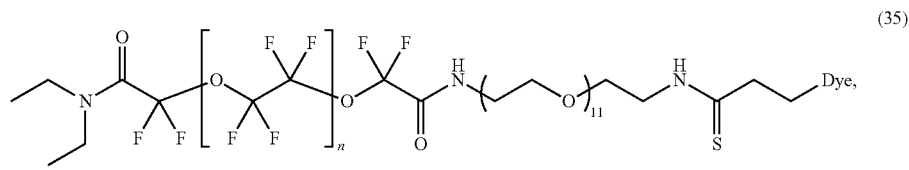

(35)

wherein
n, independently for each occurrence, represents an integer from 4 to 16; and
Dye, independently for each occurrence, represents a fluorescent detection moiety;

compound of formula 12, a compound of formula 35, and a compound of formula 1;

compound of formula 13 and a compound of formula 36:

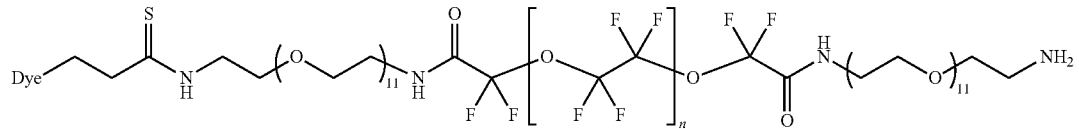

wherein
n, independently for each occurrence, represents an integer from 4 to 16; and
Dye, independently for each occurrence, represents a fluorescent detection moiety; or compound of formula 13 and a compound of formula 37:

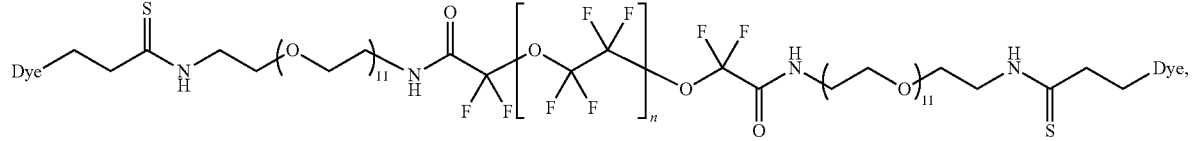

(37)

wherein
n, independently for each occurrence, represents an integer from 4 to 16; and
Dye, independently for each occurrence, represents a fluorescent detection moiety.

3. A composition comprising
A) one or more compounds of claim 1 and a compound of formula 1a,

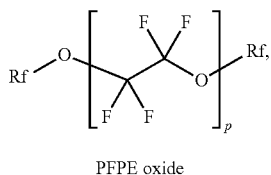

PFPE oxide wherein
p represents an integer from 8 to 13; and
Rf is $CF_3$ and/or $CF_2CF_3$ in a ratio of 2:1;
wherein the composition optionally comprises 80-95% v/v of the compound of formula 1a; or
B) one or more compounds of claim 1 and perfluoro-15-crown-5 ether, wherein the composition optionally comprises 80-95% v/v of perfluoro-15-crown-5 ether.

4. An emulsion comprising a compound of claim 1.

5. An emulsion selected from the group consisting of:
an emulsion comprising a compound of formula 1, which compound is as defined in claim 1, a compound of formula 16, which compound is as defined in claim 2, a compound of formula 17:

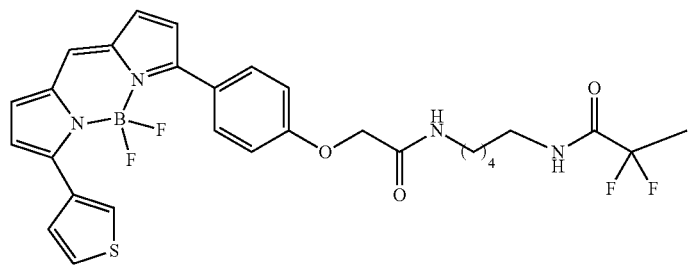

(17)

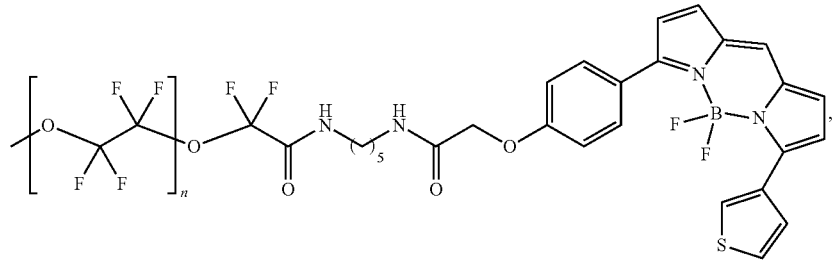

wherein
n, independently for each occurrence, represents an integer from 4 to 16,
a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;
an emulsion comprising a compound of formula 1, a compound of formula 16, a compound of formula 17, a compound of formula 1a, which compound is as defined in claim 3, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;
an emulsion comprising a compound of formula 1, a compound of formula 16, a compound of formula 17, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about an emulsion comprising a compound of formula 1, a compound of formula 16, a compound of formula 17, a polylethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;
an emulsion comprising a compound of formula 1, a compound of formula 16, a compound of formula 17, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;
an emulsion comprising a compound of formula 1, a compound of formula 16, a compound of formula 17, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;

an emulsion comprising a compound of formula 1, a compound of formula 18:

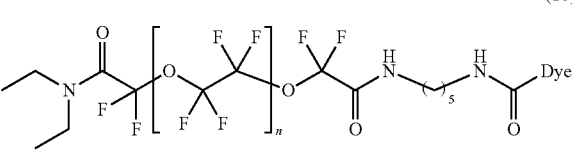

(18)

wherein
n, independently for each occurrence, represents an integer from 4 to 16, a compound of formula 19:

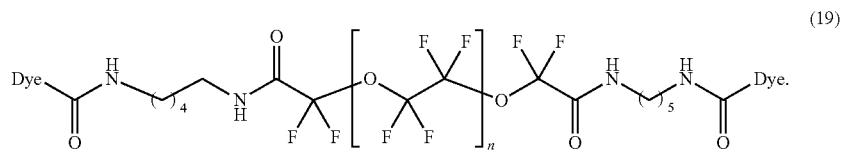

wherein
n, independently for each occurrence, represents an integer from 4 to 16,
a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;
an emulsion comprising a compound of formula 1, a compound of formula 18, a compound of formula 19, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;
an emulsion comprising a compound of formula 1, a compound of formula 18, a compound of formula 19, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;
an emulsion comprising a compound of formula 1, a compound of formula 18, a compound of formula 19, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;
an emulsion comprising a compound of formula 1, a compound of formula 18, a compound of formula 19, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;
an emulsion comprising a compound of formula 1, a compound of formula 18, a compound of formula 19, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;
an emulsion comprising a compound of formula 1, a compound of formula 40, which compound is as defined in claim 2, a compound of formula 41:

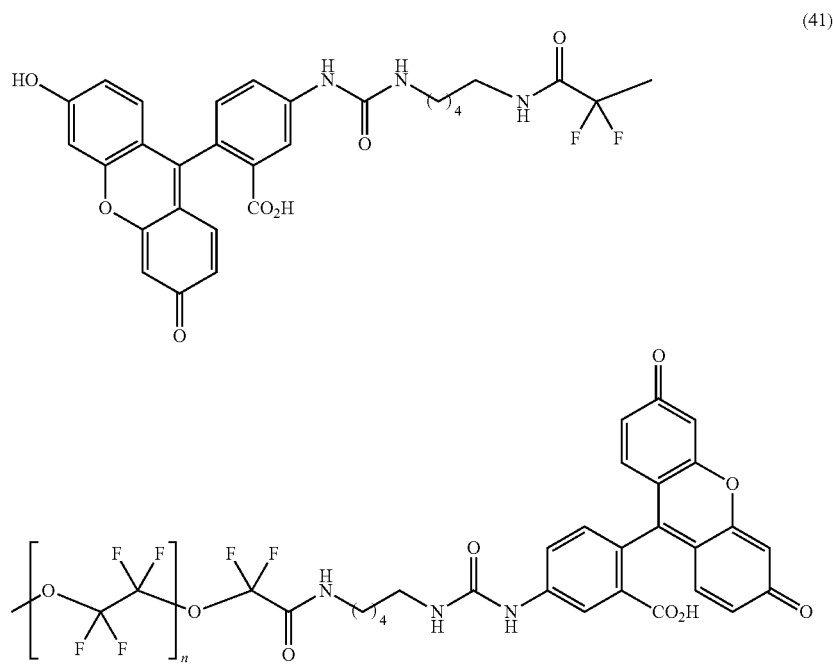

wherein
n, independently for each occurrence, represents an integer from 4 to 16,
a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;

an emulsion comprising a compound of formula 1, a compound of formula 40, a compound of formula 41, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;

an emulsion comprising a compound of formula 1, a compound of formula 40, a compound of formula 41, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;

an emulsion comprising a compound of formula 1, a compound of formula 40, a compound of formula 41, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;

an emulsion comprising a compound of formula 1, a compound of formula 40, a compound of formula 41, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;

an emulsion comprising a compound of formula 1, a compound of formula 40, a compound of formula 41, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;

an emulsion comprising a compound of formula 1, a compound of formula 1a, a poly(ethylene oxide)-poly(ethylene oxide) (PEO-PPO-PEO) tri-block copolymer with an average molecular weight of 8400, an average number of PEO units of about 153, and an average number of PPO units of about 29, and protamine sulfate;

an emulsion comprising a compound of formula 1, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;

an emulsion comprising a compound of formula 1, a compound of formula 1a, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;

an emulsion comprising a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;

an emulsion comprising a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;

an emulsion comprising a compound of formula 1a and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;

an emulsion comprising a compound of formula 1, a compound of formula 16, a compound of formula 17, perfluoro-(5-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;

an emulsion comprising a compound of formula 1, a compound of formula 16, a compound of formula 17, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;

an emulsion comprising a compound of formula 1, a compound of formula 16, a compound of formula 17, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;

an emulsion comprising a compound of formula 1, a compound of formula 18, a compound of formula 19, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;

an emulsion comprising a compound of formula 1, a compound of formula 18, a compound of formula 19, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;

an emulsion comprising a compound of formula 1, a compound of formula 18, a compound of formula 19, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;

an emulsion comprising a compound of formula 1, a compound of formula 40, a compound of formula 41, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;

an emulsion comprising a compound of formula 1, a compound of formula 40, a compound of formula 41, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;

an emulsion comprising a compound of formula 1, a compound of formula 40, a compound of formula 41, perfluoro-(5-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;

an emulsion comprising a compound of formula 1, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;

an emulsion comprising a compound of formula 1, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;

an emulsion comprising a compound of formula 1, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;

an emulsion comprising a compound of formula 1a, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and protamine sulfate;

an emulsion comprising a compound of formula 1a, perfluoro-15-crown-5 ether, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine;

an emulsion comprising a compound of formula 1a, perfluoro-15-crown-5 ether, and a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29;

an emulsion comprising a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is anon-ionic solubiliser comprising glycerol polyethylene glycol ricinoleate;

an emulsion comprising a compound of formula 1a, a compound of formula 1, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene ricinoleate;

an emulsion comprising a compound of formula 1a, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is anon-ionic solubiliser comprising glycerol polyethylene glycol ricinoleate;

an emulsion comprising a compound of formula 1a, a compound of formula 1, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate;

an emulsion comprising a compound of formula 1, a compound of formula 16, a compound of formula 17, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate;

an emulsion comprising a compound of formula 1, a compound of formula 18, a compound of formula 19, perfluoro-15-crown-5 ether, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is anon-ionic solubiliser comprising glycerol polyethylene glycol ricinoleate;

an emulsion comprising a compound of formula 1, a compound of formula 40, a compound of formula 41, perfluoro-(5-crown-15 ether, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is a non-ionic solubiliser comprising glycerol polyethylene glycol ricinoleate;

an emulsion comprising a compound of formula 1, a compound of formula 16, a compound of formula 17, a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is anon-ionic solubiliser comprising glycerol polyethylene glycol ricinoleate;

an emulsion comprising a compound of formula 1, a compound of formula 18, a compound of formula 19, a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is anon-ionic solubiliser comprising glycerol polyethylene glycol ricinoleate; and an emulsion comprising a compound of formula 1, a compound of formula 40, a compound of formula 41, a compound of formula 1a, a poly(ethylene oxide)-poly(propylene oxide)-poly(ethylene oxide) (PEO-PPO-PEO) tri-block copolymer with an average molecular weight of 6500, an average number of PEO units of about 74, and an average number of PPO units of about 56, and an emulsifier, wherein the emulsifier is anon-ionic solubiliser comprising glycerol polyethylene glycol ricinoleate.

6. A method for preparing a composition comprising a compound of formula 1 and a compound of formula 38:

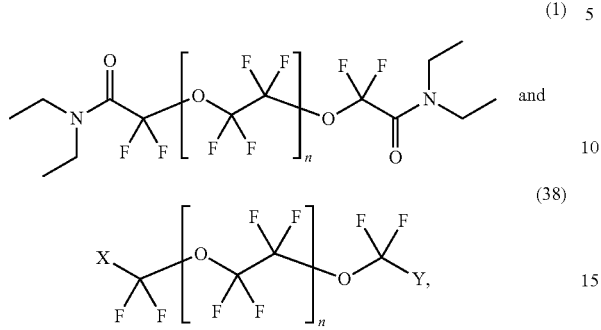

wherein
n, independently for each occurrence, represents an integer from 4 to 16; and
one or both of X and Y is an amide other than diethyl amide, comprising:
1) reacting perfluoropolyether methyl ester (39),

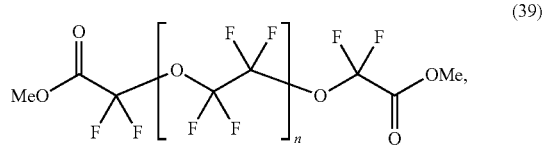

having two methyl ester end groups with a primary or secondary aliphatic amine other than diethyl amine;
2) reacting unmodified methyl ester end groups with excess diethyl amine;
3) removing unreacted diethyl amine; and
4) optionally removing non-volatile unreacted amine by selective extraction in fluorinated solvents or fluoropus phase solid extraction and filtration.

7. A method for preparing an emulsion of claim 4 or 5, comprising using low energy methods, wherein the low energy method optionally comprises a thin film method.

8. A method for preparing an emulsion of claim 4 or 5 comprising high energy methods, wherein the high energy method is optionally microfluidization or sonication.

9. A method for
I) labeling a cell, the method comprising contacting the cell ex vivo with a fluorocarbon imaging reagent comprising a compound of claim 1, under conditions such that the fluorocarbon imaging reagent becomes associated with the cell;
II) detecting a cell in a subject, the method comprising:
 a) administering to the subject a cell that is labeled with a fluorocarbon imaging reagent comprising a compound of claim 1; and
 b) examining at least a portion of the subject by a nuclear magnetic resonance technique, thereby detecting a labeled cell in the subject;
III) detecting transplanted cells in a transplant recipient, the method comprising:
 a) administering cells for transplant to a transplant recipient, at least a portion of which cells for transplant are labeled with a fluorocarbon imaging reagent comprising a compound of claim 1; and
 b) examining at least a portion of the subject by a nuclear magnetic resonance technique, thereby detecting the labeled cells;
IV) quantifying cell number in vivo, the method comprising:
 a) administering to the subject cells that are labeled with a fluorocarbon imaging reagent comprising a compound of claim 1;
 b) examining at least a portion of the subject by a nuclear magnetic resonance technique, thereby detecting labeled cells in the subject; and
 c) quantifying the number of labeled cells in a region of interest (ROI);
V) labeling a cell, the method comprising contacting the cell in vivo with a fluorocarbon imaging reagent comprising a compound of claim 1, under conditions such that the fluorocarbon imaging reagent becomes associated with the cell; or
VI) detecting a cell in a subject, the method comprising:
 a) administering to the subject a fluorocarbon imaging reagent comprising a compound of claim 1; and
 b) examining at least a portion of the subject by a nuclear magnetic resonance technique, thereby detecting a labeled cell in the subject.

10. A labeled cellular formulation for administration to a subject, the formulation comprising:
 a) a cell; and
 h) a fluorocarbon imaging reagent comprising a compound of claim 1, that is associated with the cell.

11. The compound of claim 1, wherein the compound is the compound of formula 1.
12. The compound of claim 1, wherein the compound is the compound of formula 2.
13. The compound of claim 1, wherein the compound is the compound of formula 6.
14. The compound of claim 1, wherein the compound is the compound of formula 7.
15. The compound of claim 1, wherein the compound is the compound of formula 10.
16. The compound of claim 1, wherein the compound is the compound of formula 11.
17. The compound of claim 1, wherein the compound is the compound of formula 12.
18. The compound of claim 1, wherein the compound is the compound of formula 13.
19. The compound of claim 1, wherein the compound is the compound of formula 14.
20. The compound of claim 1, wherein the compound is the compound of formula 15.
21. The composition of claim 2, wherein the composition comprises a compound of formula 16 and a compound of formula 1.
22. The composition of claim 2, wherein the composition comprises a compound of formula 40 and a compound of formula 1.
23. The composition of claim 2, wherein the composition comprises a compound of formula 12 and a compound of formula 29.
24. The emulsion of claim 5, wherein the emulsion comprises a compound of formula 1, a compound of formula 16, a compound of formula 17, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and prolamine sulfate.
25. The emulsion of claim 5, wherein the emulsion comprises a compound of formula 1, a compound of formula 16, a compound of formula 17, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine.

26. The emulsion of claim 5, wherein the emulsion comprises a compound of formula 1, a compound of formula 40, a compound of formula 41, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and prolamine sulfate.

27. The emulsion of claim 5, wherein the emulsion comprises a compound of formula 1, a compound of formula 40, a compound of formula 41, a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine.

28. The emulsion of claim 5, wherein the emulsion comprises a compound of formula 1a, a poly(ethylene oxide)-poly(propylene oxide)-poly(ethylene oxide) (PEO-PPO-PEO) tri-block copolymer with an average molecular weight of 8400, an average number of PEO units of about 153, and an average number of PPO units of about 29, and polyethylamine.

29. An emulsion comprising a composition of claim 2.

30. An emulsion comprising a composition of claim 3.

* * * * *